United States Patent
Jeon et al.

(10) Patent No.: US 10,510,966 B2
(45) Date of Patent: Dec. 17, 2019

(54) ORGANIC LIGHT-EMITTING DEVICE

(71) Applicants: SAMSUNG ELECTRONICS CO., LTD., Suwon-si, Gyeonggi-do (KR); Samsung SDI Co., Ltd., Yongin-si, Gyeonggi-do (KR)

(72) Inventors: Soonok Jeon, Seoul (KR); Masaki Numata, Hwaseong-si (KR); Saeyoun Lee, Suwon-si (KR); Hiroshi Miyazaki, Hwaseong-si (KR); Jhunmo Son, Yongin-si (KR); Myungsun Sim, Suwon-si (KR); Namheon Lee, Suwon-si (KR); Sooghang Ihn, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 168 days.

(21) Appl. No.: 15/291,477

(22) Filed: Oct. 12, 2016

(65) Prior Publication Data
US 2017/0352816 A1 Dec. 7, 2017

(30) Foreign Application Priority Data
Jun. 1, 2016 (KR) .................. 10-2016-0068106

(51) Int. Cl.
| H01L 51/54 | (2006.01) |
| C09K 11/06 | (2006.01) |
| H01L 51/00 | (2006.01) |
| C09K 11/02 | (2006.01) |
| C07D 487/04 | (2006.01) |
| H05B 33/14 | (2006.01) |
| H01L 51/50 | (2006.01) |

(52) U.S. Cl.
CPC ........ H01L 51/0072 (2013.01); C07D 487/04 (2013.01); C09K 11/025 (2013.01); C09K 11/06 (2013.01); H01L 51/0067 (2013.01); H05B 33/14 (2013.01); C09K 2211/1007 (2013.01); C09K 2211/1059 (2013.01); H01L 51/5012 (2013.01); H01L 2251/308 (2013.01)

(58) Field of Classification Search
CPC .... H05B 33/14; C07D 487/00; C07D 487/02; C07D 487/04; C09K 11/025; C09K 11/06; C09K 2211/00; C09K 2211/10; C09K 2211/1007; C09K 2211/1059; H01L 51/0032; H01L 51/0067; H01L 51/0072; H01L 51/0073; H01L 51/0074; H01L 51/50; H01L 51/5012; H01L 51/5016; H01L 2251/00; H01L 2251/5376
USPC ....... 428/690, 691, 917, 411.4, 336; 427/58, 427/66; 313/500–512; 257/40, 88–104, 257/E51.001–E51.052; 252/301.16–301.35

See application file for complete search history.

(56) References Cited

U.S. PATENT DOCUMENTS

| 2015/0171340 A1 | 7/2015 | Lee et al. |
| 2016/0197286 A1 * | 7/2016 | Kawamura ............ C09K 11/06 257/40 |
| 2017/0062718 A1 | 3/2017 | Numata et al. |

FOREIGN PATENT DOCUMENTS

| KR | 10-2010-0131939 A | 12/2010 | |
| KR | 10-2015-0070860 A | 6/2015 | |
| KR | 10-2015-0127548 A | 11/2015 | |
| KR | 10-2015-0128590 A | 11/2015 | |
| KR | 10-2017-0025990 A | 3/2017 | |
| WO | WO-2014092083 A1 * | 6/2014 | ............. C09K 11/06 |

OTHER PUBLICATIONS

Uoyama et al. Nature 2012, 492, 234-240 (Year: 2012).*

* cited by examiner

Primary Examiner — Andrew K Bohaty
(74) Attorney, Agent, or Firm — Cantor Colburn LLP

(57) ABSTRACT

An organic light-emitting device including a first electrode, a second electrode facing the first electrode, and an organic layer disposed between the first electrode and the second electrode, wherein the organic layer has an emission layer, wherein the emission layer includes a host and a thermally activated delayed fluorescent dopant, wherein the dopant includes a condensed cyclic compound represented by Formula 1, and wherein an amount of the dopant is smaller than that of the host:

$$Ar_1\text{—}Ar_2 \qquad \text{Formula 1}$$

wherein $Ar_1$ and $Ar_2$ are the same as described in the specification.

20 Claims, 1 Drawing Sheet

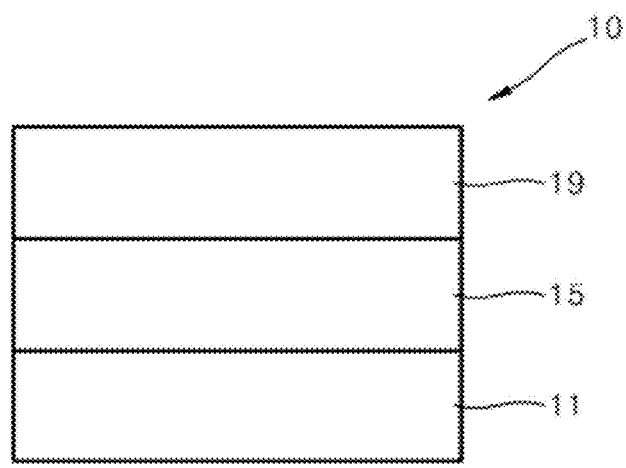

ORGANIC LIGHT-EMITTING DEVICE

CROSS-REFERENCE TO RELATED APPLICATION

This application claims priority to and the benefit of Korean Patent Application No. 10-2016-0068106, filed on Jun. 1, 2016, in the Korean Intellectual Property Office, the content of which is incorporated herein in its entirety by reference.

BACKGROUND

1. Field

The present disclosure relates to an organic light-emitting device.

2. Description of the Related Art

Organic light-emitting devices (OLEDs) are self-emission devices that have wide viewing angles, high contrast ratios, and short response times. In addition, OLEDs display excellent brightness, driving voltage and response speed characteristics, compared to devices in the art.

For example, an organic light-emitting device may include an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode layer. Holes provided from the anode may move toward the emission layer through the hole transport region, and electrons provided from the cathode may move toward the emission layer through the electron transport region. Carriers, such as holes and electrons, recombine in the emission layer to produce excitons. These excitons may transit from an excited state to the ground state, thereby generating light.

Various types of organic light emitting devices are known. However, there still remains a need in OLEDs having low driving voltage, high efficiency, high brightness, and long lifespan.

SUMMARY

Provided is an organic light-emitting device having low driving voltage, high efficiency, and long lifespan.

Additional aspects will be set forth in part in the description which follows and, in part, will be apparent from the description, or may be learned by practice of the presented embodiments.

According to an aspect of an embodiment, an organic light-emitting device includes:

a first electrode;

a second electrode facing the first electrode; and an organic layer disposed between the first electrode and the second electrode, wherein the organic layer includes an emission layer, wherein the emission layer includes a host and a dopant, wherein the dopant includes a condensed cyclic compound represented by Formula 1, and wherein an amount of the dopant is smaller than that of the host:

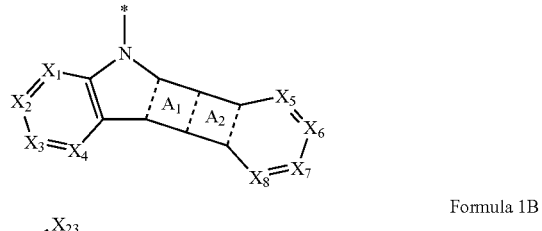
Formula 1
Ar$_1$—Ar$_2$

Formula 1A

Formula 1B

Formula 2A

Formula 2B

In Formula 1,

Ar$_1$ may be a group represented by Formula 1A, Ar$_2$ may be a group represented by Formula 1B, in Formula 1A, ring A$_1$ may be a group represented by Formula 2A, and ring A$_2$ may be a group represented by Formula 2B, in Formulae 1A, 1B, 2A, and 2B, X$_1$ may be C(R$_1$) or N, X$_2$ may be C(R$_2$) or N, X$_3$ may be C(R$_3$) or N, X$_4$ may be C(R$_4$) or N, X$_5$ may be C(R$_5$) or N, X$_6$ may be C(R$_6$) or N, X$_7$ may be C(R$_7$) or N, and X$_8$ may be C(R$_8$) or N, X$_{11}$ may be selected from O, S, N[(L$_{11}$)$_{a11}$-(R$_{11}$)$_{b11}$], C[(L$_{11}$)$_{a11}$-(R$_{11}$)$_{b11}$][(L$_{12}$)$_{a12}$-(R$_{12}$)$_{b12}$], Si[(L$_{11}$)$_{a11}$-(R$_{11}$)$_{b11}$][(L$_{12}$)$_{a12}$-(R$_{12}$)$_{b12}$], and Ge[(L$_{11}$)$_{a11}$-(R$_{11}$)$_{b11}$][(L$_{12}$)$_{a12}$-(R$_{12}$)$_{b12}$], X$_{21}$ may be C(R$_{21}$) or N, X$_{22}$ may be C(R$_{22}$) or N, X$_{23}$ may be C(R$_{23}$) or N, X$_{24}$ may be C(R$_{24}$) or N, and X$_{25}$ may be C(R$_{25}$) or N, X$_{26}$ may be C(R$_{26}$), N, or a binding site to Ar$_1$, X$_{27}$ may be C(R$_{27}$), N, or a binding site to Ar$_1$, X$_{28}$ may be C(R$_{28}$), N, or a binding site to Ar$_1$, X$_{29}$ may be C(R$_{29}$), N, or a binding site to Ar$_1$, and X$_{30}$ may be C(R$_{30}$), N, or a binding site to Ar$_1$, at least one selected from X$_{21}$ to X$_{30}$ may be N, and at least one selected from X$_{26}$ to X$_{30}$ may be a binding site to Ar$_1$, L$_{11}$ and L$_{12}$ may each independently be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 and a12 may each independently be an integer selected from 0 to 3, $R_1$ to $R_{12}$ and $R_{21}$ to $R_{30}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), b11 and b12 may each independently be an integer selected from 1 to 3, the number of cyano group(s) included in the condensed cyclic compound represented by Formula 1 may be 1 or greater,

* indicates a binding site to a neighboring atom, at least one substituent selected from substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_0$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, and a substituted or unsubstituted monovalent non-aromatic condensed heteropolycyclic group.

BRIEF DESCRIPTION OF THE DRAWING

These and/or other aspects will become apparent and more readily appreciated from the following description of the embodiments, taken in conjunction with the FIGURE, which is a schematic diagram of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

According to an aspect of the present inventive concept, an organic light-emitting device includes:
a first electrode;
a second electrode facing the first electrode; and
an organic layer that is disposed between the first electrode and the second electrode, wherein
the organic layer includes an emission layer,
wherein the emission layer includes a host and a dopant,
wherein the dopant includes a condensed cyclic compound represented by Formula 1, and
wherein an amount of the dopant is smaller than that of the host:

$$Ar_1\text{—}Ar_2, \quad \text{Formula 1}$$

wherein, $Ar_1$ in Formula 1 may be a group represented by Formula 1A:

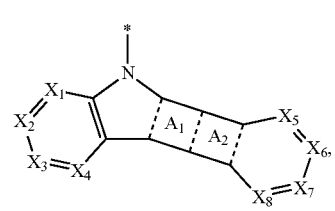

Formula 1A wherein, in Formula 1A, ring $A_1$ may be a group represented by Formula 2A, and is condensed with both a neighboring 5-membered ring and ring $A_2$ by sharing carbon atoms therebetween.

In Formula 1A, ring $A_2$ may be a group represented by Formula 2B, and is condensed with both ring $A_1$ and a neighboring 6-membered ring by sharing carbon atoms therebetween.

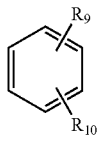

Formula 2A

Formula 2B

Descriptions of Formulae 1A, 1B, 2A, and 2B will be provided below.

In Formula 1A, $X_1$ may be $C(R_1)$ or N, $X_2$ may be $C(R_2)$ or N, $X_3$ may be $C(R_3)$ or N, $X_4$ may be $C(R_4)$ or N, $X_5$ may be $C(R_5)$ or N, $X_6$ may be $C(R_6)$ or N, $X_7$ may be $C(R_7)$ or N, and $X_8$ may be $C(R_8)$ or N.

For example, when at least one selected from $X_1$ to $X_8$ in Formula 1A is N, $Ar_1$ may not include a cyano group, and $Ar_2$ may include at least one cyano group.

In various embodiments, in Formula 1A, when $X_1$ is $C(R_1)$, $X_2$ is $C(R_2)$, $X_3$ is $C(R_3)$, $X_4$ is $C(R_4)$, $X_5$ is $C(R_5)$, $X_6$ is $C(R_6)$, $X_7$ is $C(R_7)$, and $X_8$ is $C(R_8)$, i) $Ar_1$ may not include a cyano group, and $Ar_2$ may include at least one cyano group;

ii) $Ar_1$ may include at least one cyano group, and $Ar_2$ may not include a cyano group; or iii) $Ar_1$ and $Ar_2$ may each independently include at least one cyano group, but embodiments are not limited thereto.

In Formula 2B, $X_{11}$ may be selected from O, S, N[$(L_{11})_{a11}$-$(R_{11})_{b11}$], C[$(L_{11})_{a11}$-$(R_{11})_{b11}$][$(L_{12})_{a12}$-$(R_{12})_{b12}$], Si[$(L_{11})_{a11}$-$(R_{11})_{b11}$][$(L_{12})_{a12}$-$(R_{12})_{b12}$], and Ge[$(L_{11})_{a11}$-$(R_{11})_{b11}$][$(L_{12})_{a12}$-$(R_{12})_{b12}$].

For example, in Formula 2B, $X_{11}$ may be N[$(L_{11})_{a11}$-$(R_{11})_{b11}$], and a group represented by *-[$(L_{11})_{a11}$-$(R_{11})_{b11}$] may include at least one cyano group; or $X_{11}$ may be selected from C[$(L_{11})_{a11}$-$(R_{11})_{b11}$][$(L_{12})_{a12}$-$(R_{12})_{b12}$], Si[$(L_{11})_{a11}$-$(R_{11})_{b11}$][$(L_{12})_{a12}$-$(R_{12})_{b12}$], and Ge[$(L_{11})_{a11}$-$(R_{11})_{b11}$][$(L_{12})_{a12}$-$(R_{12})_{b12}$], and at least one selected from a group represented by *-[$(L_{11})_{a11}$-$(R_{11})_{b11}$] and a group represented by *-[$(L_{12})_{a12}$-$(R_{12})_{b12}$] may include at least one cyano group.

In Formula 2B, $L_{11}$ and $L_{12}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_{11}$ and $L_{12}$ in Formula 2B may each independently be selected from:

a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, and a dibenzothiophenylene group; and a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, and a dibenzothiophenylene group, each substituted with at least one selected from deuterium, a cyano group, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, and —Si($Q_{31}$)($Q_{32}$)($Q_{33}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In various embodiments, $L_{11}$ and $L_{12}$ in Formula 2B may each independently be selected from:

a phenylene group; and a phenylene group substituted with at least one selected from deuterium, a cyano group, a $C_1$-$C_{10}$ alkyl group, a $C_1$-$C_{10}$ alkoxy group, a phenyl group, a biphenyl group, and a terphenyl group.

In Formula 2B, a11 and a12 may each independently be an integer selected from 0 to 3.

In Formula 2B, a11 indicates the number of groups $L_{11}$, wherein when a11 is 0, *-$(L_{11})_{a11}$-*' is a single bond. When a11 in Formula 2B is 2 or more, 2 or more groups $L_{11}$ may be identical to or different from each other. In Formula 2B, a12 indicates the number of groups $L_{12}$, wherein when a12 is 0, *-$(L_{12})_{a12}$-*' is a single bond. When a12 in Formula 2B is 2 or more, 2 or more groups $L_{12}$ may be identical to or different from each other.

In an embodiment, a11 and a12 in Formula 2B may each independently be 0, 1, or 2.

In various embodiments, a11 and a12 in Formula 2B may each independently be 0 or 1.

For example, $Ar_1$ in Formula 1 may be represented by one selected from Formulae 1A(1) to 1A(6):

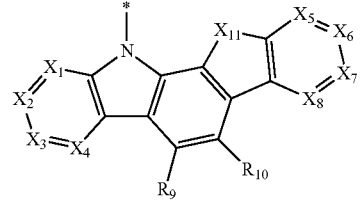

Formula 1A(1)

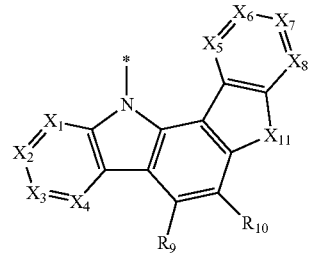

Formula 1A(2)

-continued

Formula 1A(3)
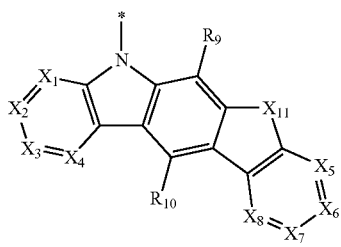

Formula 1A(4)
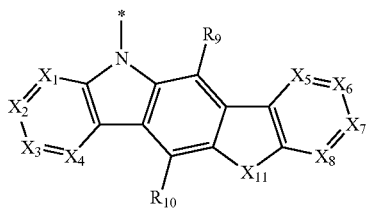

Formula 1A(5)
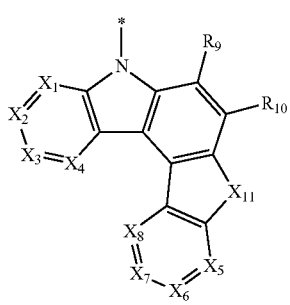

Formula 1A(6)
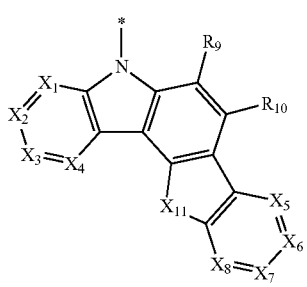

In Formulae 1A(1) to 1A(6), $X_1$ to $X_8$, $X_{11}$, $R_9$, and $R_{10}$ may be understood by referring to the descriptions thereof provided herein in the present specification, and * indicates a binding site to a neighboring atom (e.g., $Ar_2$).

In Formula 1, $Ar_2$ may be a group represented by Formula 1B:

Formula 1B
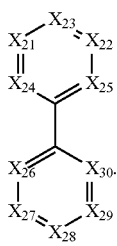

In Formula 1B, $X_{21}$ may be $C(R_{21})$ or N, $X_{22}$ may be $C(R_{22})$ or N, $X_{23}$ may be $C(R_{23})$ or N, $X_{24}$ may be $C(R_{24})$ or N, and $X_{25}$ may be $C(R_{25})$ or N, $X_{26}$ may be $C(R_{26})$, N, or a binding site to $Ar_1$, $X_{27}$ may be $C(R_{27})$, N, or a binding site to $Ar_1$, $X_{28}$ may be $C(R_{28})$, N, or a binding site to $Ar_1$, $X_{29}$ may be $C(R_{29})$, N, or a binding site to $Ar_1$, and $X_{30}$ may be $C(R_{30})$, N, or a binding site to $Ar_1$, and at least one selected from $X_{21}$ to $X_{30}$ may be N, and at least one selected from $X_{26}$ to $X_{30}$ may be a binding site to $Ar_1$.

For example, $Ar_2$ in Formula 1 may be represented by one selected from Formulae 1B(1) to 1B(3):

Formula 1B(1)
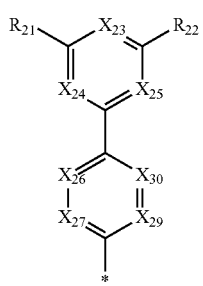

Formula 1B(2)
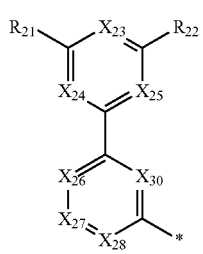

Formula 1B(3)
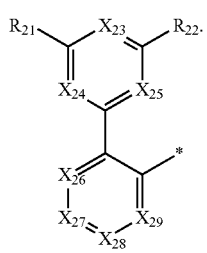

In Formulae 1B(1) to 1B(3), $X_{23}$ to $X_{25}$, $R_{21}$, and $R_{22}$ may be understood by referring to the descriptions thereof provided herein in the present specification, $X_{26}$ may be $C(R_{26})$ or N, $X_{27}$ may be $C(R_{27})$ or N, $X_{28}$ may be $C(R_{28})$ or N, $X_{29}$ may be $C(R_{29})$ or N, and $X_{30}$ may be $C(R_{30})$ or N, at least one selected from $X_{23}$ to $X_{27}$, $X_{29}$, and $X_{30}$ in Formula 1B(1) may be N, at least one selected from $X_{23}$ to $X_{28}$ and $X_{30}$ in Formula 1B(2) may be N, at least one selected from $X_{23}$ to $X_{29}$ in Formula 1B(3) may be N, and

* indicates a binding site to a neighboring atom (e.g., $Ar_1$).

In Formulae 1A, 1B, 2A, and 2B, $R_1$ to $R_{12}$ and $R_{21}$ to $R_{30}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$).

For example, in Formulae 1A, 1B, 2A, and 2B, $R_1$ to $R_{12}$, and $R_{21}$ to $R_{30}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and —Si($Q_{31}$)($Q_{32}$)($Q_{33}$); and —Si($Q_1$)($Q_2$)($Q_3$), and $Q_1$ to $Q_3$ and $Q_{31}$ to $Q_{33}$ may each independently be selected from hydrogen, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group.

In various embodiments, in Formulae 1A, 1B, 2A, and 2B, $R_1$ to $R_{12}$ and $R_{23}$ to $R_{30}$ may each independently be selected from:

hydrogen, deuterium, a cyano group, a $C_1$-$C_{20}$ alkyl group, a phenyl group, a biphenyl group, a terphenyl group, a fluorenyl group, a dibenzofuranyl group, a dibenzothiophenyl group, and a dibenzosilolyl group;

a $C_1$-$C_{20}$ alkyl group each substituted with at least one selected from deuterium and a cyano group;

a phenyl group, a biphenyl group, a terphenyl group, a fluorenyl group, a dibenzofuranyl group, a dibenzothiophenyl group, and a dibenzosilolyl group; and a phenyl group, a biphenyl group, a terphenyl group, a fluorenyl group, a dibenzofuranyl group, a dibenzothiophenyl group, and a dibenzosilolyl group, each substituted with at least one selected from deuterium, a cyano group, a $C_1$-$C_{20}$ alkyl group, a phenyl group, a biphenyl group, and a terphenyl group, $R_{21}$ and $R_{22}$ may each independently be selected from:

a phenyl group, a biphenyl group, a terphenyl group, a fluorenyl group, a dibenzofuranyl group, a dibenzothiophenyl group, and a dibenzosilolyl group; and a biphenyl group, a terphenyl group, a fluorenyl group, a dibenzofuranyl group, a dibenzothiophenyl group, and a dibenzosilolyl group, each substituted with at least one selected from deuterium, a cyano group, a $C_1$-$C_{20}$ alkyl group, a phenyl group, a biphenyl group, and a terphenyl group, but embodiments are not limited thereto.

In various embodiments, in Formulae 1A, 1B, 2A, and 2B, $R_1$ to $R_{12}$ and $R_{23}$ to $R_{30}$ may each independently be selected from:

hydrogen, deuterium, a cyano group, a $C_1$-$C_{20}$ alkyl group, a phenyl group, a biphenyl group, a terphenyl group, a fluorenyl group, a dibenzofuranyl group, a dibenzothiophenyl group, and a dibenzosilolyl group;

a $C_1$-$C_{20}$ alkyl group substituted with at least one selected from deuterium and a cyano group;

a phenyl group, a biphenyl group, a terphenyl group, a fluorenyl group, a dibenzofuranyl group, a dibenzothiophenyl group, and a dibenzosilolyl group; and groups represented by Formulae 5-1 to 5-15, and $R_{21}$ and $R_{22}$ may each independently be selected from:

a phenyl group, a biphenyl group, a terphenyl group, a fluorenyl group, a dibenzofuranyl group, a dibenzothiophenyl group, and a dibenzosilolyl group; and groups represented by Formulae 5-1 to 5-15, but embodiments are not limited thereto:

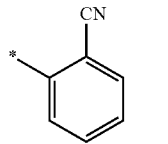
5-1

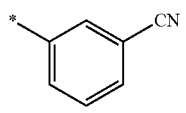
5-2

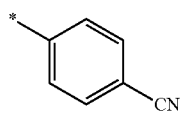
5-3

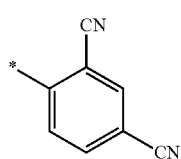
5-4

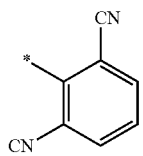
5-5

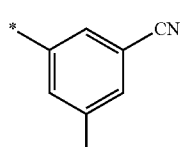
5-6

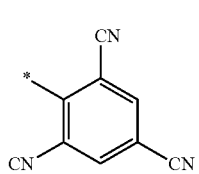
5-7

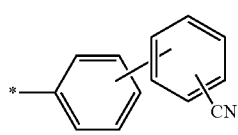
5-8

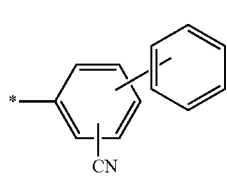
5-9

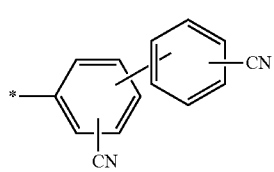
5-10

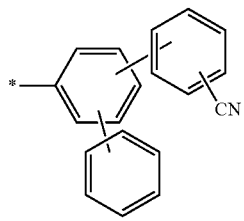
5-11

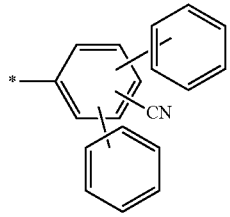
5-12

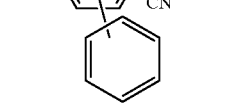
5-13

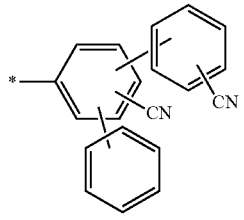
5-13

5-14

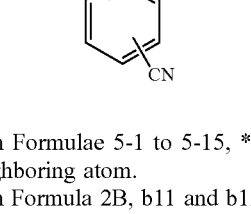
5-15

In Formulae 5-1 to 5-15, * indicates a binding site to a neighboring atom.

In Formula 2B, b11 and b12 may each independently be an integer selected from 1 to 3. In Formula 2B, b11 indicates the number of groups $R_{11}$, wherein when b11 is 2 or more, 2 or more groups $R_{11}$ may be identical to or different from each other. In Formula 2B, b12 indicates the number of groups $R_{12}$, wherein when b12 is 2 or more, 2 or more groups $R_{12}$ may be identical to or different from each other.

The number of cyano group(s) included in the condensed cyclic compound represented by Formula 1 may be 1 or greater.

For example, the number of a cyano group(s) included in the condensed cyclic compound represented by Formula 1 may be 1, 2, 3, or 4.

That is, the condensed cyclic compound represented by Formula 1 includes at least one cyano group, and such introduction of the cyano group leads to improved thermal stability and color purity of the condensed cyclic compound, thereby resulting in a stable spectrum of light emitted from the organic light-emitting device including the condensed cyclic compound.
The condensed cyclic compound represented by Formula 1 may be one selected from Compounds 1 to 192, but embodiments are not limited thereto:
1
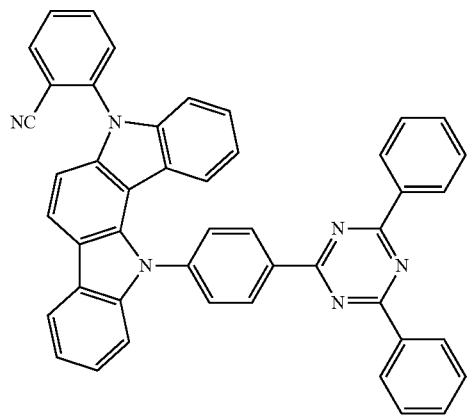
2
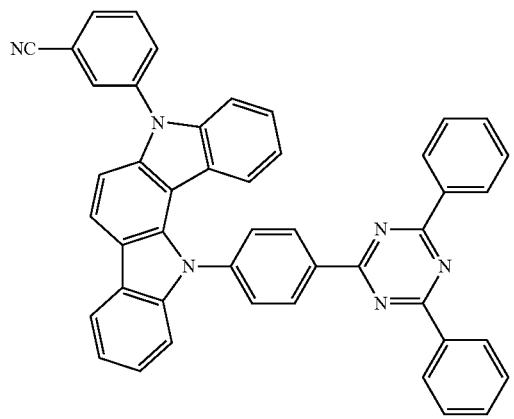
3
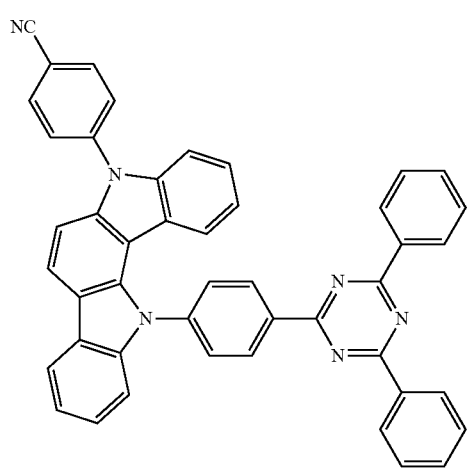
-continued
4
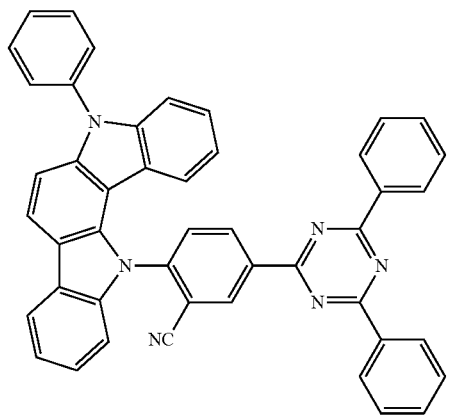
5
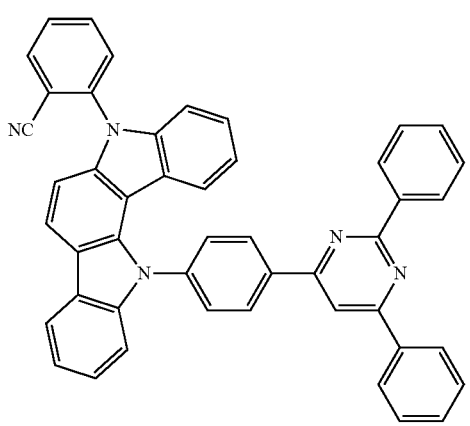
6
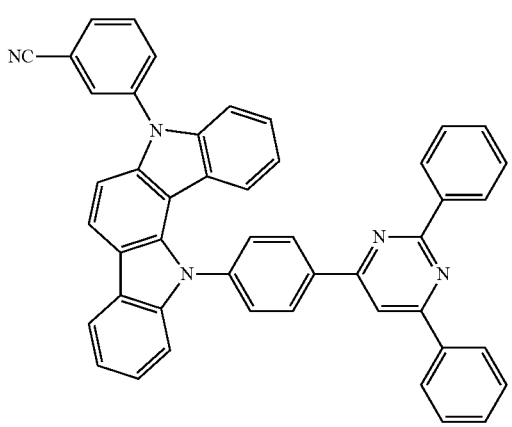

-continued
7
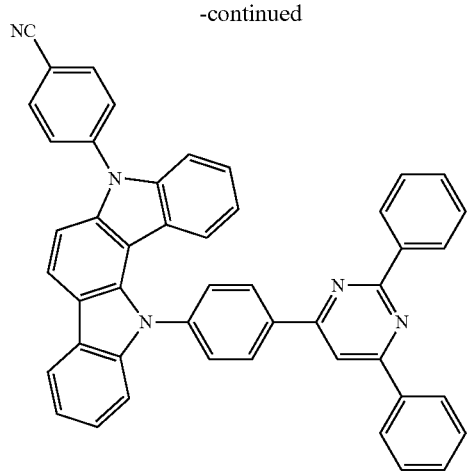
8
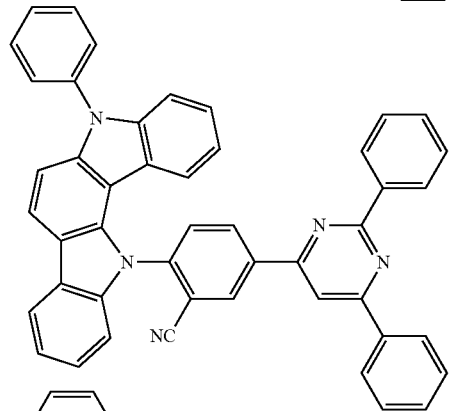
9
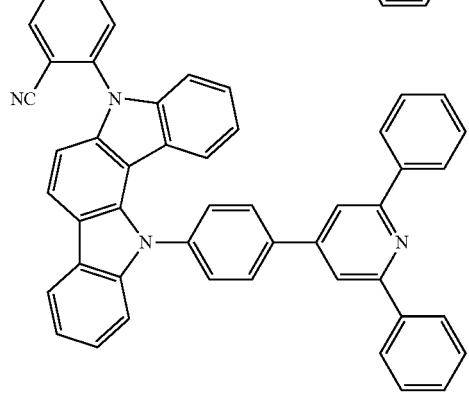
10
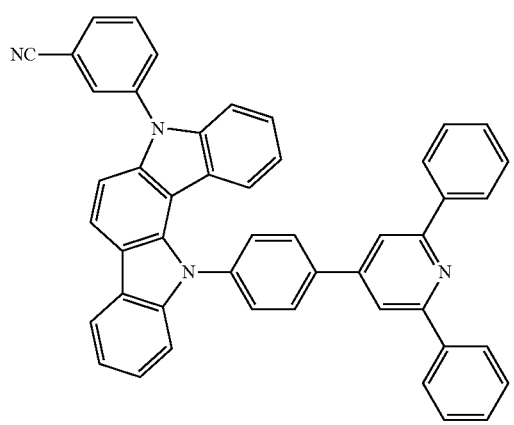
11
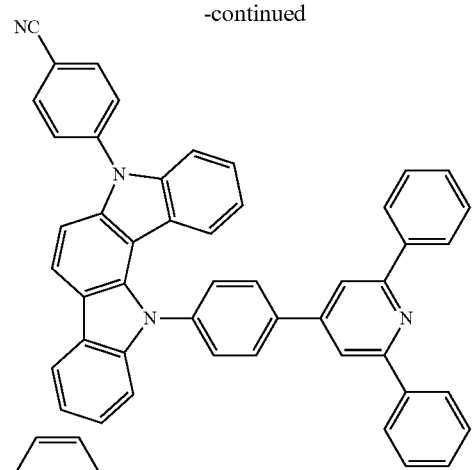
12
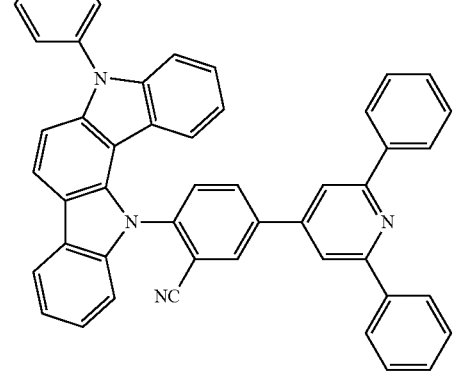
13
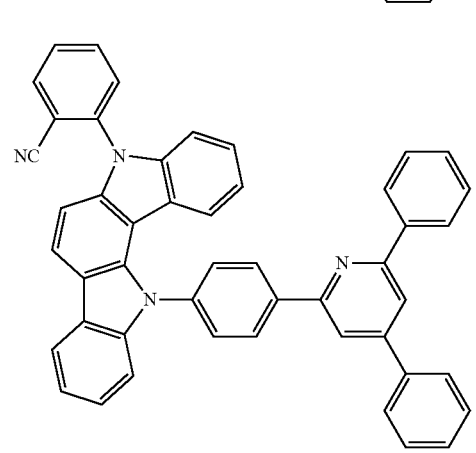
14
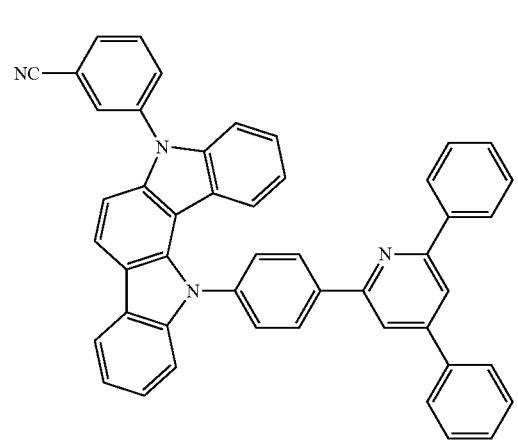

-continued
19
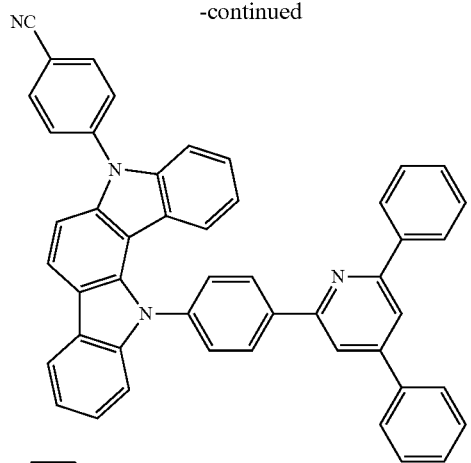
16
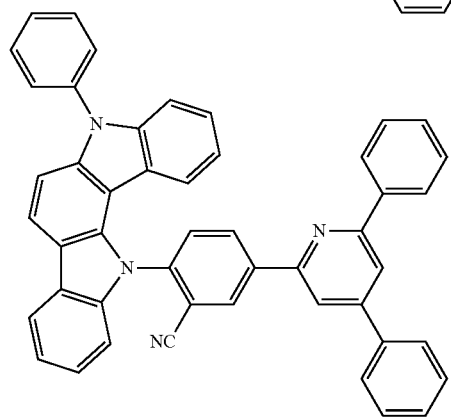
17
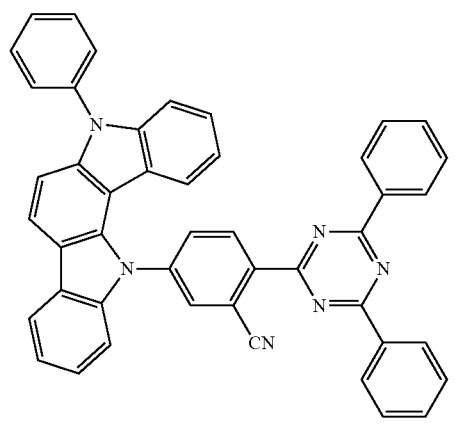
18
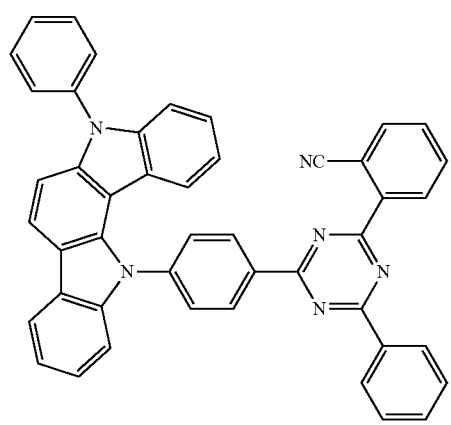
-continued
19
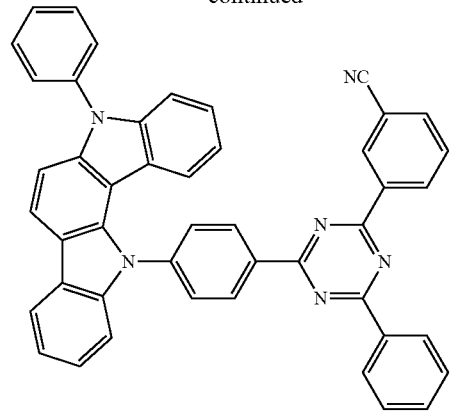
20
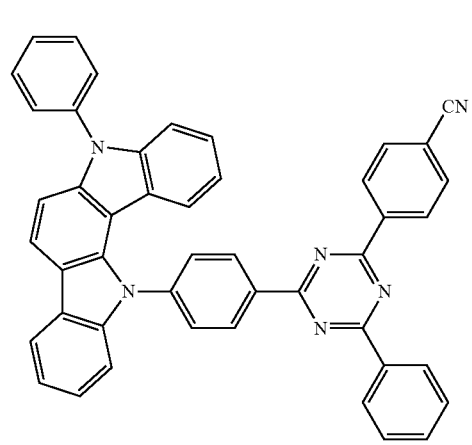
21
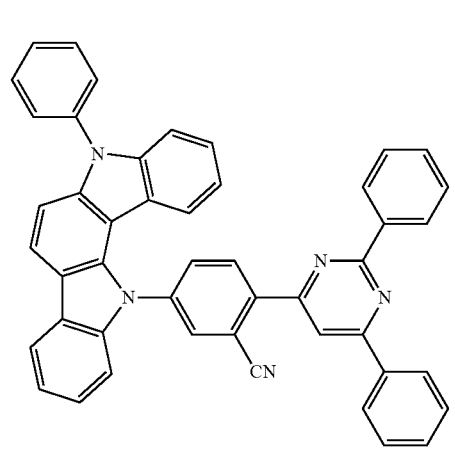
22
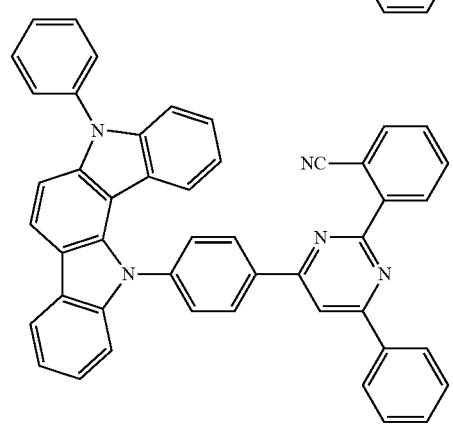

23
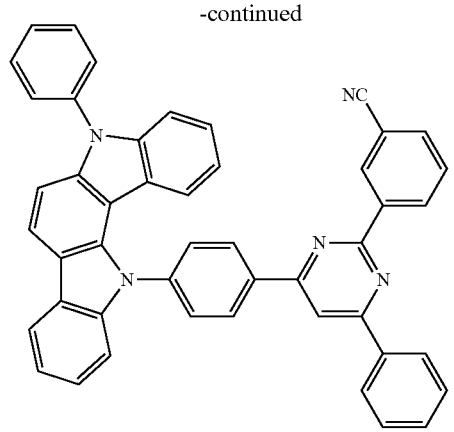
24
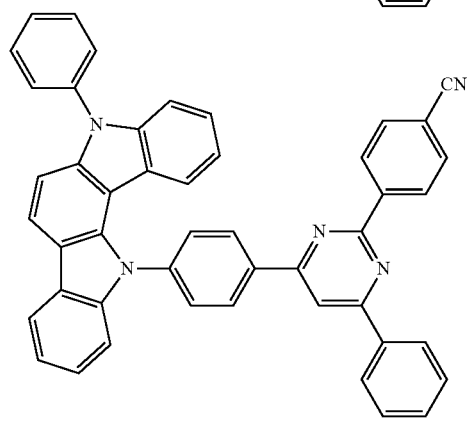
25
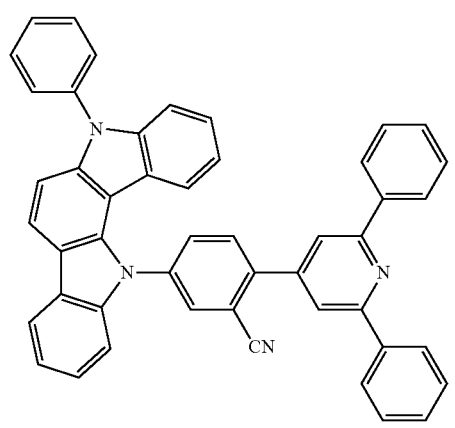
26
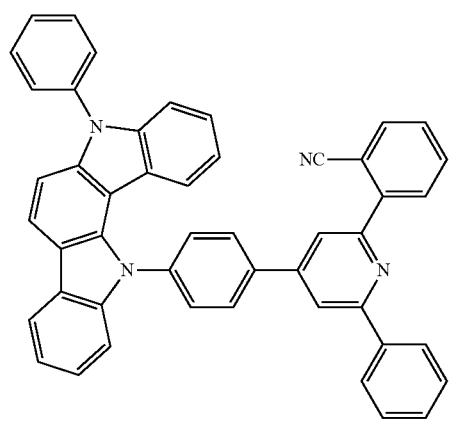
27
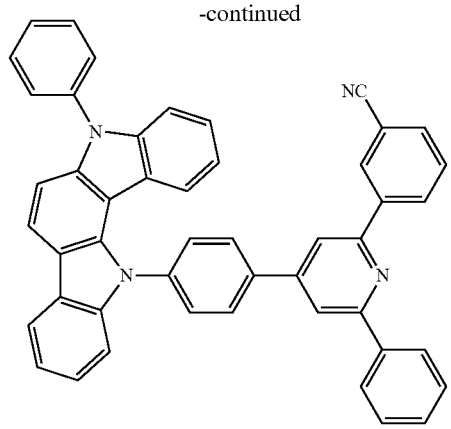
28
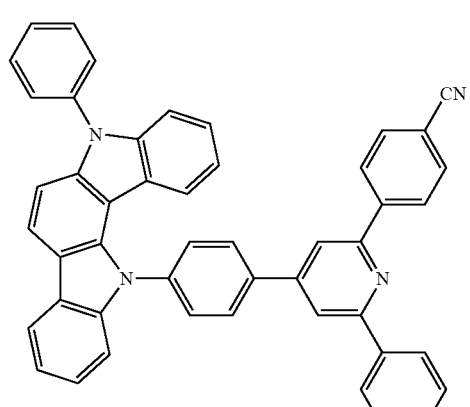
29
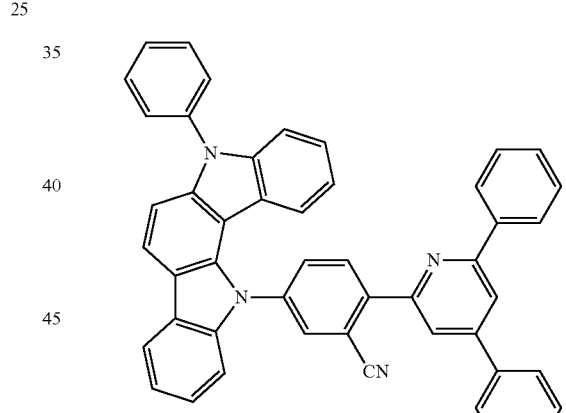
30
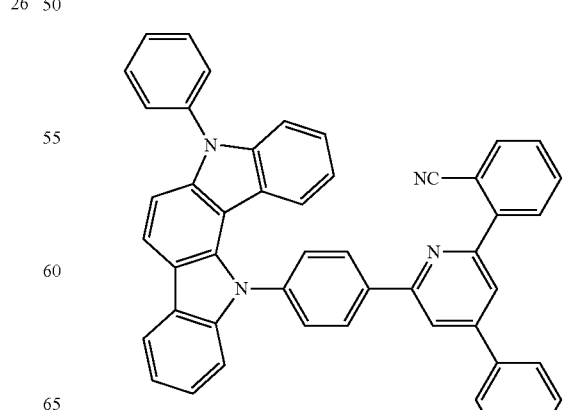

31
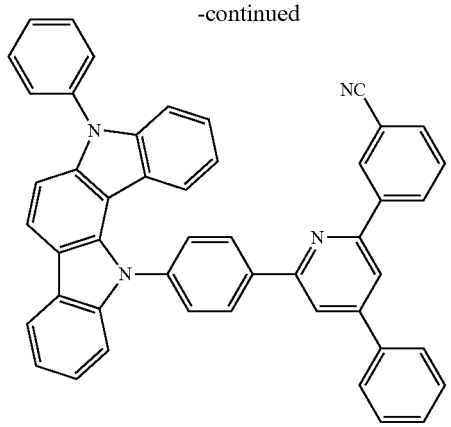
32
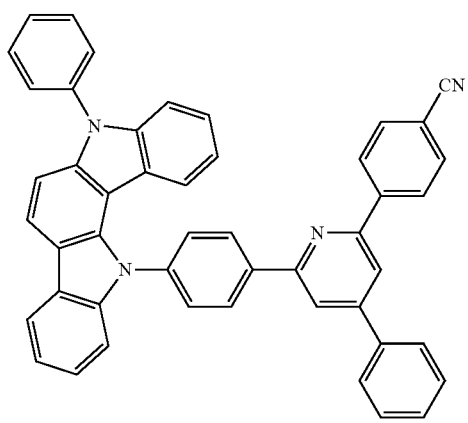
33
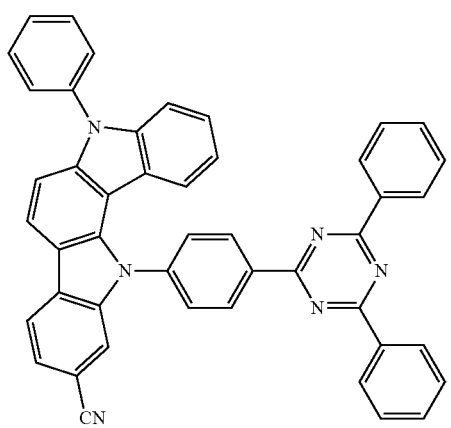
34
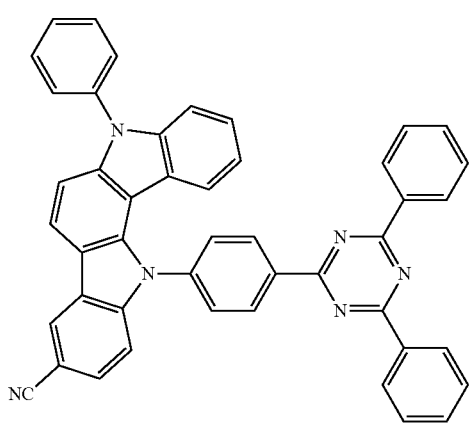
35
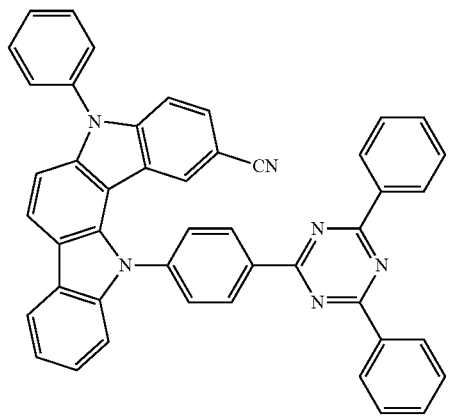
36
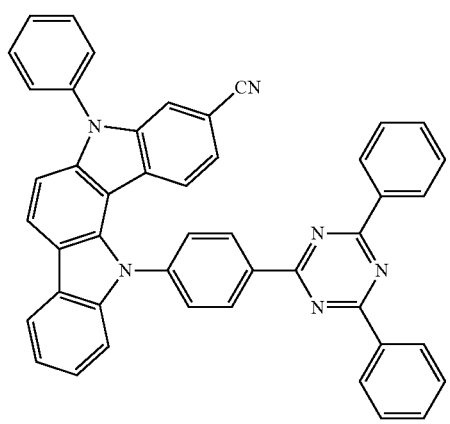
37
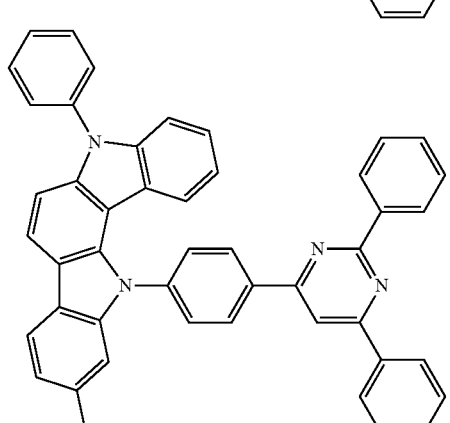
38
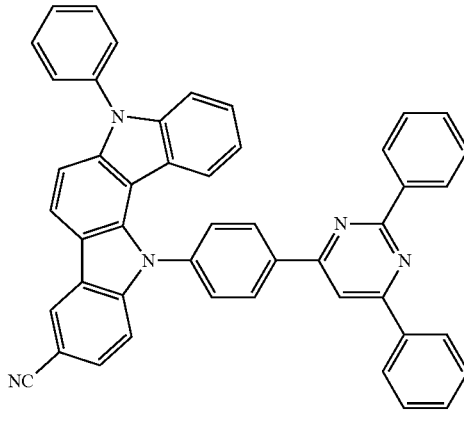

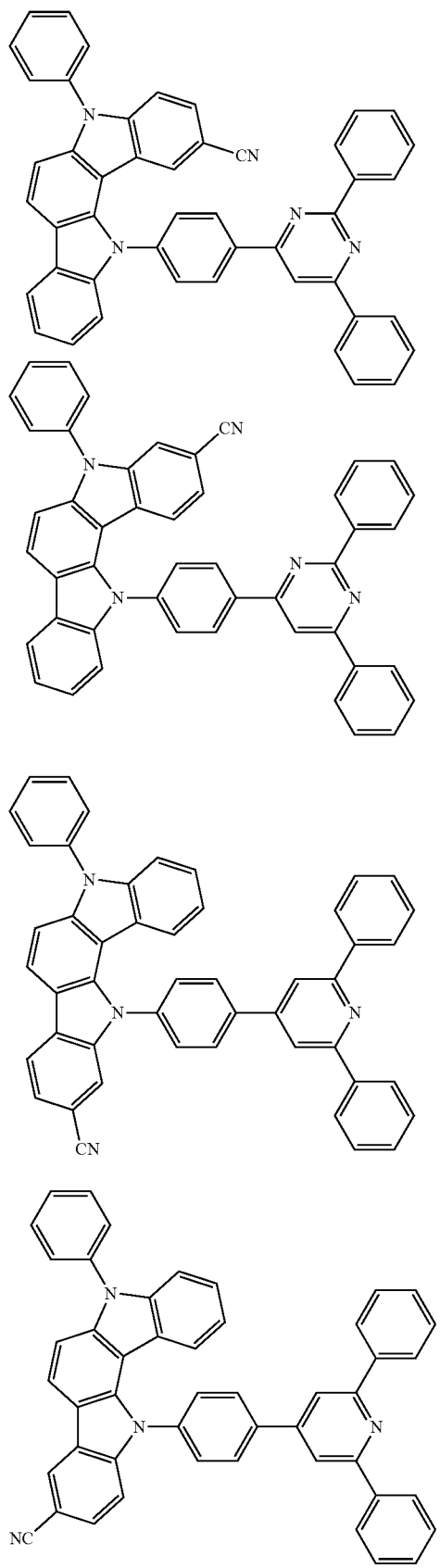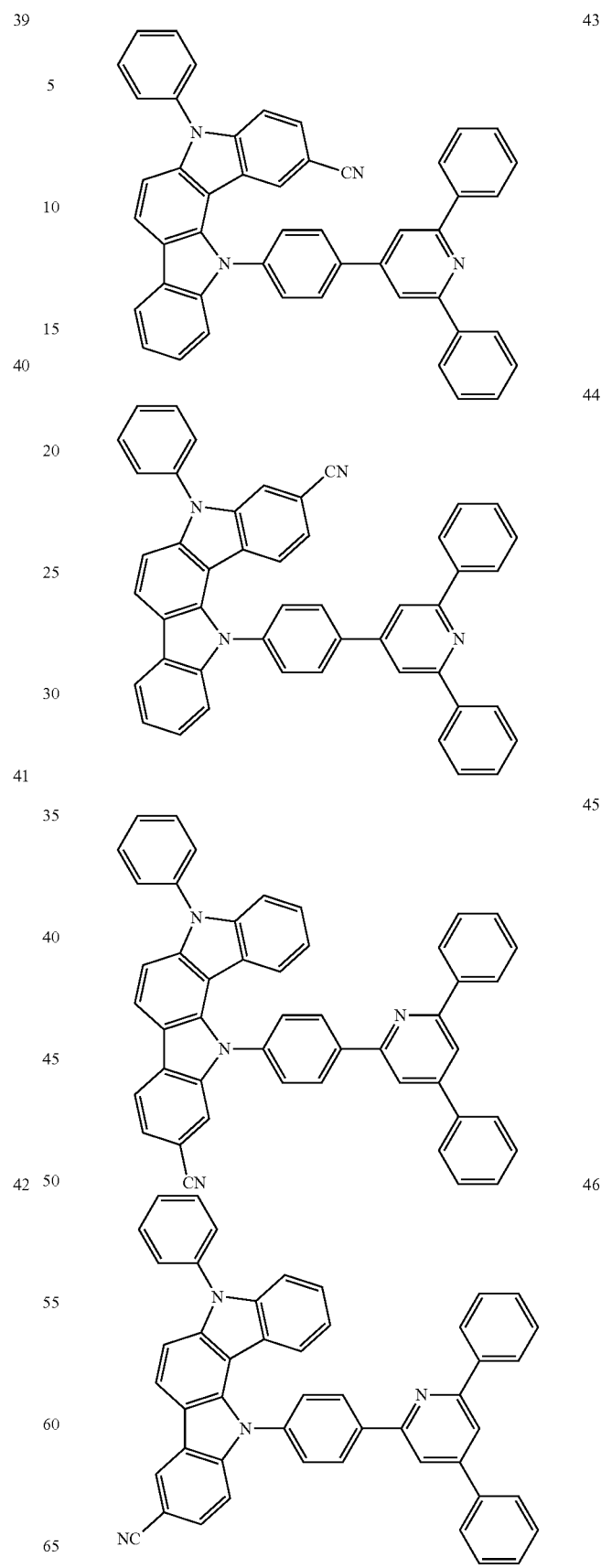

47
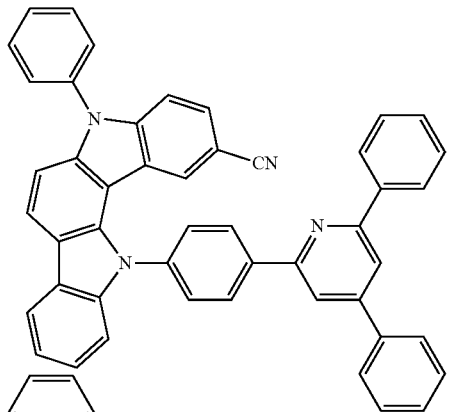
48
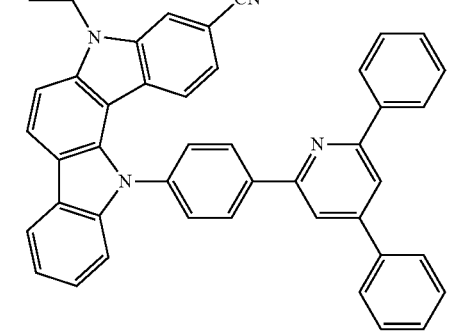
49
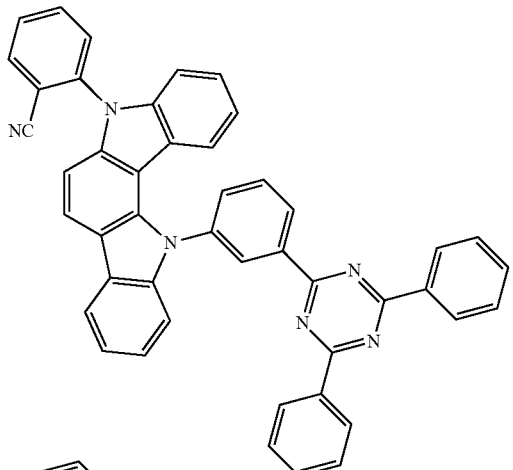
50
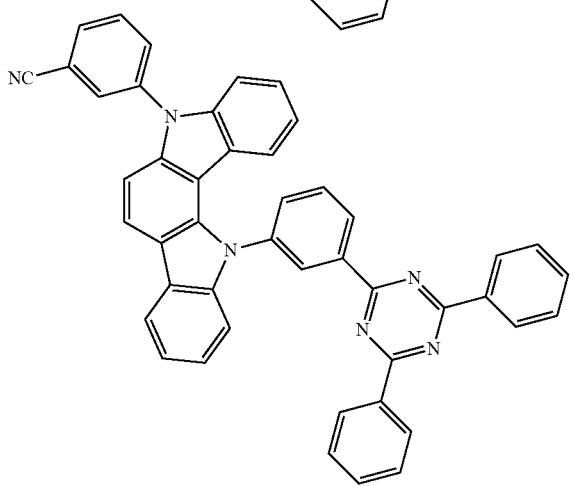
51
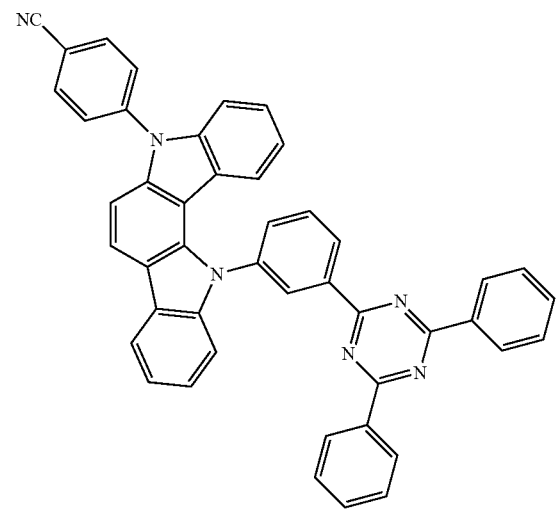
52
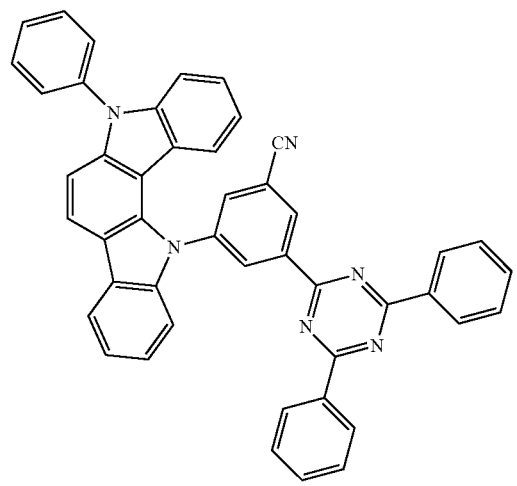
53
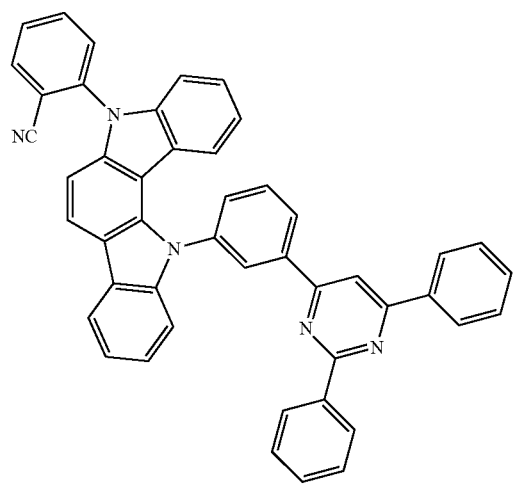

54
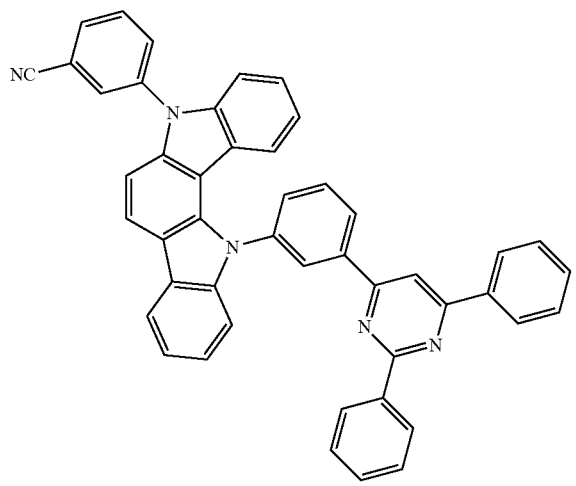
55
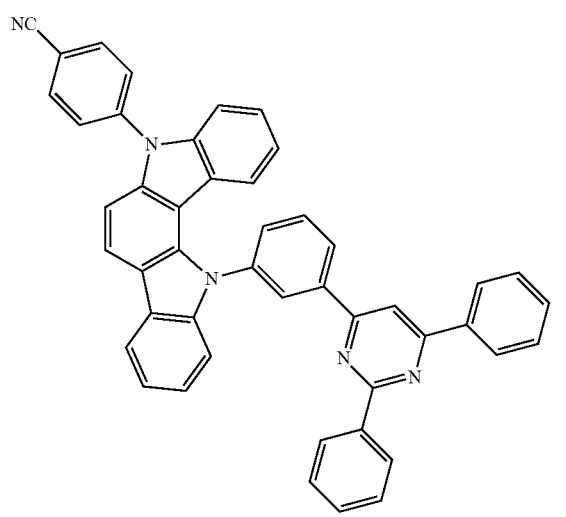
56
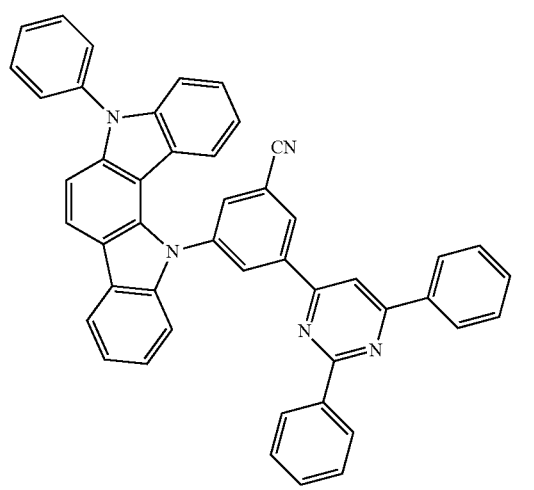
57
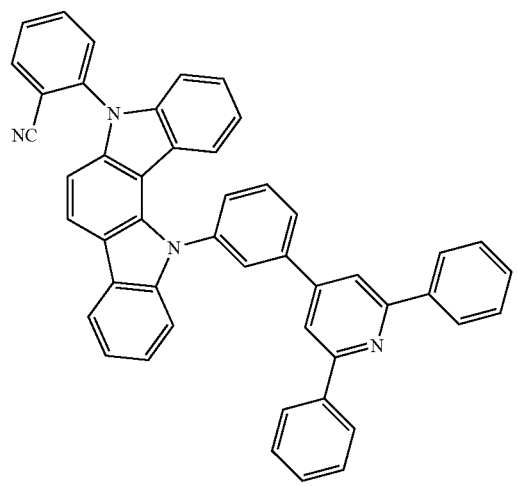
58
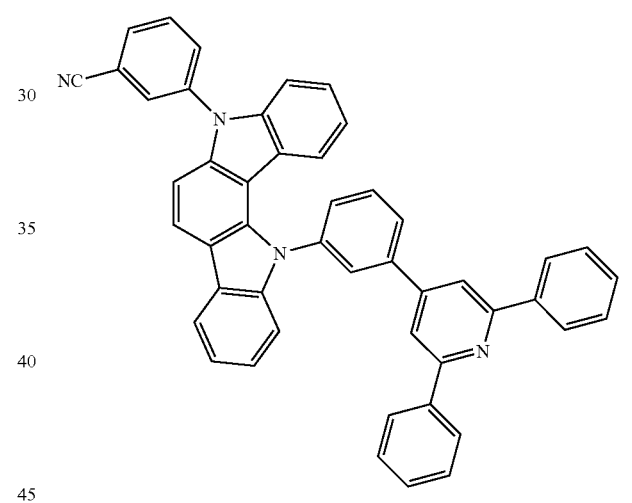
59
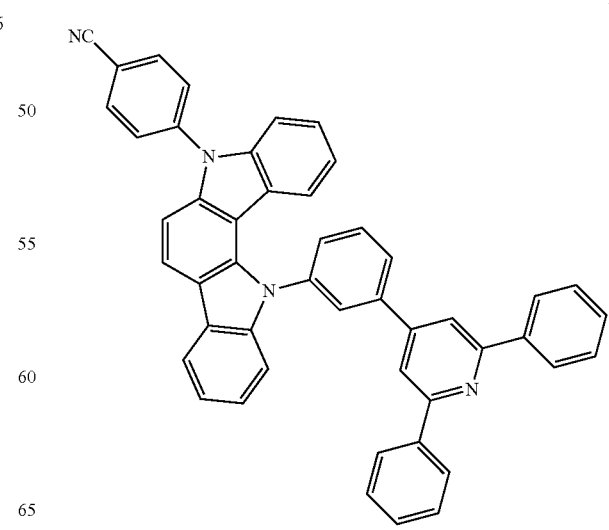

60
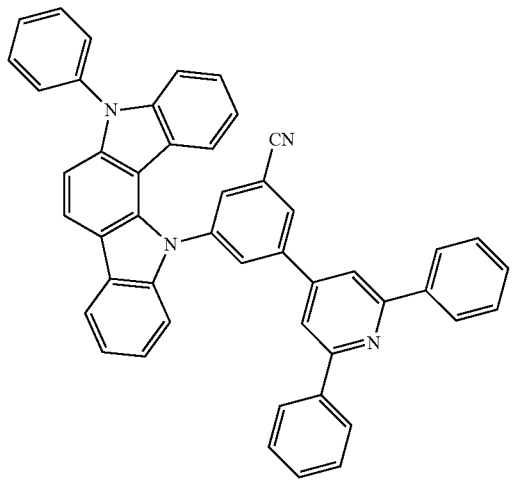
63
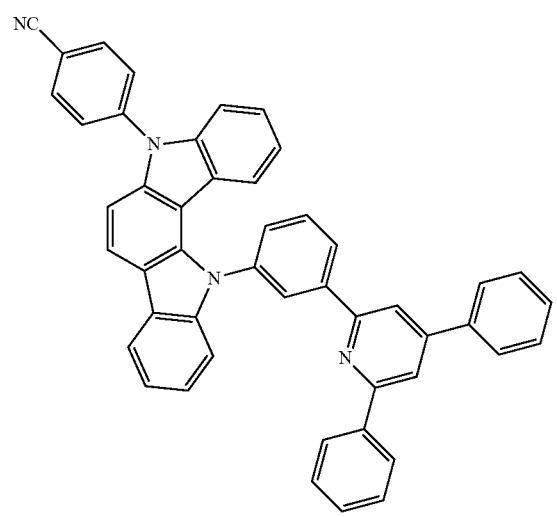
61
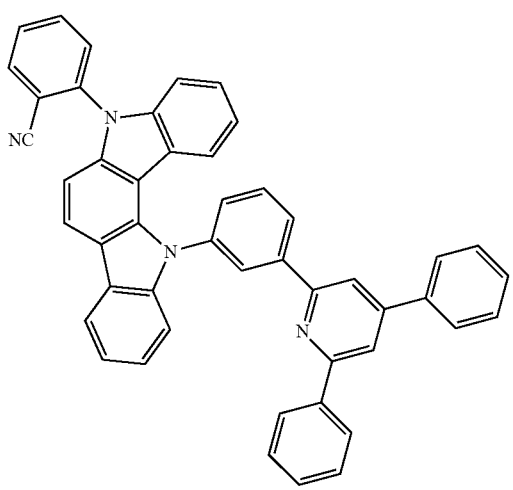
64
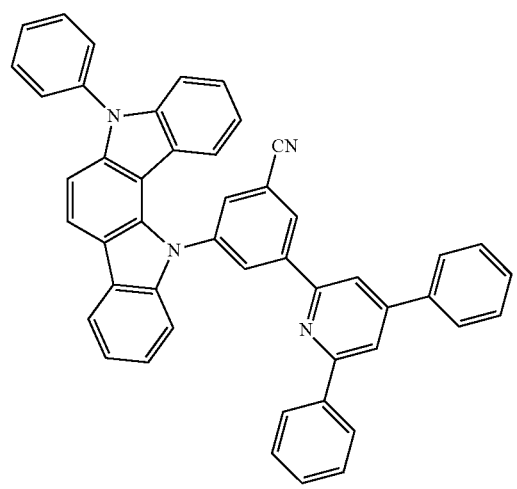
62
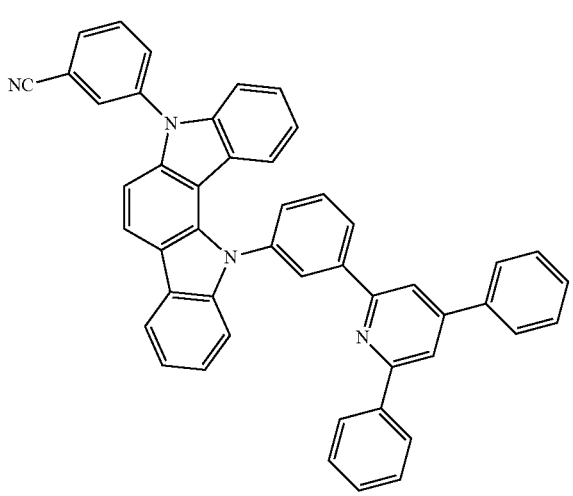
65
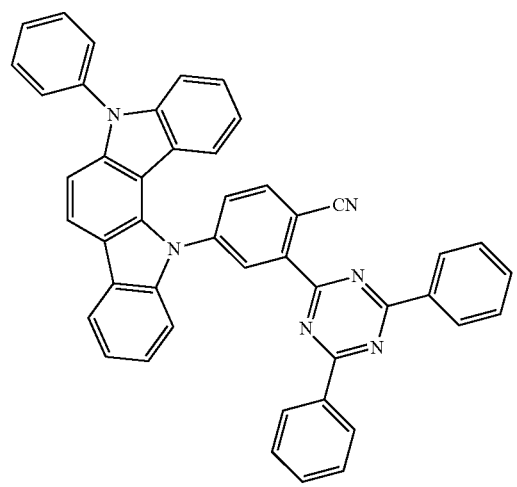

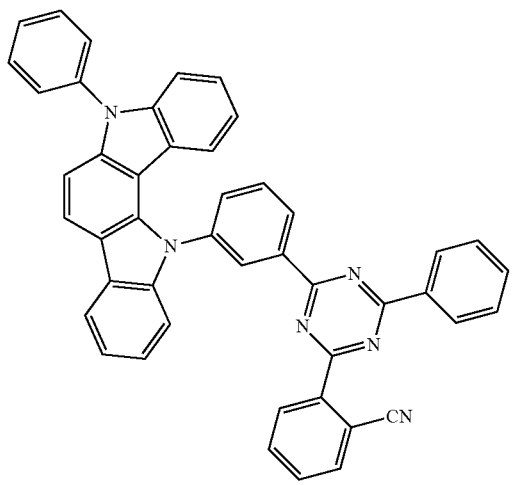
66
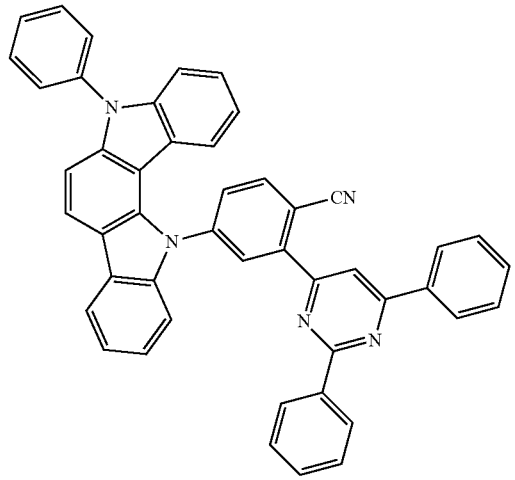
69
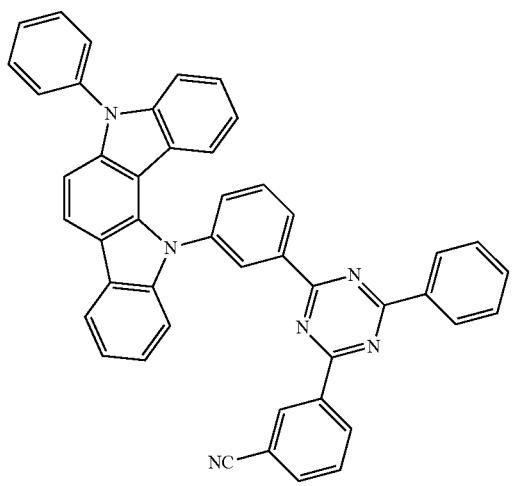
67
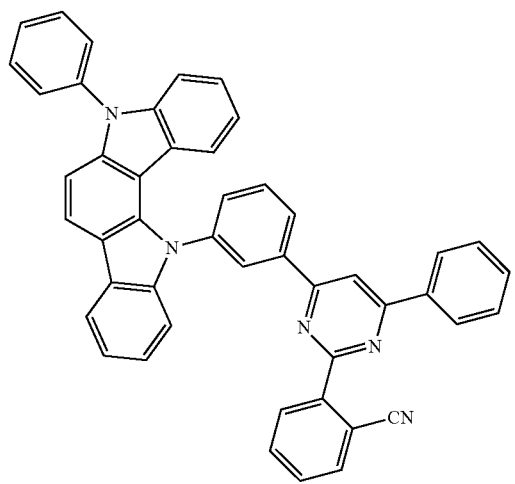
70
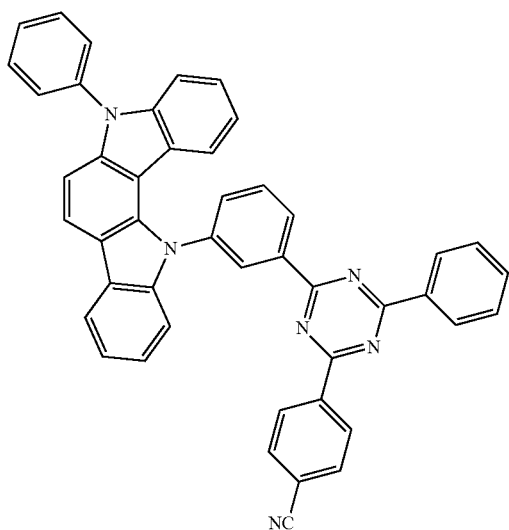
68
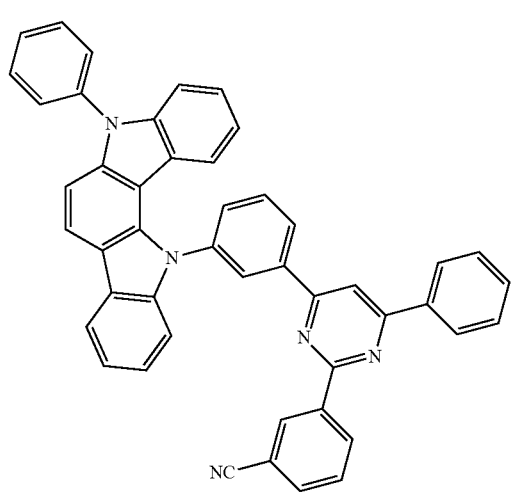
71

72
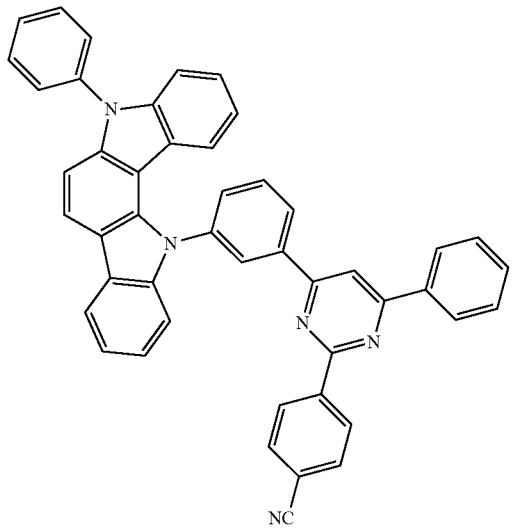
75
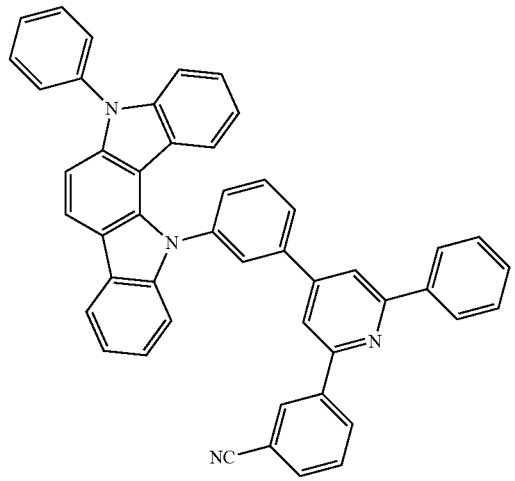
73
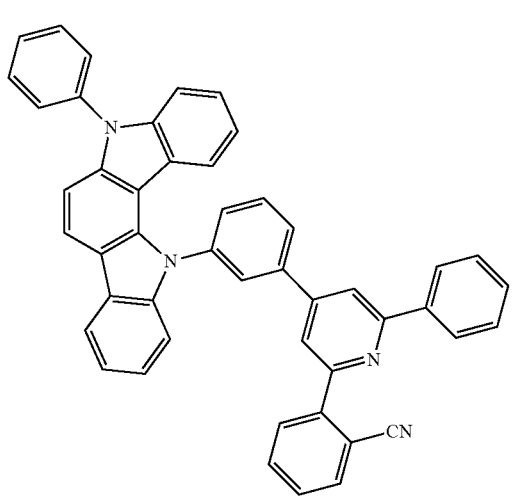
76
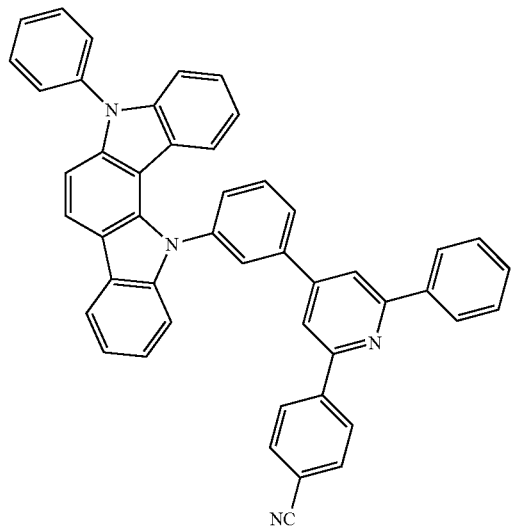
74
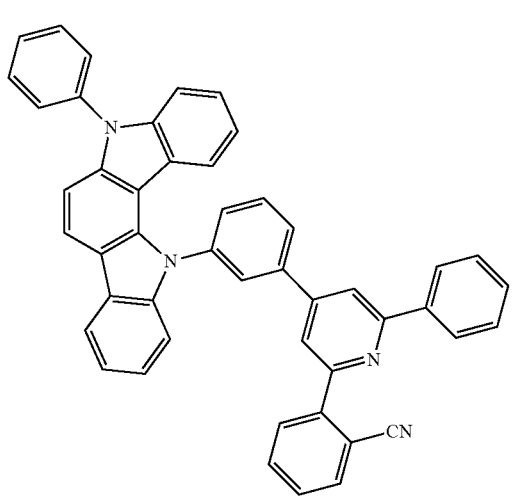
77
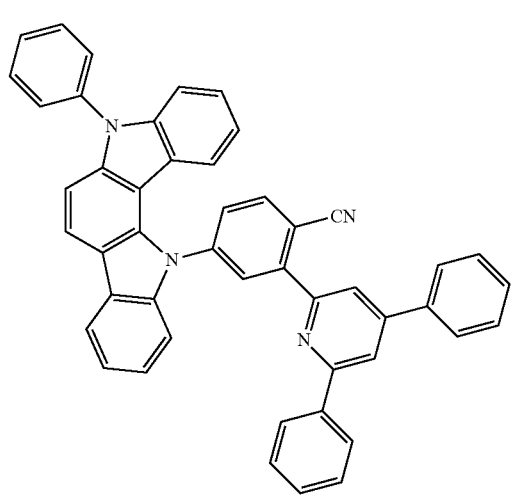

78
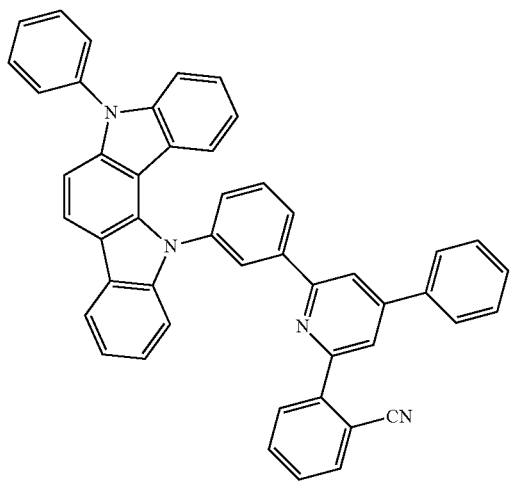
79
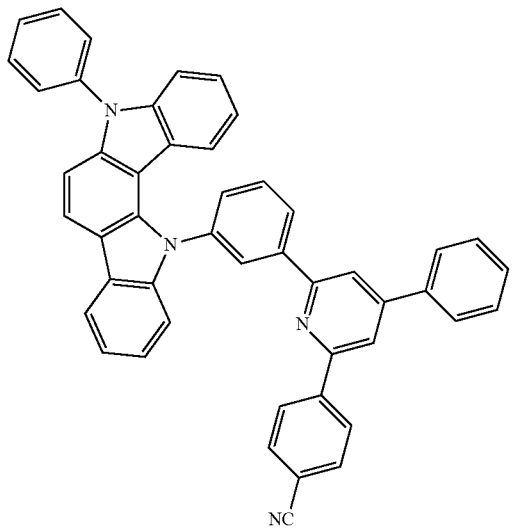
80
81
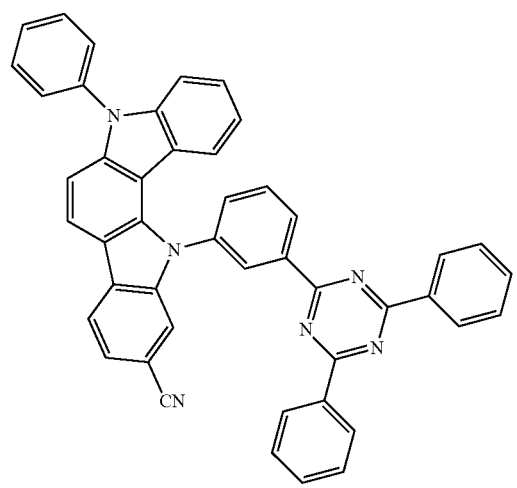
82
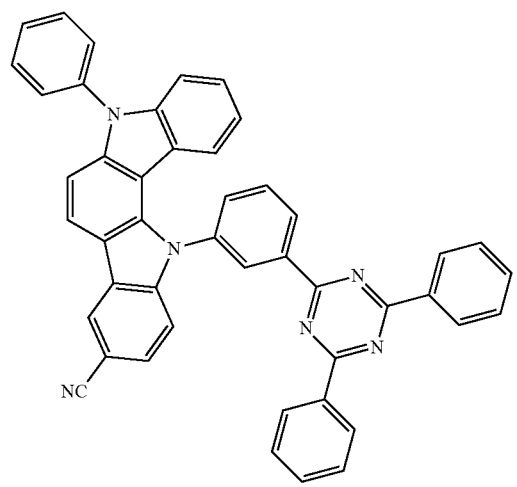
83

84
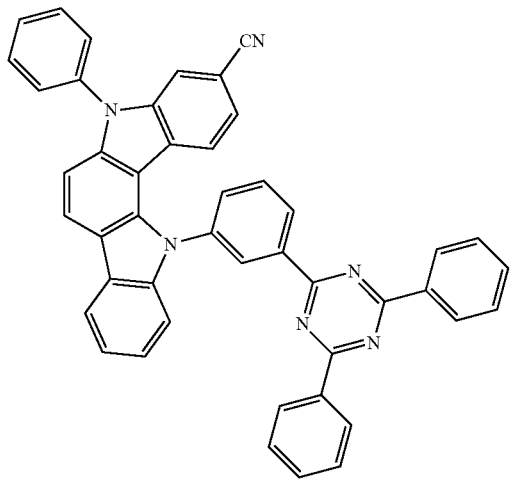
85
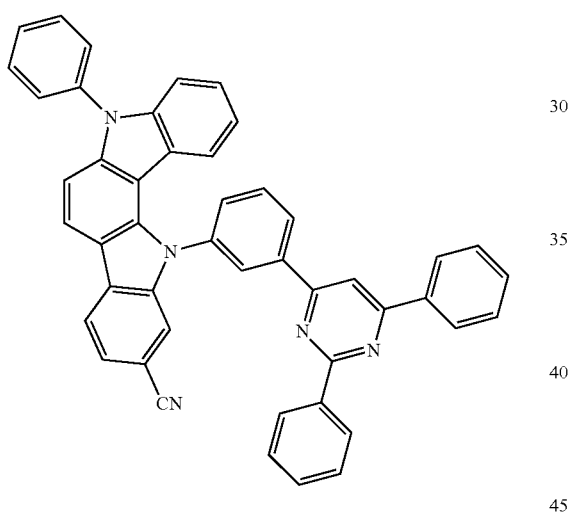
86
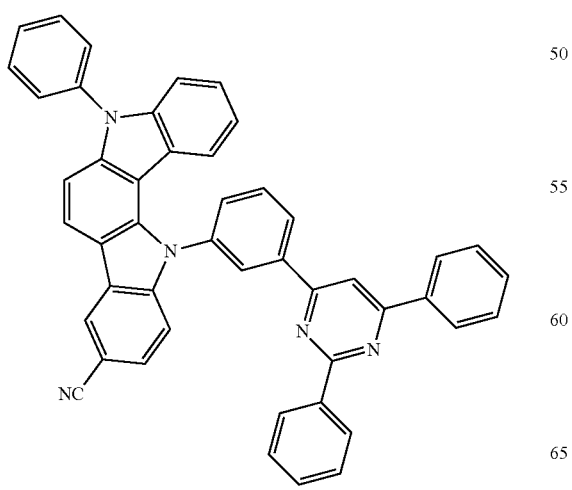
87
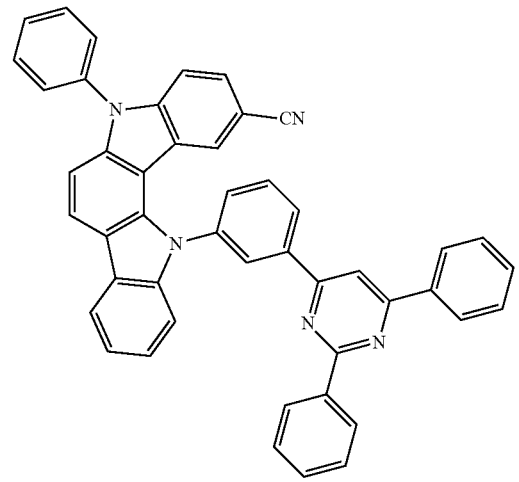
88
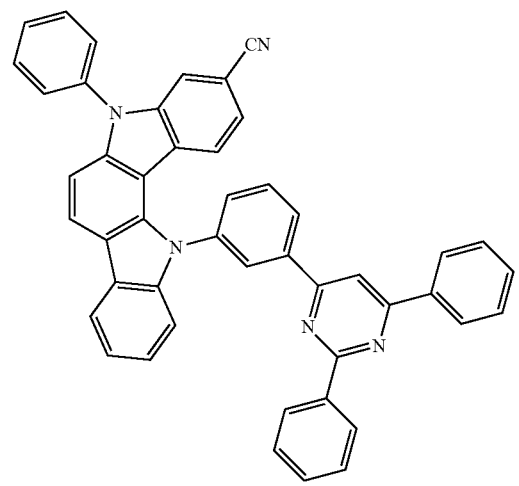
89
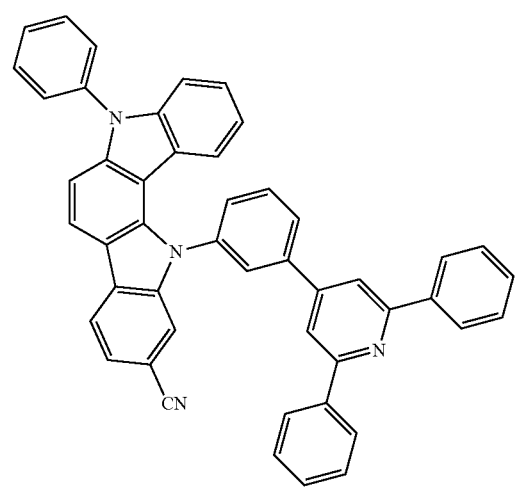

90
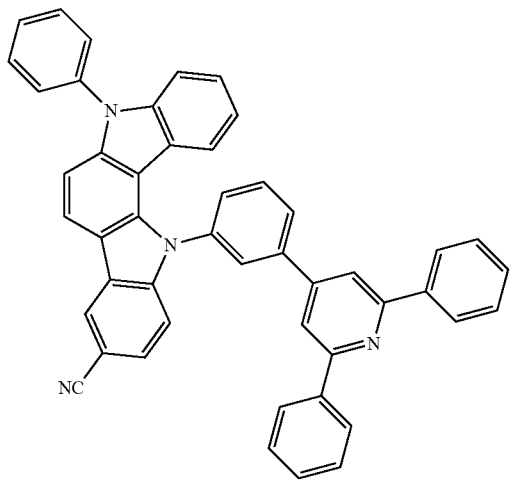
91
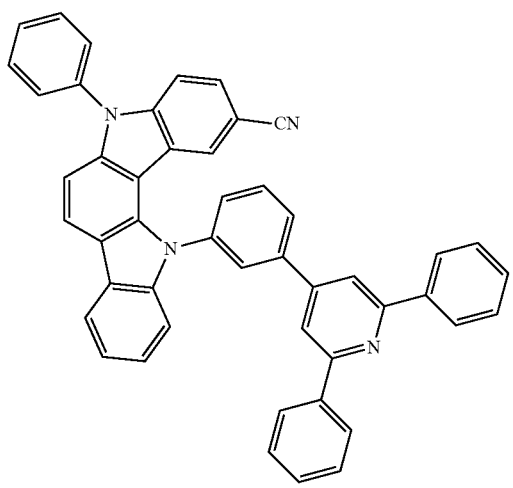
92
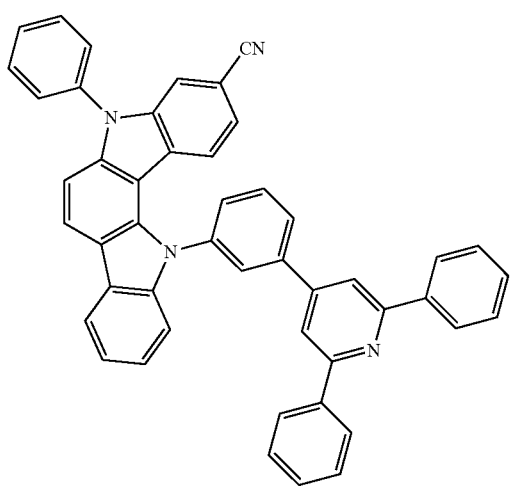
93
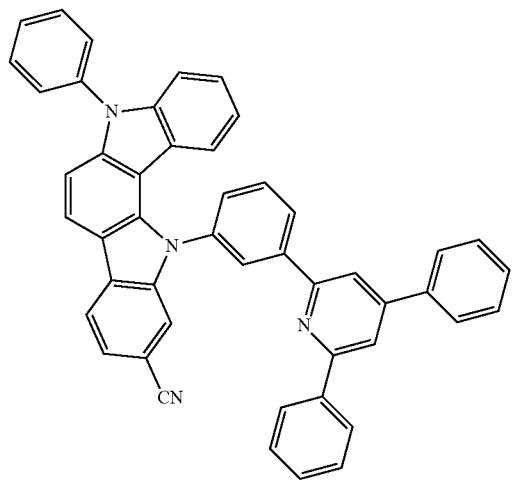
94
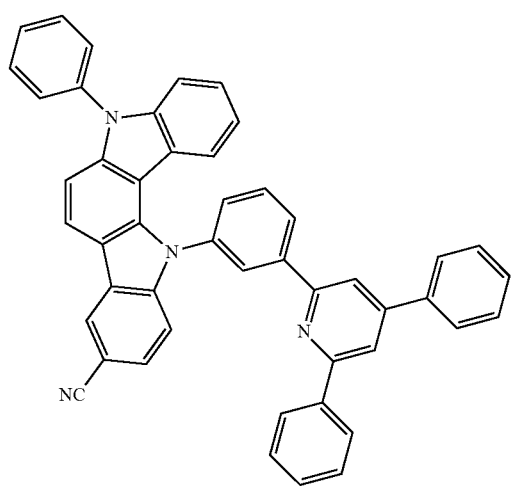
95
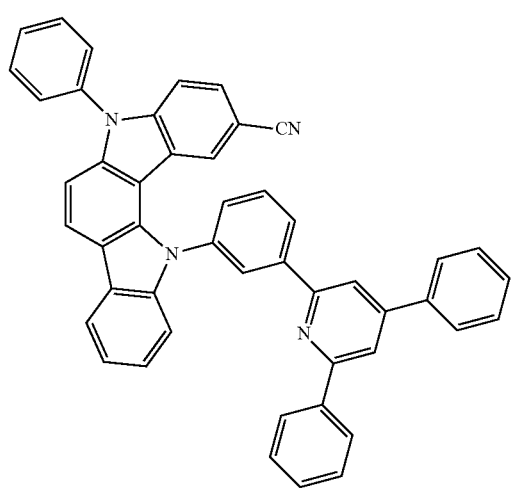

96
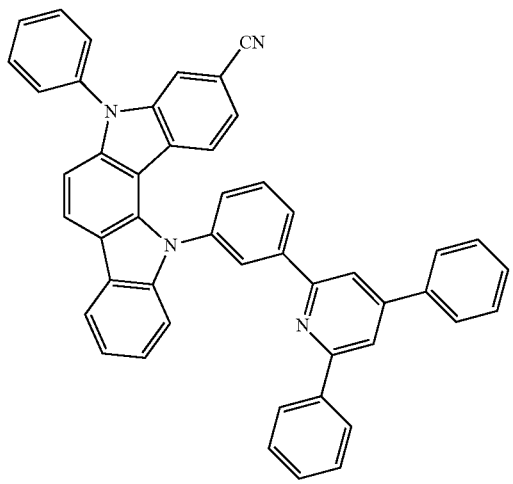
97
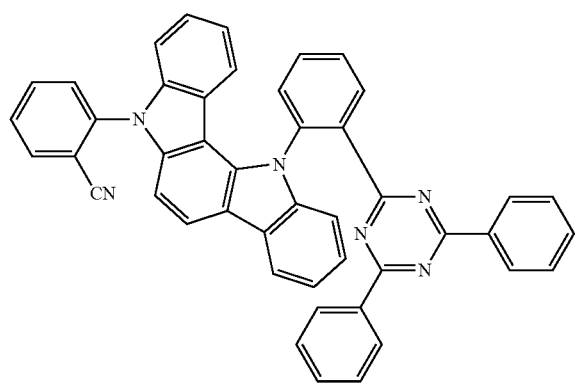
98
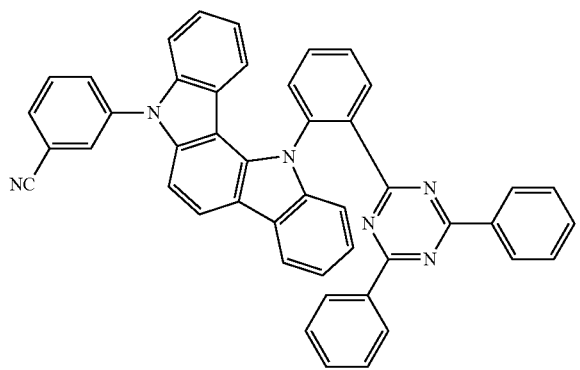
99
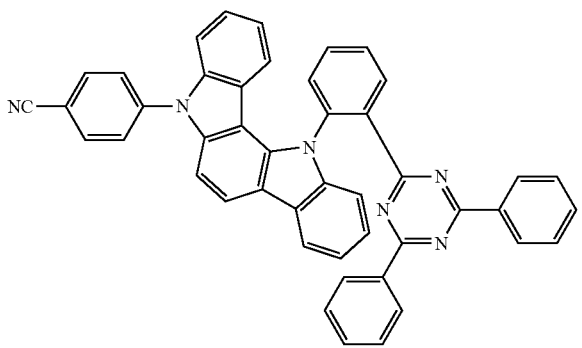
100
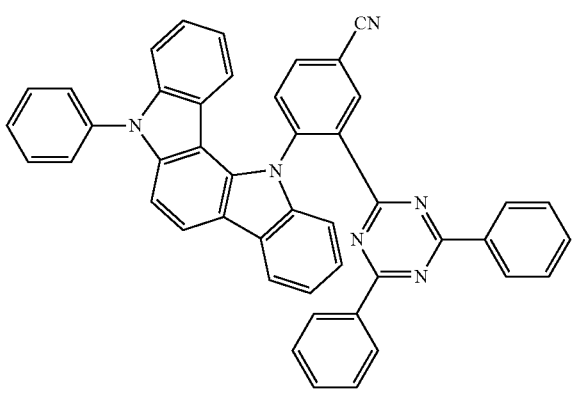
101
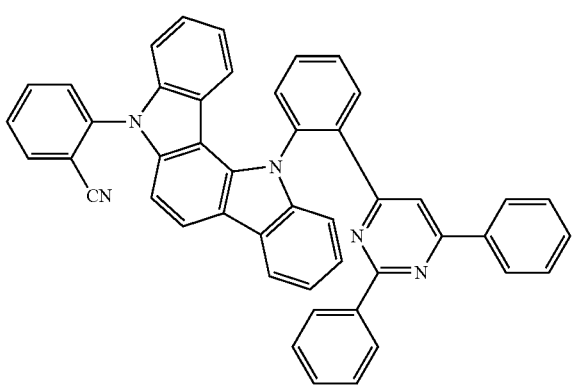
102
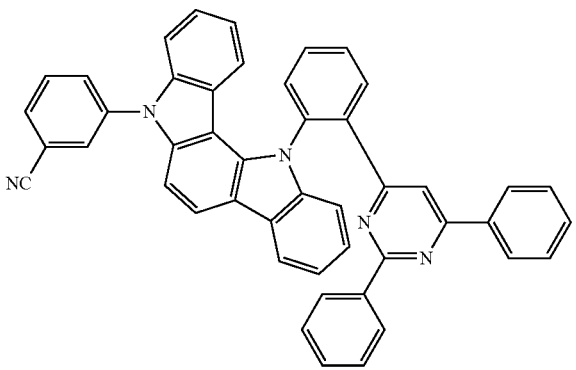
103
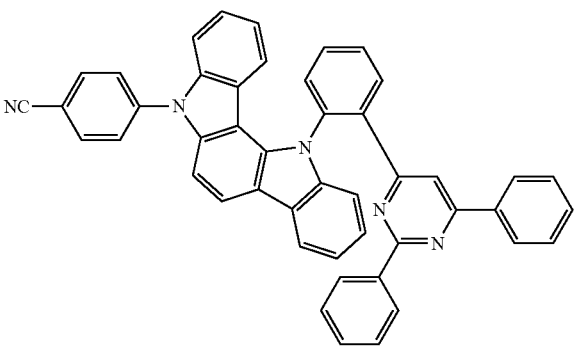

104
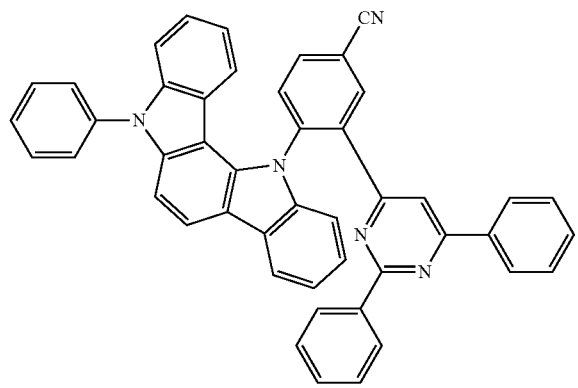
105
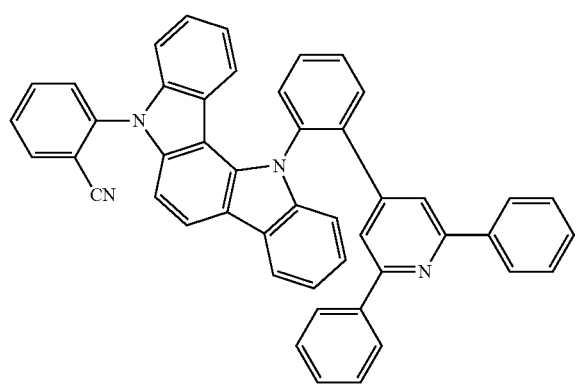
106
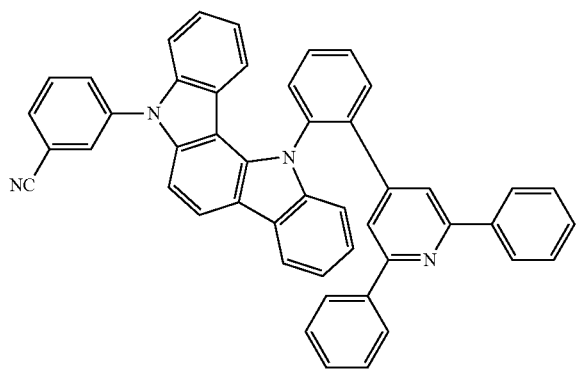
107
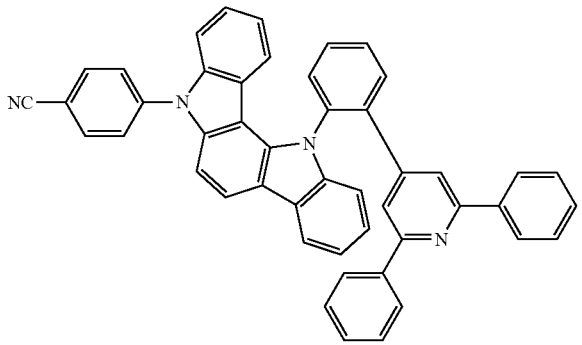
108
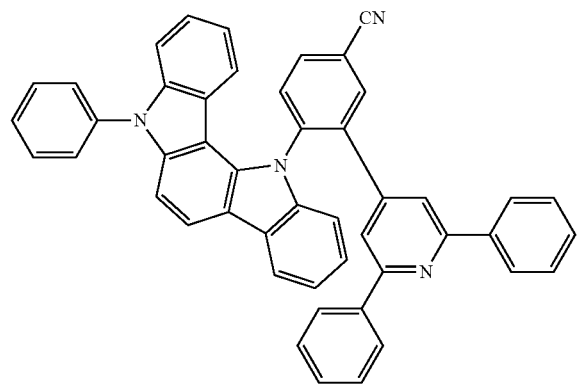
109
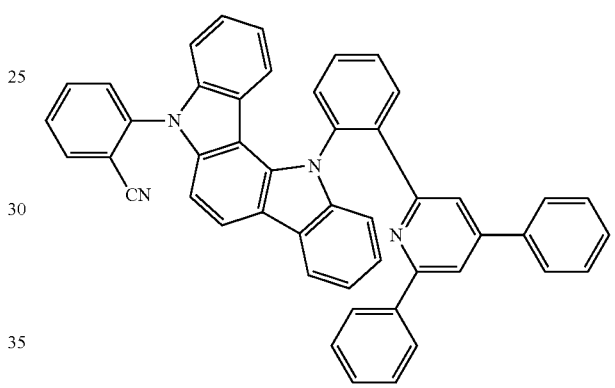
110
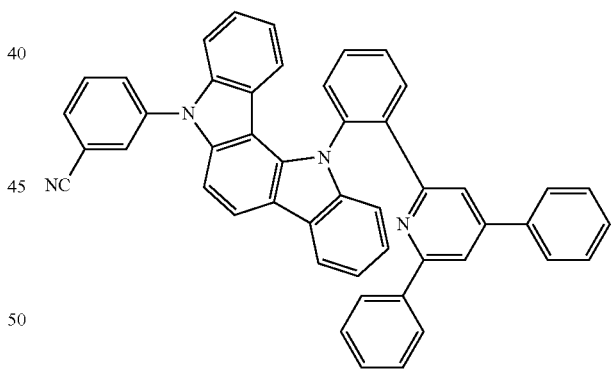
111
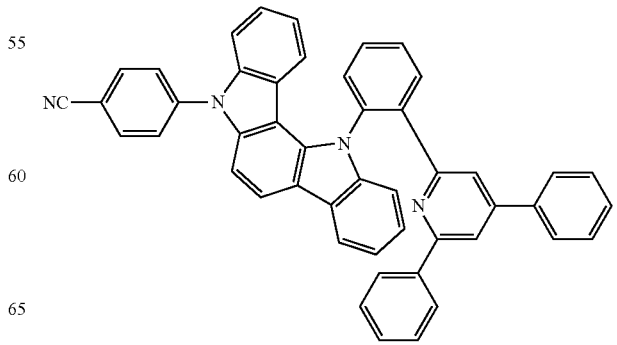

112
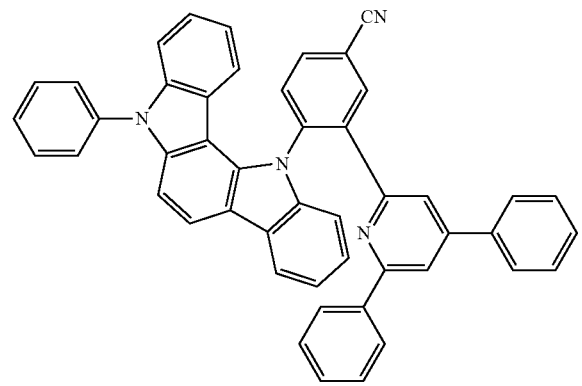
113
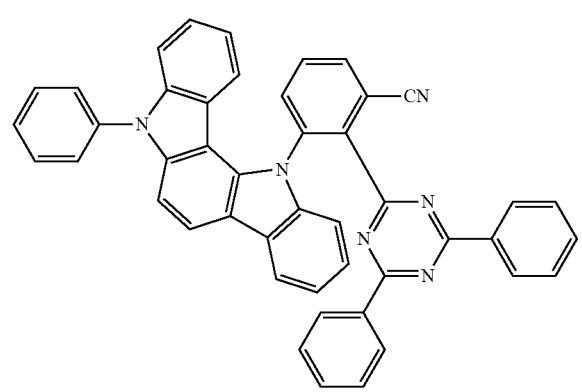
114
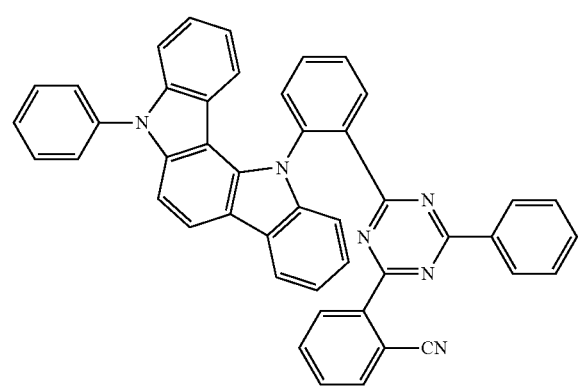
115
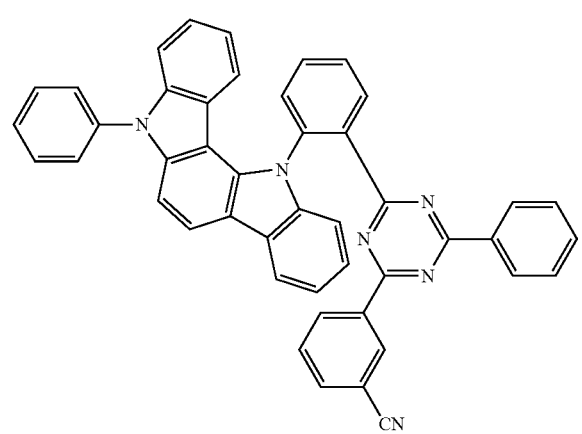
116
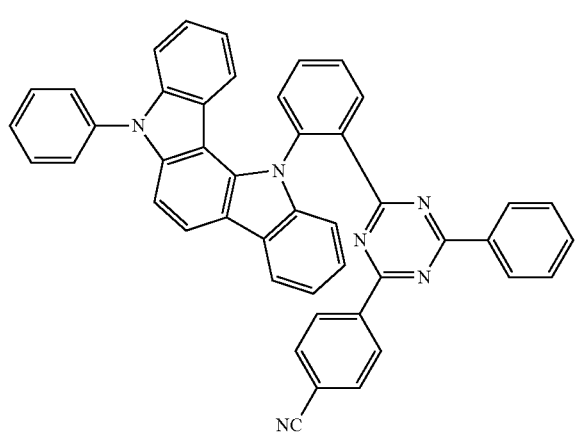
117
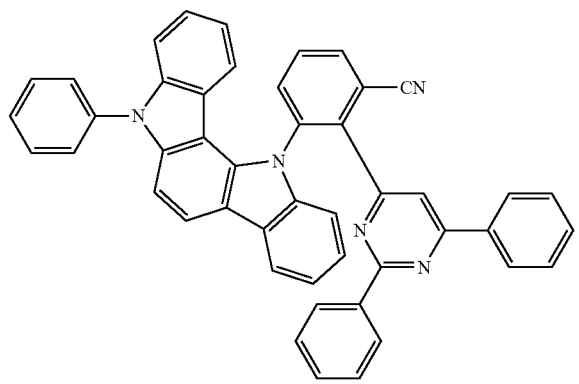
118
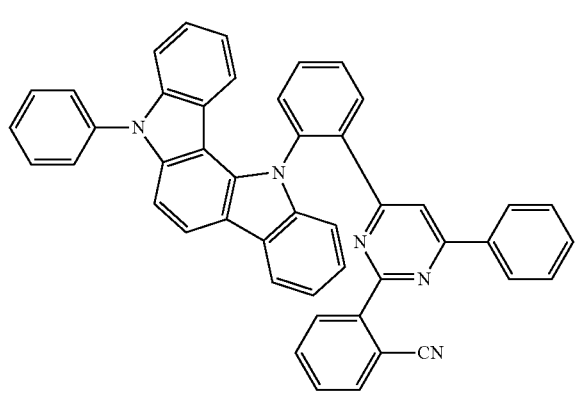

-continued
119
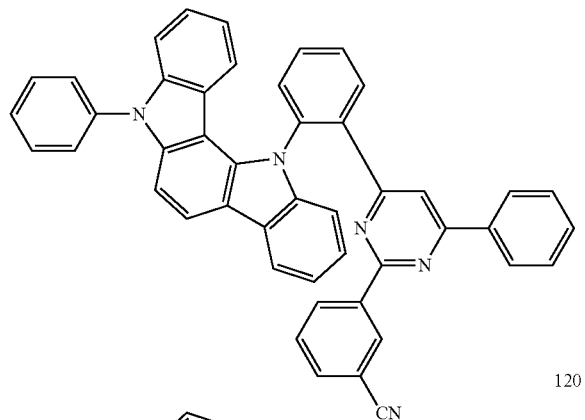
120
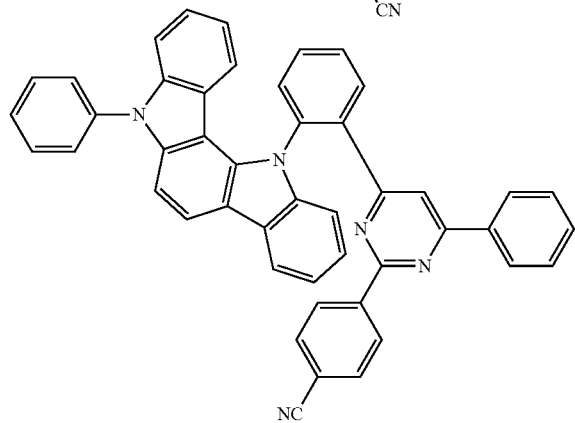
121
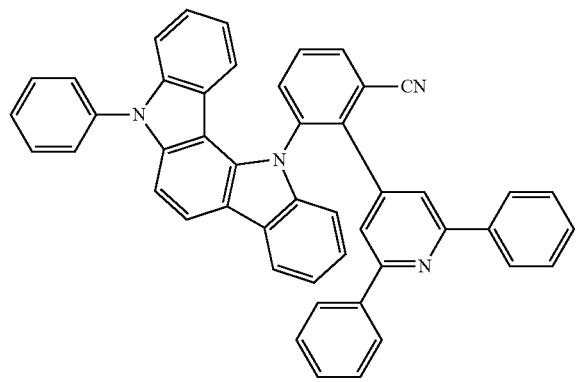
122
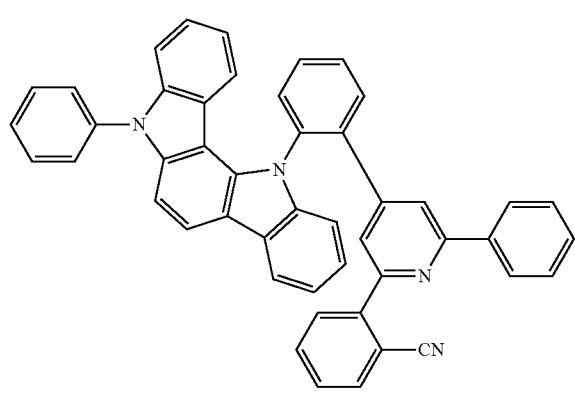
-continued
123
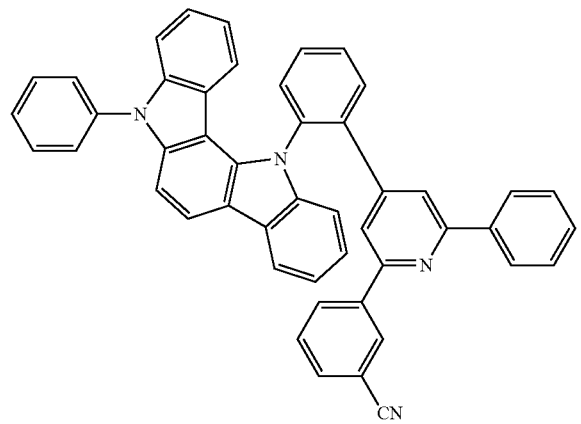
124
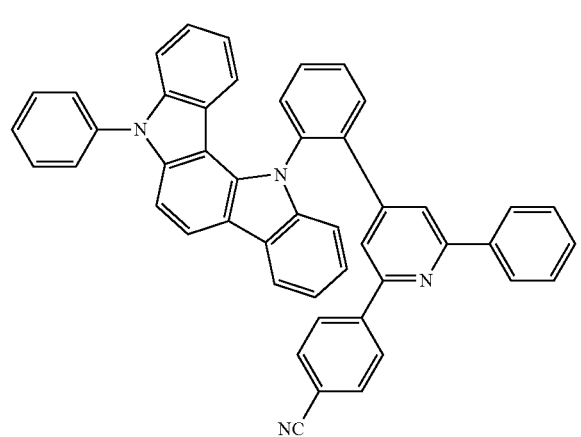
125
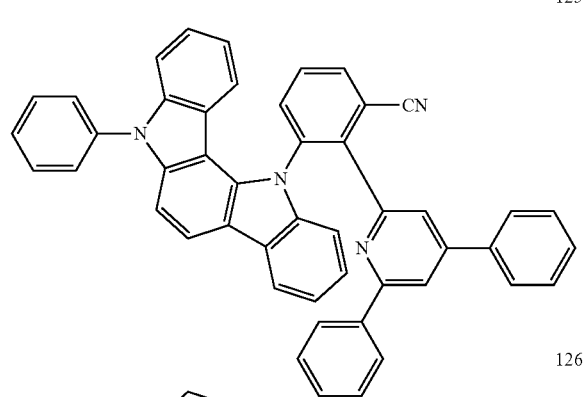
126
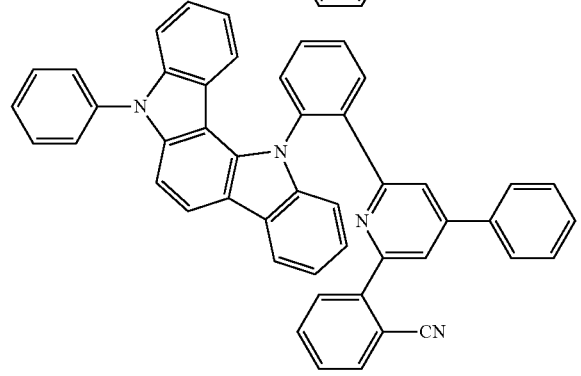

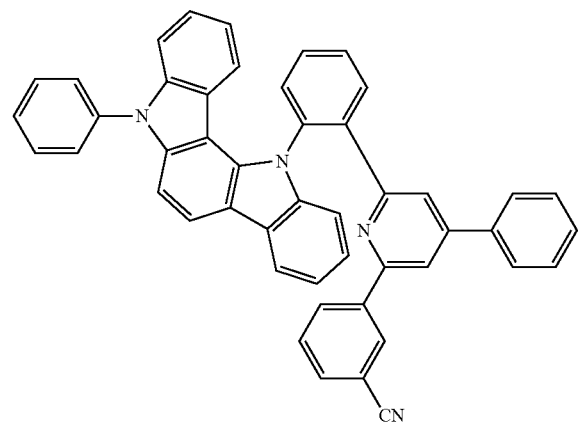
127
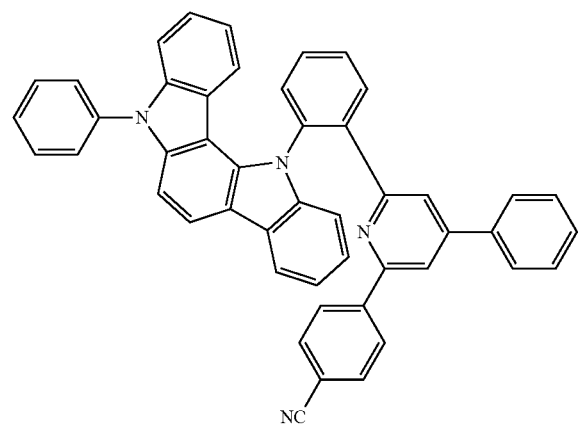
128
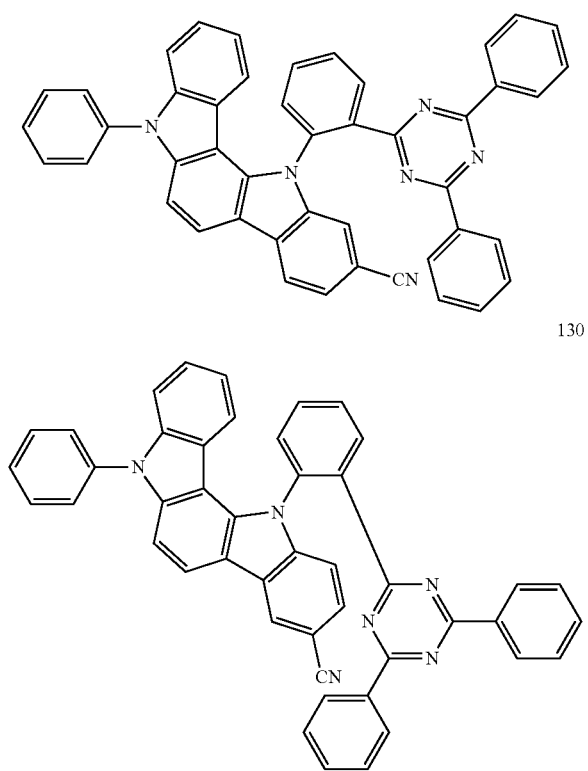
129
130
131
132
133
134

-continued
135
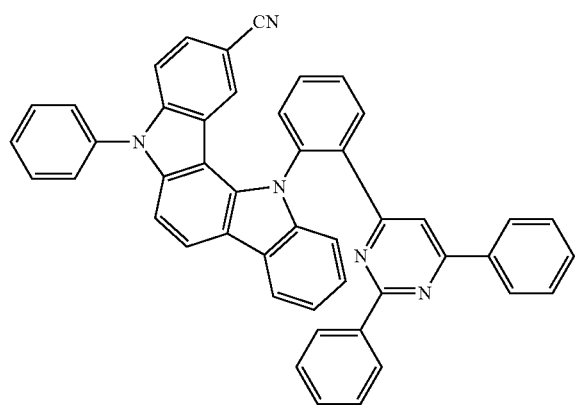
136
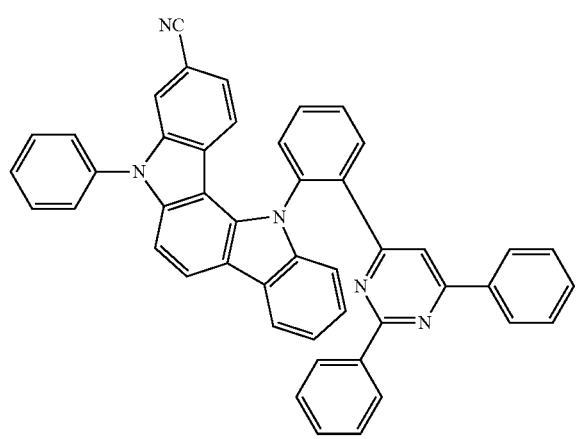
137
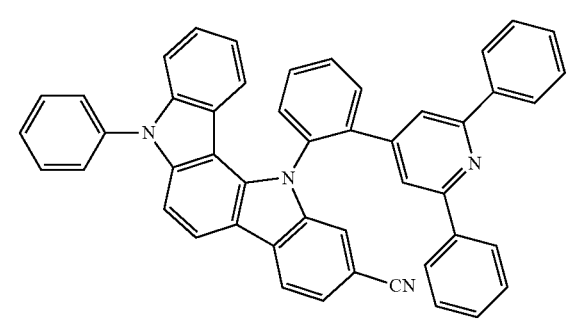
138
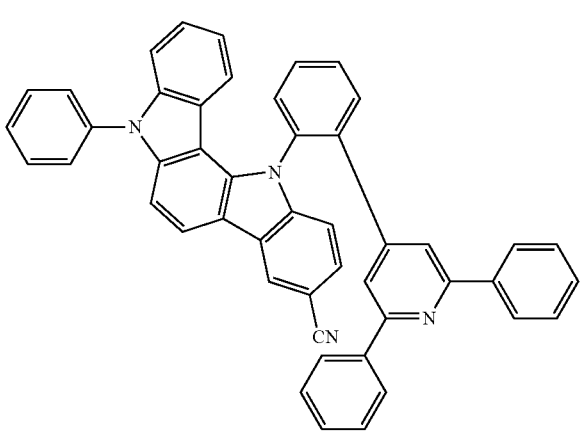
-continued
139
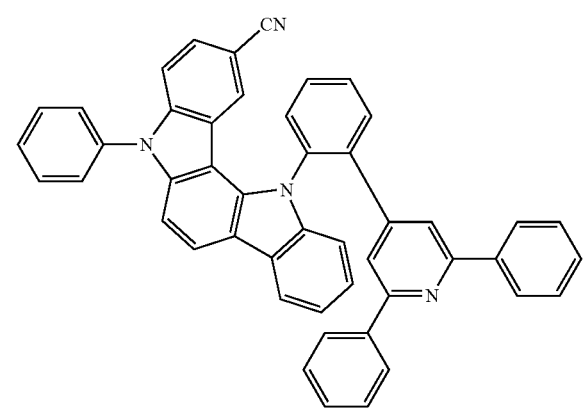
140
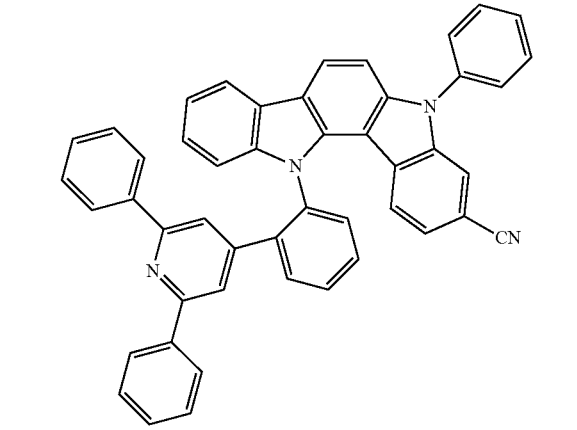
141
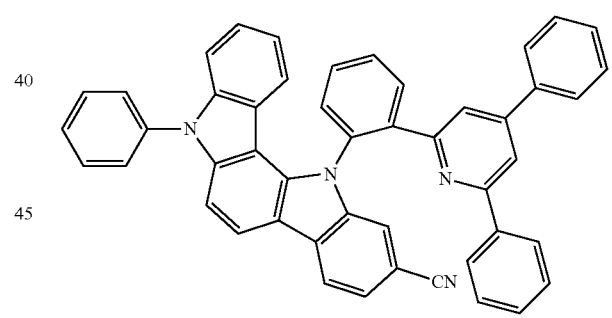
142
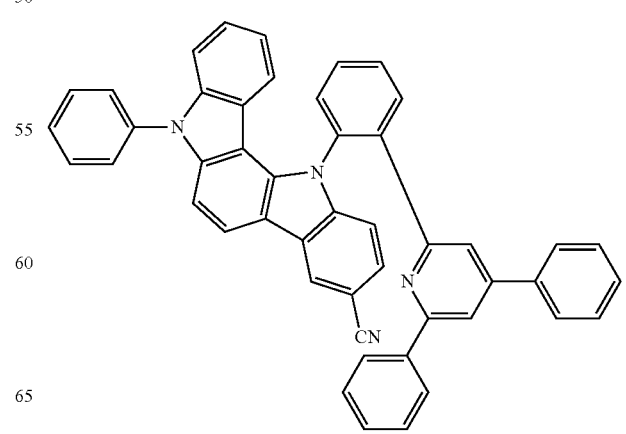

143
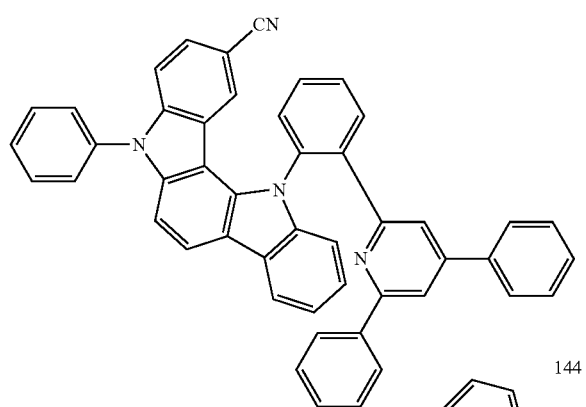
144
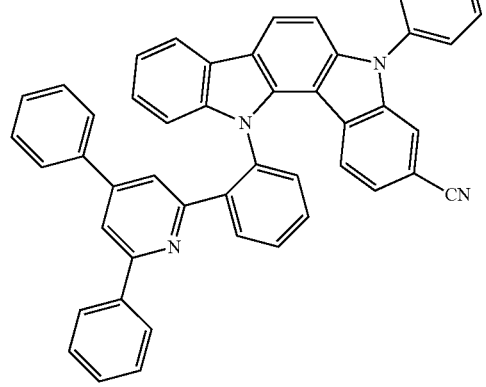
145
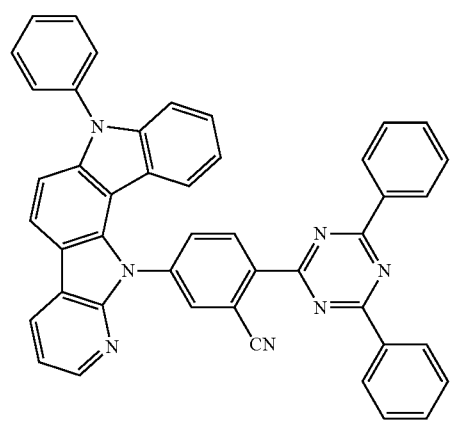
146
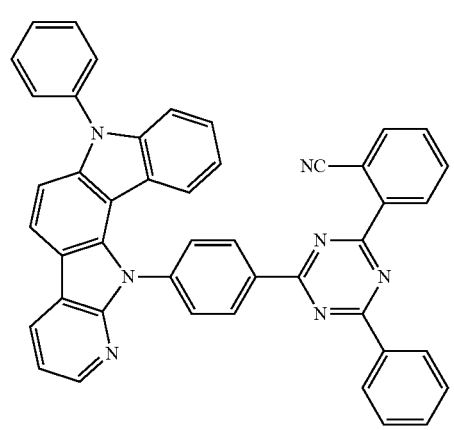
147
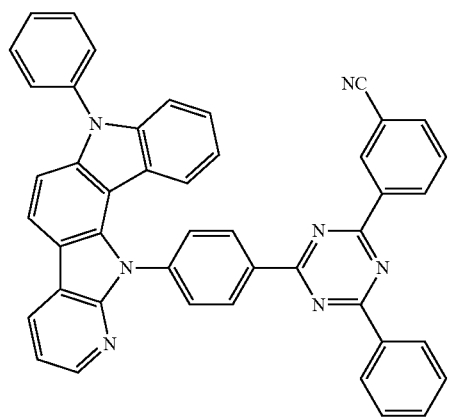
148
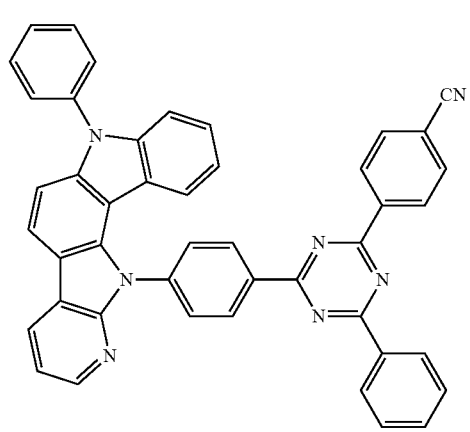
149
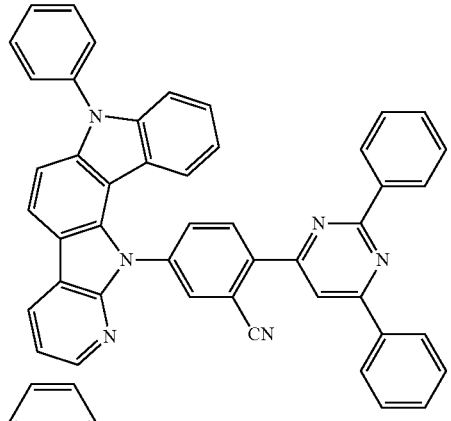
150
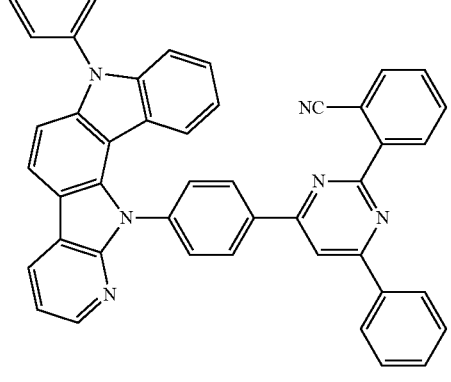

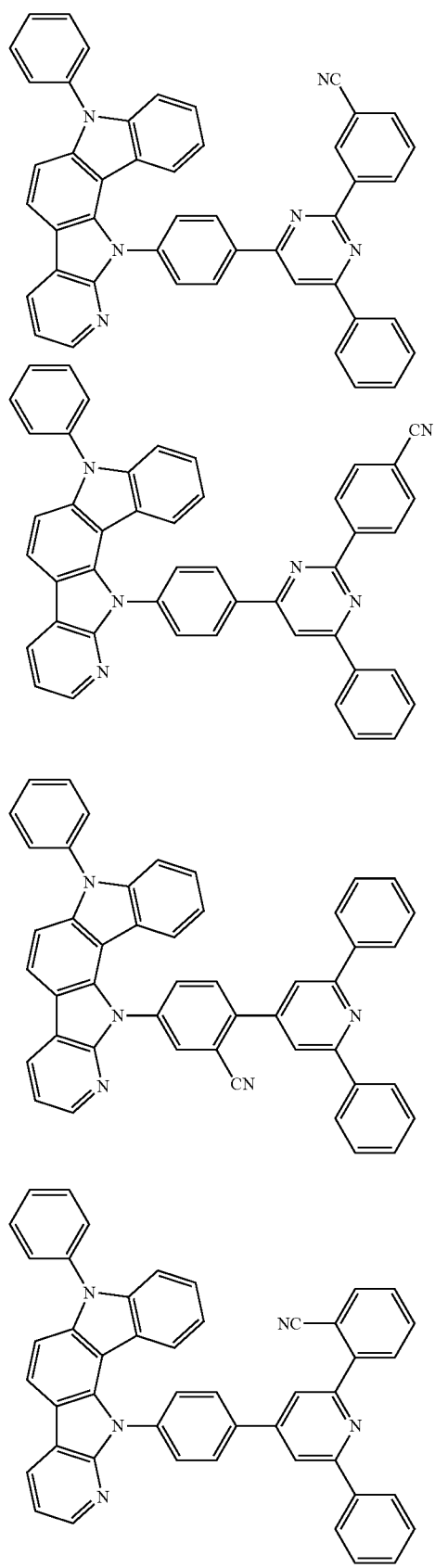
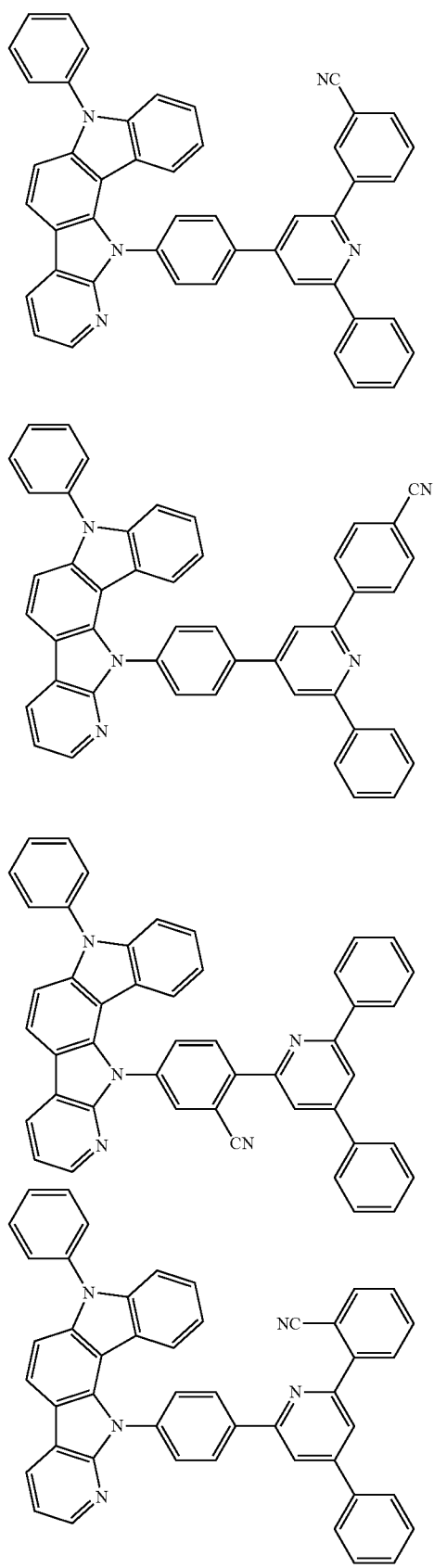

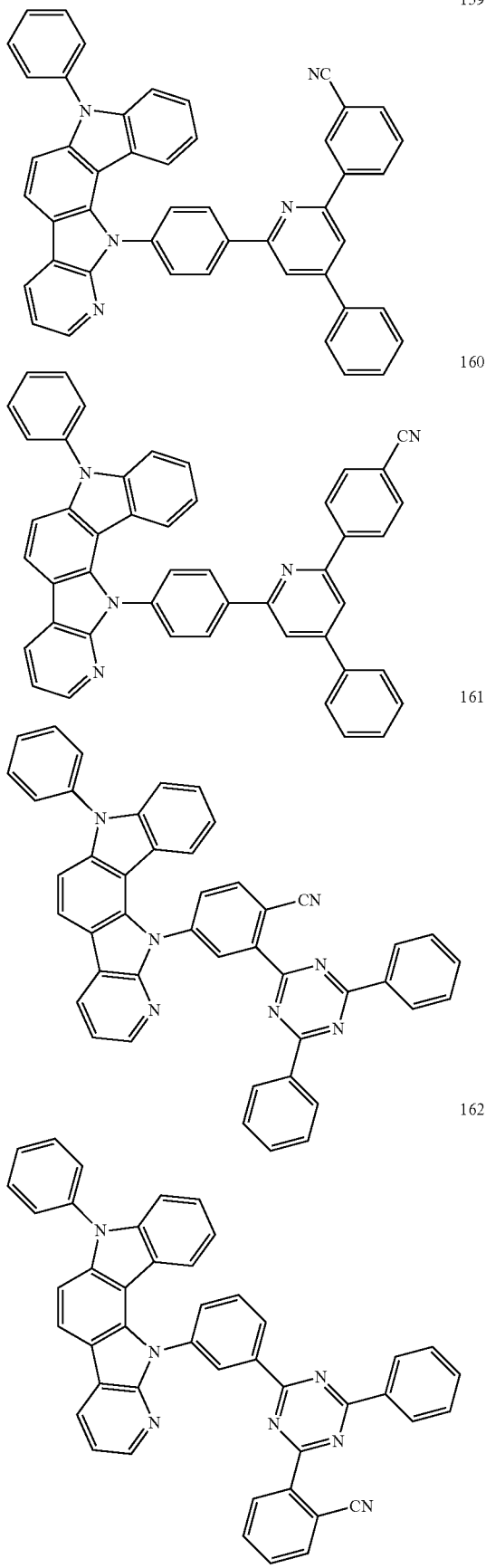
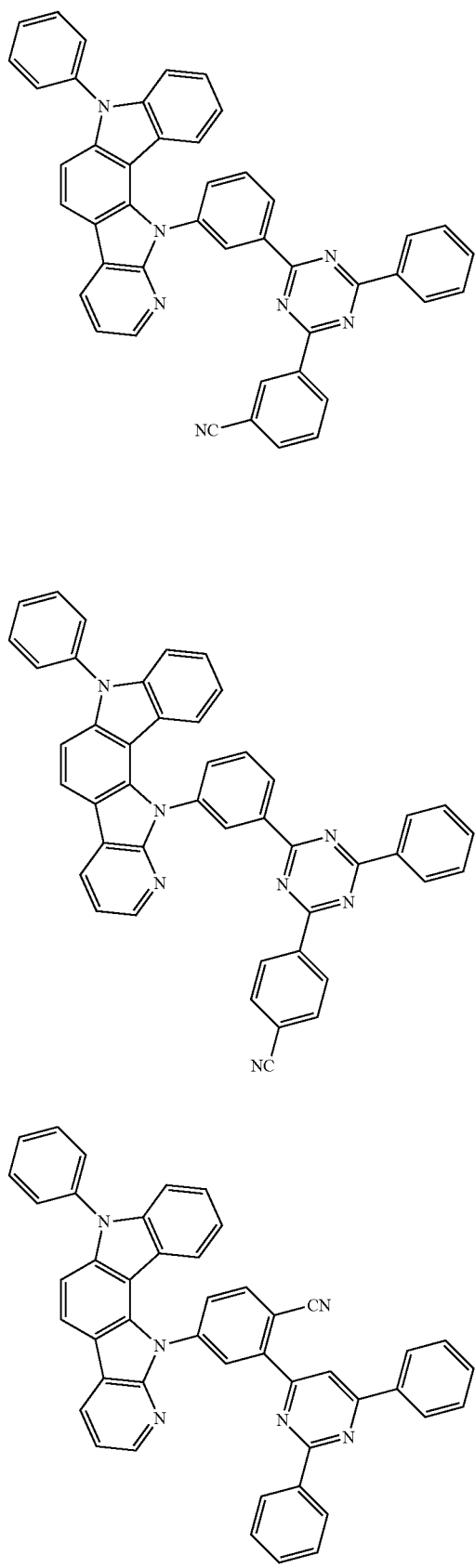

166
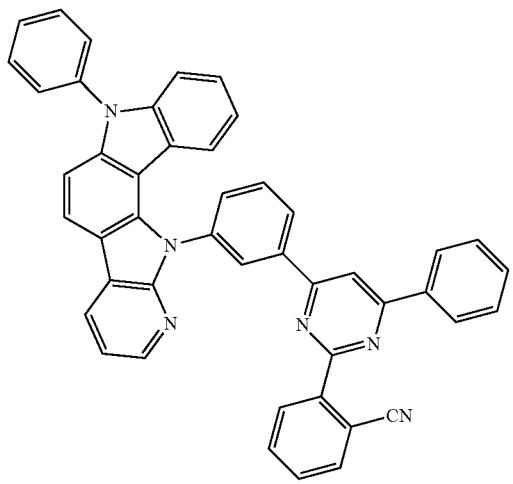
167
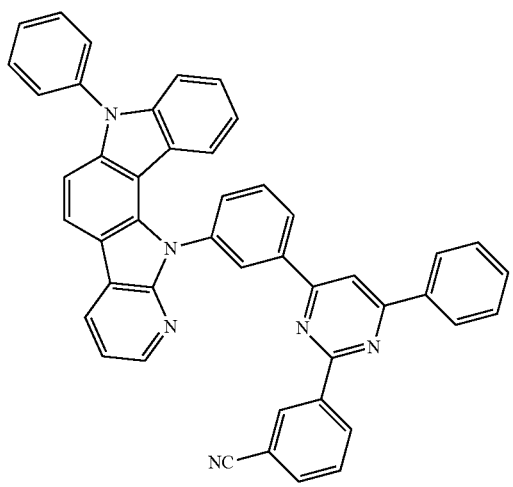
168
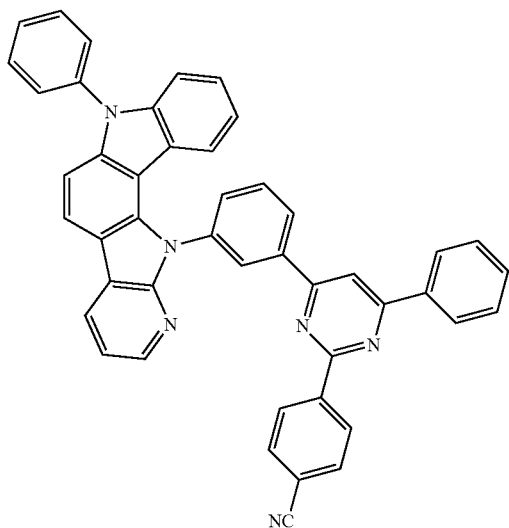
169
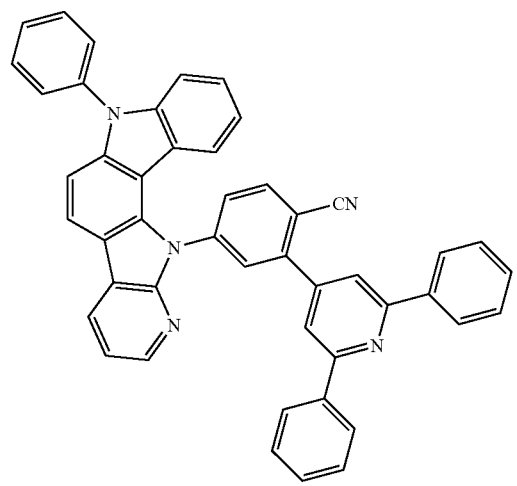
170
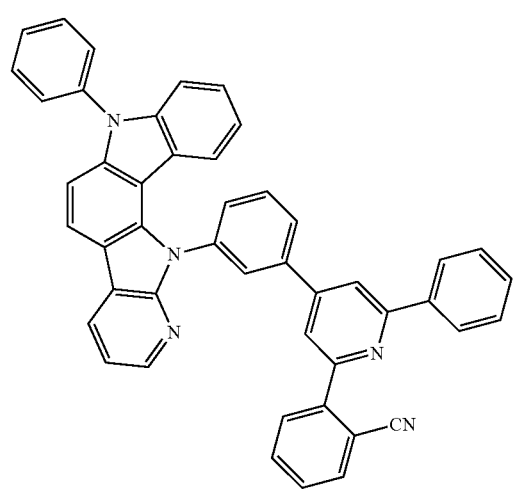
171
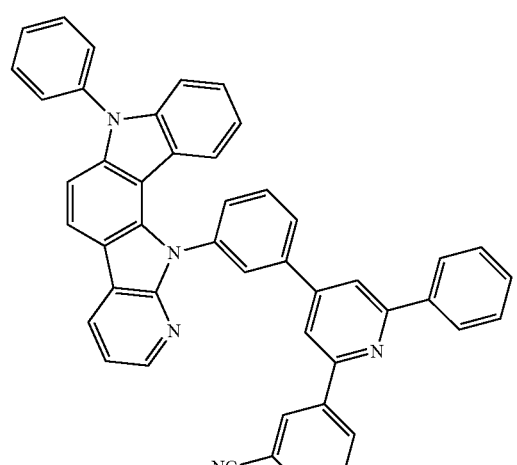

172
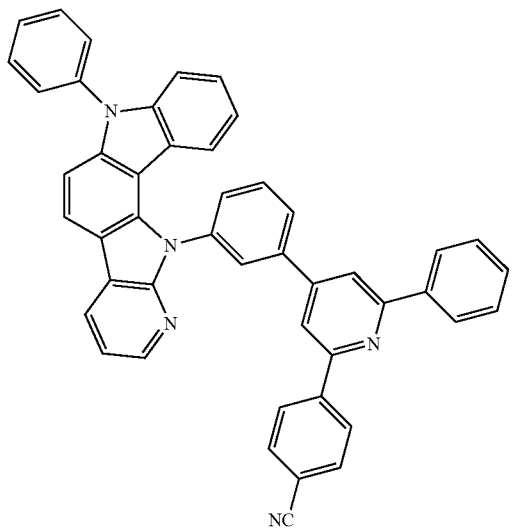
173
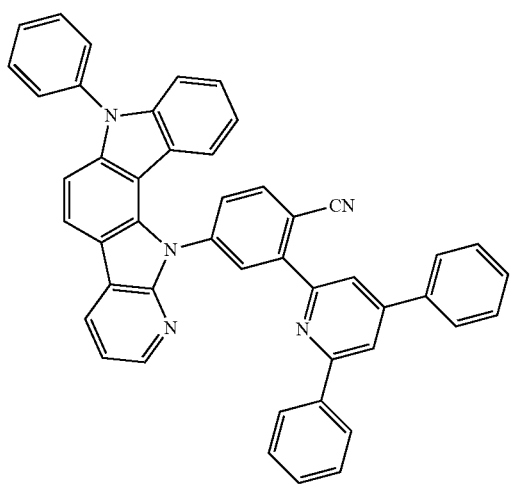
174
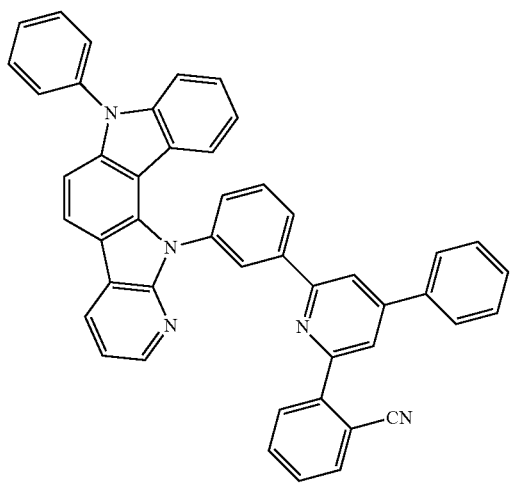
175
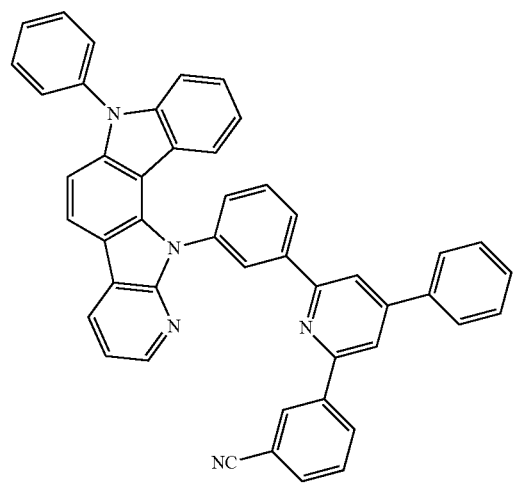
176
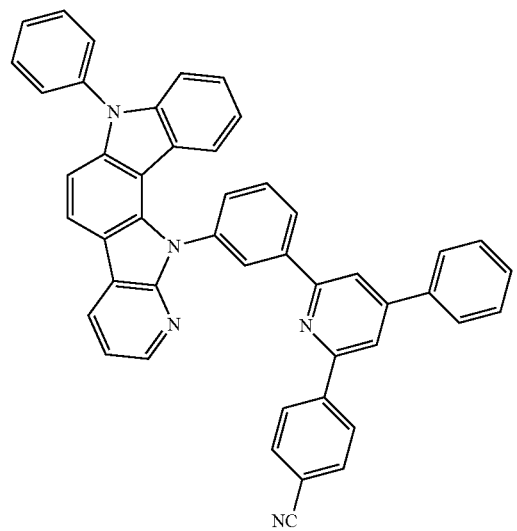
177
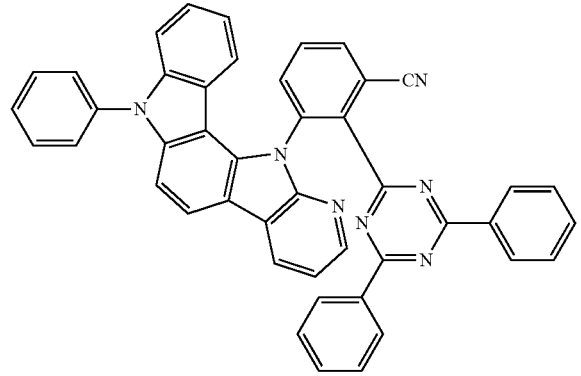

-continued
178
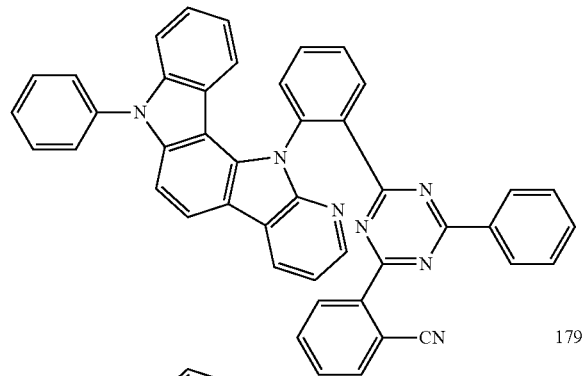
179
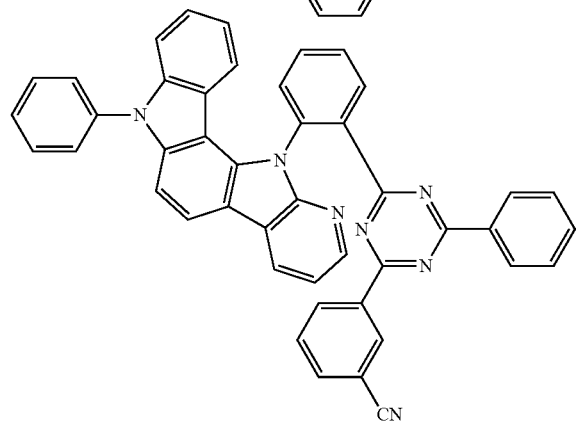
180
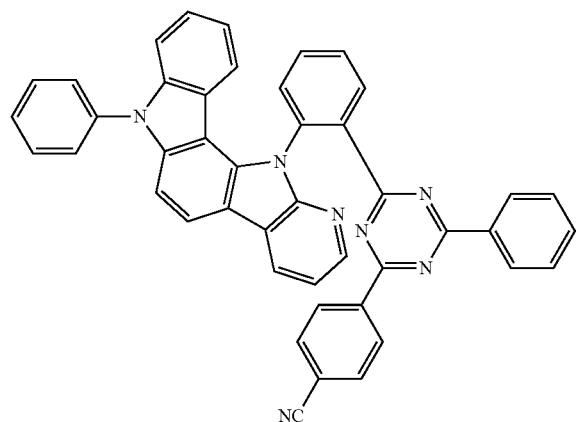
181
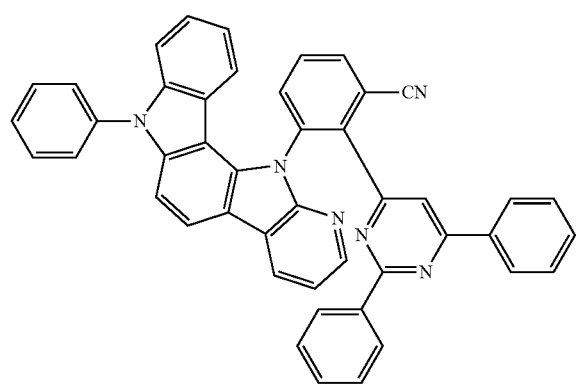
-continued
182
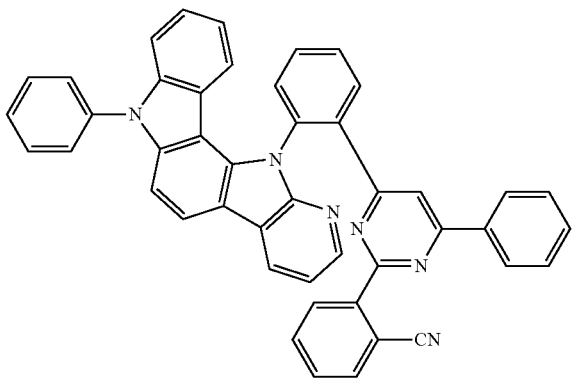
183
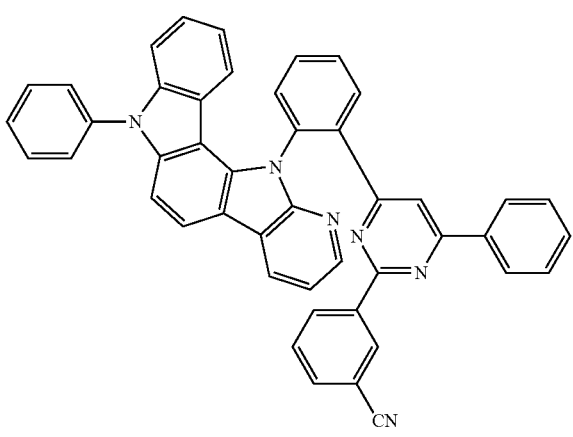
184
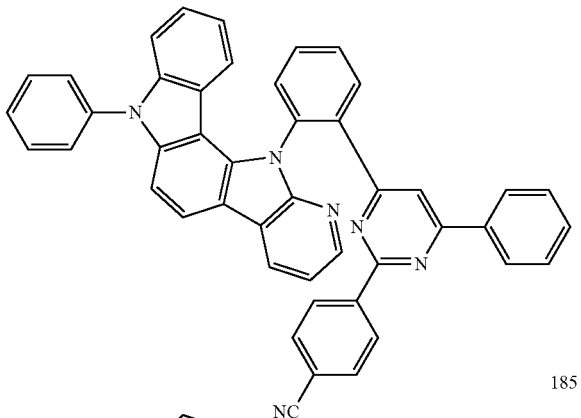
185
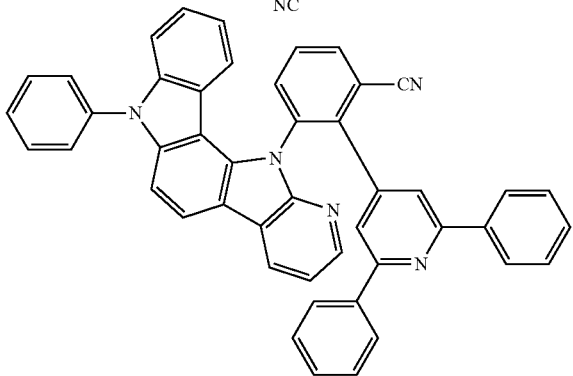

186

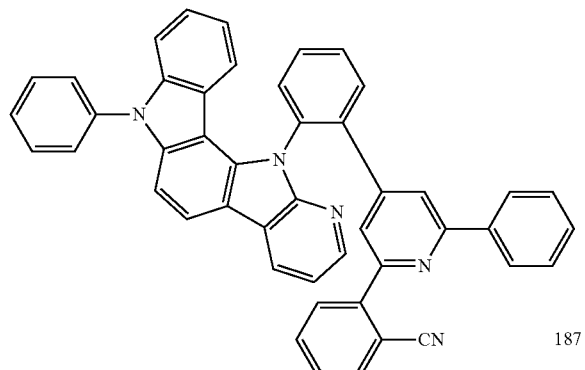

187

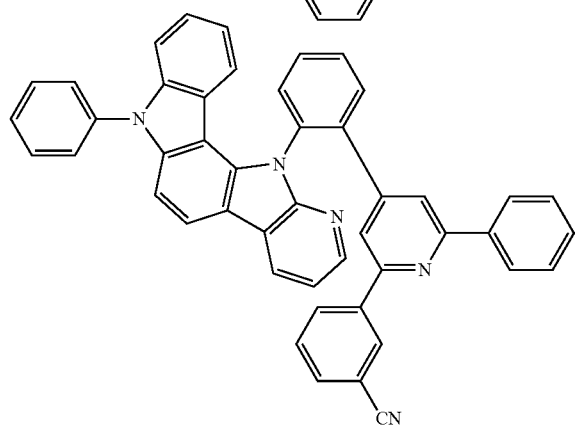

188

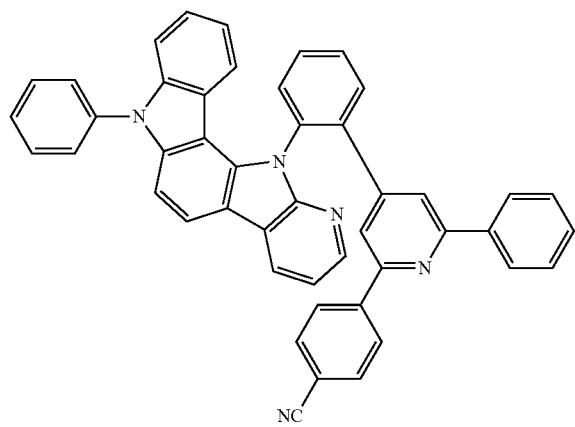

189

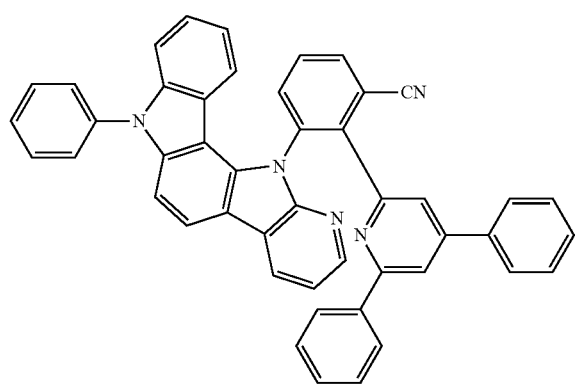

190

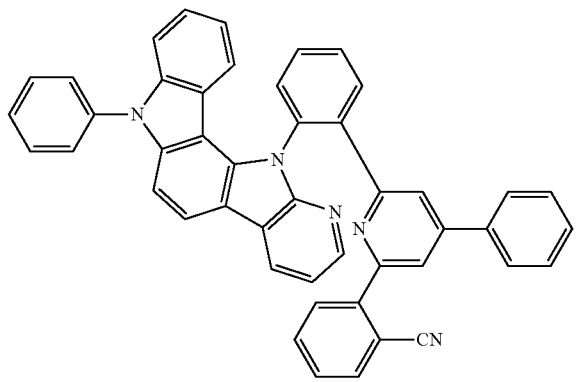

191

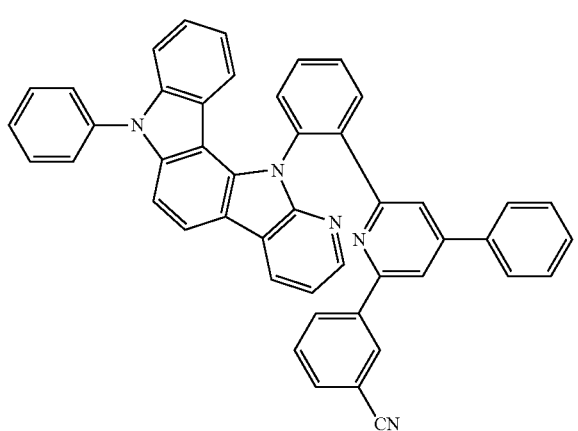

192

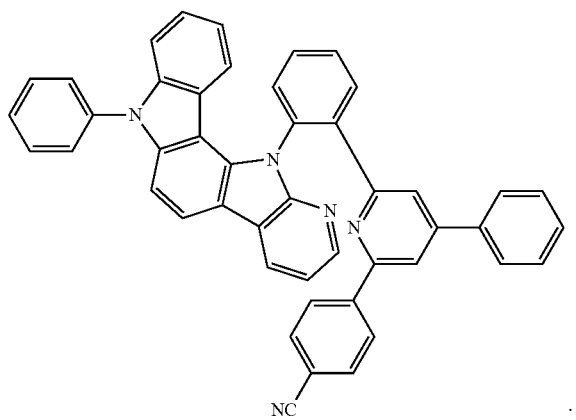

In various embodiments, the host may be selected from:

compounds including at least one selected from a fluorene-based ring, a carbazole-based ring, a dibenzofuran-based ring, a dibenzothiophene-based ring, an indenocarbazole-based ring, an indolocarbazole-based ring, a benzofurocarbazole-based ring, a benzothienocarbazole-based ring, an acridine-based ring, a dihydroacridine-based ring, and a triindolobenzene-based ring; or a silicon-based compound and a phosphine oxide-based compound.

For example, the host may be selected from compounds represented by Formulae 11-1 to 11-3, but embodiments are not limited thereto:

$Ar_{11}$—$(L_{101})_{a101}$—$(Ar_{12})_{c1}$  Formula 11-1

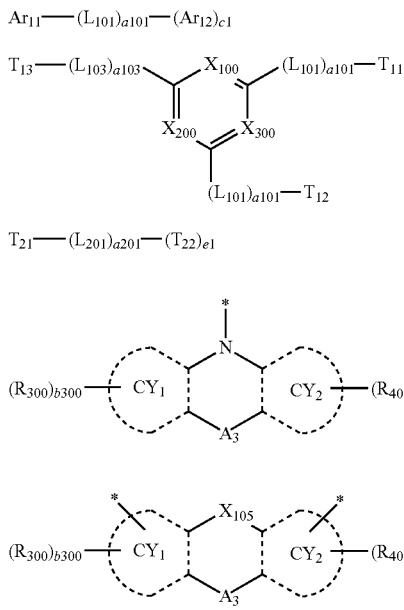

Formula 11-2

$T_{21}$—$(L_{201})_{a201}$—$(T_{22})_{e1}$  Formula 11-3

Formula 13

Formula 14

In Formulae 11-1 to 11-3, 13, and 14, $Ar_{11}$ and $Ar_{12}$ may each independently be selected from groups represented by Formulae 13 and 14, $X_{105}$ may be $N(R_{202})$, O, or S, $X_{100}$ may be N or $C(T_{14})$, $X_{200}$ may be N or $C(T_{15})$, and $X_{300}$ may be N or $C(T_{16})$, wherein at least one selected from $X_{100}$ to $X_{300}$ is N, $T_{21}$ and $T_{22}$ may each independently be selected from *-$(L_{201})_{a201}$-$Si(Q_{41})(Q_{42})(Q_{43})$ and *-$(L_{201})_{a201}$-$P(=O)(Q_{51})(Q_{52})$, $L_{101}$ to $L_{103}$ and $L_{201}$ may each independently be selected from:

a single bond, O, S, $Si(Q_{61})(Q_{62})$, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{71})(Q_{72})(Q_{73})$, a101 to a103 and a201 may each independently be an integer selected from 0 to 5, wherein when a101 is 2 or more, 2 or more groups $L_{101}$ may be identical to or different from each other, when a102 is 2 or more, 2 or more groups $L_{102}$ may be identical to or different from each other, when a103 is 2 or more, 2 or more groups $L_{103}$ may be identical to or different from each other, and when a201 is 2 or more, 2 or more groups $L_{201}$ may be identical to or different from each other, $CY_1$ and $CY_2$ may each independently be selected from a benzene group, a naphthalene group, a fluorene group, a carbazole group, a benzocarbazole group, an indolocarbazole group, a dibenzofuran group, and a dibenzothiophene group, $A_3$ may be selected from:

a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{81})(Q_{82})(Q_{83})$, $T_{11}$ to $T_{16}$, $R_{202}$, $R_{300}$, and $R_{400}$ may each independently be selected from hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, and —$Si(Q_{91})(Q_{92})(Q_{93})$, b300 and b400 may each independently be an integer selected from 0 to 10, c1 and e1 may each independently be 0, 1, 2, or 3,

* indicates a binding site to a neighboring atom, at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, and —Si($Q_{101}$)($Q_{102}$)($Q_{103}$), and $Q_{41}$ to $Q_{43}$, $Q_{51}$ to $Q_{52}$, $Q_{61}$ to $Q_{62}$, $Q_{71}$ to $Q_{73}$, $Q_{81}$ to $Q_{83}$, $Q_{91}$ to $Q_{93}$, and $Q_{101}$ to $Q_{103}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In Formula 11-1, $Ar_{11}$ and $Ar_{12}$ may each independently be selected from groups represented by Formulae 13-1 to 13-8 and 14-1 to 14-8:

Formula 13-1

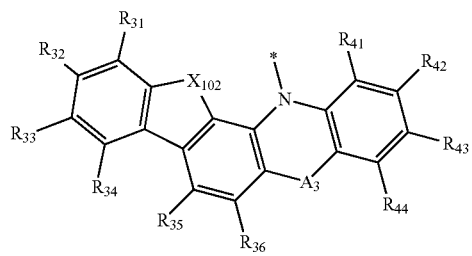

Formula 13-2

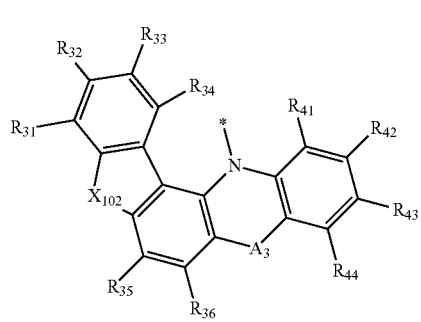

Formula 13-3

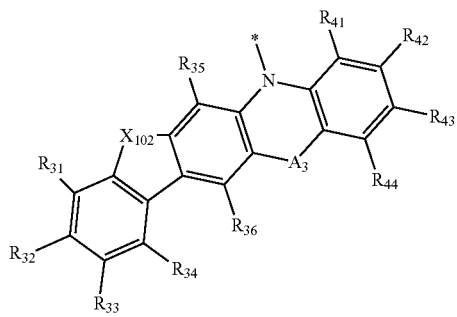

Formula 13-4

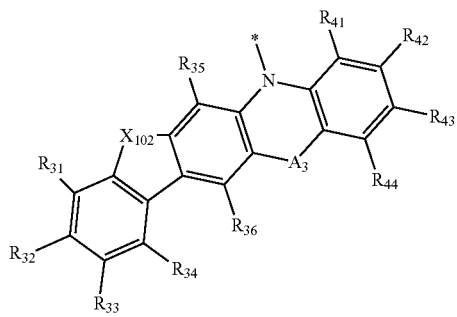

Formula 13-5

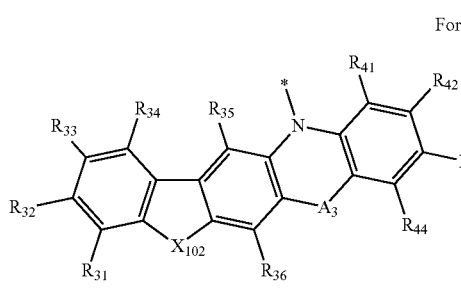

Formula 13-6

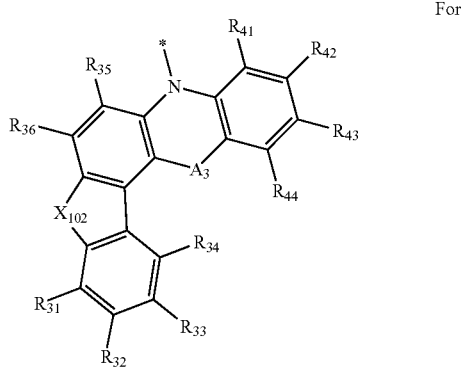

Formula 13-7

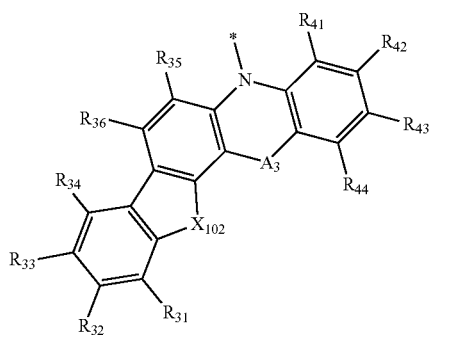

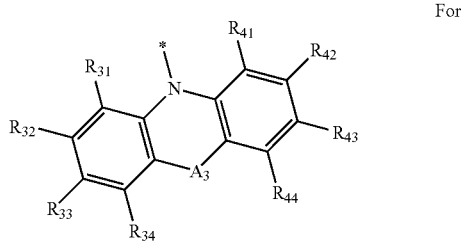

Formula 13-8
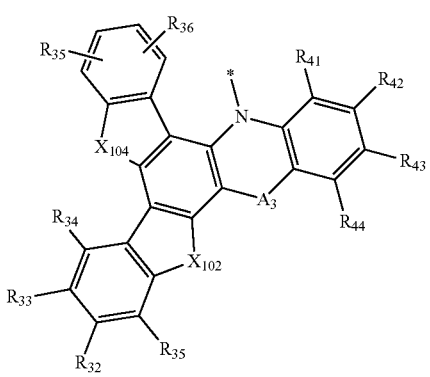

Formula 14-1
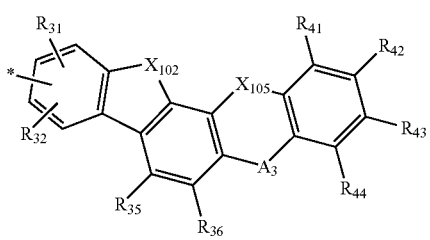

Formula 14-2
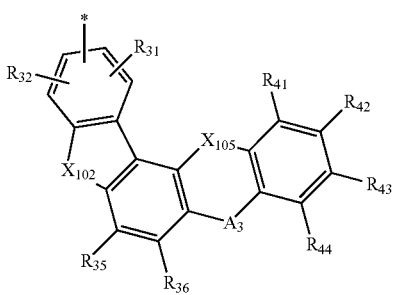

Formula 14-3
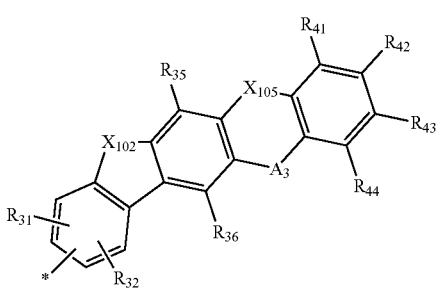

Formula 14-4
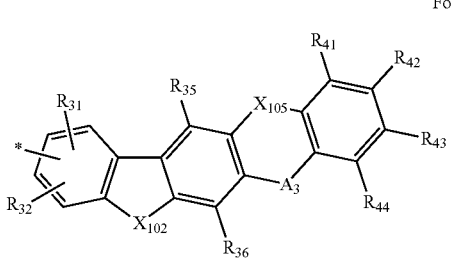

Formula 14-5
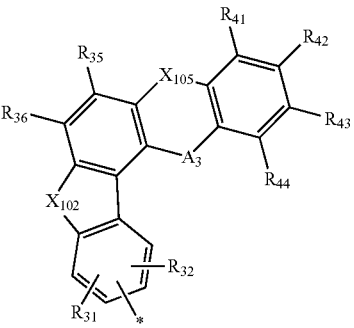

Formula 14-6
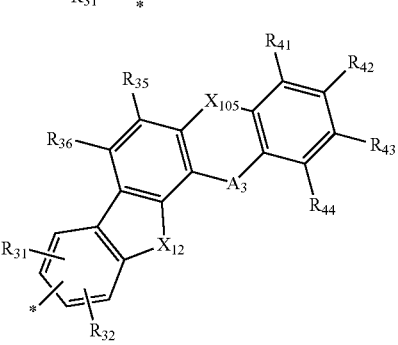

Formula 14-7
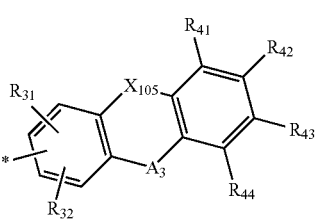

Formula 14-8
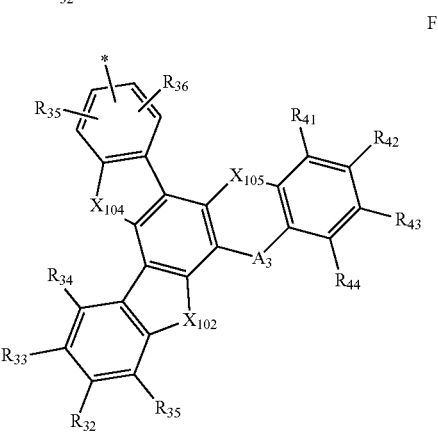

In Formulae 13-1 to 13-8 and 14-1 to 14-8, $X_{102}$ and $X_{104}$ may each independently be $C(R_{37})(R_{38})$, $N(R_{39})$, O, or S, $X_{105}$ and $A_3$ may each independently be understood by referring to the descriptions thereof provided herein in the present specification, $R_{31}$ to $R_{39}$ may each independently be understood by referring to the description of $R_{300}$ provided herein, $R_{41}$ to $R_{44}$ may each independently be understood by referring to the description of $R_{400}$ provided herein, and

* indicates a binding site to a neighboring atom.

In an embodiment, in Formulae 13, 14, 13-1 to 13-8, and 14-1 to 14-8, $A_3$ may be selected from:

a single bond, a $C_1$-$C_2$ alkylene group, and a $C_2$ alkenylene group; and a $C_1$-$C_2$ alkylene group and a $C_2$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{81}$)($Q_{82}$)($Q_{83}$), $R_{202}$, $R_{30}$ to $R_{39}$, and $R_{40}$ to $R_{44}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a carbazolyl group, a dibenzofuranyl group, and a dibenzothiophenyl group;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and —Si($Q_{91}$)($Q_{92}$)($Q_{93}$), and $Q_{81}$ to $Q_{83}$ and $Q_{91}$ to $Q_{93}$ may each independently be selected from hydrogen, a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In various embodiments, in Formula 11-1, $Ar_{11}$ and $Ar_{12}$ may each independently be selected from groups represented by Formulae 17-1 to 17-19 and 18-1 to 18-8, but embodiments are not limited thereto:

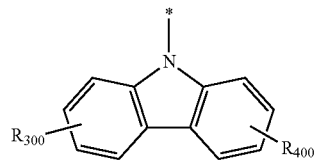

Formula 17-1

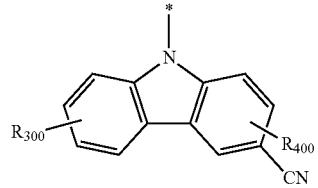

Formula 17-2

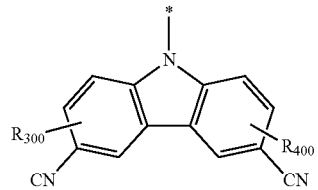

Formula 17-3

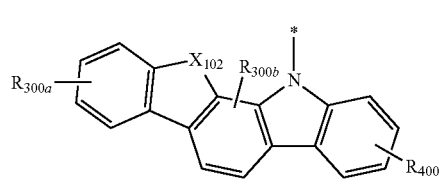

Formula 17-4

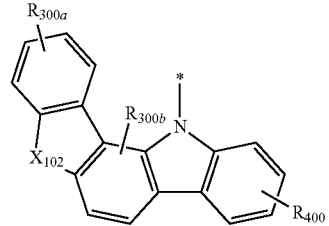

Formula 17-5

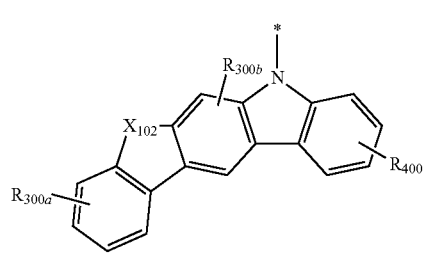

Formula 17-6

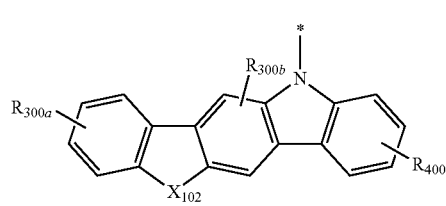

Formula 17-7

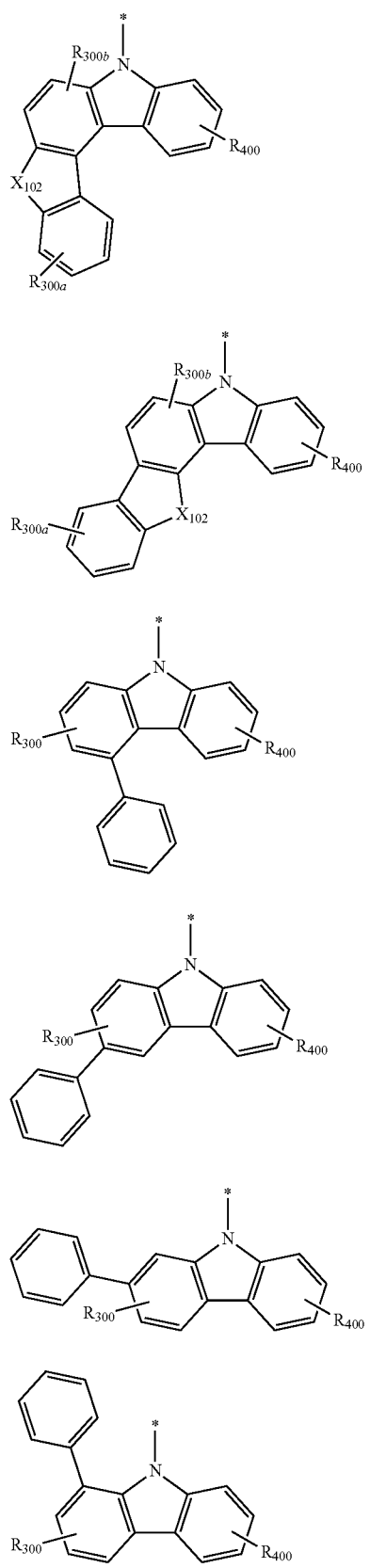
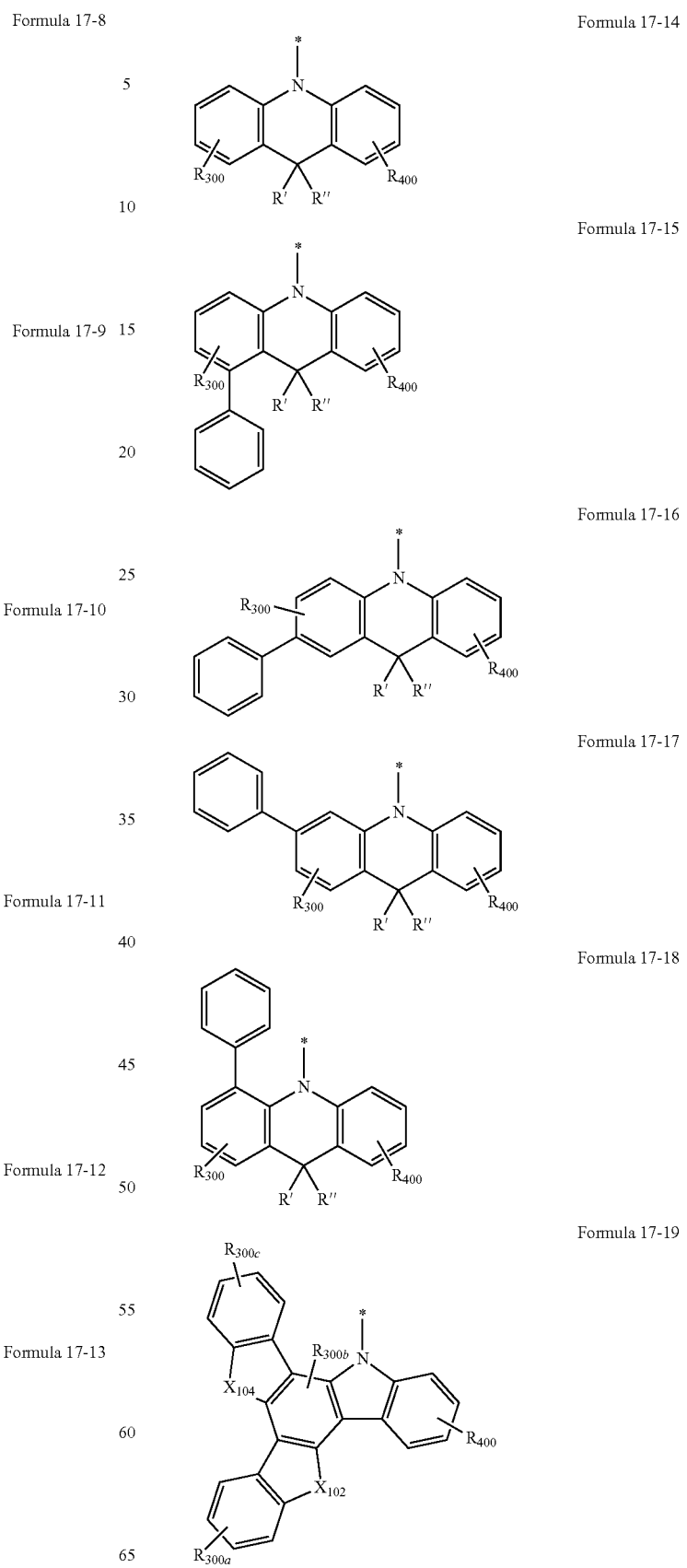

-continued

Formula 18-1
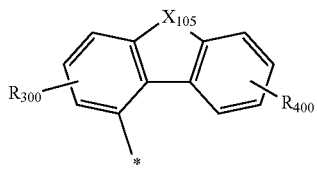

Formula 18-2
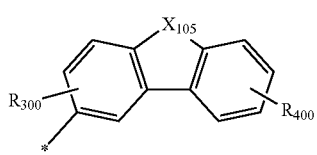

Formula 18-3
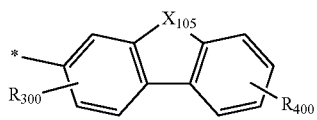

Formula 18-4
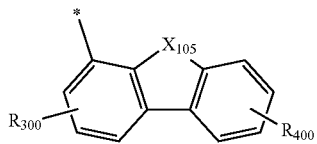

Formula 18-5
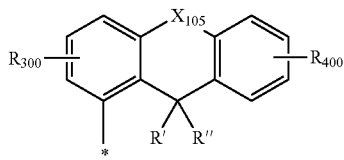

Formula 18-6
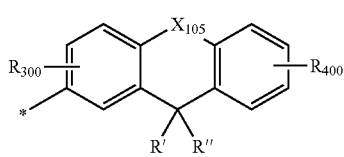

Formula 18-7
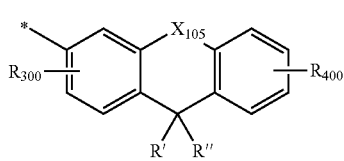

Formula 18-8
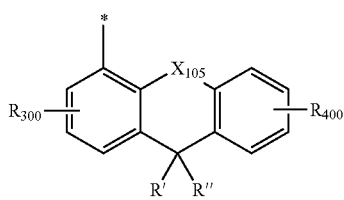

In Formulae 17-1 to 17-19 and 18-1 to 18-8, $X_{102}$ and $X_{104}$ may each independently be $C(R_{37})(R_{38})$, $N(R_{39})$, O, or S, $X_{105}$ may be $N(R_{202})$, O, or S, R' and R" may each independently be selected from hydrogen, deuterium, a $C_1$-$C_{10}$ alkyl group, a $C_1$-$C_{10}$ alkoxy group, a phenyl group, a biphenyl group, a terphenyl group, a naphthyl group, a fluorenyl group, a carbazolyl group, a dibenzofuranyl group, and a dibenzothiophenyl group, $R_{202}$, $R_{300}$, and $R_{400}$ may each independently be understood by referring to the descriptions thereof provided herein in the present specification, $R_{300a}$ to $R_{300c}$ may be understood by referring to the description of $R_{300}$ provided herein, and

* indicates a binding site to a neighboring atom.

For example, in Formulae 17-1 to 17-19 and 18-1 to 18-8, $R_{202}$, $R_{300}$, $R_{300a}$ to $R_{300c}$, and $R_{400}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;

a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$, a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and —$Si(Q_{91})(Q_{92})(Q_{93})$, and $Q_{91}$ to $Q_{93}$ may each independently be selected from hydrogen, a $C_1$-$C_{10}$ alkyl group, a $C_1$-$C_{10}$ alkoxy group, a phenyl group, a biphenyl group, a terphenyl group, and a naphthyl group, but embodiments are not limited thereto.

In various embodiments, in Formulae 11-1 to 11-3, $L_{101}$ to $L_{103}$ and $L_{201}$ may each independently be selected from a single bond, O, S, $Si(Q_{61})(Q_{62})$, and groups represented by Formulae 3-1 to 3-56:

Formula 3-1
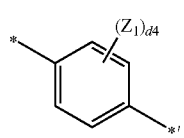

Formula 3-2
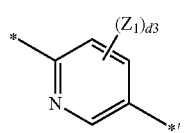

Formula 3-3

-continued
Formula 3-4
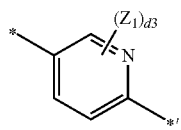
Formula 3-5
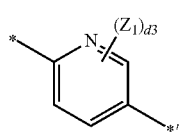
Formula 3-6
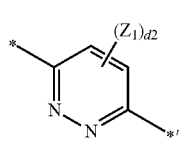
Formula 3-7
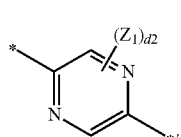
Formula 3-8
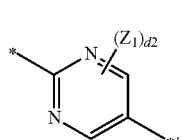
Formula 3-9
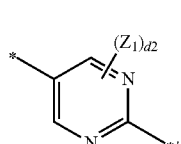
Formula 3-10
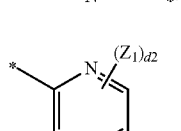
Formula 3-11
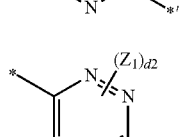
Formula 3-12
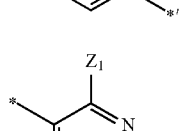
Formula 3-13
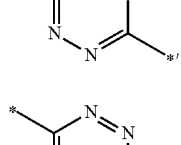
Formula 3-14
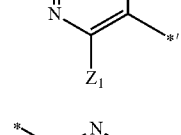
-continued
Formula 3-15
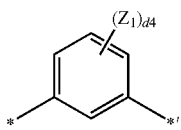
Formula 3-16
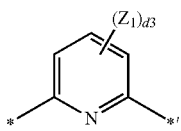
Formula 3-17
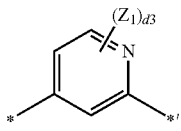
Formula 3-18
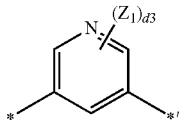
Formula 3-19
Formula 3-20
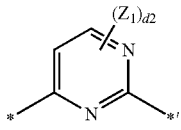
Formula 3-21
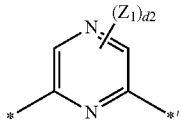
Formula 3-22
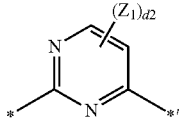
Formula 3-23
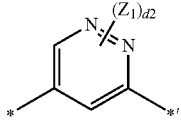
Formula 3-24
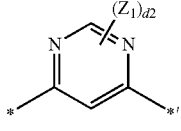
Formula 3-25
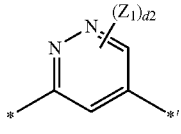

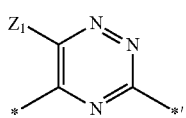
Formula 3-25
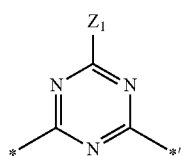
Formula 3-27
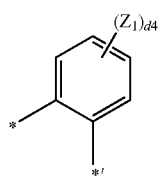
Formula 3-28
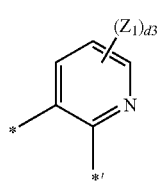
Formula 3-29
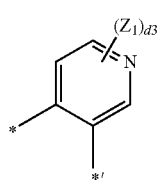
Formula 3-30
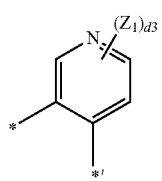
Formula 3-31
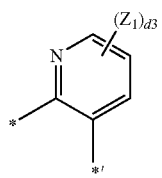
Formula 3-32
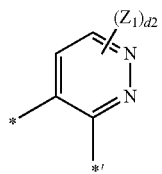
Formula 3-33
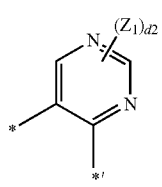
Formula 3-26
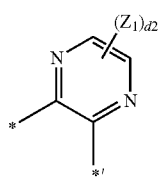
Formula 3-34
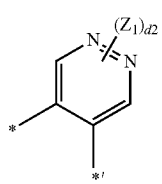
Formula 3-35
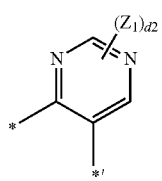
Formula 3-36
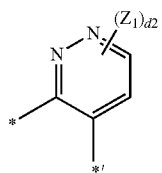
Formula 3-37
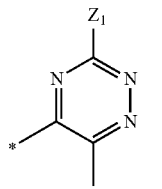
Formula 3-38
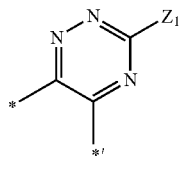
Formula 3-39
Formula 3-40
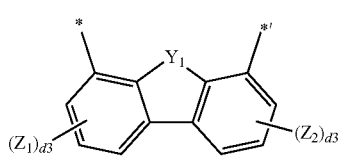
Formula 3-41

-continued

Formula 3-42
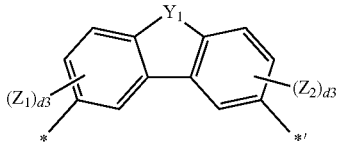

Formula 3-43
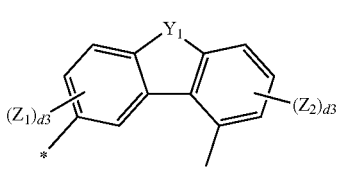

Formula 3-44
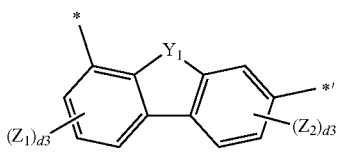

Formula 3-45
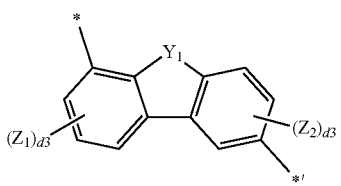

Formula 3-46
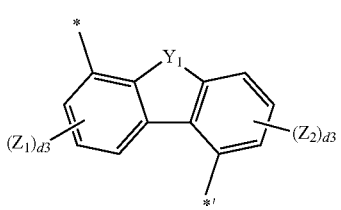

Formula 3-47
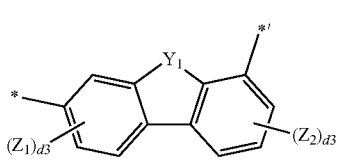

Formula 3-48
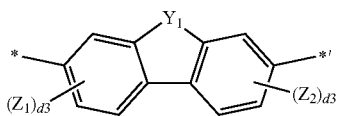

Formula 3-49
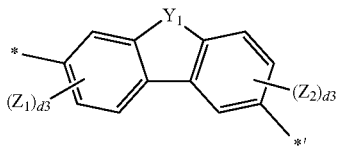

Formula 3-50
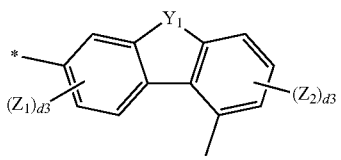

Formula 3-51
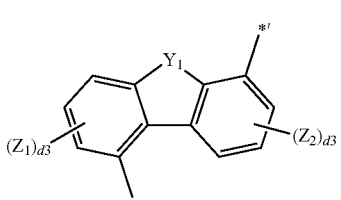

Formula 3-52
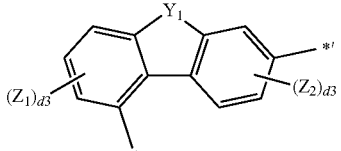

Formula 3-53
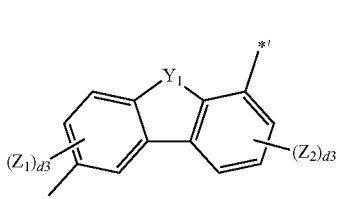

Formula 3-54
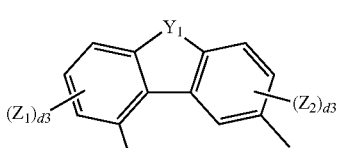

Formula 3-55
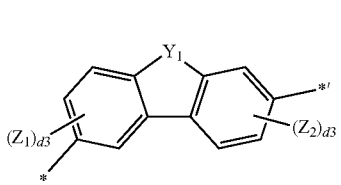

Formula 3-56
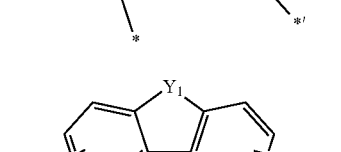

In Formulae 3-1 to 3-56, $Y_1$ may be selected from O, S, $C(Z_3)(Z_4)$, and $N(Z_5)$, $Z_1$ to $Z_5$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si$(Q_{71})(Q_{72})(Q_{73})$, $Q_{71}$ to $Q_{73}$ may each independently be selected from hydrogen, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group, d4 may be an integer selected from 0 to 4, d3 may be an integer selected from 0 to 3, d2 may be an integer selected from 0 to 2, and

* and *' each indicate a binding site to a neighboring atom.

In an embodiment, in Formulae 11-1 to 11-3, $L_{101}$ to $L_{103}$ and $L_{201}$ may each independently be selected from a single bond, O, S, $Si(Q_{61})(Q_{62})$, and groups represented by Formulae 3-1 to 3-56, wherein at least one of groups $L_{101}$ in the number of a101, at least one of groups $L_{102}$ in the number of a102, at least one of groups $L_{103}$ in the number of a103, or at least one of groups $L_{201}$ in the number of a201 may be selected from O, $Si(Q_{61})(Q_{62})$, and groups represented by Formulae 3-15 to 3-56.

In various embodiments, the groups represented by *-$(L_{101})_{a101}$-*', *-$(L_{102})_{a102}$-*', *-$(L_{103})_{a103}$-*', and *-$(L_{201})_{a201}$-*' may be selected from groups represented by Formulae 3-41 to 3-56, but embodiments are not limited thereto.

In various embodiments, the groups represented by *-$(L_{101})_{a101}$-*', *-$(L_{102})_{a102}$-*', *-$(L_{103})_{a103}$-*', and *-$(L_{201})_{a201}$-*' may be selected from a single bond and groups represented by Formulae 4-1 to 4-42, but embodiments are not limited thereto:

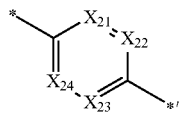

Formula 4-1

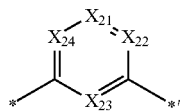

Formula 4-2

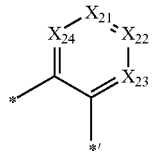

Formula 4-3

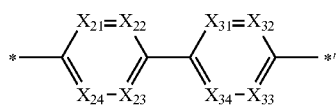

Formula 4-4

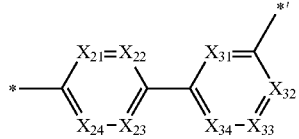

Formula 4-5

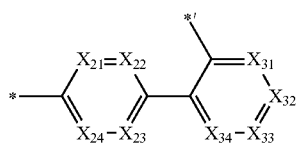

Formula 4-6

-continued

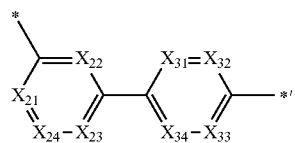

Formula 4-7

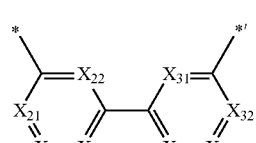

Formula 4-8

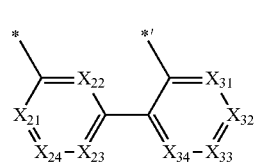

Formula 4-9

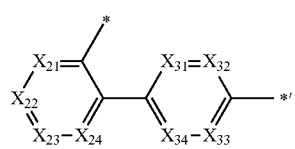

Formula 4-10

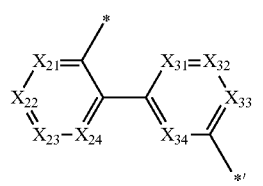

Formula 4-11

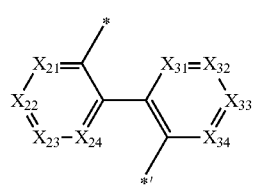

Formula 4-12

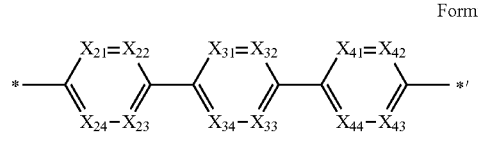

Formula 4-13

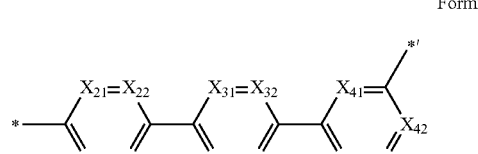

Formula 4-14

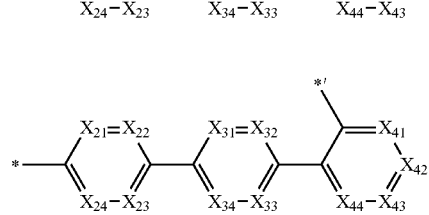

Formula 4-15

Formula 4-16
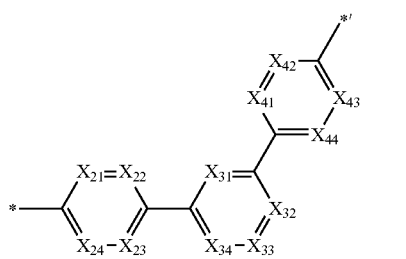
Formula 4-17
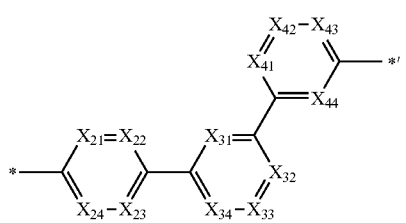
Formula 4-18
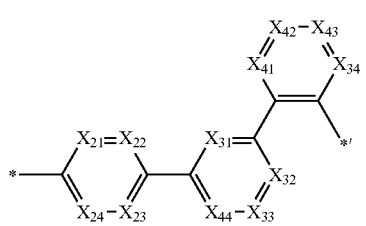
Formula 4-19
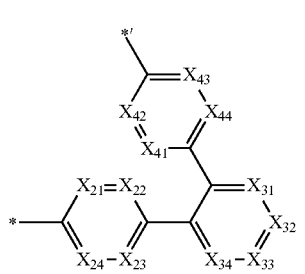
Formula 4-20
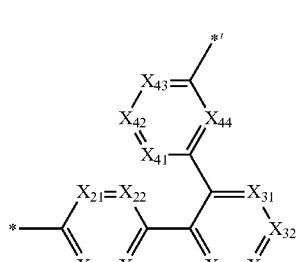
Formula 4-21
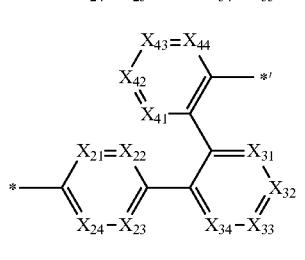
Formula 4-22
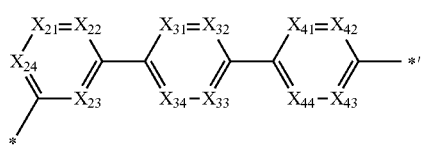
Formula 4-23
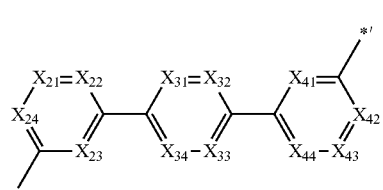
Formula 4-24
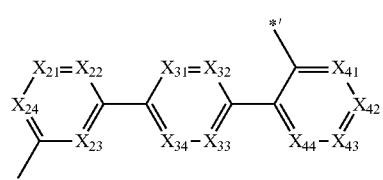
Formula 4-25
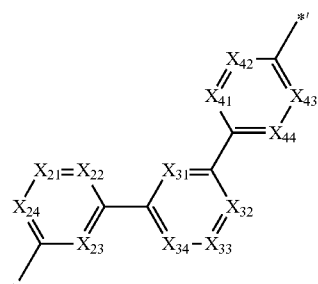
Formula 4-26
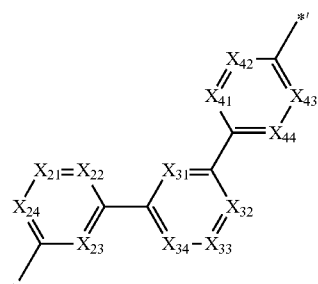
Formula 4-27
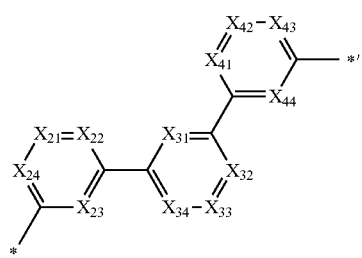
Formula 4-28
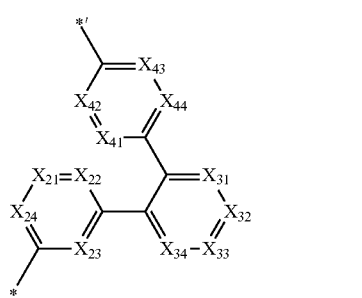

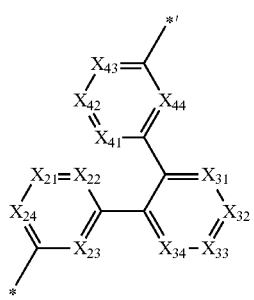
Formula 4-29
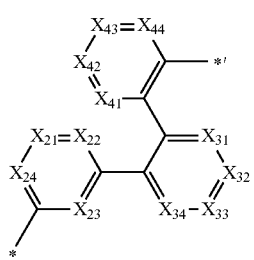
Formula 4-30
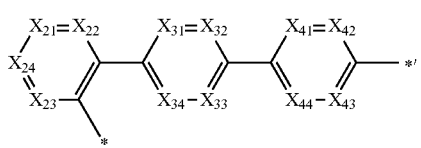
Formula 4-31
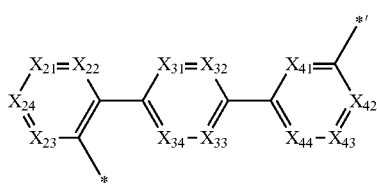
Formula 4-32
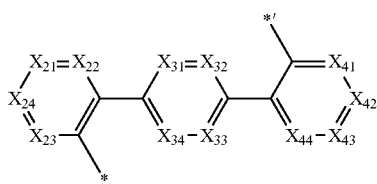
Formula 4-33
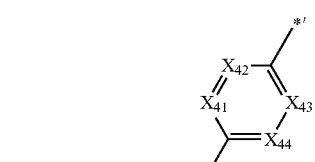
Formula 4-34
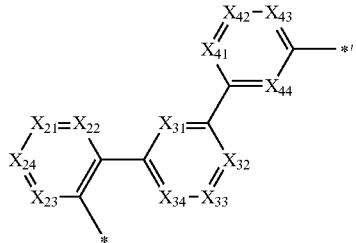
Formula 4-35
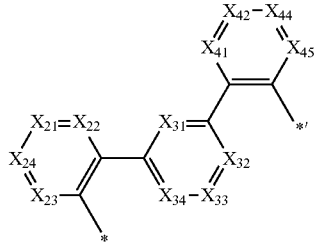
Formula 4-36
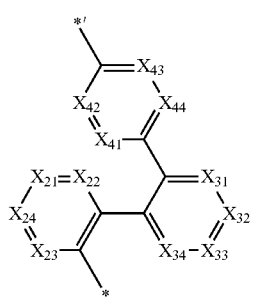
Formula 4-37
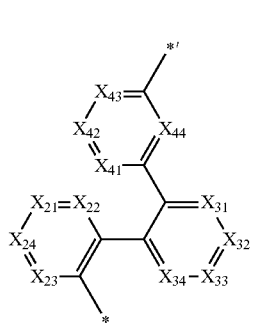
Formula 4-38
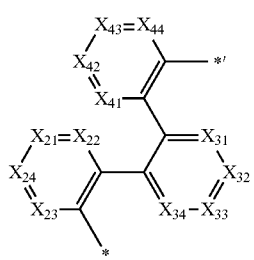
Formula 4-39
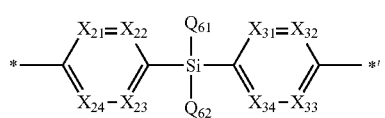
Formula 4-40

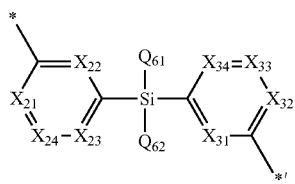

Formula 4-41

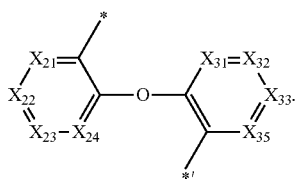

Formula 4-42

In Formulae 4-1 to 4-42, $X_{41}$ may be N or $C(Z_{41})$, $X_{42}$ may be N or $C(Z_{42})$, $X_{43}$ may be N or $C(Z_{43})$, $X_{44}$ may be N or $C(Z_{44})$, $X_{51}$ may be N or $C(Z_{51})$, $X_{52}$ may be N or $C(Z_{52})$, $X_{53}$ may be N or $C(Z_{53})$, $X_{54}$ may be N or $C(Z_{54})$, $X_{61}$ may be N or $C(Z_{61})$, $X_{62}$ may be N or $C(Z_{62})$, $X_{63}$ may be N or $C(Z_{63})$, and $X_{64}$ may be N or $C(Z_{64})$, wherein a case where each of $X_{41}$ to $X_{44}$ is N, a case where each of $X_{51}$ to $X_{54}$ is N, and a case where each of $X_{61}$ to $X_{64}$ is N are excluded, $Z_{41}$ to $Z_{44}$, $Z_{51}$ to $Z_{54}$, and $Z_{61}$ to $Z_{64}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{71})(Q_{72})(Q_{73})$, $Q_{71}$ to $Q_{73}$ may each independently be selected from hydrogen, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group, and

* and *' each indicate a binding site to a neighboring atom.

In Formula 11-2, two or three selected from $X_{100}$ to $X_{300}$ may be N.

For example, in Formula 11-2, $T_{11}$ to $T_{16}$ may each independently be selected from:

hydrogen, deuterium, —F, a cyano group, a $C_1$-$C_{10}$ alkyl group, a $C_1$-$C_{10}$ alkoxy group —$CF_3$, —$CF_2H$, and —$CFH_2$;

a $C_1$-$C_{10}$ alkyl group and a $C_1$-$C_{10}$ alkoxy group, each substituted with at least one selected from deuterium, —F, a cyano group —$CF_3$, —$CF_2H$, and —$CFH_2$;

a phenyl group, a biphenyl group, a terphenyl group, a pyridinyl group, a pyrimidinyl group, a triazinyl group, a carbazolyl group, a dibenzofuranyl group, and a dibenzothiophenyl group;

a phenyl group, a biphenyl group, a terphenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a $C_1$-$C_{10}$ alkyl group, a $C_1$-$C_{10}$ alkoxy group, —$CF_3$, —$CF_2H$, —$CFH_2$, a phenyl group, a biphenyl group, a terphenyl group, a pyridinyl group, a pyrimidinyl group, a triazinyl group, a carbazolyl group, a dibenzofuranyl group, and a dibenzothiophenyl group; and —$Si(Q_{91})(Q_{92})(Q_{93})$, and $Q_{91}$ to $Q_{93}$ may each independently be selected from hydrogen, a $C_1$-$C_{10}$ alkyl group, a $C_1$-$C_{10}$ alkoxy group, a phenyl group, a biphenyl group, a terphenyl group, a pyridinyl group, a pyrimidinyl group, a triazinyl group, a carbazolyl group, a dibenzofuranyl group, and a dibenzothiophenyl group, but embodiments are not limited thereto.

In various embodiments, in Formula 11-3, $T_{21}$ and $T_{22}$ may each independently be selected from *-$(L_{201})_{a201}$-Si$(Q_{41})(Q_{42})(Q_{43})$ and *-$(L_{201})_{a201}$-P(=O)$(Q_{51})(Q_{52})$, and $Q_{41}$ to $Q_{43}$ and $Q_{51}$ to $Q_{52}$ may each independently be selected from:

a phenyl group, a biphenyl group, a terphenyl group, a pyridinyl group, a pyrimidinyl group, a triazinyl group, a carbazolyl group, a dibenzofuranyl group, and a dibenzothiophenyl group; and a phenyl group, a biphenyl group, a terphenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a $C_1$-$C_{10}$ alkyl group, a $C_1$-$C_{10}$ alkoxy group, —$CF_3$, —$CF_2H$, —$CFH_2$, a phenyl group, a biphenyl group, a terphenyl group, a pyridinyl group, a pyrimidinyl group, a triazinyl group, a carbazolyl group, a dibenzofuranyl group, and a dibenzothiophenyl group, but embodiments are not limited thereto.

In an embodiment, the host may include at least one cyano group. For example, the host may be a compound that is represented by one selected from Formulae 11-1 to 11-3 and includes at least one cyano group, but embodiments are not limited thereto.

For example, the host may be selected from Compounds H1 to H24:

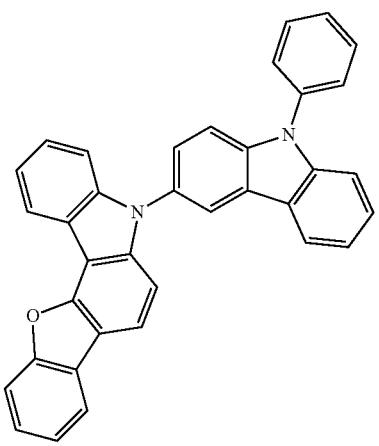

H1

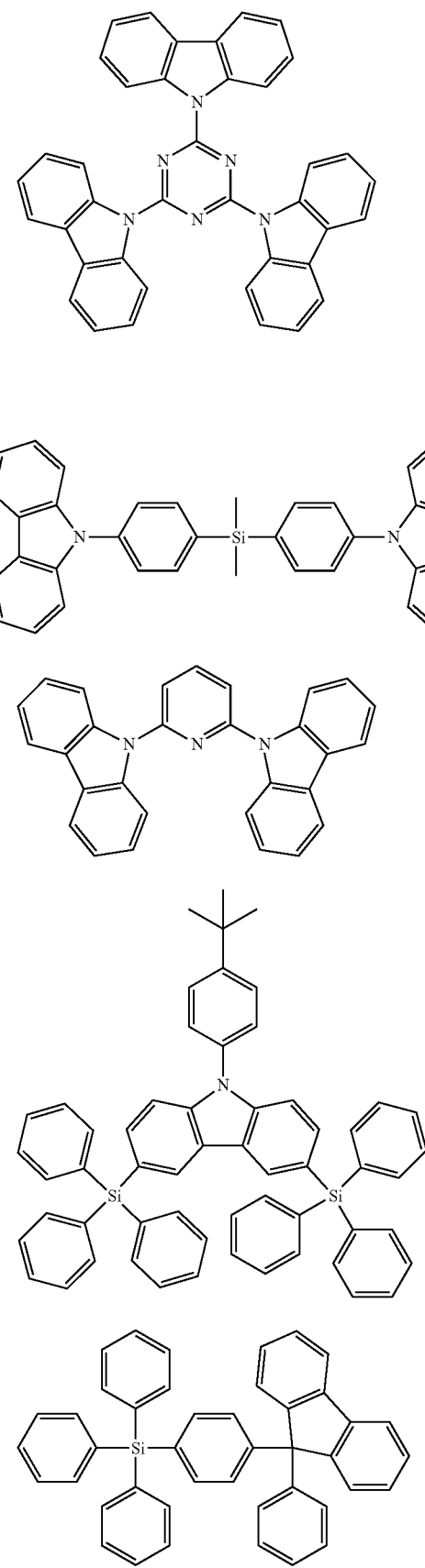
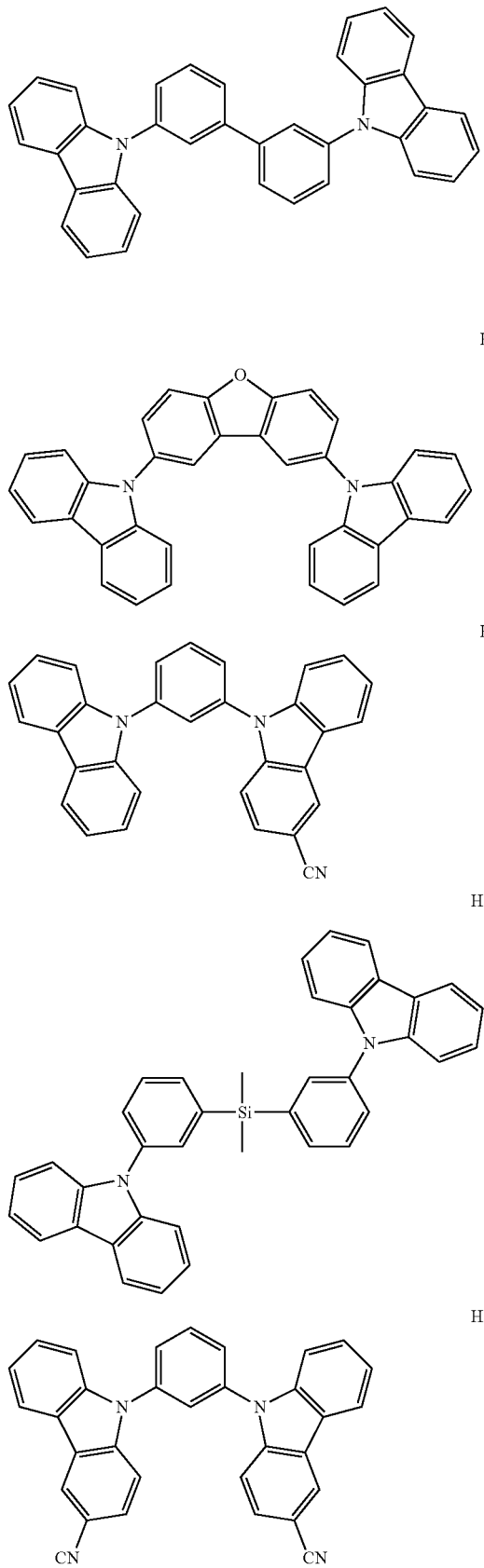

H12 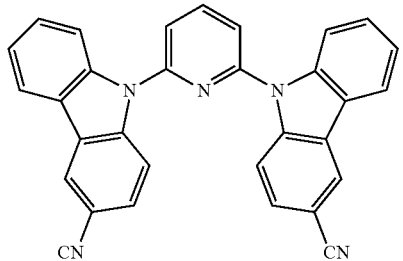
H13 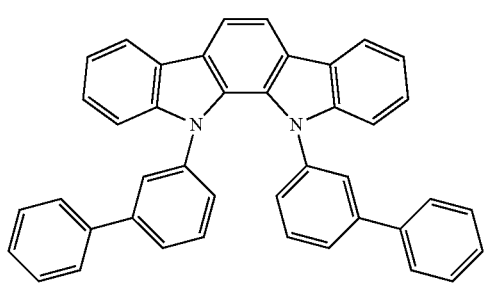
H14 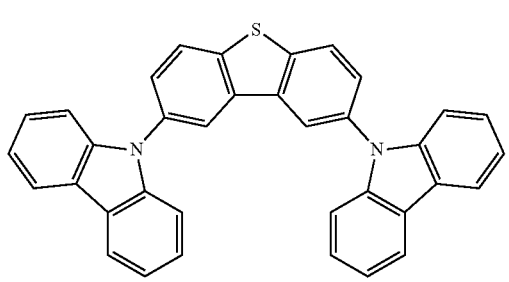
H15 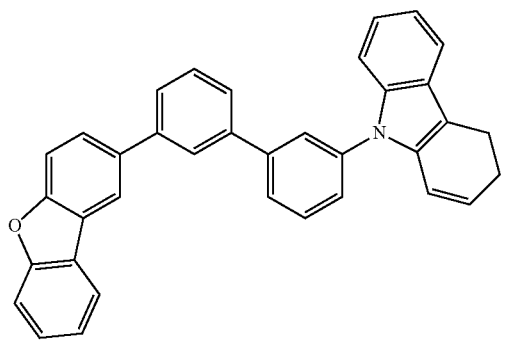
H16 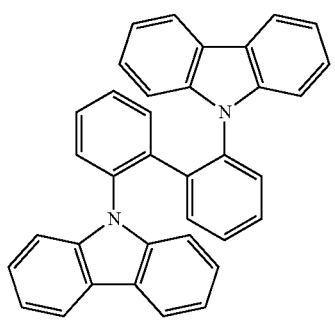
H17 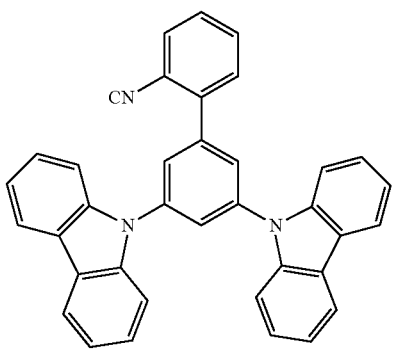
H18 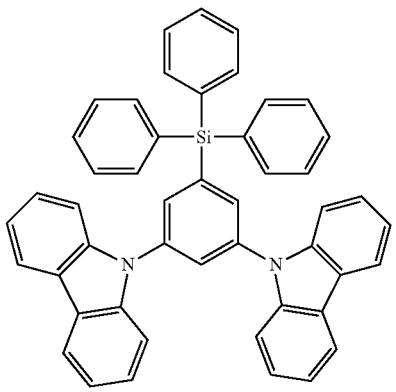
H19 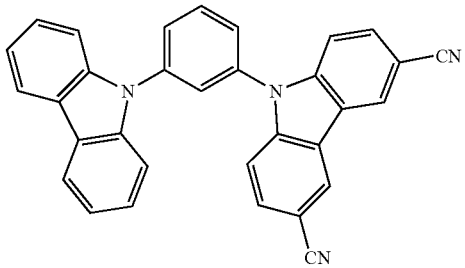
H20 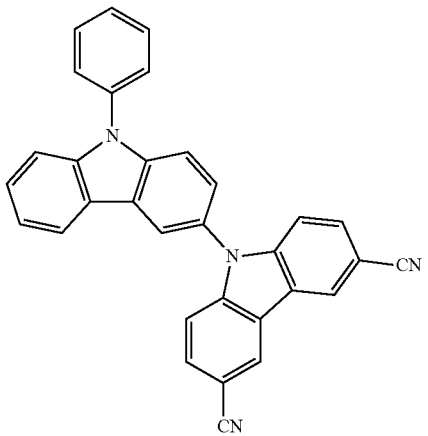

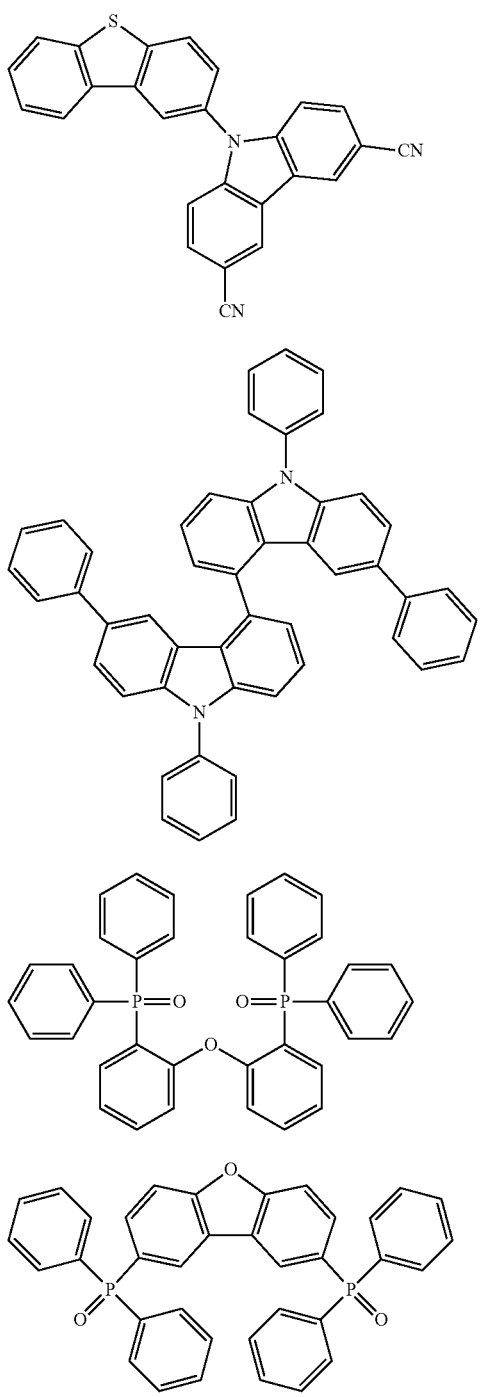

In an embodiment, the dopant may include a thermal activated delayed fluorescent dopant, wherein the thermal activated delayed fluorescent dopant may be the condensed cyclic compound represented by Formula 1.

In various embodiments, the thermal activated delayed fluorescent dopant may satisfy Equations 1 and 2:

$$E_{S1(TD)} - E_{T1(TD)} \leq -0.3 \text{ electron Volts} \qquad \text{Equation 1}$$

$$E_{S1(TD)} > 2.6 \text{ electron Volts.} \qquad \text{Equation 2}$$

In Equations 1 and 2, $E_{S1(TD)}$ denotes a singlet state (S₁) energy level (unit: electron volts (eV)) of the thermal activated delayed fluorescent dopant, and $E_{T1(TD)}$ denotes a triplet state (T₁) energy level (unit: eV) of the thermal activated delayed fluorescent dopant.

The organic light-emitting device, which includes the dopant satisfying Equation 1, may emit blue light.

In addition, the organic light-emitting device, which includes the dopant satisfying Equation 2, may efficiently exhibit thermally activated delayed fluorescence characteristics, thereby having high efficiency.

The FIGURE is a diagram schematically illustrating a cross-section of an organic light-emitting device 10. Hereinafter, the structure of the organic light-emitting device 10 according to an embodiment and a method of manufacturing the organic light-emitting device 10, according to an embodiment, will be described in connection with the FIGURE. The organic light-emitting device 10 includes a first electrode 11, an organic layer 15, and a second electrode 19 that are sequentially stacked in the stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be formed by, for example, depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may include indium tin oxide (ITO), indium zinc oxide (IZO), tin oxide ($SnO_2$), or zinc oxide (ZnO). In various embodiments, metals, such as magnesium (Mg), aluminum (Al), aluminum-lithium (Al—Li), calcium (Ca), magnesium-indium (Mg—In), and magnesium-silver (Mg—Ag), may be used as the material for forming the first electrode 11.

The first electrode 11 may have a single-layered structure, or a multi-layered structure including two or more layers. For example, the first electrode 11 may have a three-layered structure of ITO/Ag/ITO, but embodiments are not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In various embodiments, the hole transport region may have a structure of hole injection layer/hole transport layer or have a structure of hole injection layer/hole transport layer/electron blocking layer, wherein, for each structure, constituting layers are sequentially stacked from the first electrode 11 in the stated order.

When the hole transport region includes a hole injection layer, the hole injection layer may be formed on the first electrode 11 by using one or more suitable methods, such as vacuum deposition, spin coating, casting, or Langmuir-Blodgett (LB) deposition.

When the hole injection layer is formed by vacuum deposition, the deposition conditions may vary according to a compound that is a material used to form the hole injection layer, and a structure and thermal characteristics of the hole injection layer to be formed. For example, the deposition conditions may be selected from a deposition temperature range of about 100 to about 500° C., a vacuum degree range of about $10^{-8}$ to about $10^{-3}$ torr, and a deposition rate range of about 0.01 to about 100 Angstroms per second (Å/sec), but embodiments are not limited thereto.

When the hole injection layer is formed by spin coating, the coating conditions may vary depending on a compound used as a material to form the hole injection layer, and a structure and thermal characteristics of the hole injection layer to be formed. For example, the coating conditions may be selected from a coating rate range of about 2,000 to about 5,000 revolutions per minute (rpm), and a temperature at which a heat treatment is performed to remove a solvent after coating may be selected from a range of about 80° C. to about 200° C., but embodiments are not limited thereto.

Conditions for forming a hole transport layer and an electron blocking layer may be understood by referring to conditions for forming the hole injection layer.

The hole transport region may include, for example, at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly (4-styrene sulfonate) (PEDOT/PSS), polyaniline/camphor sulfonic acid (PANI/CSA), polyaniline/poly(4-styrene sulfonate) (PANI/PSS), a compound represented by Formula 201, and a compound represented by Formula 202:

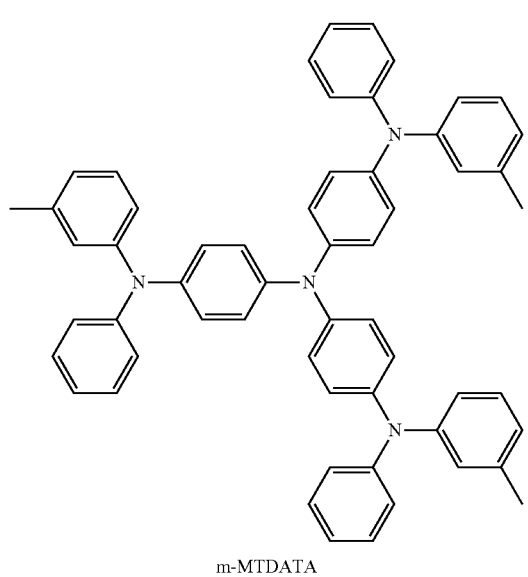

m-MTDATA

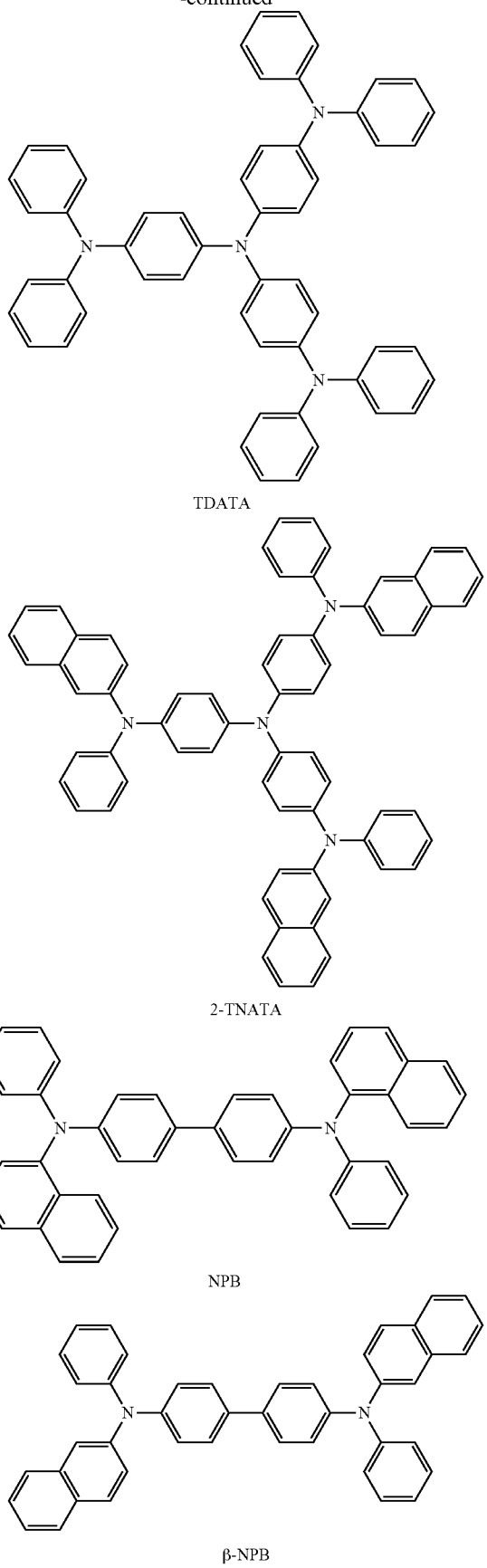

TDATA

2-TNATA

NPB

β-NPB

-continued

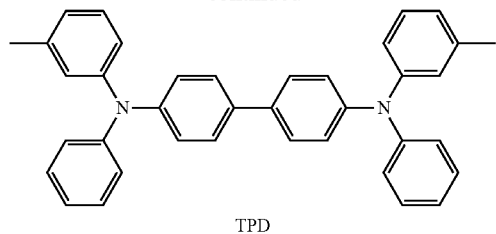

TPD

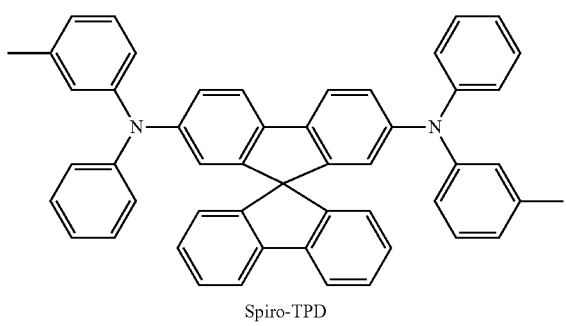

Spiro-TPD

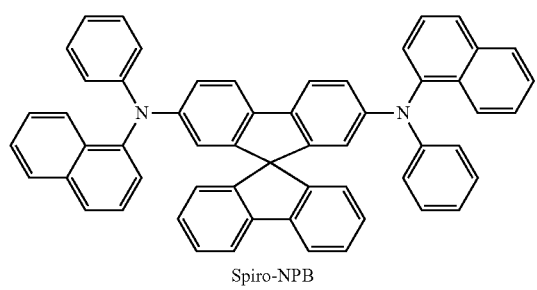

Spiro-NPB

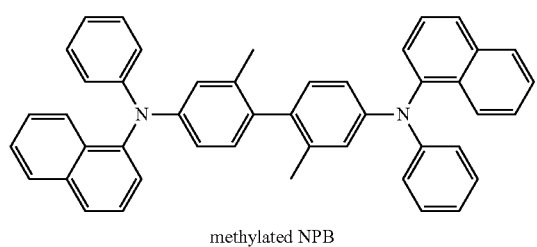

methylated NPB

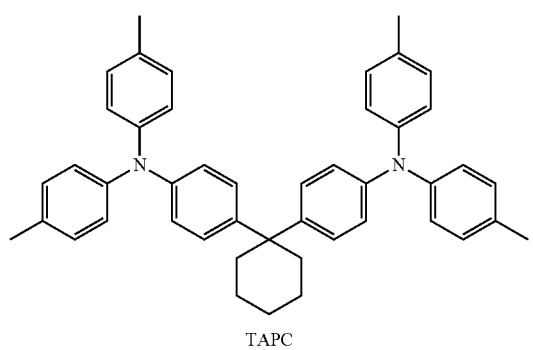

TAPC

-continued

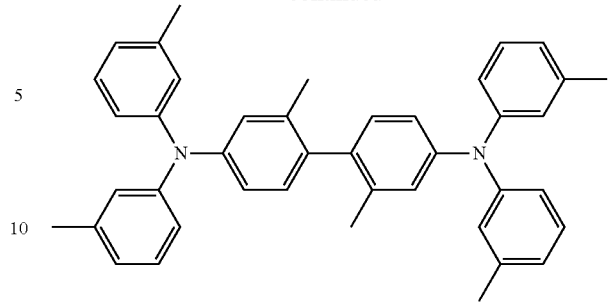

HMTPD

Formula 201

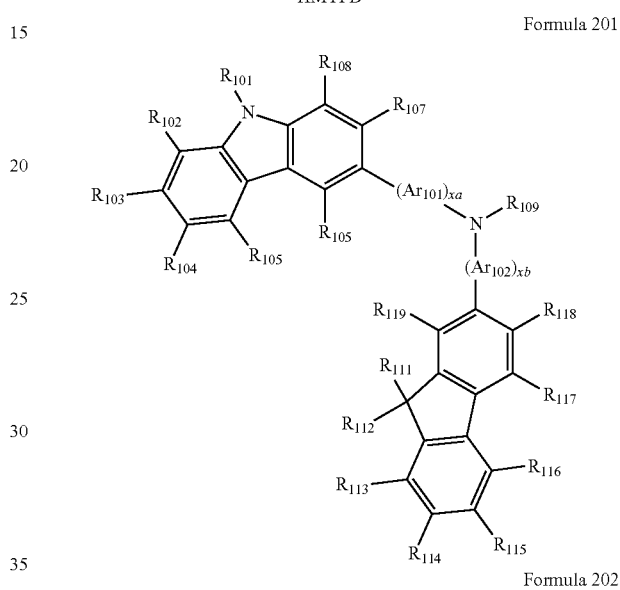

Formula 202

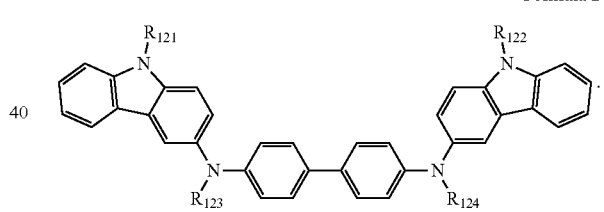

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group.

In Formula 201, xa and xb may each independently be an integer selected from 0 to 5, or may be 0, 1, or 2. For example, xa may be 1, and xb may be 0, but embodiments are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_1$ alkyl group (for example, a methyl group, an ethyl group, a propyl group, a butyl group, pentyl group, or a hexyl group), and a $C_1$-$C_{10}$ alkoxy group (for example, a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and
m
a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but embodiments are not limited thereto:

Formula 201A

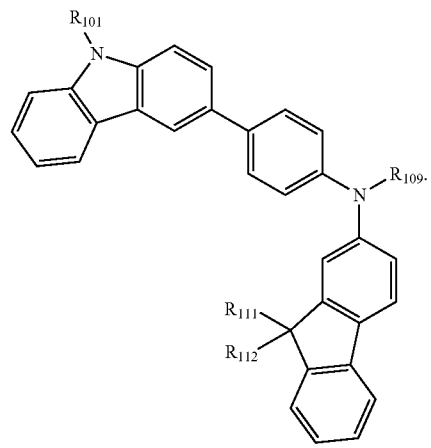

In Formula 201A, $R_{101}$, $R_{111}$, $R_{112}$, and $R_{109}$ may be understood by referring to the descriptions thereof provided herein.

For example, the compound represented by Formula 201 and the compound represented by Formula 202 may each independently include Compounds HT1 to HT20, but embodiments are not limited thereto:

HT1

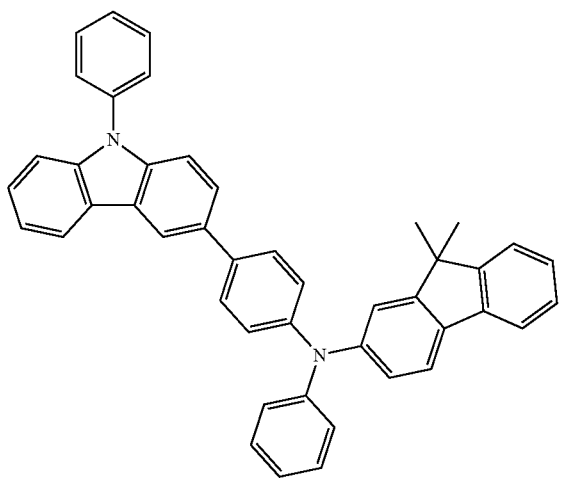

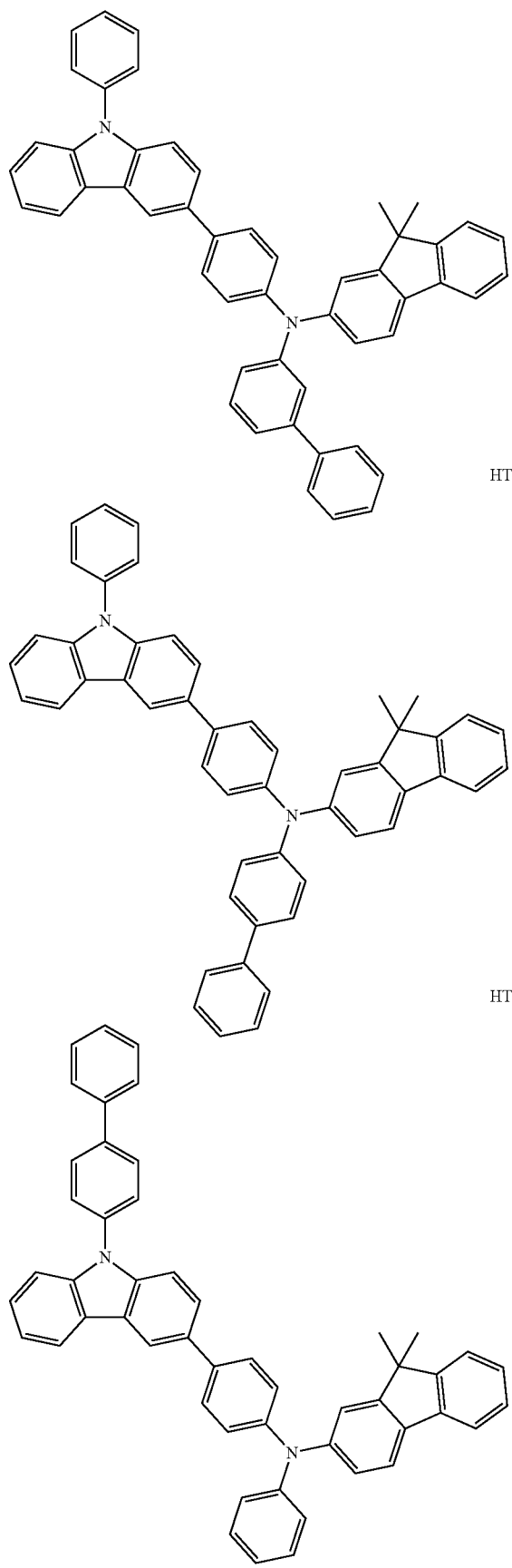
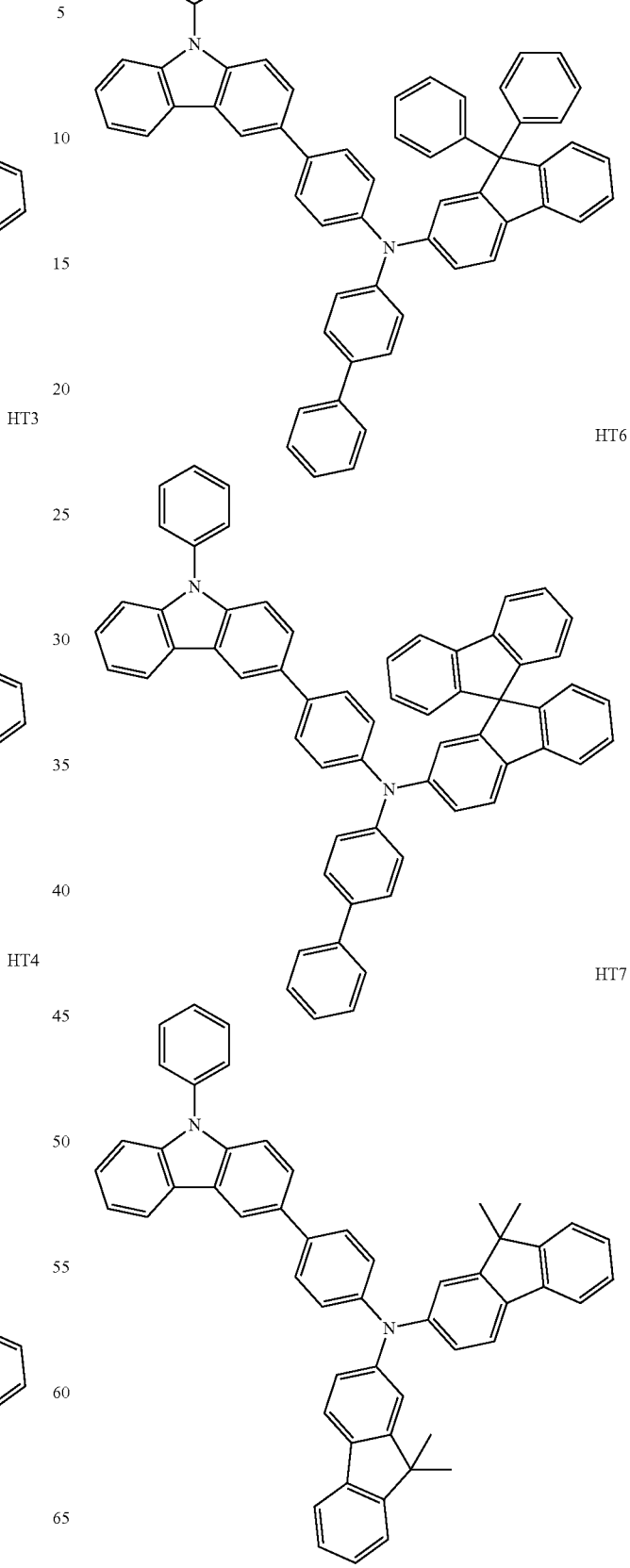

HT8
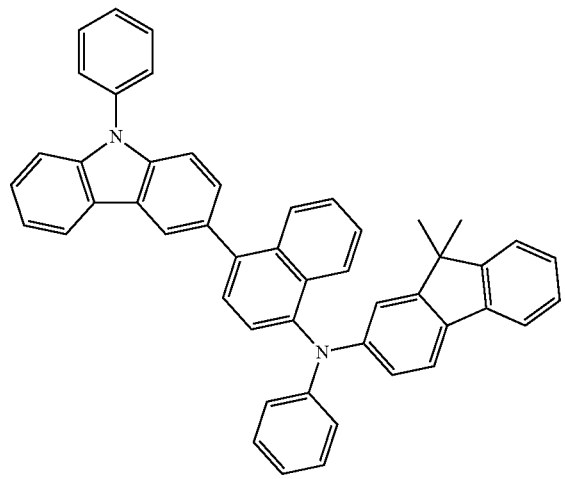
HT9
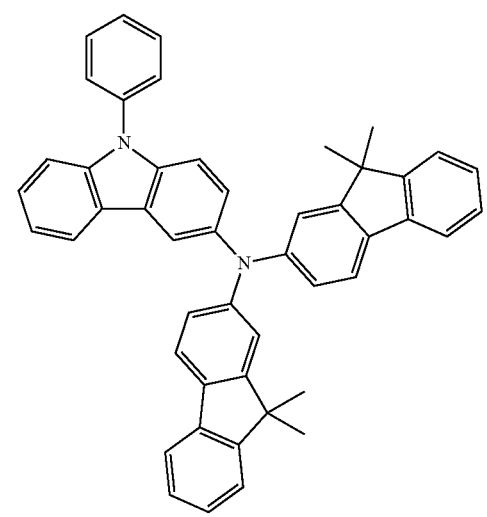
HT10
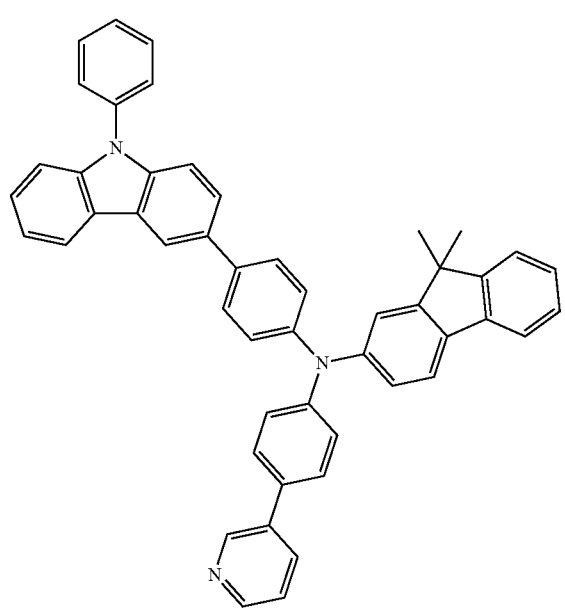
HT11
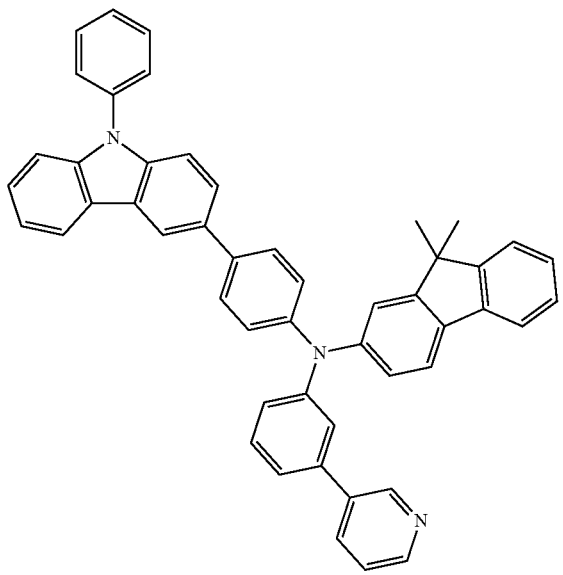
HT12
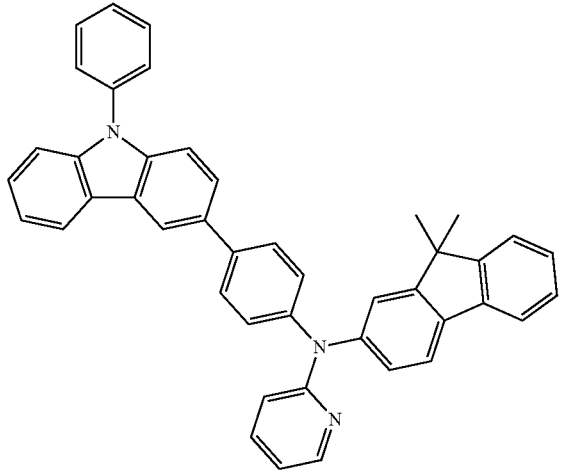
HT13
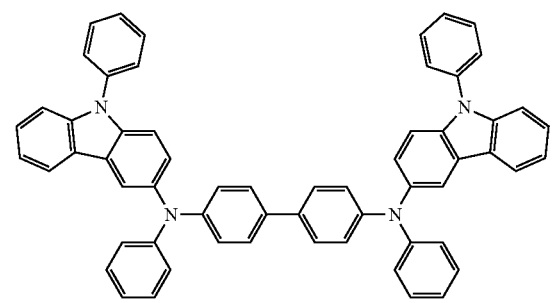

HT14 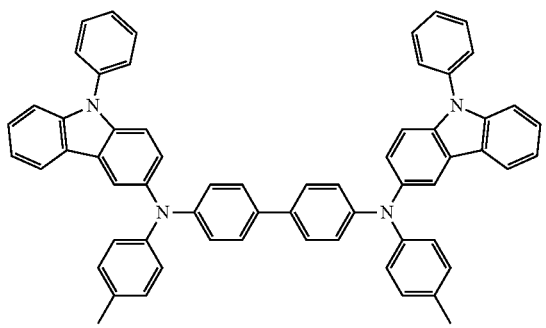

HT15 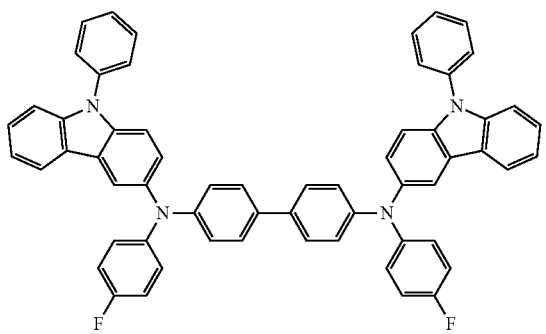

HT16 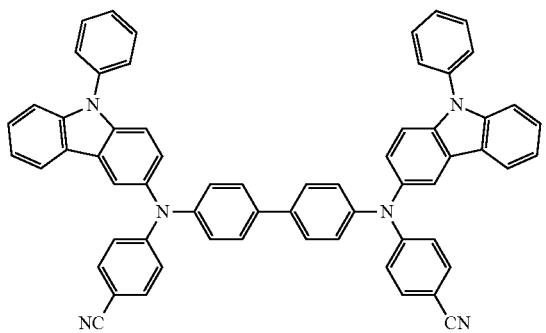

HT17 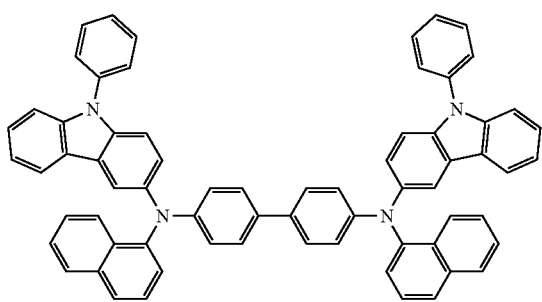

HT18 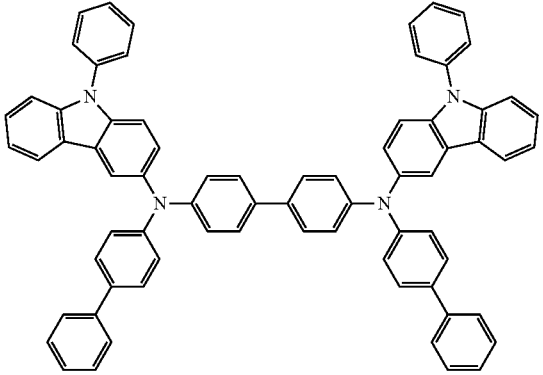

HT19

HT20 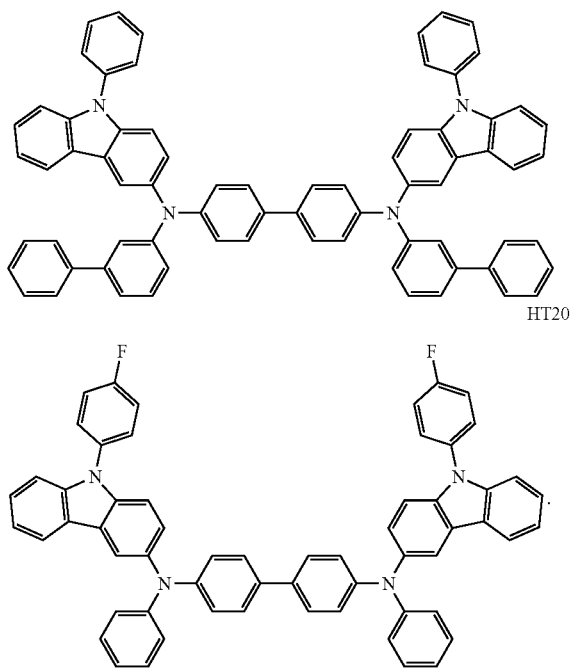

A thickness of the hole transport region may be in a range of about 100 Angstroms (Å), for example, about 100 Å to about 1,000 Å. When the hole transport region includes at least one of a hole injection layer and a hole transport layer, the thickness of the hole injection layer may be in a range of about 100 Å to about 10,000 Å, for example, about 100 Å to about 1,000 Å, and the thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to materials described above, a charge-generating material for the improvement of conductive properties. The charge-generating material may be homogeneously or non-homogeneously dispersed in the hole transport region.

The charge-generating material may be, for example, a p-dopant. The p-dopant may be one selected from a quinone derivative, a metal oxide, and a cyano group-containing compound, but embodiments are not limited thereto. Non-limiting examples of the p-dopant include quinone derivatives, such as tetracyanoquinonedimethane (TCNQ) and 2,3,5,6-tetrafluoro-tetracyano-1,4-benzoquinonedimethane (F4-TCNQ); metal oxides, such as tungsten oxide and molybdenum oxide; and cyano group-containing compounds, such as Compounds HT-D1 and HP-1, but embodiments are not limited thereto:

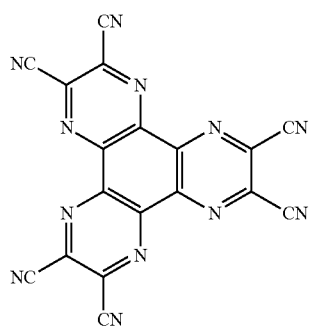

Compound HT-D1

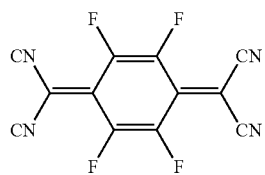

F4-TCNQ

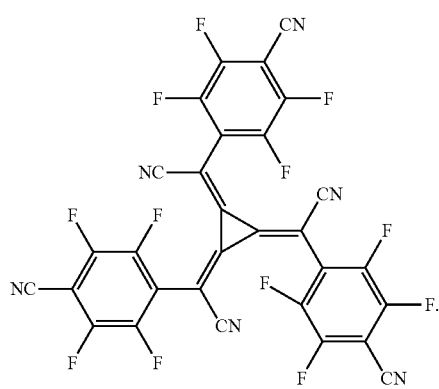

HP-1

The hole transport region may further include a buffer layer.

The buffer layer may compensate for an optical resonance distance according to a wavelength of light emitted from the emission layer, and thus a light-emission efficiency of the formed organic light-emitting device may be improved.

The hole transport region may further include an electron blocking layer. The electron blocking layer may include a material known in the art, for example, mCP, but embodiments are not limited thereto:

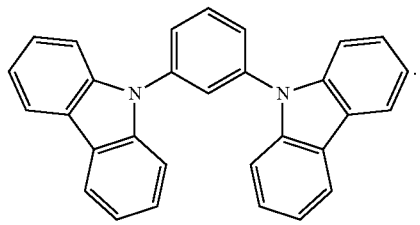

mCP

The emission layer may be formed in the hole transport region by using one or more suitable methods, such as vacuum deposition, spin coating, casting, or LB deposition. When the emission layer is formed by vacuum deposition and spin coating, the deposition and coating conditions may vary depending on a compound that is used to form the emission layer, but generally, may be determined by referring to the deposition and coating conditions for the hole injection layer.

When the organic light-emitting device 10 is a full-color organic light-emitting device, the emission layer may be patterned into a red emission layer, a green emission layer, and a blue emission layer. In various embodiments, the emission layer may have a structure in which a red emission layer, a green emission layer, and/or a blue emission layer are stacked on each other, to thereby emit white light.

The emission layer may include the dopant. When the dopant includes the compound represented by Formula 1, a blue fluorescence emission organic light-emitting device having low driving voltage, high efficiency, long lifespan characteristics, and excellent color purity at the same time and emitting blue light may be implemented.

An amount of the thermal activated delayed fluorescent dopant in the emission layer may be generally in a range of about 0.01 to about 50 parts by weight based on 100 parts by weight of the host, but embodiments are not limited thereto.

A thickness of the emission layer may be in a range of about 100 Å to about 1,000 Å, for example, about 200 Å to about 600 Å. While not wishing to be bound by theory, it is understood that when the thickness of the emission layer is within these ranges, excellent light-emitting characteristics may be exhibited without a substantial increase in driving voltage.

Next, the electron transport region is disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure electron transport layer/electron injection layer, but embodiments are not limited thereto.

The electron transport layer may have a single-layered structure, or a multi-layered structure including two or more materials.

Conditions for forming a hole blocking layer, an electron transport layer, and an electron injection layer in the electron transport region may be understood by referring to conditions for forming the hole injection layer.

When the electron transport region includes a hole blocking layer, the hole blocking layer may include, for example, at least one of BCP and Bphen, but embodiments are not limited thereto:

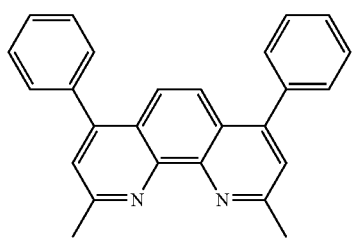

BCP

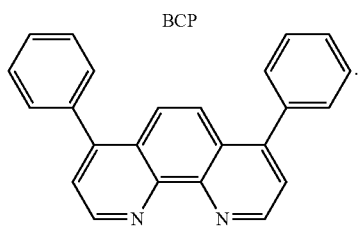

Bphen

In various embodiments, the hole blocking layer may include a compound selected from the materials provided above as the host. For example, the hole blocking layer may include Compound H24, but embodiments are not limited thereto.

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, satisfactory hole blocking characteristics may be obtained without a substantial increase in driving voltage.

The electron transport layer may further include at least one selected from BCP, Bphen, Alq$_3$, BAlq, TAZ, and NTAZ:

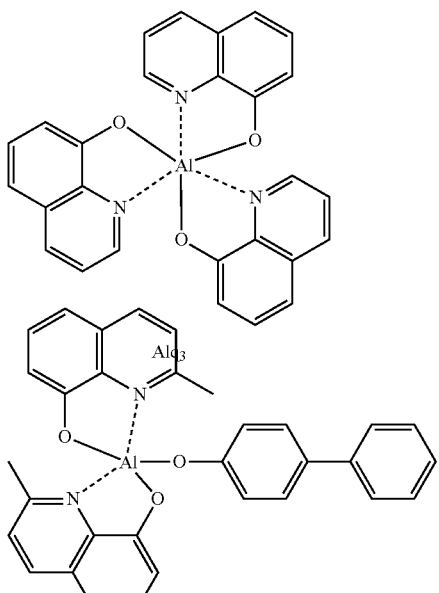

BAlq

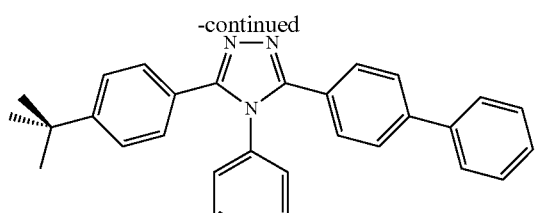

TAZ

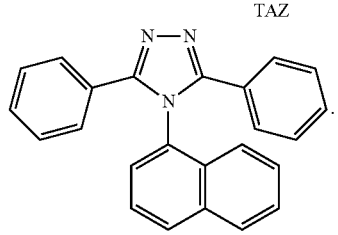

NTAZ

In various embodiments, the electron transport layer may include at least one selected from Compounds ET1, ET2, and ET3, but embodiments are not limited thereto:

ET1

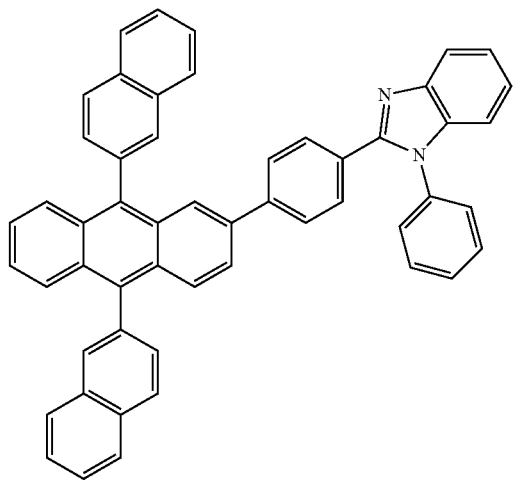

ET2

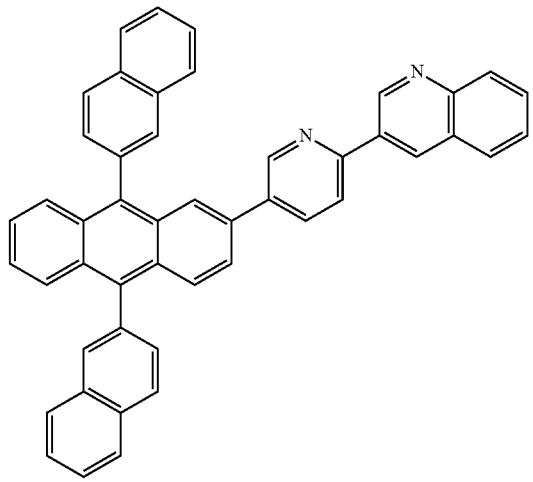

ET3

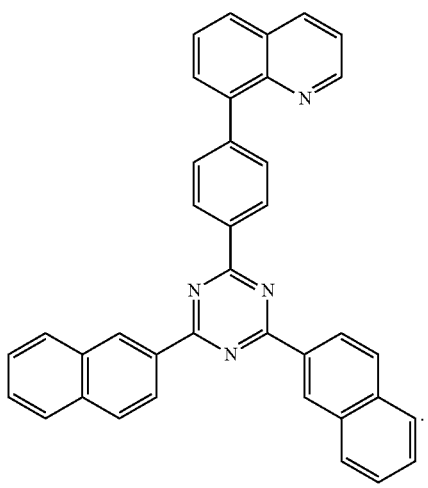

A thickness of the electron transport layer may be in a range of about 100 Å to about 1,000 Å, for example, about 150 Å to about 500 Å. When the thickness of the electron transport layer is within these ranges, satisfactory electron transport characteristics may be obtained without a substantial increase in driving voltage.

The electron transport layer may further include, in addition to the materials described above, a metal-containing material.

The metal-containing material may include a lithium (Li) complex. The Li complex may include, for example, Compound ET-D1 (lithium quinolate (LiQ)) or Compound ET-D2:

ET-D1

ET-D2

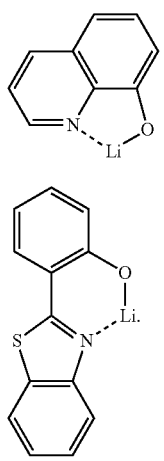

In addition, the electron transport region may include an electron injection layer that facilitates electron injection from the second electrode 19.

The electron injection layer may include at least one selected from LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within these ranges, satisfactory electron injection characteristics may be obtained without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, Li, Mg, Al, Al—Li, Ca, Mg—In, or Mg—Ag may be used as a material for forming the second electrode 19. In various embodiments, to manufacture a top emission-type light-emitting device, a transmissive electrode formed using ITO or IZO may be used as the second electrode 19.

Hereinbefore, the organic light-emitting device 10 has been described with reference to the FIGURE, but is not limited thereto.

A "$C_1$-$C_{60}$ alkyl group," as used herein, refers to a linear or branched aliphatic saturated hydrocarbon monovalent group having 1 to 60 carbon atoms. Examples thereof include a methyl group, an ethyl group, a propyl group, an isobutyl group, a sec-butyl group, a tert-butyl group, a pentyl group, an iso-amyl group, and a hexyl group. A "$C_1$-$C_{60}$ alkylene group," as used herein, refers to a divalent group having substantially the same structure as the $C_1$-$C_{60}$ alkyl group.

A "$C_1$-$C_{60}$ alkoxy group," as used herein, refers to a monovalent group represented by —$OA_{101}$ (where $A_{101}$ is the $C_1$-$C_{60}$ alkyl group). Examples thereof include a methoxy group, an ethoxy group, and an isopropyloxy group.

A "$C_2$-$C_{60}$ alkenyl group," as used herein, refers to a hydrocarbon group having at least one carbon-carbon double bond at one or more positions along the hydrocarbon chain (e.g., in the middle or at either terminal end of the $C_2$-$C_{60}$ alkyl group). Examples thereof include an ethenyl group, a propenyl group, and a butenyl group. A "$C_2$-$C_{60}$ alkenylene group," as used herein, refers to a divalent group having substantially the same structure as the $C_2$-$C_{60}$ alkenyl group.

A "$C_2$-$C_{60}$ alkynyl group," as used herein, refers to a hydrocarbon group having at least one carbon-carbon triple bond at one or more positions along the hydrocarbon chain (e.g., in the middle or at either terminal end of the $C_2$-$C_{60}$ alkyl group). Examples thereof include an ethynyl group and a propynyl group. A "$C_2$-$C_{60}$ alkynylene group," as used herein, refers to a divalent group having substantially the same structure as the $C_2$-$C_{60}$ alkynyl group.

A "$C_3$-$C_{10}$ cycloalkyl group," as used herein, refers to a monovalent saturated hydrocarbon monocyclic saturated group having 3 to 10 carbon atoms. Examples thereof include a cyclopropyl group, a cyclobutyl group, a cyclopentyl group, a cyclohexyl group, and a cycloheptyl group. A "$C_3$-$C_{10}$ cycloalkylene group," as used herein, refers to a divalent group having substantially the same structure as the $C_3$-$C_{10}$ cycloalkyl group.

A "$C_1$-$C_{10}$ heterocycloalkyl group," as used herein, refers to a monovalent saturated monocyclic group having at least one heteroatom selected from N, O, P, and S as a ring-forming atom in addition to 1 to 10 carbon atoms. Examples thereof include a tetrahydrofuranyl group and a tetrahydrothiophenyl group. A "$C_1$-$C_{10}$ heterocycloalkylene group," as used herein, refers to a divalent group having substantially the same structure as the $C_1$-$C_{10}$ heterocycloalkyl group.

A "$C_3$-$C_{10}$ cycloalkenyl group," as used herein, refers to a monovalent saturated monocyclic group that has 3 to 10 carbon atoms and at least one carbon-carbon double bond in the ring thereof, and which is not aromatic. Examples thereof include a cyclopentenyl group, a cyclohexenyl group, and a cycloheptenyl group. A "$C_3$-$C_{10}$ cycloalkenylene group," as used herein, refers to a divalent group having substantially the same structure as the $C_3$-$C_{10}$ cycloalkenyl group.

A "$C_1$-$C_{10}$ heterocycloalkenyl group," as used herein refers to a monovalent monocyclic group that has at least one heteroatom selected from N, O, P, and S as a ring-forming atom in addition to 1 to 10 carbon atoms, and at least one carbon-carbon double bond in the ring. Examples of the $C_1$-$C_{10}$ heterocycloalkenyl group include a 2,3-dihydrofuranyl group and a 2,3-dihydrothiophenyl group. A "$C_1$-$C_{10}$ heterocycloalkenylene group," as used herein, refers to a divalent group having substantially the same structure as the $C_1$-$C_{10}$ heterocycloalkenyl group.

A "$C_6$-$C_{60}$ aryl group," as used herein, refers to a monovalent group having a cyclic aromatic system having 6 to 60 carbon atoms, and a "$C_6$-$C_{60}$ arylene group," as used herein, refers to a divalent group having an aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other or may be linked with each other via a single bond.

A "$C_1$-$C_{60}$ heteroaryl group," as used herein, refers to a monovalent group having a heterocyclic aromatic system that has at least one heteroatom selected from N, O, P, and S as a ring-forming atom in addition to 1 to 60 carbon atoms. A "$C_1$-$C_{60}$ heteroarylene group," as used herein, refers to a divalent group having a heterocyclic aromatic system that has at least one heteroatom selected from N, O, P, and S as a ring-forming atom in addition to 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other or may be linked with each other via a single bond.

A "$C_6$-$C_{60}$ aryloxy group," as used herein, refers to a group represented by —$OA_{102}$ (wherein $A_{102}$ is the $C_6$-$C_{60}$ aryl group), a "$C_6$-$C_{60}$ arylthio group," as used herein, refers to a group represented by —$SA_{103}$ (wherein $A_{103}$ is the $C_6$-$C_{60}$ aryl group), and a "$C_7$-$C_{60}$ arylalkyl group," as used herein, refers to a group represented by -$A_{104}A_{105}$ (wherein $A_{105}$ is a $C_6$-$C_{59}$ aryl group and $A_{104}$ is a $C_1$-$C_{54}$ alkylene group).

The term "$C_1$-$C_{60}$ heteroaryloxy group" as used herein indicates —$OA_{106}$ (wherein $A_{106}$ is a $C_1$-$C_{60}$ heteroaryl group), the term "$C_1$-$C_{60}$ heteroarylthio group" as used herein indicates —$SA_{107}$ (wherein $A_{107}$ is a $C_1$-$C_{60}$ heteroaryl group), and the term "$C_2$-$C_{60}$ heteroarylalkyl group" as used herein indicates -$A_{108}A_{109}$ (wherein $A_{109}$ is a $C_1$-$C_{59}$ heteroaryl group and $A_{108}$ is a $C_1$-$C_{59}$ alkylene group).

A "monovalent non-aromatic condensed polycyclic group," as used herein refers to a monovalent group that has two or more rings condensed to each other, has only carbon atoms as ring-forming atoms (for example, 8 to 60 carbon atoms), and which is non-aromatic in the entire molecular structure. An example of the monovalent non-aromatic condensed polycyclic group includes a fluorenyl group. A "divalent non-aromatic condensed polycyclic group," as used herein, refers to a divalent group having substantially the same structure as the monovalent non-aromatic condensed polycyclic group.

A "monovalent non-aromatic condensed heteropolycyclic group," as used herein, refers to a monovalent group that has two or more rings condensed to each other, has at least one heteroatom selected from N, O, Si, P, and S as a ring-forming atom in addition to carbon atoms (for example, 1 to 60 carbon atoms), and which is non-aromatic in the entire molecular structure. An example of the monovalent non-aromatic condensed heteropolycyclic group includes a carbazolyl group. A "divalent non-aromatic condensed heteropolycyclic group," as used herein, refers to a divalent group having substantially the same structure as the monovalent non-aromatic condensed heteropolycyclic group.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ may each independently be selected from hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, and a substituted or unsubstituted monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

The term "room temperature," as used herein, refers to a temperature of about 25° C.

Hereinafter, a compound according to embodiments and an organic light-emitting device according to embodiments will be described in detail with reference to Synthesis Examples and Examples below, but the present inventive concept is not limited thereto. The expression "'B' was used instead of 'A'" used in describing Synthesis Examples means that the number of molar equivalents of 'B' used was identical to the number of molar equivalents of 'A'.

EXAMPLES

Synthesis Example 1: Synthesis of Compound 1

Synthesis of Intermediate 1

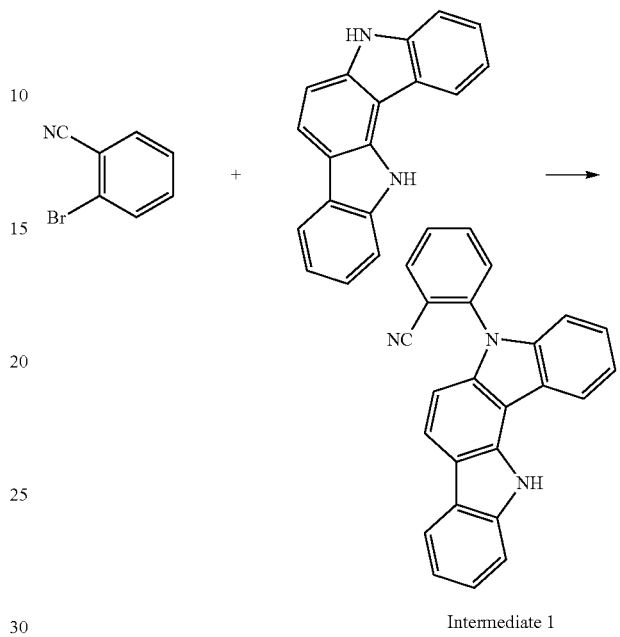

Intermediate 1

10 grams (g) (56.23 millimoles, mmol) of 1-bromobenzonitrile, 12 g (46.86 mmol) of 5,12-dihydroindolocarbazole, 0.45 g (2.34 mmol) of iodine oxide, 1.07 g (9.37 mmol) of trans-1,2-diaminocyclohexane, and 19.9 g (93.71 mmol) of potassium phosphate were dissolved in 300 milliliters (ml) of 1,4-dioxane, and the resulting solution was allowed to react for 12 hours at a temperature of about 110° C. After completing the reaction and quenching the reaction solution by adding 500 ml of toluene thereto, the resulting reaction solution was filtered with celite to remove a solvent therefrom. Then, the filtered crude product was purified by column chromatography with a mixture of dichloromethane and hexane as an eluent, thereby obtaining 11.8 g (yield: 71%) of 3-indolo[3,2-a]carbazole-5(12H)-yl)benzonitrile (i.e., Intermediate 1). The structure of the synthesized compound was identified using MALDI-TOF mass spectrum (MS).

MALDI-TOF (calculated: 357.1 g/mol, measured: [M+H]$^+$=358 g/mol)

Synthesis of Compound 1

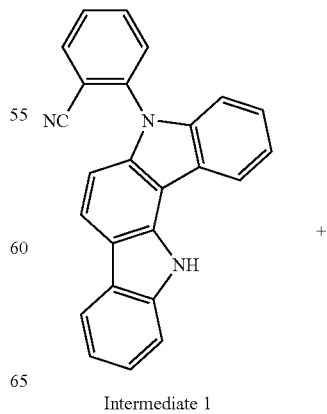

+

Intermediate 1

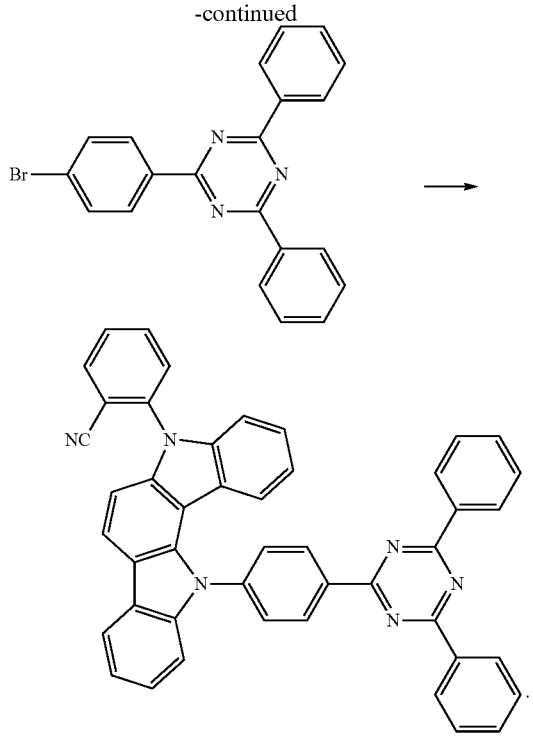

Compound 1

10 g (28 mmol) of 3-indolo[3,2-a]carbazole-5(12H)-yl) benzonitrile (i.e., Intermediate 1), 16.26 g (42 mmol) of 2-(4-bromophenyl)-4,6-diphenyl-1,3,5-a triazine, and 5.38 g (56 mmol) of sodium tert-butoxide were dissolved in 140 ml of toluene. The reaction temperature was raised to 140° C., and 10 mole percent (mol %) of a palladium catalyst and 20 mol % of tri-tert-butylphosphine were added to the mixed solution. The resulting mixed solution was allowed to react. After completing the reaction and quenching the reaction solution by adding 300 ml of methanol thereto, the resulting reaction was filtered, and the filtered crude product was dried. The dried product was purified by column chromatography using a mixture of dichloromethane and hexane as an eluent, thereby obtaining 9.3 g (yield: 50%) of Compound 1. The structure of the synthesized compound was identified using MALDI-TOF mass spectrometry (MS).

MALDI-TOF (calculated: 664.2 g/mol, measured: $[M+H]^+$=665 g/mol)

Synthesis Example 2: Synthesis of Compound 2

Synthesis of Intermediate 2

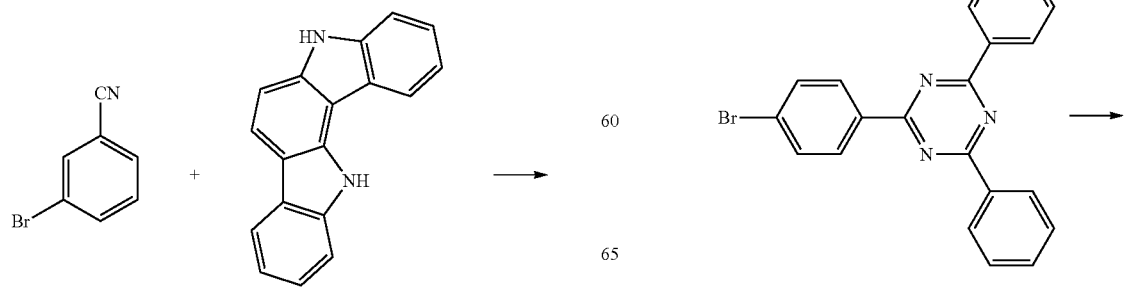

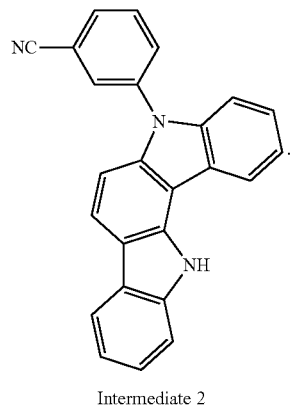

Intermediate 2

Intermediate 2 was synthesized in the same manner as Intermediate 1 of Synthesis Example 1, except that 2-bromo-benzonitrile was used instead of 1-bromo-benzonitrile. The structure of the synthesized compound was identified using a MALDI-TOF mass spectrometer.

MALDI-TOF (calculated: 357.1 g/mol, measured: $[M+H]^{30}$ =358 g/mol)

Synthesis of Compound 2

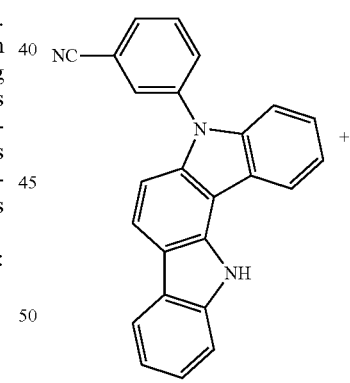

Intermediate 2

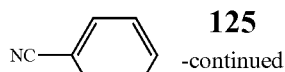

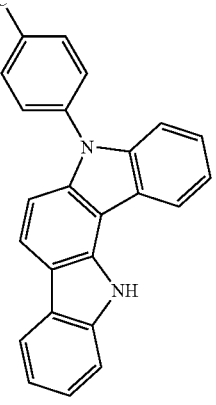

Compound 2

Compound 2 was synthesized in the same manner as Compound 1 of Synthesis Example 1, except that Intermediate 2 was used instead of Intermediate 1. The structure of the synthesized compound was identified using a MALDI-TOF mass spectrometer.

MALDI-TOF (calculated: 664.2 g/mol, measured: $[M+H]^+$=665 g/mol)

Synthesis Example 3: Synthesis of Compound 3

Synthesis of Intermediate 3

Intermediate 3

Intermediate 3 was synthesized in the same manner as Intermediate 1 of Synthesis Example 1, except that 3-bromo-benzonitrile was used instead of 1-bromo-benzonitrile. The structure of the synthesized compound was identified using a MALDI-TOF mass spectrometer.

MALDI-TOF (calculated: 357.1 g/mol, measured: $[M+H]^+$=358 g/mol)

Synthesis of Compound 3

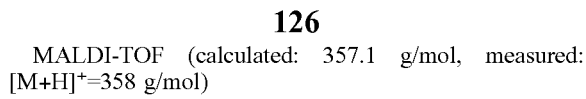

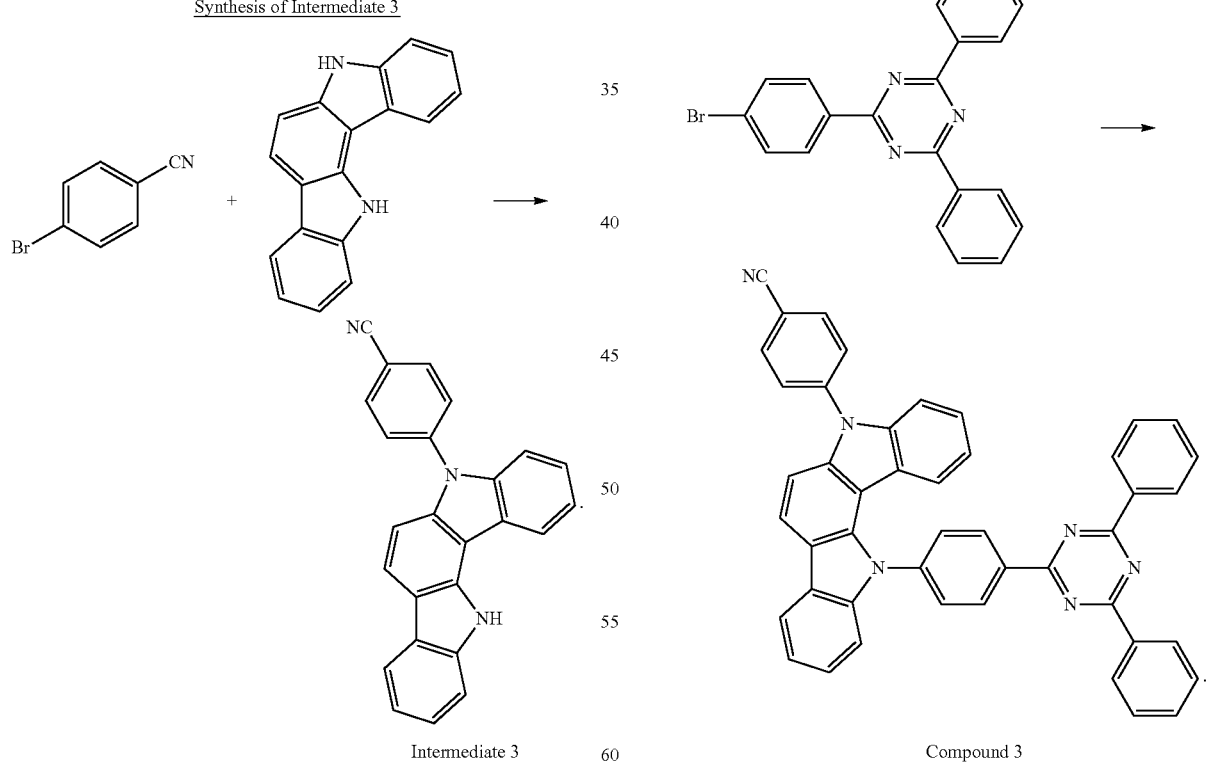

Intermediate 3

Compound 3

Compound 3 was synthesized in the same manner as Compound 1 of Synthesis Example 1, except that Intermediate 3 was used instead of Intermediate 1.

The structure of the synthesized compound was identified using a MALDI-TOF mass spectrometer.

MALDI-TOF (calculated: 664.2 g/mol, measured: [M+H]⁺=665 g/mol)

Synthesis Example 4: Synthesis of Compound 33

Synthesis of Intermediate 4

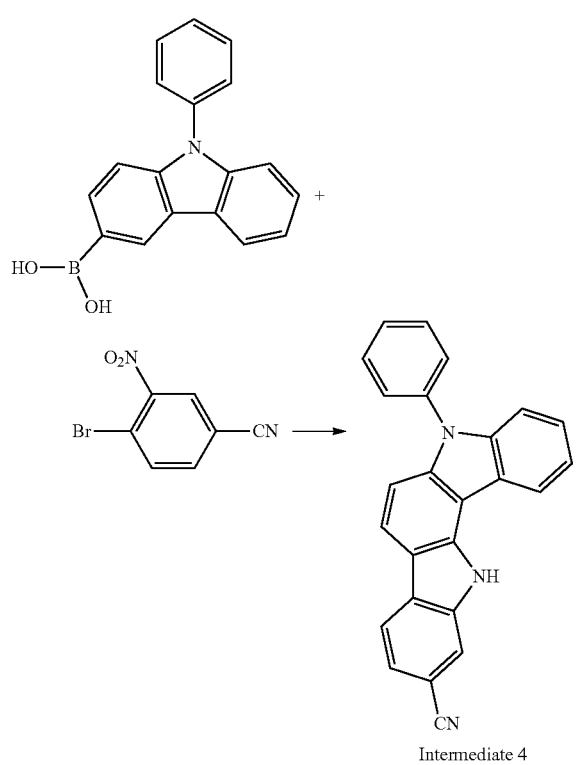

Intermediate 4

15.18 g (52.85 mmol) of 9-phenyl-9H-carbazole-3-yl-boronic acid, 10 g (44.04 mmol) of 4-bromo-3-nitrobenzonitrile, and 0.05 percent by weight (wt %) of a palladium catalyst were dissolved in 25 ml of toluene, 25 ml of 2 molar (M) potassium carbonate was added thereto, and the resulting reaction solution was stirred for 24 hours. After completing the reaction, the resulting reaction solution was extracted using chloroform to remove a solvent therefrom. Then, the resulting solid product was dried. 3 equivalents of triphenylphosphine were added thereto, and the mixture was stirred in dichlorobenzene for 12 hours at a temperature of 160° C. After completing the reaction, 100 ml of methanol was slowly added to the mixture, to thereby filter the resulting reaction solution. The filtered crude product obtained therefrom was dried and purified by column chromatography with a mixture of dichloromethane and hexane as an eluent, thereby obtaining 4.87 g (yield: 31%) of Intermediate 4. The structure of the synthesized compound was identified using a MALDI-TOF mass spectrometer.

MALDI-TOF (calculated: 357.1 g/mol, measured: [M+H]⁺=358 g/mol)

Synthesis of Compound 33

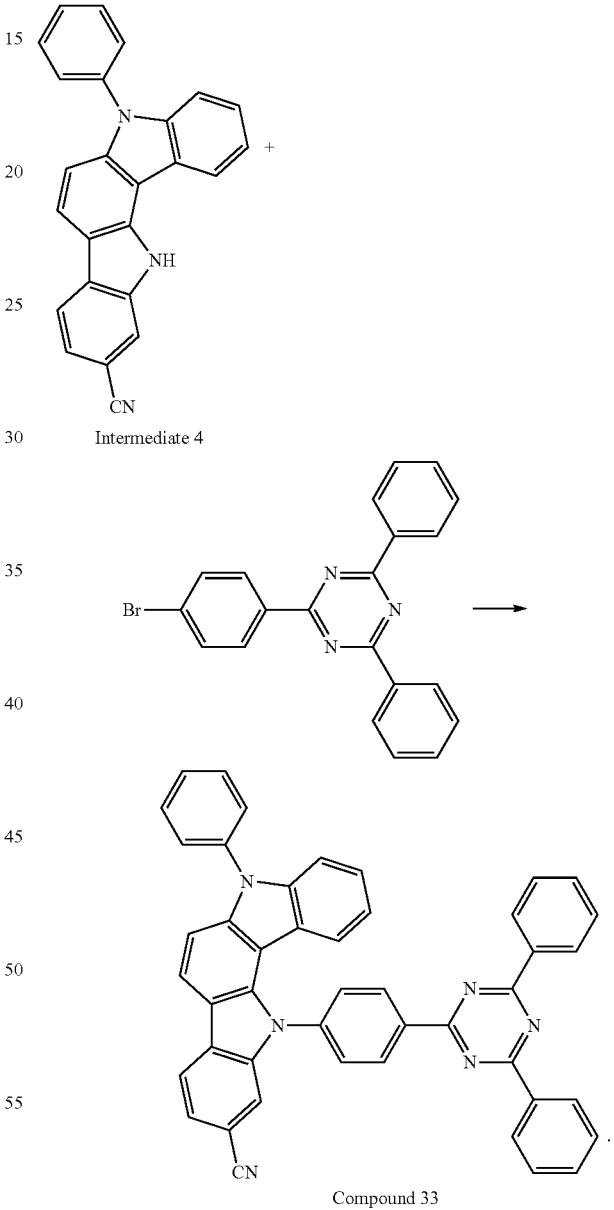

Intermediate 4

Compound 33

Compound 33 was synthesized in the same manner as Compound 1 of Synthesis Example 1, except that Intermediate 4 was used instead of Intermediate 1. The structure of the synthesized compound was identified using a MALDI-TOF mass spectrometer.

MALDI-TOF (calculated: 664.2 g/mol, measured: [M+H]$^+$=665 g/mol)

Synthesis Example 5: Synthesis of Compound 17

Synthesis of Intermediate 5-1

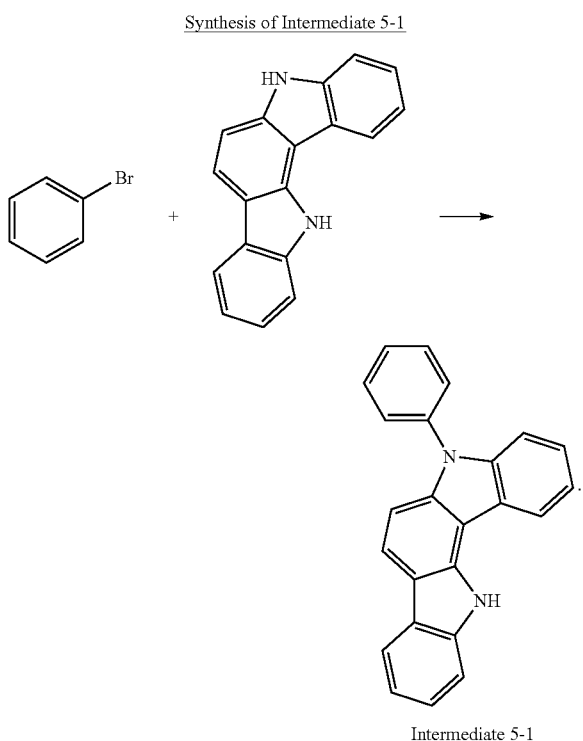

Intermediate 5-1

Intermediate 5-1 was synthesized in the same manner as Intermediate 1 of Synthesis Example 1, except that bromobenzene was used instead of 1-bromo-benzonitrile. The structure of the synthesized compound was identified using a MALDI-TOF mass spectrometer.

MALDI-TOF (calculated: 332.1 g/mol, measured: [M+H]$^+$=333 g/mol)

Synthesis of Intermediate 5-2

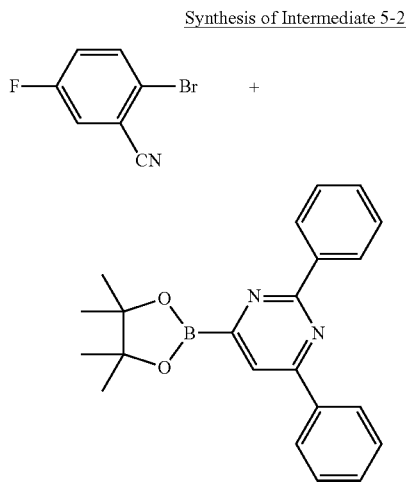

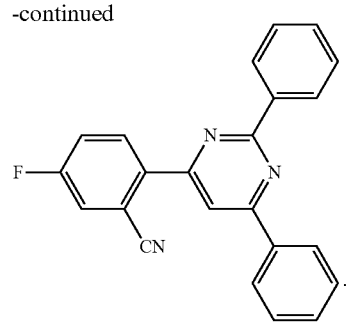

Intermediate 5-2

10 g (50.27 mmol) of 2-bromo-5-fluorobenzonitrile, 19.8 g (55.29 mmol) of 2,4-diphenyl-6-(4,4,5,5-tetramethyl-1,3,2-dioxaboro-2-yl)pyridine, 5 mol % of a palladium catalyst, and 20.84 g (150.8 mmol) of potassium carbonate were added to 100 ml of a solution in which tetrahydrofuran and water were mixed at a ratio of 1:1. The resulting solution was then allowed to react for 6 hours at a temperature of about 80° C. After completing the reaction, 200 ml of methanol was slowly added thereto, to thereby filter the resulting reaction solution. The filtered crude product obtained therefrom was dried and purified by column chromatography using a mixture of dichloromethane and hexane as an eluent, thereby obtaining 16.3 g (yield: 92%) of Intermediate 5-2. The structure of the synthesized compound was identified using a MALDI-TOF mass spectrometer.

MALDI-TOF (calculated: 351.1 g/mol, measured: [M+H]$^+$=352 g/mol)

Synthesis of Compound 17

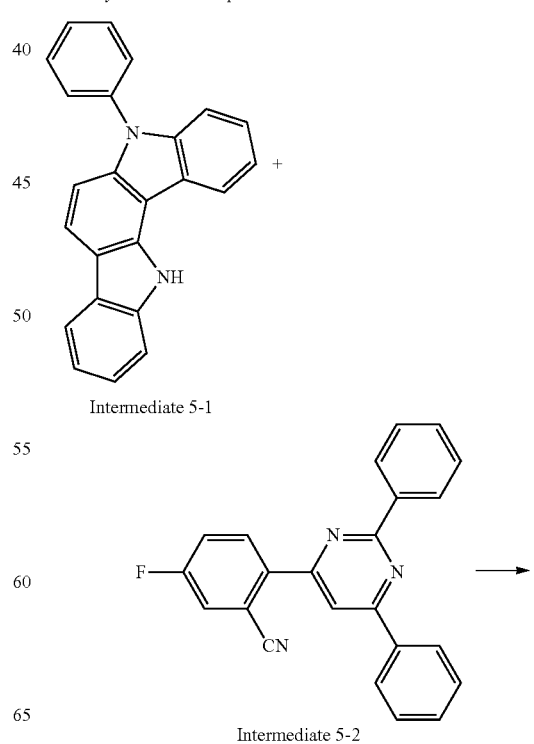

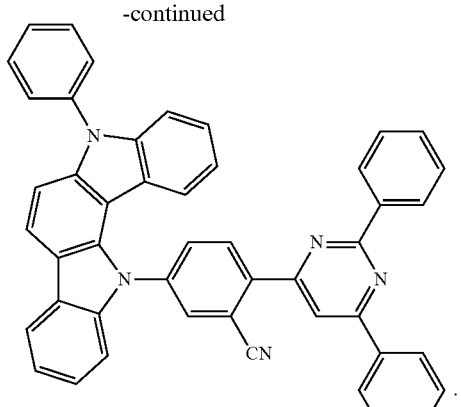

Compound 17

0.88 g (36.13 mmol) of 60% sodium hydride was washed with hexane three times and dried in a vacuum oven for 2 hours. The dried resulting product was added to 30 ml of tetrahydrofuran, and the mixed solution was stirred for 30 minutes in a nitrogen atmosphere. 12 g (36.13 mmol) of 5-phenyl-5,12-dihydroindolocarbazole was added to the reaction solution, and the reaction solution was allowed to react for 10 minutes at a temperature of about 0° C. Then, 13.96 g (39.74 mmol) of 2-(2,6-diphenylpyrimidine-4-yl)5-fluorobenzonitrile was slowly added to the reaction solution. After the reaction was allowed for 1 hour at room temperature, the reaction temperature was raised to 80° C., and the reaction was continued for 10 hours. After completing the reaction, an extraction process was performed on the resulting reaction solution using dichloromethane to remove a solvent therefrom, and the resulting product was purified by column chromatography using a mixture of dichloromethane and hexane as an eluent, thereby obtaining 8.8 g (yield: 69%) of Compound 5. The structure of the synthesized compound was identified using a MALDI-TOF mass spectrometer.

MALDI-TOF (calculated: 663.2 g/mol, measured: $[M+H]^+$=664 g/mol)

Evaluation Example 1: Evaluation of Thermal Characteristics of Synthesized Compounds Compounds 1, 2, 3, 17, and 33 were subjected to the thermogravimetric analysis (TGA) and the differential scanning calorimetry (DSC) to perform thermal analysis thereon (under conditions including $N_2$ atmosphere, temperature ranges from room temperature to 800° C. (10° C./min) for the TGA and from room temperature to 400° C. for the DSC, and Pan Type of Pt Pan in disposable Al Pan (for the TGA) and disposable Al pan (for the DSC)), and the results are shown in Table 1.

TABLE 1

| Compound No. | Tg (° C.) | Td (° C.) |
|---|---|---|
| Compound 1 | Non-measurable | 392.8 |
| Compound 2 | 161 | 328.7 |
| Compound 3 | 170.2 | 344 |
| Compound 17 | 151.6 | 390 |
| Compound 33 | 177 | 388 |

According to Table 1, it was confirmed that Compounds 1, 2, 3, 17, and 33 had excellent thermal stability.

Evaluation Example 2: Full Width at Half Maximum (FWHM) of Synthesized Compounds Compound 1 was diluted in toluene at a concentration of $10^{-5}$ M, and then, an in-solution photoluminescence (PL) spectrum of Compound 1 was measured using an ISC PC1 spectrofluorometer equipped with a xenon lamp. PL spectra of Compounds 2, 3, 17, and 33 were measured repeatedly in the same manner as in Compound 1, so that FWHM of each of Compound 2, 3, 17, and 33 was calculated based on the measured PL spectra thereof. The results are shown in Table 2.

TABLE 2

| Compound No. | FWHM (nm) |
|---|---|
| Compound 1 | 78 |
| Compound 2 | 79 |
| Compound 3 | 77 |
| Compound 17 | 87 |
| Compound 33 | 71 |

Referring to Table 2, it was confirmed that, depending on a position of a substituent, i.e., a cyano group, Compounds 1, 2, 3, and 17 showed changes in FWHM thereof. In addition, it was confirmed that Compound 33 showed the smallest FWHM.

Example 1: Preparation of Organic Light-Emitting Device Including Condensed Cyclic Compound Represented by Formula 1 as Thermal Activated Delayed Fluorescence Dopant A glass substrate on which an ITO electrode (i.e., a first electrode or an anode) having a thickness of 1,500 Angstroms (Å) was formed was ultrasonically cleaned using distilled water. After completing the washing of the glass substrate using distilled water, the glass substrate was ultrasonically washed again using a solvent, such as isopropyl alcohol, acetone, or methanol, and then, dried. The glass substrate was transported to a plasma washing machine, washed using oxygen plasma for 5 minutes, and then, transported to a vacuum evaporator.

Compounds HT3 and HP-1 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 150 Å, thereby forming a hole transport region.

Compound H23 (as a host) and Compound 2 (as a thermal activated delayed fluorescent dopant) were co-deposited on the hole transport region at a ratio of 85:15 to form an emission layer having a thickness of 300 Å.

Compound H24 was vacuum-deposited on the emission layer to form a hole blocking layer having a thickness of 100 Å, Compound ET3 and Liq were vacuum-deposited together on the hole blocking layer to form an electron transport layer having a thickness of 250 Å, and Liq was deposited on the electron transport layer to form an electron injection layer having a thickness of 5 Å. Then, Al was deposited on the electron injection layer to form an Al second electrode (i.e., a cathode) having a thickness of 1,000 Å, thereby completing the manufacture of an organic light-emitting device.

Examples 2 to 5 and Comparative Examples 1 and 2

Organic light-emitting devices of Examples 2 to 5 and Comparative Examples 1 and 2 were each manufactured in substantially the same manner as in Example 1-1, except that compositions of the emission layer are changed as shown in Table 3.

TABLE 3

|  | Host | Thermal activated delayed fluorescent dopant |
|---|---|---|
| Example 1 | Compound H23 | Compound 2 |
| Example 2 | Compound H23 | Compound 1 |
| Example 3 | Compound H23 | Compound 3 |
| Example 4 | Compound H23 | Compound 17 |
| Example 5 | Compound H23 | Compound 33 |
| Comparative Example 1 | Compound H23 | Compound A |
| Comparative Example 2 | Compound H23 | Compound B |

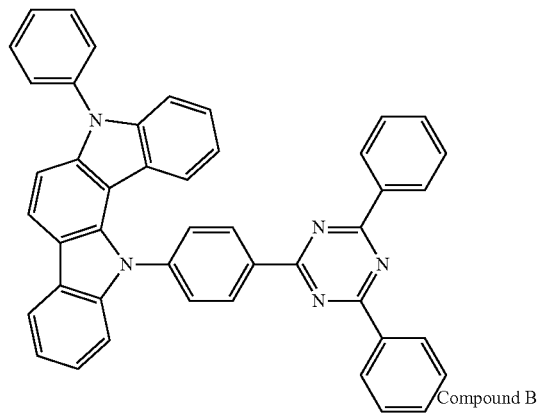

Compound A

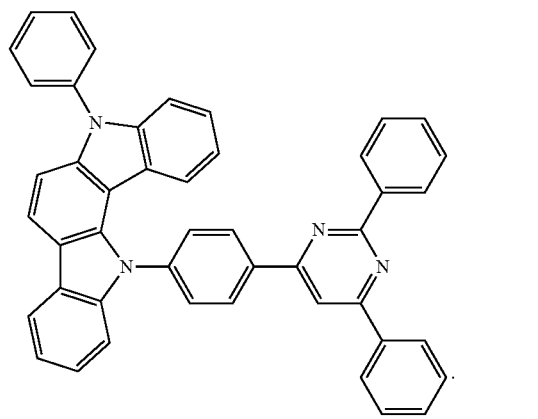

Compound B

Evaluation Example 3: Evaluation of Triplet State ($T_1$) Energy Level and Singlet State ($S_1$) Energy Level The $T_1$ energy levels and/or the $S_1$ energy levels of the thermal activated delayed fluorescent dopants utilized in the organic light-emitting devices of Examples 1 to 5 and Comparative Examples 1 and 2 are evaluated according to the descriptions shown in Table 4, and the results are shown in Table 5.

TABLE 4

| Evaluation of $S_1$ energy level | A mixture of 2-MeTHF and each compound (i.e., a mixture prepared by dissolving 1 mg of each compound in 3 cubic centimeters (cc) of 2-MeTHF) was loaded into a quartz cell. The resulting quartz cell was loaded into liquid nitrogen (77 K), and a photoluminescence spectrum thereof was measured by using a photoluminescence measuring meter. Then, $T_1$ energy levels were calculated based on peaks observed at the beginning of short wavelengths of the photoluminescence of the photoluminescence spectrum. |
|---|---|
| Evaluation of $T_1$ energy level | A mixture of 2-MeTHF and each compound (i.e., a mixture prepared by dissolving each compound in 2-MeTHF to thereby have a density of about $10^{-4}$ [M]) was loaded into a quartz cell, and a fluorescence spectrum thereof was measured by using a photoluminescence measuring device (F7000 manufactured by Hitachi). Then, $S_1$ energy levels of the mixture were calculated based on peaks observed at the beginning of short wavelengths of the fluorescence spectrum wavelength. |

TABLE 5

| Compound No. | $S_1$ energy level (eV) | $T_1$ energy level (eV) | $E_{S1} - E_{T1}$ (eV) |
|---|---|---|---|
| Compound 1 | 3.05 | 2.90 | 0.15 |
| Compound 2 | 3.05 | 2.92 | 0.13 |
| Compound 3 | 3.06 | 2.90 | 0.16 |
| Compound 17 | 2.84 | 2.92 | 0.08 |
| Compound 33 | 3.14 | 2.83 | 0.30 |
| Compound A | 2.98 | 2.89 | 0.09 |
| Compound B | 3.13 | 2.91 | 0.22 |

Referring to Table 5, it was confirmed that the organic light-emitting devices of Examples 1 to 5 all satisfied both Equations 1 and 2.

$$E_{S1(TD)} - E_{T1(TD)} \leq 0.3 \text{ electron Volts} \quad \text{Equation 1}$$

$$E_{S1(TD)} > 2.6 \text{ electron Volts.} \quad \text{Equation 2}$$

In Equations 1 and 2, $E_{S1(TD)}$ denotes a $S_1$ energy level (unit: eV) of the thermal activated delayed fluorescent dopant, and $E_{T1(TD)}$ denotes a $T_1$ energy level (unit: eV) of the thermal activated delayed fluorescent dopant.

Evaluation Example 4: Evaluation of Device Data

The driving voltage, maximum emission wavelength, CIE y, and external quantum efficiency (EQE) of the organic light-emitting devices of Examples 1 to 5 and Comparative Examples 1 and 2 were measured using a Keithley 2400 current-voltage meter and a Minolta Cs-1000A luminance meter, and the results are shown in Table 6. Here, all the data, except maximum quantum efficiency values, was measured at 500 candelas per square meter (cd/m²).

TABLE 6

| Example No. | Driving voltage (V) | Maximum emission wavelength (nm) | CIE y | EQE (%) Maximum value | Emission color |
|---|---|---|---|---|---|
| Example 1 | 5.55 | 468 | 0.3 | 19.1 | Blue |
| Example 2 | 5.79 | 468 | 0.27 | 18.2 | Blue |
| Example 3 | 5.59 | 468 | 0.293 | 18.3 | Blue |
| Example 4 | 4.02 | 516 | 0.483 | 21.3 | Blue-green |
| Example 5 | 5.96 | 460 | 0.243 | 14.1 | Blue |
| Comparative Example 1 | 8.23 | 444 | 0.184 | 10.6 | Blue |
| Comparative Example 2 | 7.45 | 480 | 0.324 | 16.7 | Blue |

Referring to Table 6, it was confirmed that the organic light-emitting devices of Examples 1 to 5 exhibited low driving voltage and excellent color purity and device efficiency (e.g., emission efficiency), compared to those of the organic light-emitting devices of Comparative Examples 1 and 2.

As described above, an organic light-emitting device according to one or more embodiments may have low driving voltage and excellent color purity and emission efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. An organic light-emitting device comprising:
   a first electrode;
   a second electrode facing the first electrode; and
   an organic layer disposed between the first electrode and the second electrode,
   wherein the organic layer comprises an emission layer,
   wherein the emission layer comprises a host and a dopant,
   wherein the dopant comprises a condensed cyclic compound represented by Formula 1, and
   wherein an amount of the dopant is smaller than that of the host:

Formula 1

Formula 1A

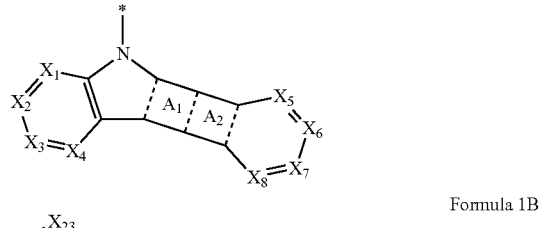

Formula 1B

Formula 2A

Formula 2B wherein, in Formula 1, $Ar_1$ is a group represented by Formula 1A, and $Ar_2$ is a group represented by Formula 1B, in Formula 1A, ring $A_1$ is a group represented by Formula 2A, and ring $A_2$ is a group represented by Formula 2B, in Formulae 1A, 1B, 2A, and 2B, $X_1$ is $C(R_1)$ or N, $X_2$ is $C(R_2)$ or N, $X_3$ is $C(R_3)$ or N, $X_4$ is $C(R_4)$ or N, $X_5$ is $C(R_5)$ or N, $X_6$ is $C(R_6)$ or N, $X_7$ is $C(R_7)$ or N, and $X_8$ is $C(R_8)$ or N, $X_{11}$ is selected from S, $N[(L_{11})_{a11}-(R_{11})_{b11}]$, $Si[(L_{11})_{a11}-(R_{11})_{b11}][(L_{12})_{a12}-(R_{12})_{b12}]$, and $Ge[(L_{11})_{a11}-(R_{11})_{b11}][(L_{12})_{a12}-(R_{12})_{b12}]$, $X_{21}$ is $C(R_{21})$ or N, $X_{22}$ is $C(R_{22})$ or N, $X_{23}$ is $C(R_{23})$ or N, $X_{24}$ is $C(R_{24})$ or N, and $X_{25}$ is $C(R_{25})$ or N, $X_{26}$ is $C(R_{26})$, N, or a binding site to $Ar_1$, $X_{27}$ is $C(R_{27})$, N, or a binding site to $Ar_1$, $X_{28}$ is $C(R_{28})$, N, or a binding site to $Ar_1$, $X_{29}$ is $C(R_{29})$, N, or a binding site to $Ar_1$, and $X_{30}$ is $C(R_{30})$, N, or a binding site to $Ar_1$, at least one selected from $X_{21}$ to $X_{30}$ is N, and at least one selected from $X_{26}$ to $X_{30}$ is a binding site to $Ar_1$, $L_{11}$ and $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 and a12 are each independently an integer selected from 0 to 3, $R_1$ to $R_{12}$ and $R_{21}$ to $R_{30}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), b11 and b12 are each independently an integer selected from 1 to 3, the number of a cyano group(s) included in the condensed cyclic compound represented by Formula 1 is 1 or greater, provided that $Ar_1$ comprises at least one cyano group,

* indicates a binding site to a neighboring atom, at least one substituent selected from the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$), and —B(Q$_{26}$)(Q$_{27}$); and —Si(Q$_{31}$)(Q$_{32}$)(Q$_{33}$), —N(Q$_{34}$)(Q$_{35}$), and —B(Q$_{36}$)(Q$_{37}$), and Q$_1$ to Q$_7$, Q$_{11}$ to Q$_{17}$, Q$_{21}$ to Q$_{27}$, and Q$_{31}$ to Q$_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group, and a substituted or unsubstituted monovalent non-aromatic condensed heteropolycyclic group.

2. The organic light-emitting device of claim 1, wherein Ar$_1$ is represented by one selected from Formulae 1A(1) to 1A(6):

Formula 1A(1)

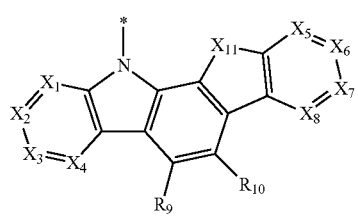

Formula 1A(2)

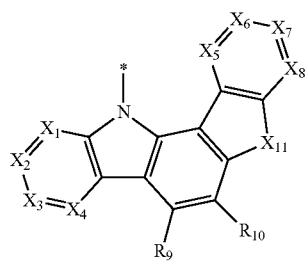

Formula 1A(3)

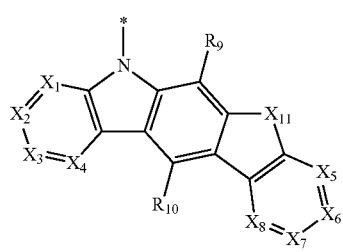

Formula 1A(4)

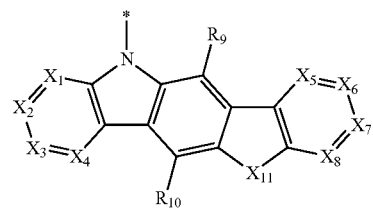

Formula 1A(5)

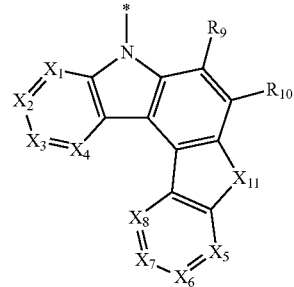

Formula 1A(6)

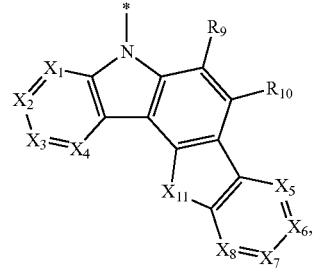

wherein, in Formulae 1A(1) to 1A(6), X$_1$ to X$_8$, X$_{11}$, R$_9$, and R$_{10}$ are understood by referring to the descriptions thereof provided in claim 1, and

* indicates a binding site to a neighboring atom.

3. The organic light-emitting device of claim 1, wherein Ar$_2$ is represented by one selected from Formulae 1B(1) to 1B(3):

Formula 1B(1)

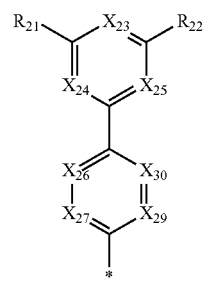

Formula 1B(2)

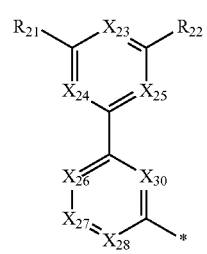

-continued

Formula 1B(3)

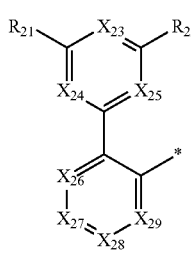

wherein, in Formulae 1B(1) to 1B(3), $X_{23}$ to $X_{25}$, $R_{21}$, and $R_{22}$ are understood by referring to the descriptions thereof provided in claim 1, $X_{26}$ is $C(R_{26})$ or N, $X_{27}$ is $C(R_{27})$ or N, $X_{28}$ is $C(R_{28})$ or N, $X_{29}$ is $C(R_{29})$ or N, and $X_{30}$ is $C(R_{30})$ or N, at least one selected from $X_{23}$ to $X_{27}$, $X_{29}$, and $X_{30}$ in Formula 1B(1) is N, at least one selected from $X_{23}$ to $X_{28}$ and $X_{30}$ in Formula 1B(2) is N, at least one selected from $X_{23}$ to $X_{29}$ in Formula 1B(3) is N, and

* indicates a binding site to a neighboring atom.

4. The organic light-emitting device of claim 1, wherein the condensed cyclic compound represented by Formula 1 comprises 1, 2, 3, or 4 cyano group(s).

5. An organic light-emitting device comprising:
a first electrode;
a second electrode facing the first electrode; and
an organic layer disposed between the first electrode and the second electrode,
wherein the organic layer comprises an emission layer,
wherein the emission layer comprises a host and a dopant,
wherein the dopant comprises a condensed cyclic compound represented by Formula 1, and
wherein an amount of the dopant is smaller than that of the host:

$$Ar_1—Ar_2 \quad \text{Formula 1}$$

$$Ar_1—Ar_2 \quad \text{Formula 1}$$

Formula 1A

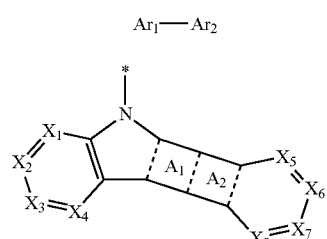

Formula 1B

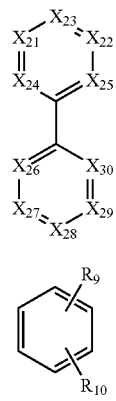

Formula 2A

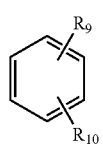

Formula 2B

wherein, in Formula 1, $Ar_1$ is a group represented by Formula 1A, and $Ar_2$ is a group represented by Formula 1B, in Formula 1A, ring $A_1$ is a group represented by Formula 2A, and ring $A_2$ is a group represented by Formula 2B, in Formulae 1A, 1B, 2A, and 2B, $X_1$ is $C(R_1)$ or N, $X_2$ is $C(R_2)$ or N, $X_3$ is $C(R_3)$ or N, $X_4$ is $C(R_4)$ or N, $X_5$ is $C(R_5)$ or N, $X_6$ is $C(R_6)$ or N, $X_7$ is $C(R_7)$ or N, and $X_8$ is $C(R_8)$ or N, $X_{11}$ is selected from O, S, $N[(L_{11})_{a11}\text{-}(R_{11})_{b11}]$, $C[(L_{11})_{a11}\text{-}(R_{11})_{b11}][(L_{12})_{a12}\text{-}(R_{12})_{b12}]$, $Si[(L_{11})_{a11}\text{-}(R_{11})_{b11}][(L_{12})_{a12}\text{-}(R_{12})_{b12}]$, and $Ge[(L_{11})_{a11}\text{-}(R_{11})_{b11}][(L_{12})_{a12}\text{-}(R_{12})_{b12}]$, $X_{21}$ is $C(R_{21})$ or N, $X_{22}$ is $C(R_{22})$ or N, $X_{23}$ is $C(R_{23})$ or N, $X_{24}$ is $C(R_{24})$ or N, and $X_{25}$ is $C(R_{25})$ or N, $X_{26}$ is $C(R_{26})$, N, or a binding site to $Ar_1$, $X_{27}$ is $C(R_{27})$, N, or a binding site to $Ar_1$ $X_{28}$ is $C(R_{28})$, N, or a binding site to $Ar_1$, $X_{29}$ is $C(R_{29})$, N, or a binding site to $Ar_1$, and $X_{30}$ is $C(R_{30})$, N, or a binding site to $Ar_1$, at least one selected from $X_{21}$ to $X_{30}$ is N, and at least one selected from $X_{26}$ to $X_{30}$ is a binding site to $Ar_1$, $L_{11}$ and $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 and a12 are each independently an integer selected from 0 to 3, $R_1$ to $R_{12}$ and $R_{21}$ to $R_{30}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), b11 and b12 are each independently an integer selected from 1 to 3, the number of a cyano group(s) included in the condensed cyclic compound represented by Formula 1 is 1 or greater,

* indicates a binding site to a neighboring atom, at least one substituent selected from the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, and a substituted or unsubstituted monovalent non-aromatic condensed heteropolycyclic group, wherein, at least one selected from $X_1$ to $X_8$ in Formula 1A is N, $Ar_1$ does not comprise a cyano group, while $Ar_2$ includes at least one cyano group.

6. The organic light-emitting device of claim 1, wherein, in Formula 1A, when $X_1$ is C($R_1$), $X_2$ is C($R_2$), $X_3$ is C($R_3$), $X_4$ is C($R_4$), $X_5$ is C($R_5$), $X_6$ is C($R_6$), $X_7$ is C($R_7$), and $X_8$ is C($R_8$), i) $Ar_1$ does not comprise a cyano group and $Ar_2$ comprises at least one cyano group;
ii) $Ar_1$ comprises at least one cyano group and $Ar_2$ does not comprise a cyano group; or
iii) $Ar_1$ group and $Ar_2$ group each comprises at least one cyano group.

7. The organic light-emitting device of claim 1, wherein, in Formula 2B, $X_{11}$ is $N[(L_{11})_{a11}\text{-}(R_{11})_{b11}]$ and a group represented by *-$[(L_{11})_{a11}\text{-}(R_{11})_{b11}]$ comprises at least one cyano group; or $X_{11}$ is selected from $Si[(L_{11})_{a11}\text{-}(R_{11})_{b11}][(L_{12})_{a12}\text{-}(R_{12})_{b12}]$, and $Ge[(L_{11})_{a11}\text{-}(R_{11})_{b11}][(L_{12})_{a12}\text{-}(R_{12})_{b12}]$, and at least one selected from a group represented by *-$[(L_{11})_{a11}\text{-}(R_{11})_{b11}]$ and a group represented by *-$[(L_{12})_{a12}\text{-}(R_{12})_{b12}]$ comprises a cyano group.

8. The organic light-emitting device of claim 1, wherein $L_{11}$ and $L_{12}$ are each independently selected from:

a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, and a dibenzothiophenylene group; and a phenylene group, a naphthylene group, a fluorenylene group, a pyridinylene group, a pyrimidinylene group, a pyrazinylene group, a pyridazinylene group, a triazinylene group, a quinolinylene group, an isoquinolinylene group, a carbazolylene group, a dibenzofuranylene group, and a dibenzothiophenylene group, each substituted with at least one selected from deuterium, a cyano group, a $C_1$-$C_{10}$ alkyl group, a $C_1$-$C_{10}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a quinolinyl group, an isoquinolinyl group, a carbazolyl group, a dibenzofuranyl group, a dibenzothiophenyl group, and —$Si(Q_{31})(Q_{32})(Q_{33})$, and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

9. The organic light-emitting device of claim 1, wherein $R_1$ to $R_{12}$ and $R_{21}$ to $R_{30}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group; and a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, a benzofuranyl group, a benzothiophenyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and —$Si(Q_{31})(Q_{32})(Q_{33})$; and —$Si(Q_1)(Q_2)(Q_3)$, and $Q_1$ to $Q_3$ and $Q_{31}$ to $Q_{33}$ are each independently selected from hydrogen, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group.

10. The organic light-emitting device of claim 1, wherein $R_1$ to $R_{12}$ and $R_{23}$ to $R_{30}$ are each independently selected from:

hydrogen, deuterium, a cyano group, a $C_1$-$C_{20}$ alkyl group, a phenyl group, a biphenyl group, a terphenyl group, a fluorenyl group, a dibenzofuranyl group, a dibenzothiophenyl group, and a dibenzosilolyl group;

a $C_1$-$C_{20}$ alkyl group substituted with at least one selected from deuterium and a cyano group;

a phenyl group, a biphenyl group, a terphenyl group, a fluorenyl group, a dibenzofuranyl group, a dibenzothiophenyl group, and a dibenzosilolyl group; and a phenyl group, a biphenyl group, a terphenyl group, a fluorenyl group, a dibenzofuranyl group, a dibenzothiophenyl group, and a dibenzosilolyl group, each substituted with at least one selected from deuterium, a cyano group, a $C_1$-$C_{20}$ alkyl group, a phenyl group, a biphenyl group, and a terphenyl group, and $R_{21}$ and $R_{22}$ are each independently selected from:

a phenyl group, a biphenyl group, a terphenyl group, a fluorenyl group, a dibenzofuranyl group, a dibenzothiophenyl group, and a dibenzosilolyl group; and a phenyl group, a biphenyl group, a terphenyl group, a fluorenyl group, a dibenzofuranyl group, a dibenzothiophenyl group, and a dibenzosilolyl group, each substituted with at least one selected from deuterium, a cyano group, a $C_1$-$C_{20}$ alkyl group, a phenyl group, a biphenyl group, and a terphenyl group.

11. The organic light-emitting device of claim 1, wherein $R_1$ to $R_{12}$ and $R_{23}$ to $R_{30}$ are each independently selected from:

hydrogen, deuterium, a cyano group, a $C_1$-$C_{20}$ alkyl group, a phenyl group, a biphenyl group, a terphenyl group, a fluorenyl group, a dibenzofuranyl group, a dibenzothiophenyl group, and a dibenzosilolyl group;

a $C_1$-$C_{20}$ alkyl group substituted with at least one selected from deuterium and a cyano group;

a phenyl group, a biphenyl group, a terphenyl group, a fluorenyl group, a dibenzofuranyl group, a dibenzothiophenyl group, and a dibenzosilolyl group; and groups represented by Formulae 5-1 to 5-15, and $R_{21}$ and $R_{22}$ are each independently selected from:

a phenyl group, a biphenyl group, a terphenyl group, a fluorenyl group, a dibenzofuranyl group, a dibenzothiophenyl group, and a dibenzosilolyl group; and groups represented by Formulae 5-1 to 5-15:

5-1
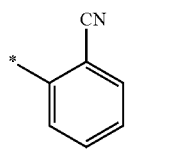

5-2
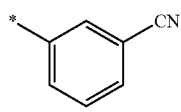

5-3
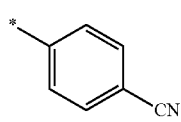

5-4
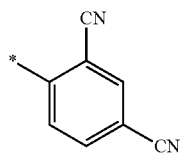

5-5
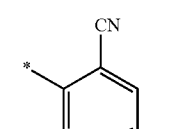

5-6
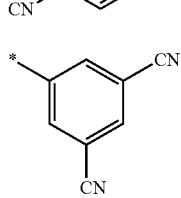

-continued 5-7
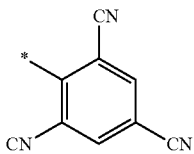

5-8
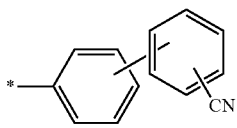

5-9
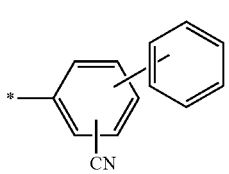

5-10
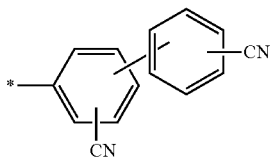

5-11
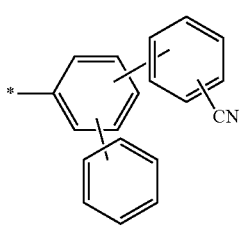

5-12
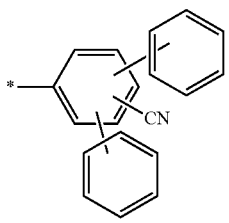

5-13
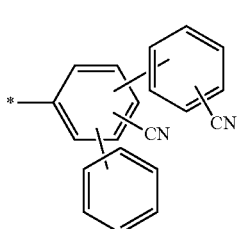

5-14
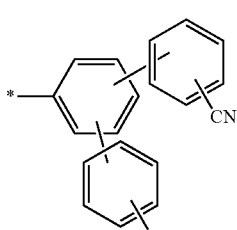

5-15

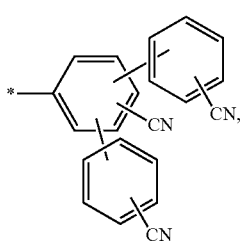

wherein * in Formulae 5-1 to 5-15 indicates a binding site to a neighboring atom.

12. An organic light-emitting device comprising:
a first electrode;
a second electrode facing the first electrode; and
an organic layer disposed between the first electrode and the second electrode,
wherein the organic layer comprises an emission layer,
wherein the emission layer comprises a host and a dopant,
wherein an amount of the dopant is smaller than that of the host, and
wherein the dopant comprises at least one selected from Compounds 1-3, 5-7, 9-20, and 22 to 192:

1

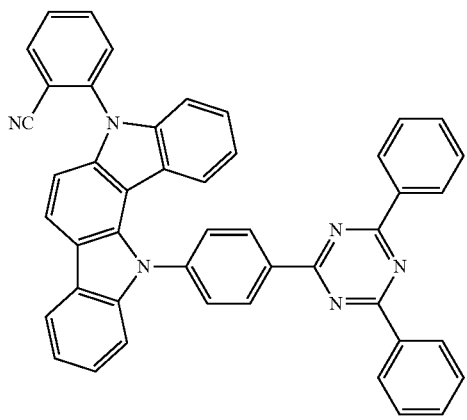

2

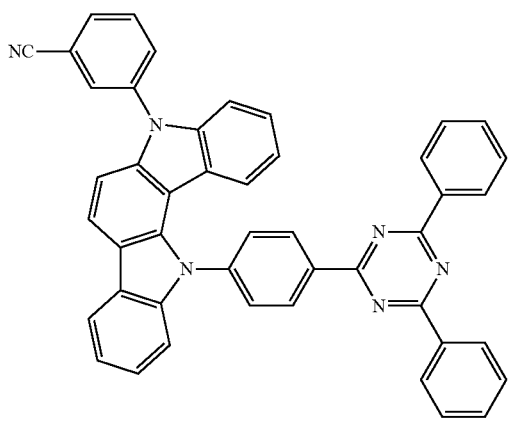

3

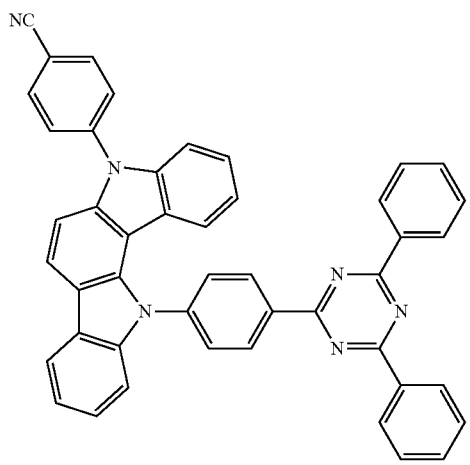

5

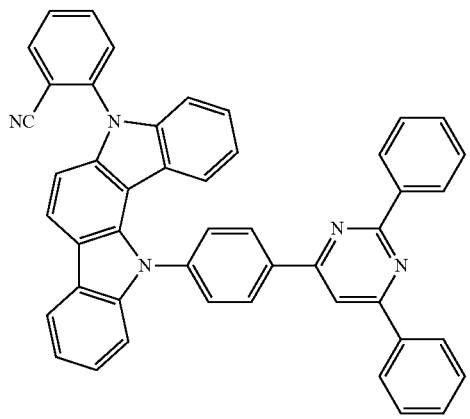

6

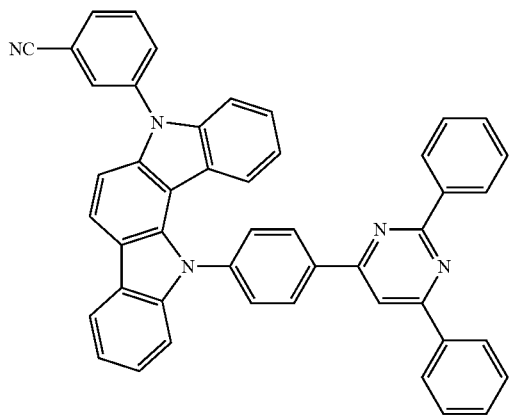

151
-continued
7
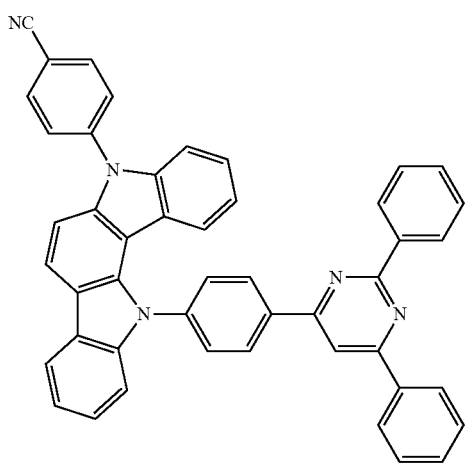
9
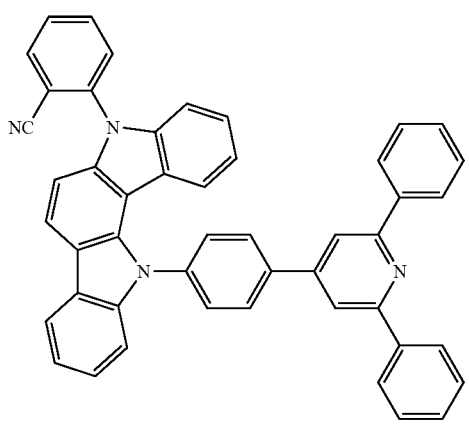
10
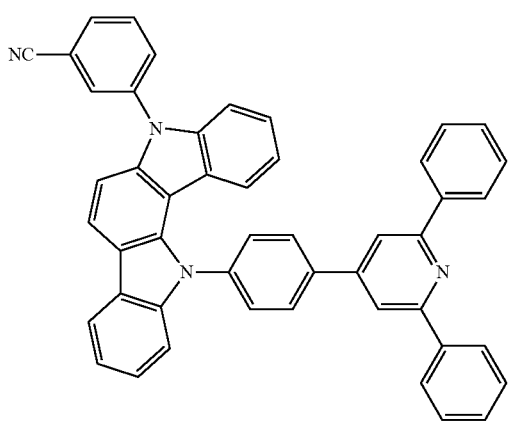
152
-continued
11
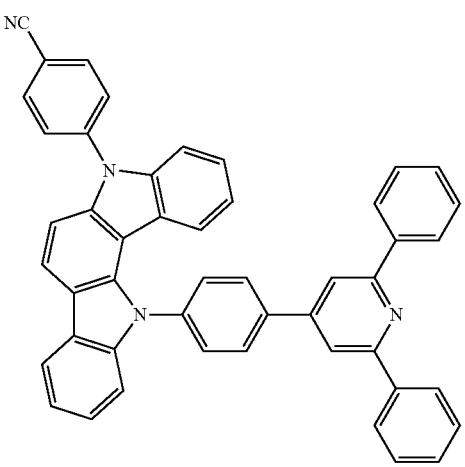
12
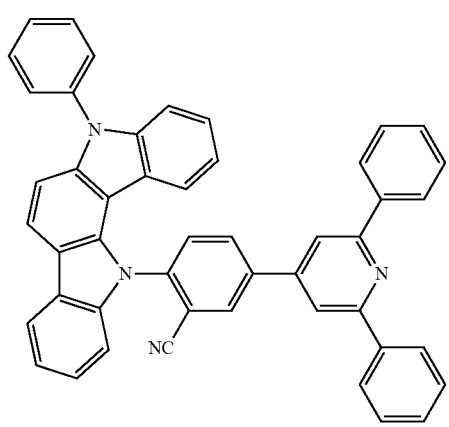
13
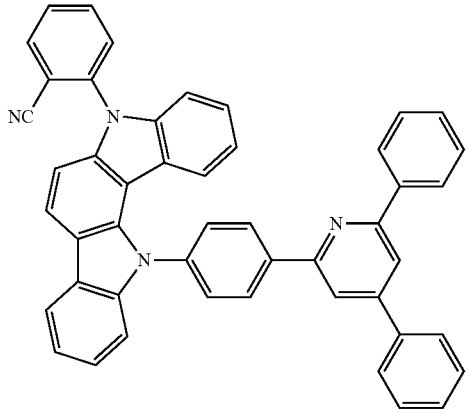

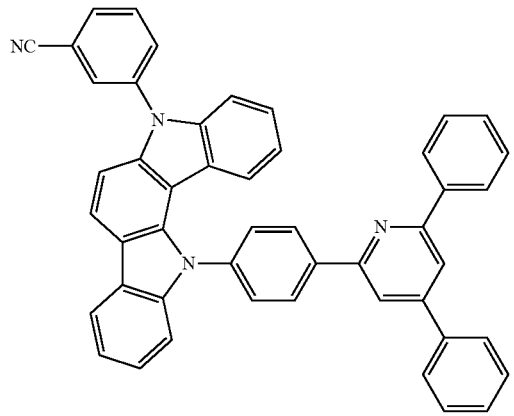
14
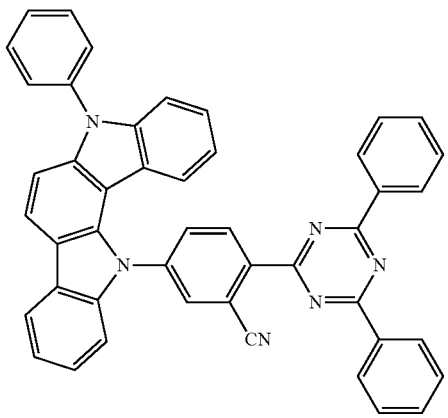
17
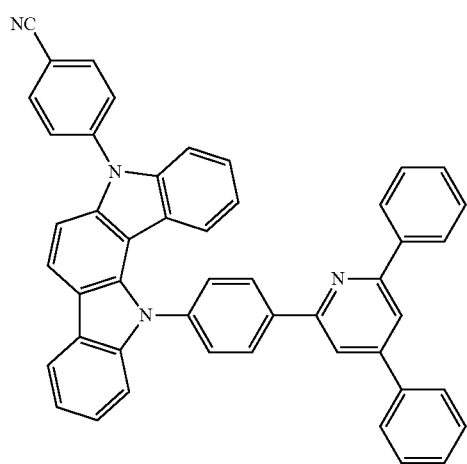
15
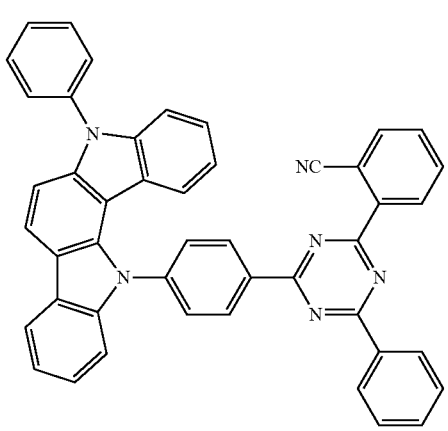
18
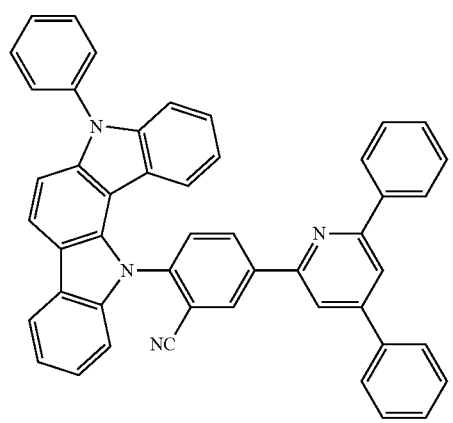
16
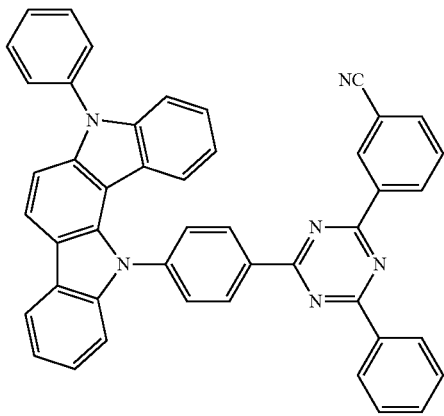
19

155
-continued
20
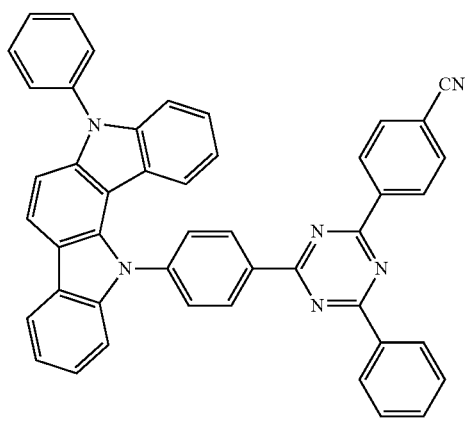
22
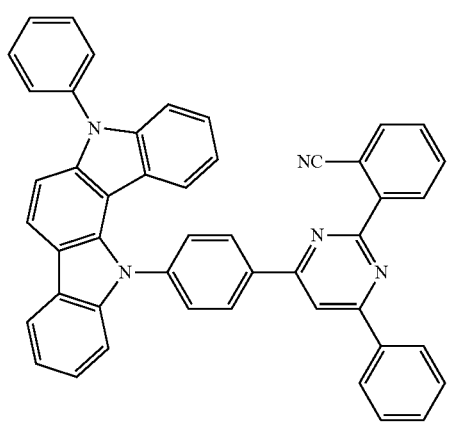
23
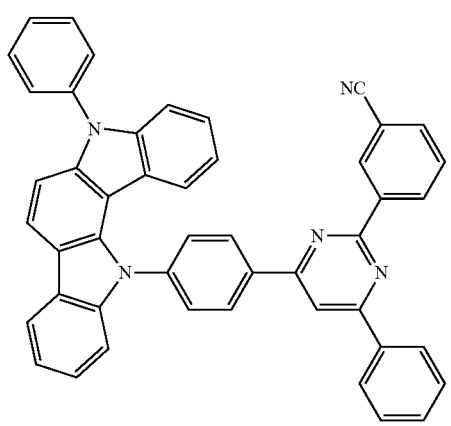
156
-continued
24
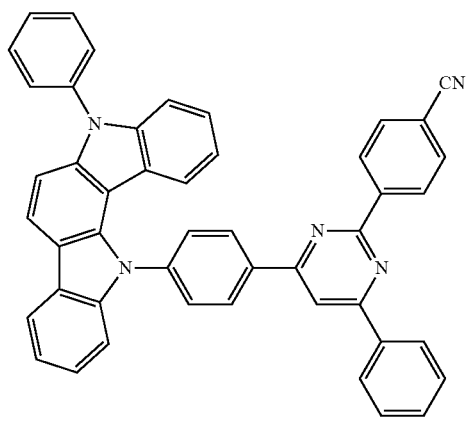
25
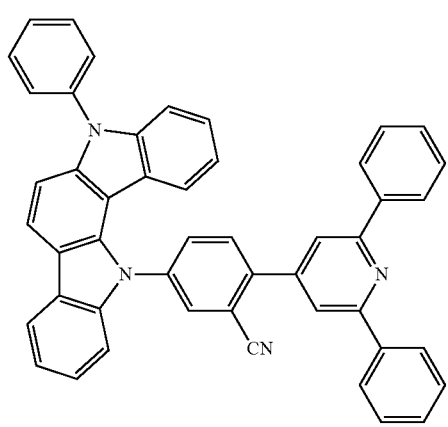
26
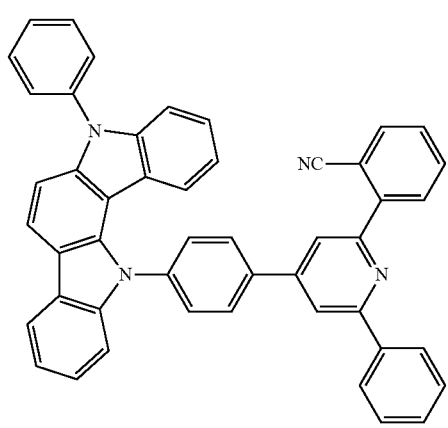

-continued
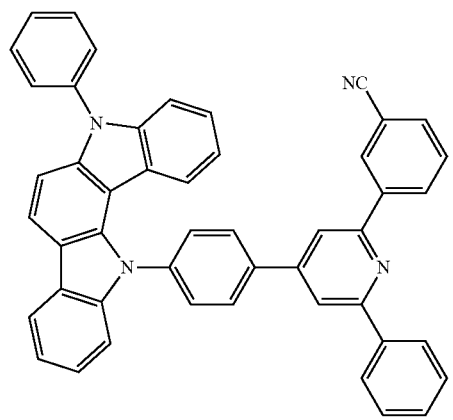
27
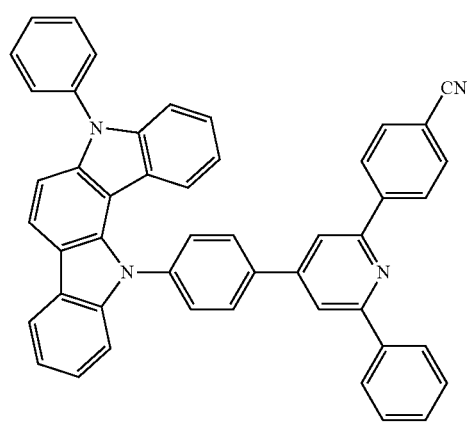
28
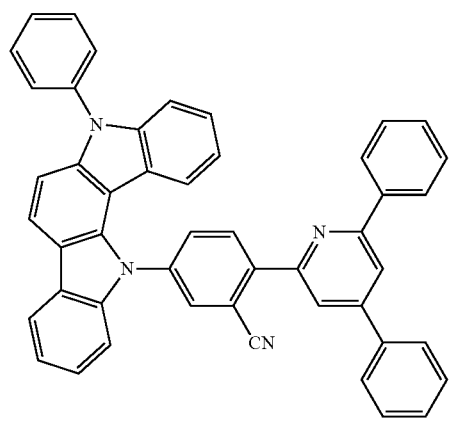
29
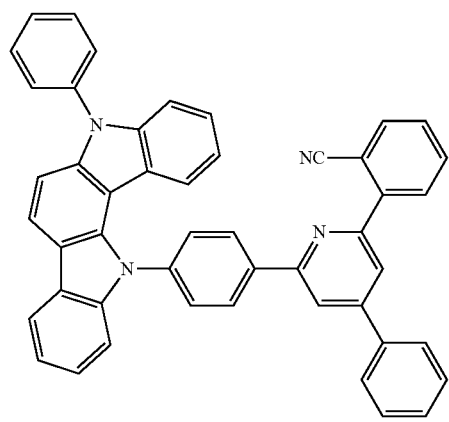
30
-continued
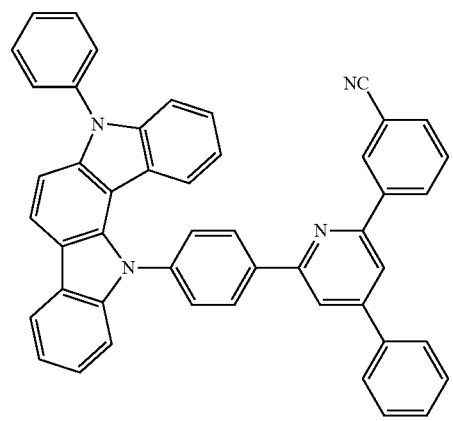
31
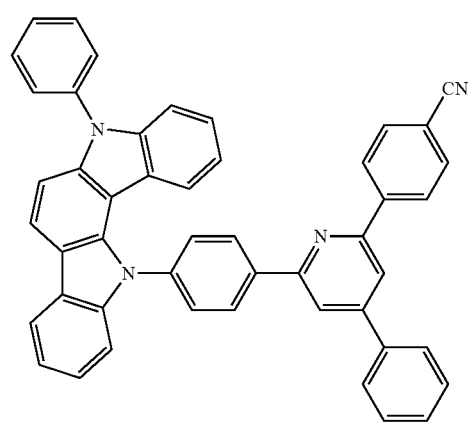
32
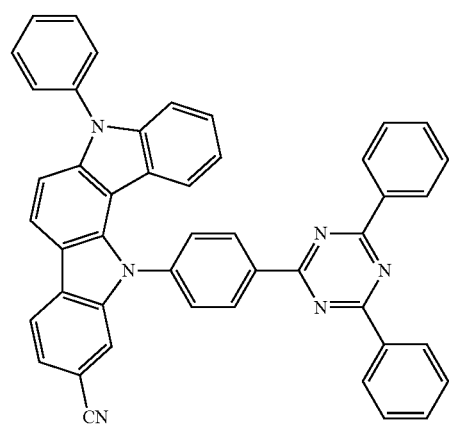
33

34
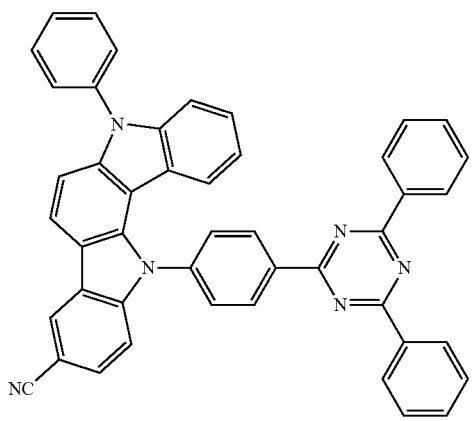
37
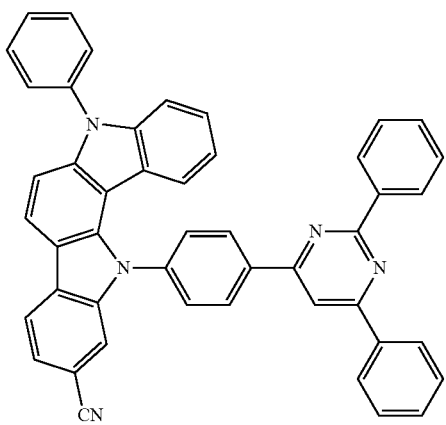
35
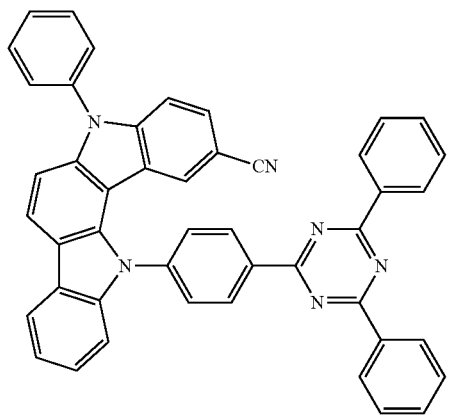
38
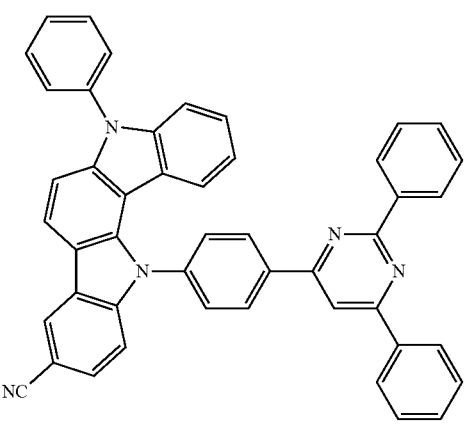
36
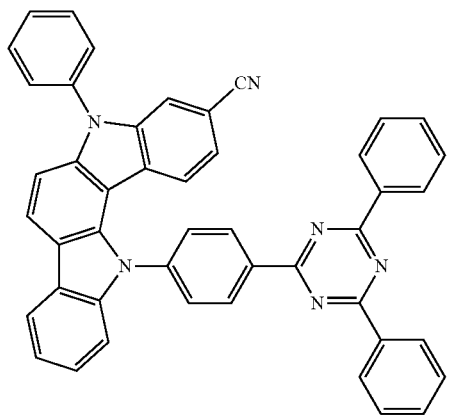
39
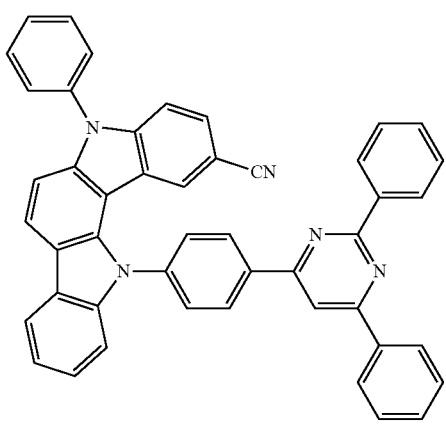

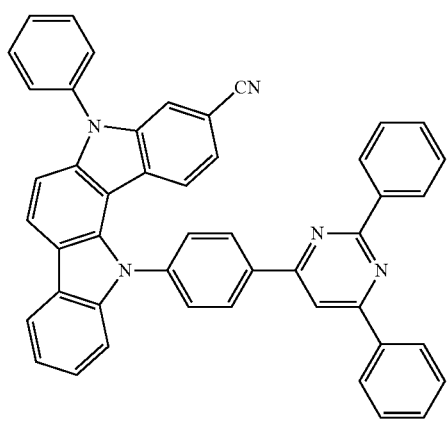
40
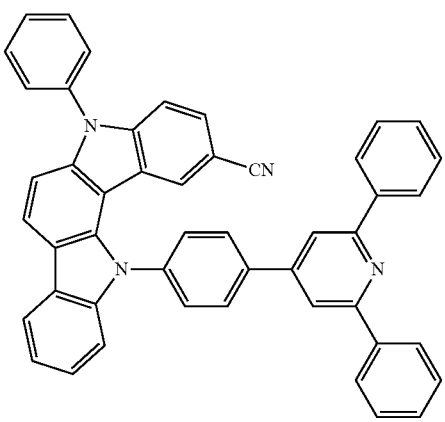
43
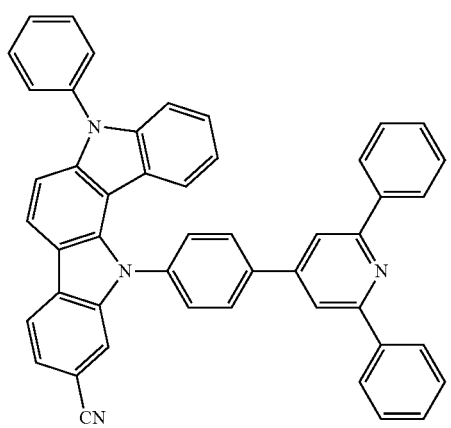
41
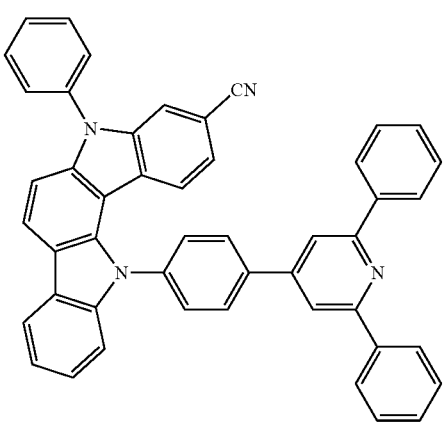
44
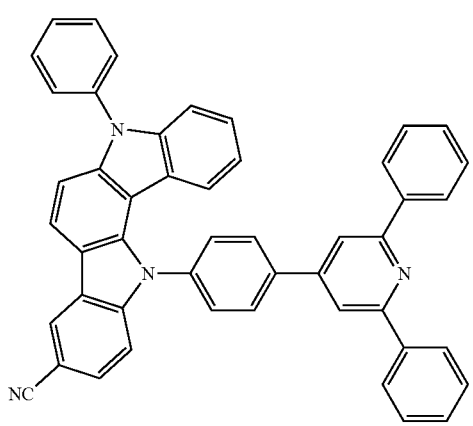
42
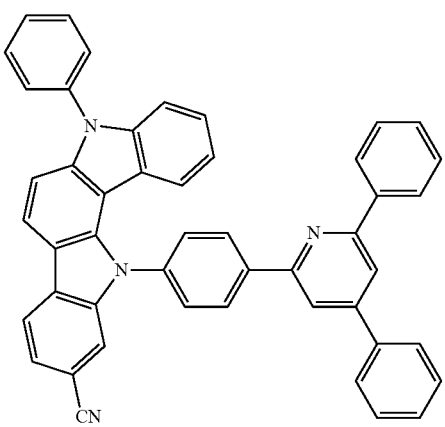
45

46
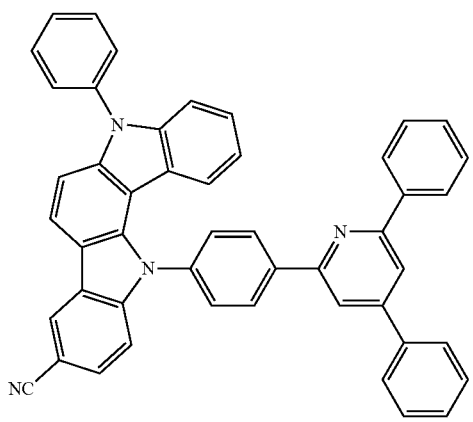
47
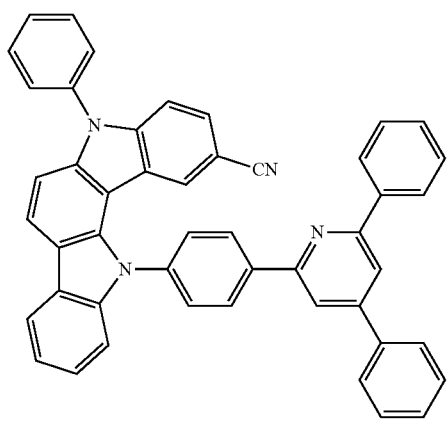
48
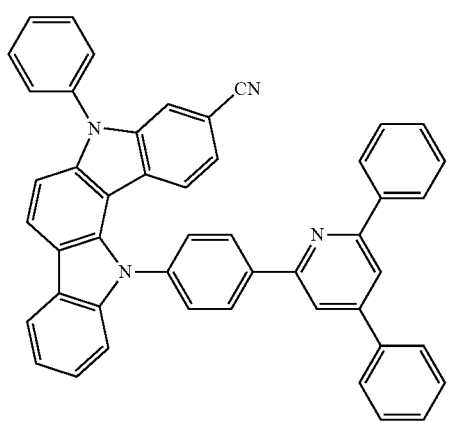
49
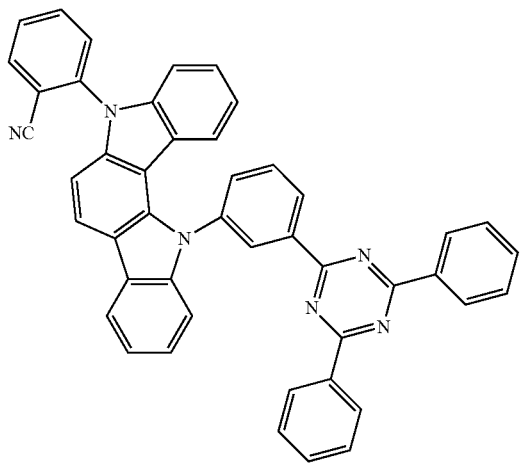
50
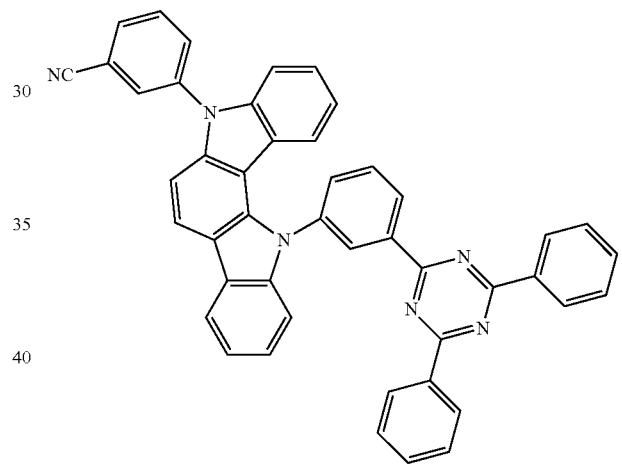
51
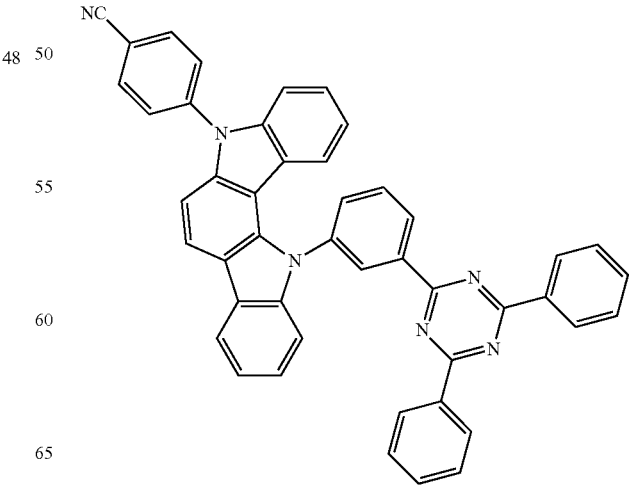

52
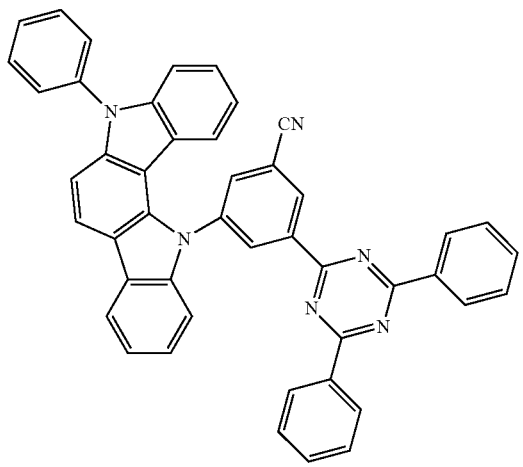
53
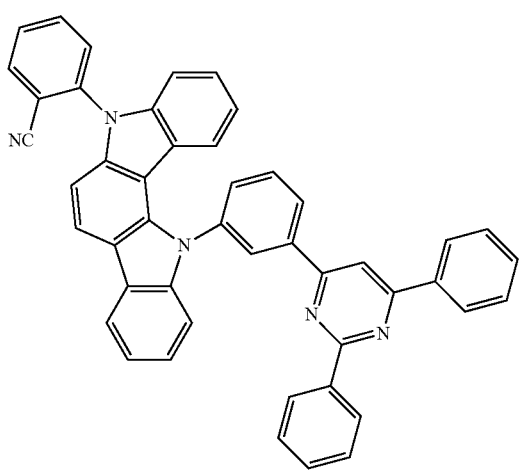
54
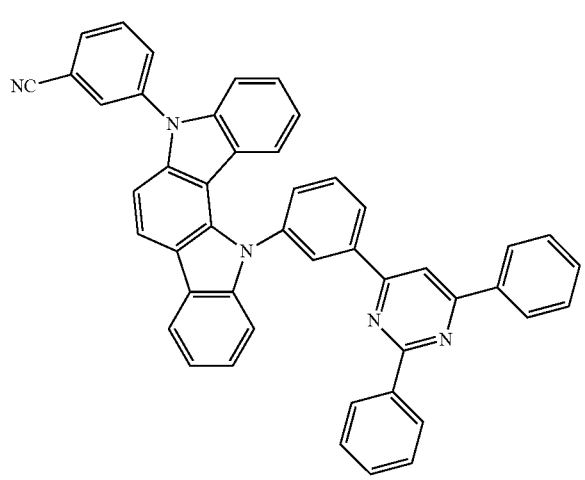
55
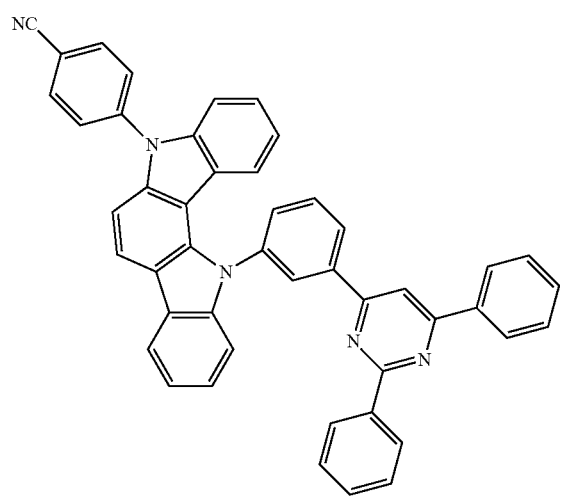
56
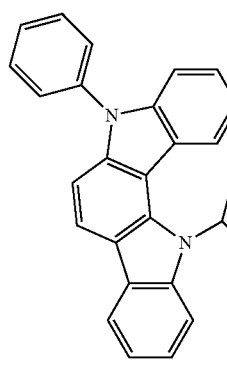
57
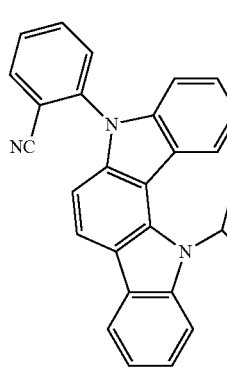

167
-continued
58
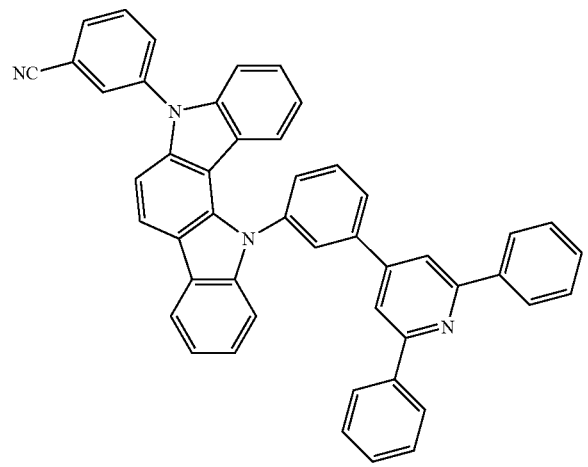
59
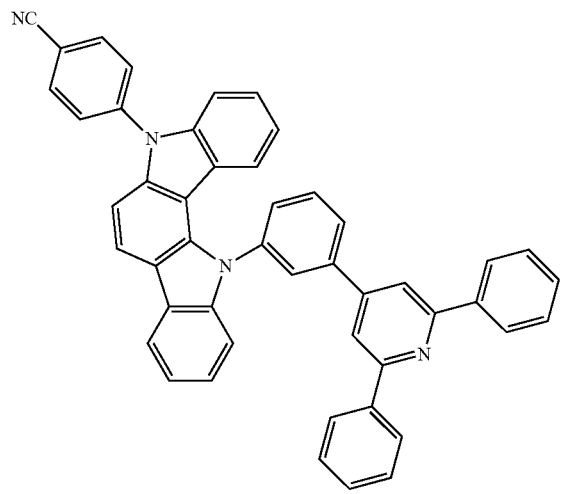
60
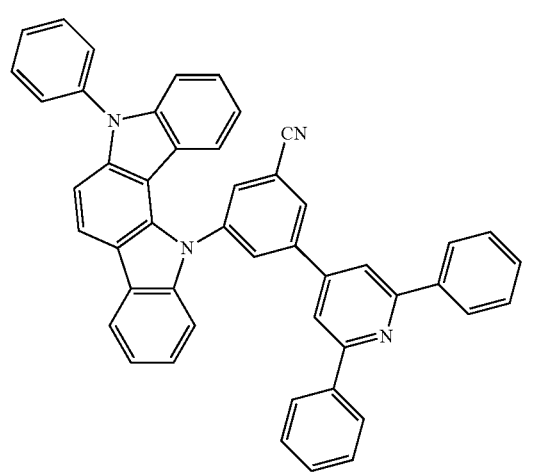
168
-continued
61
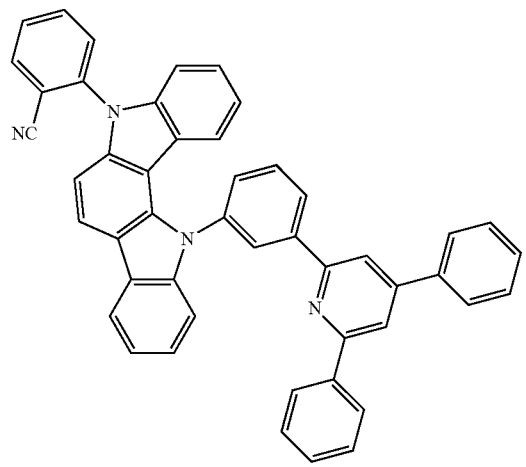
62
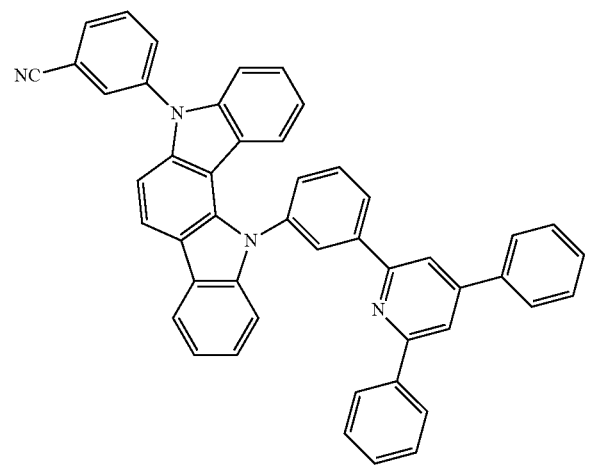
63
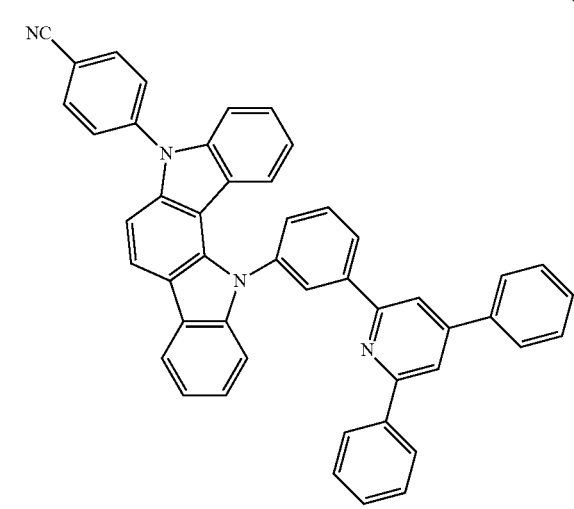

169
-continued
64
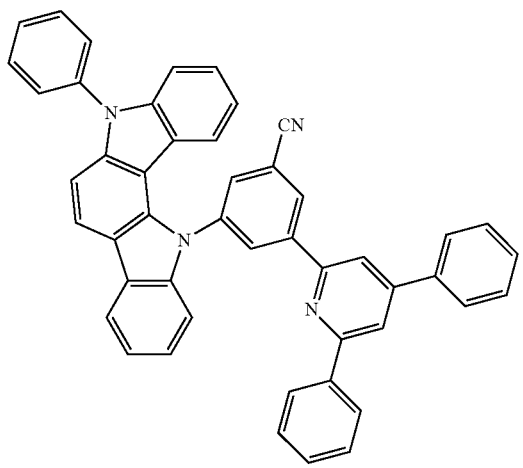
65
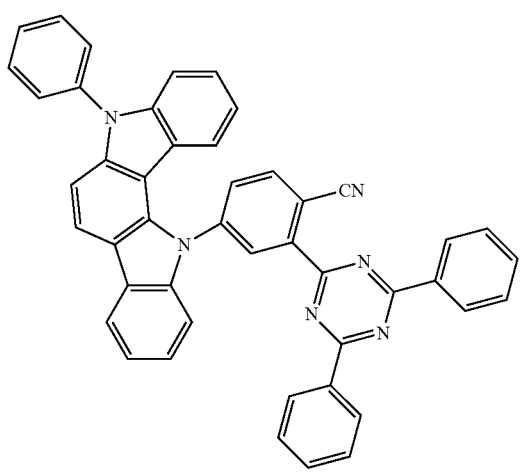
66
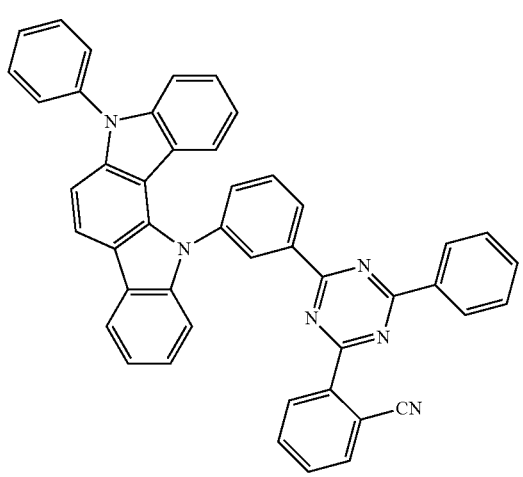
170
-continued
67
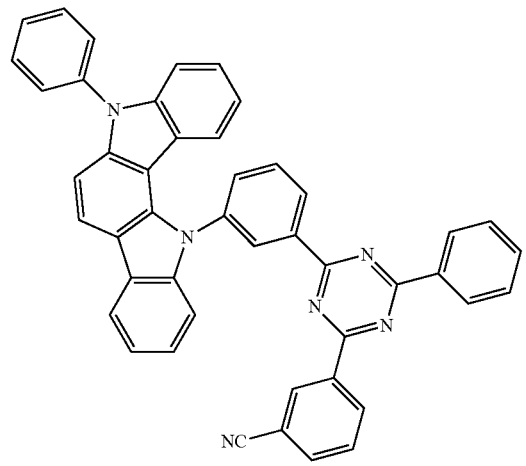
68
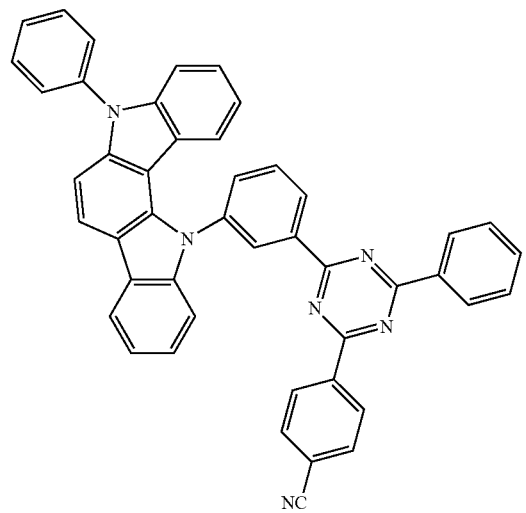
69
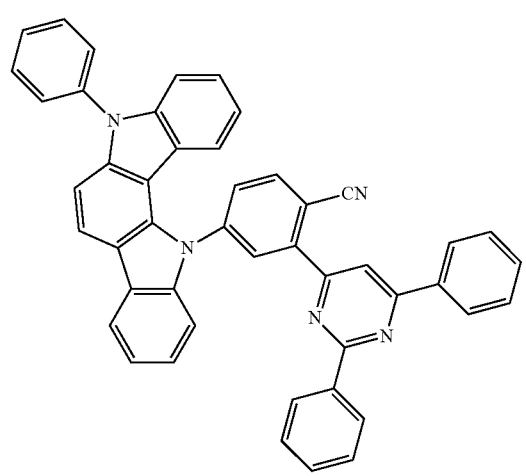

-continued
70
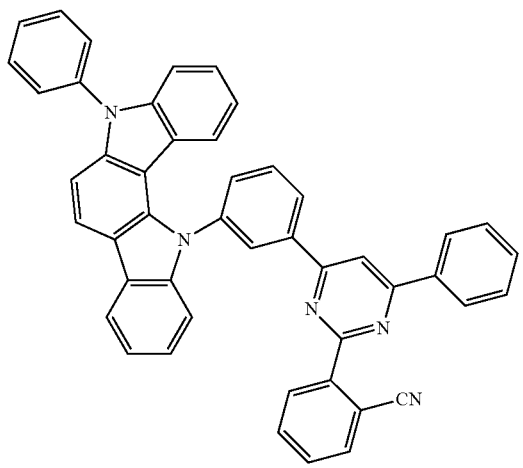
73
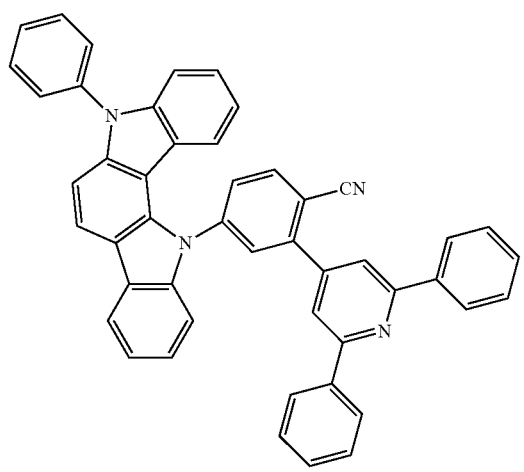
71
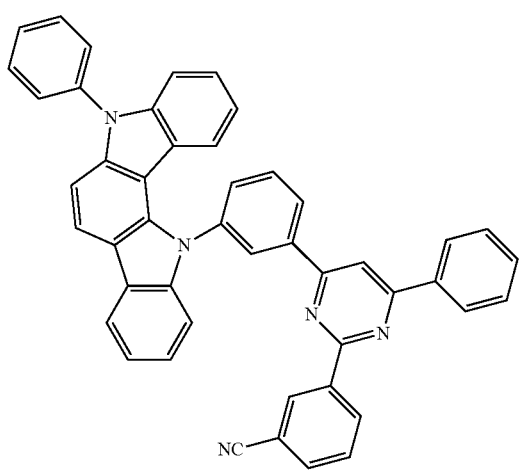
74
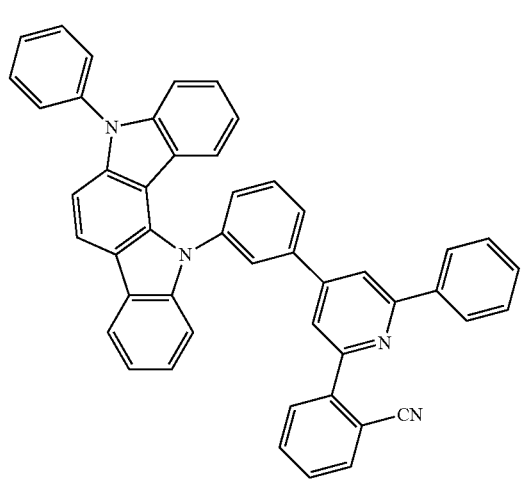
72
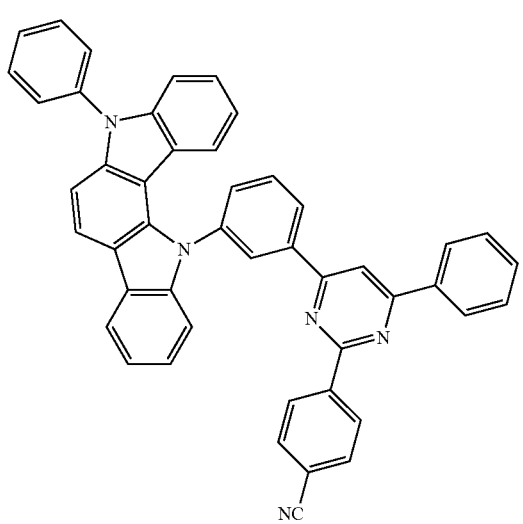
75
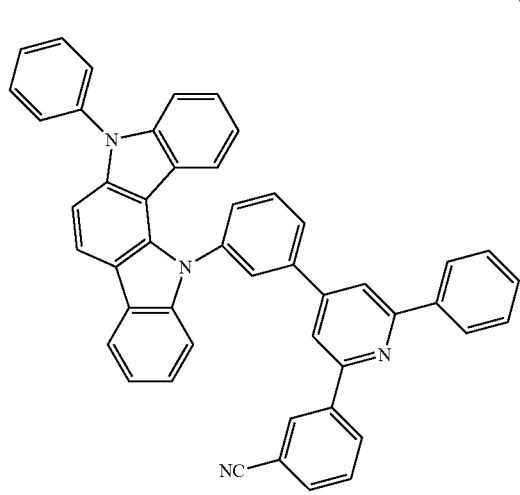

76
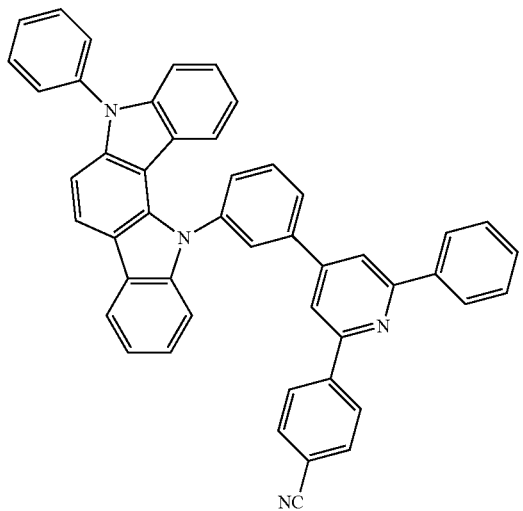
77
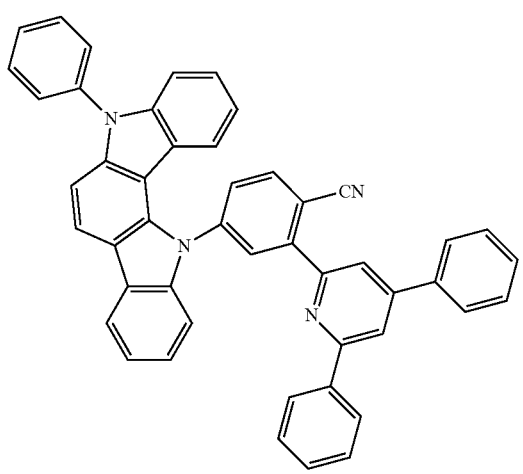
79
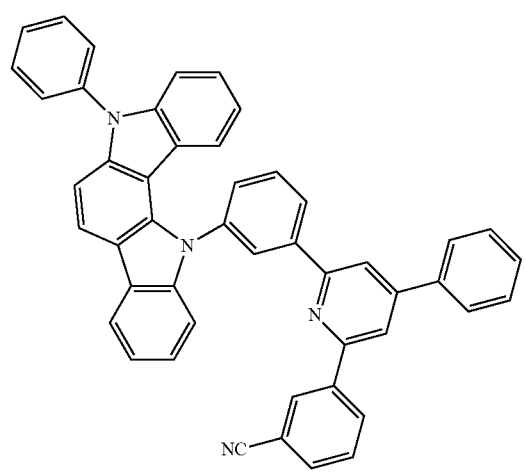
80
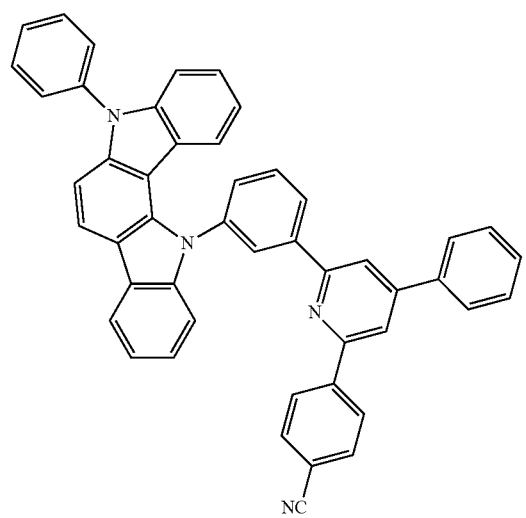
78
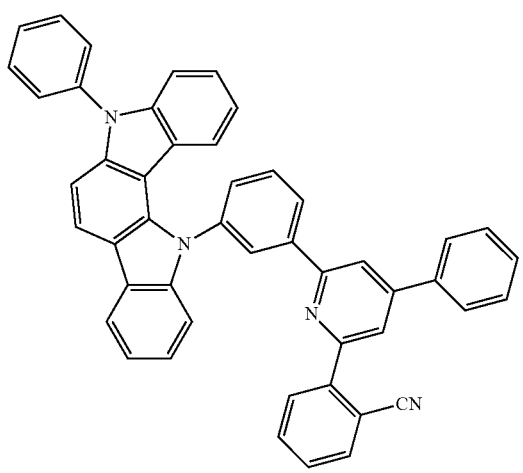
81
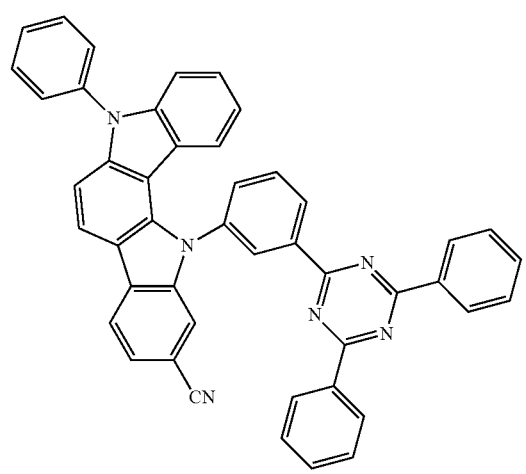

82
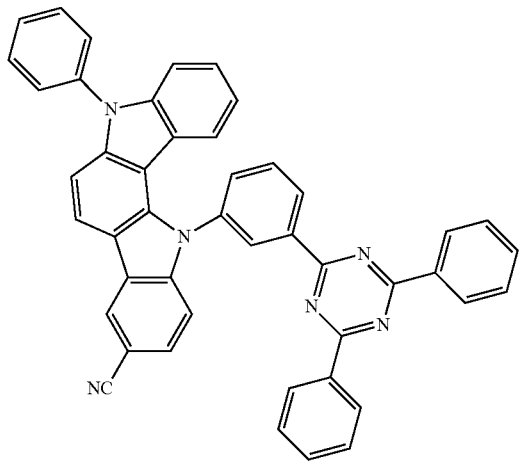
83
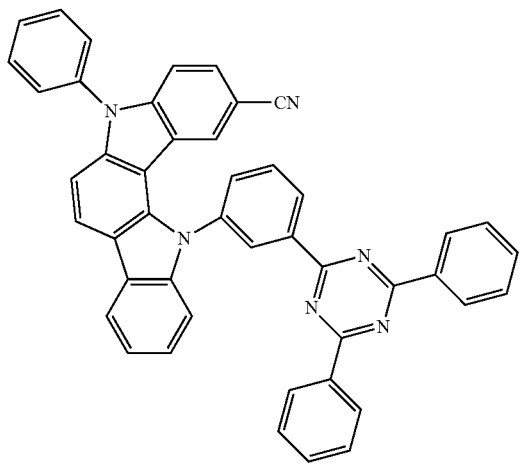
84
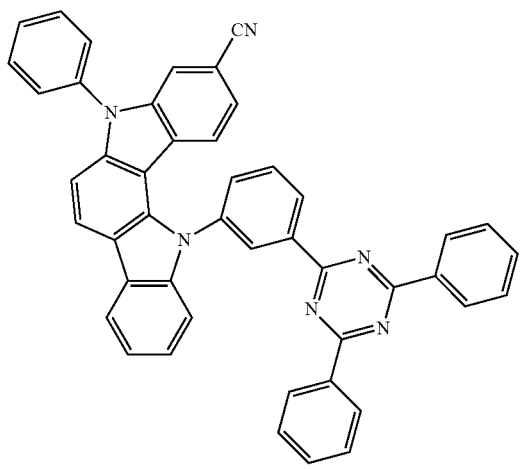
85
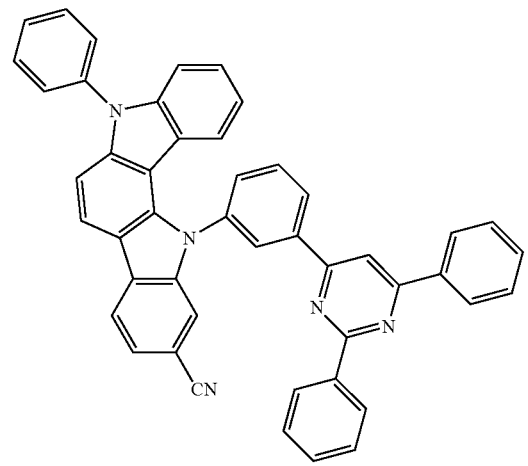
86
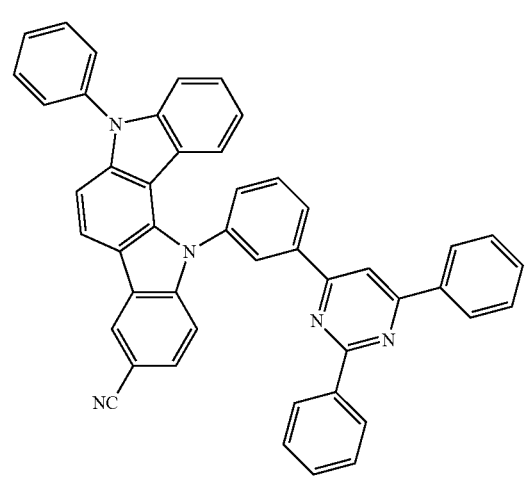
87
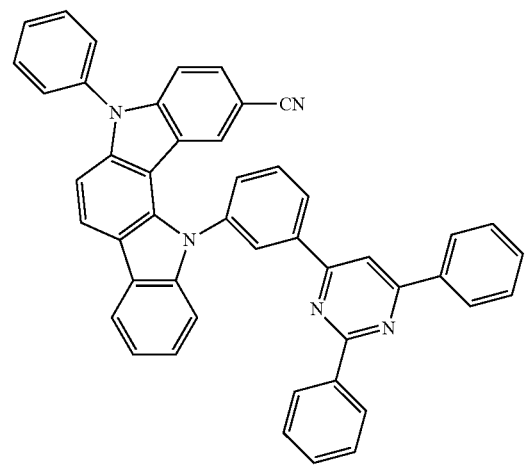

88
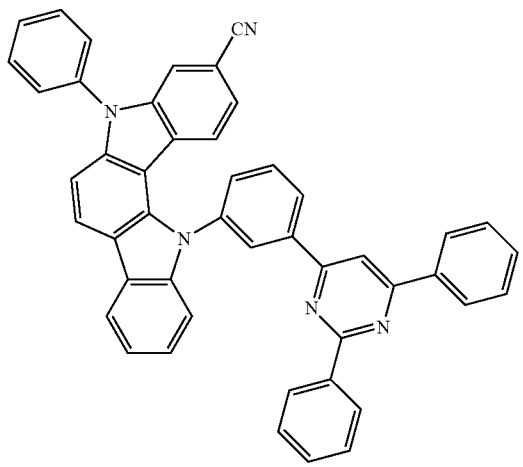
89
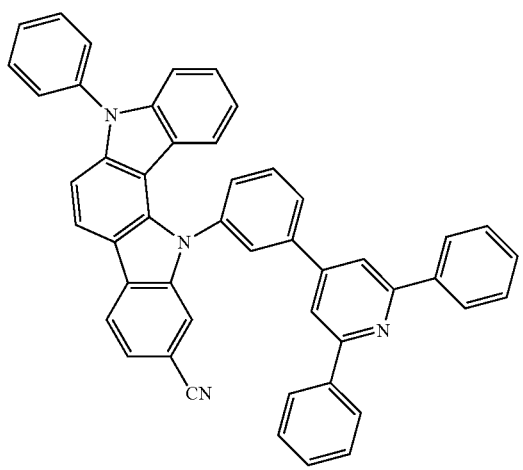
90
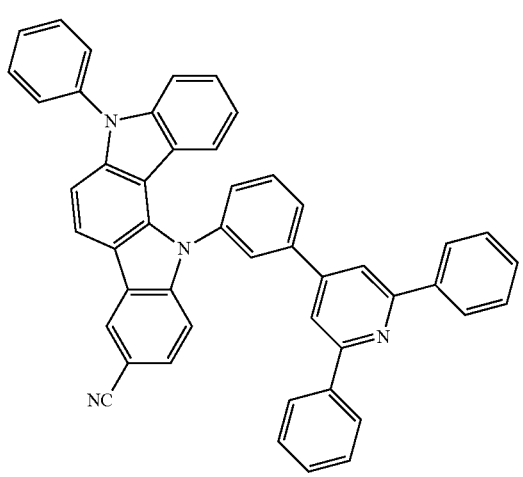
91
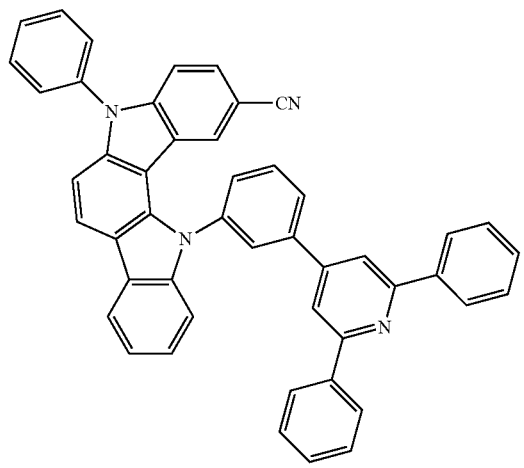
92
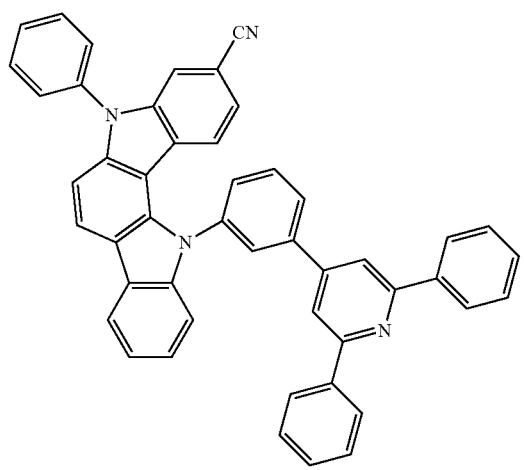
93
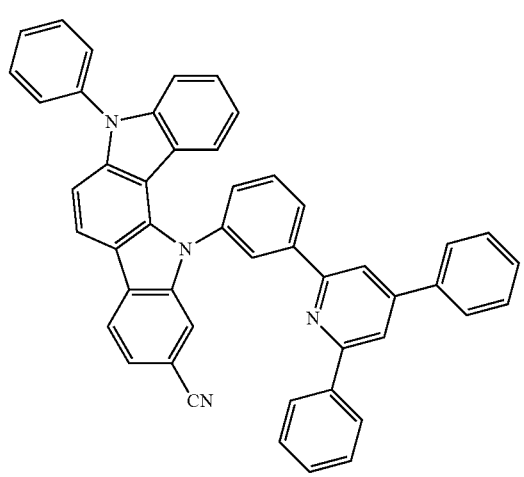

94
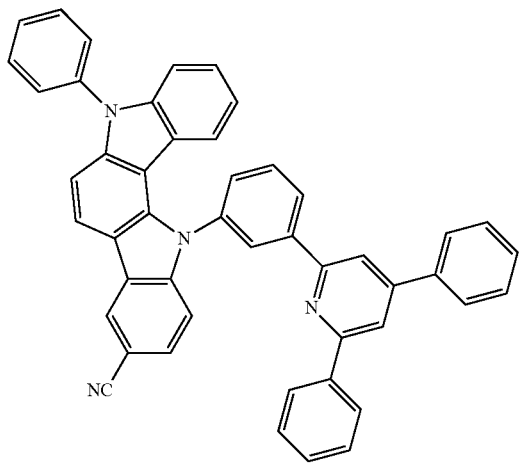
95
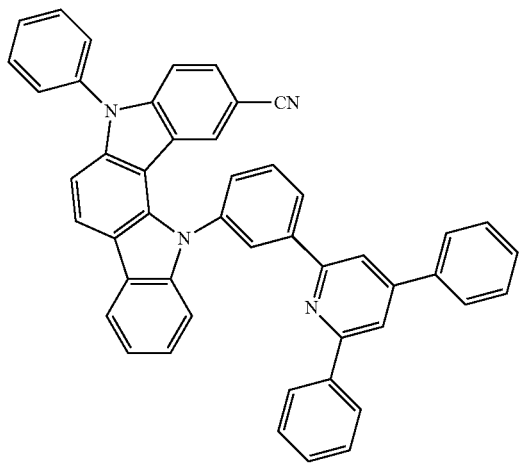
96
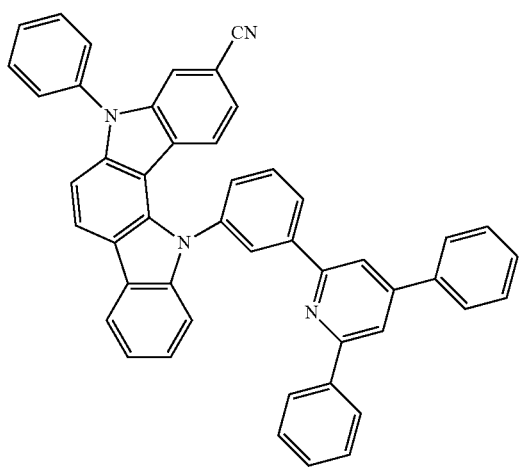
97
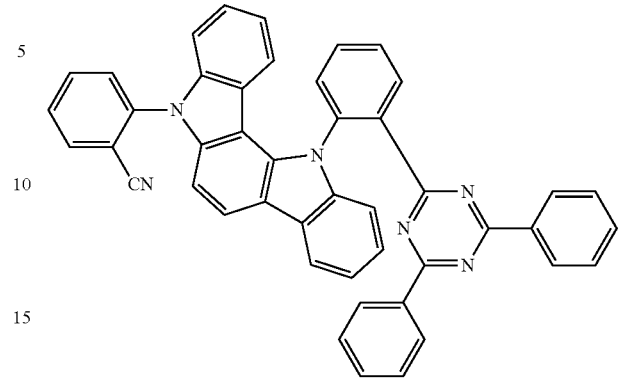
98
99
100
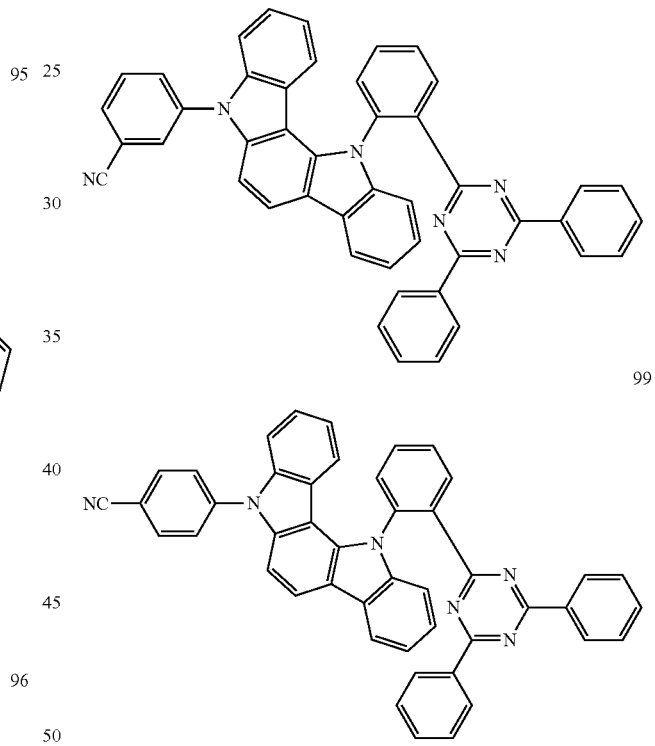

-continued
101
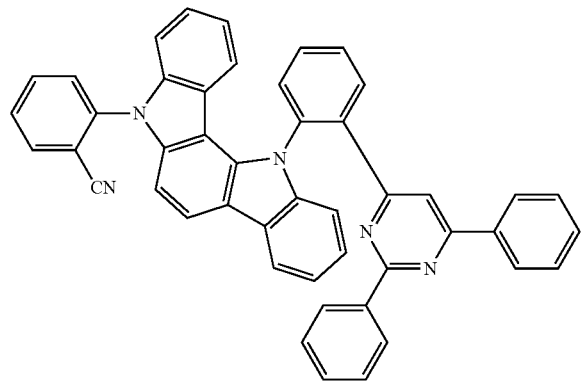
102
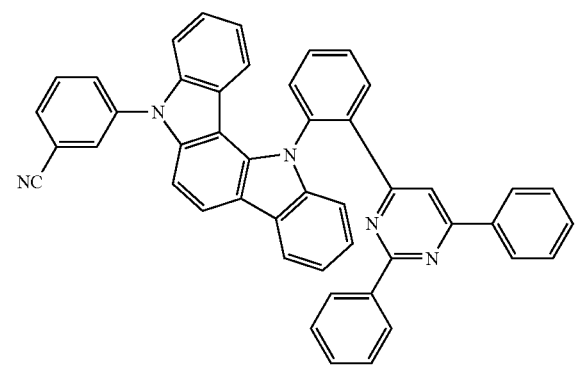
103
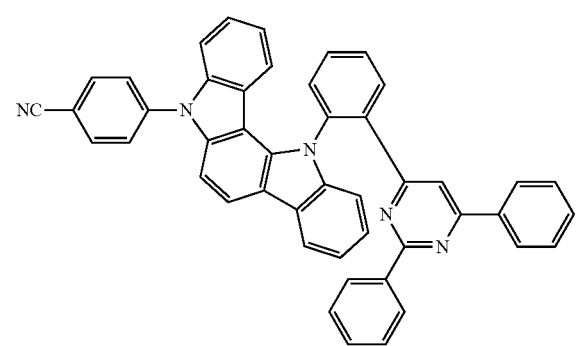
104
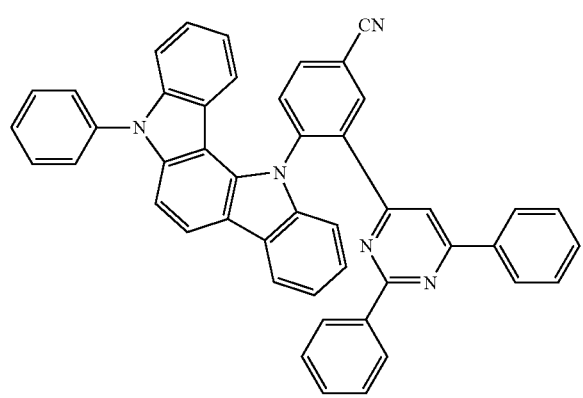
-continued
105
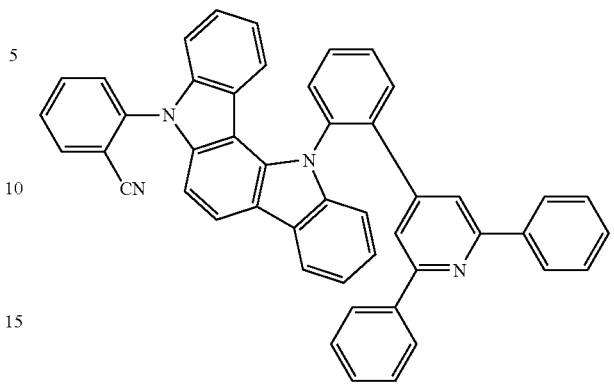
106
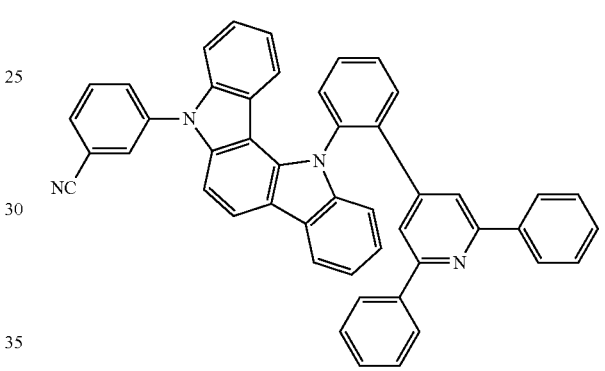
107
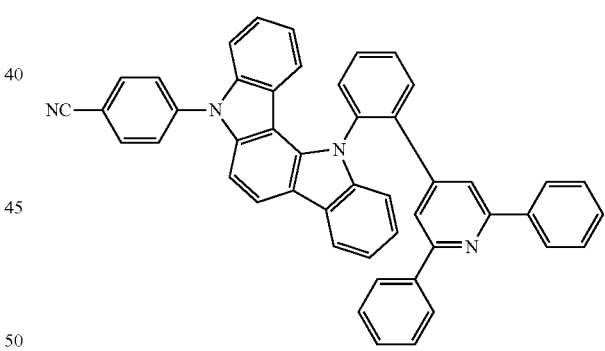
108
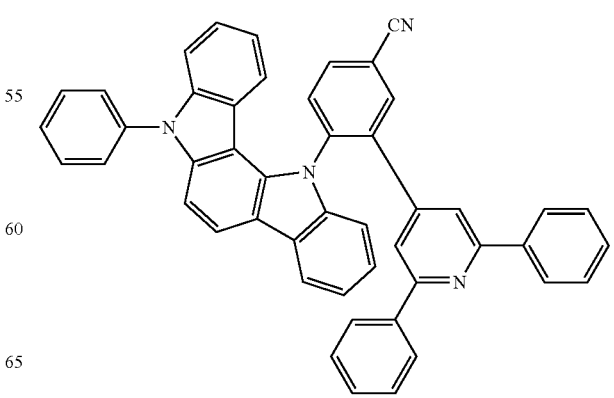

-continued
109
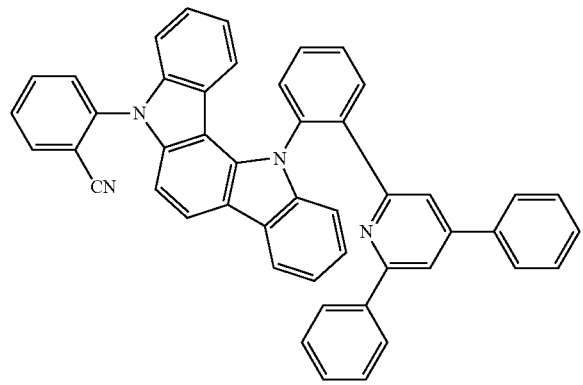
110
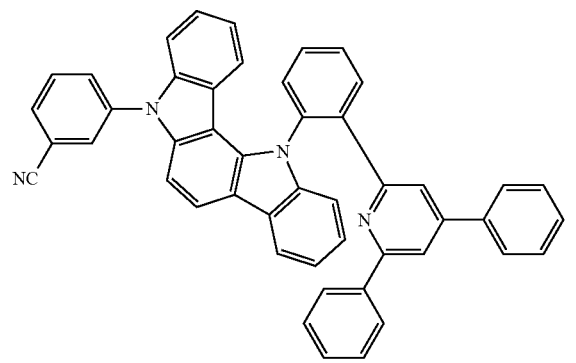
111
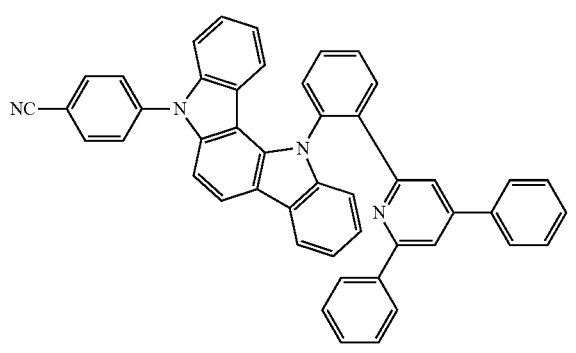
112
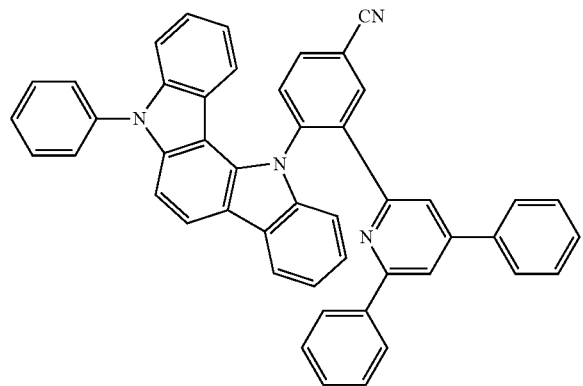
-continued
113
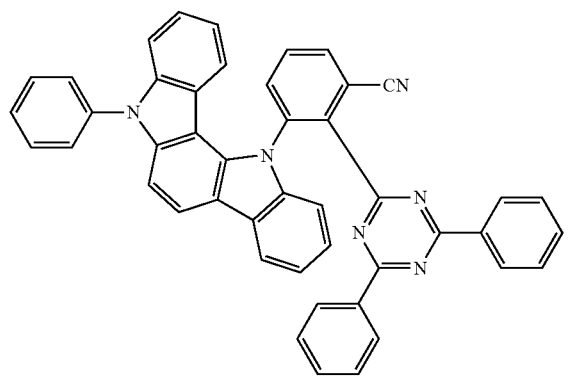
114
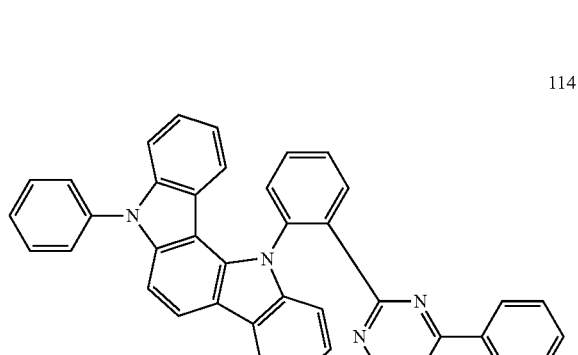
115
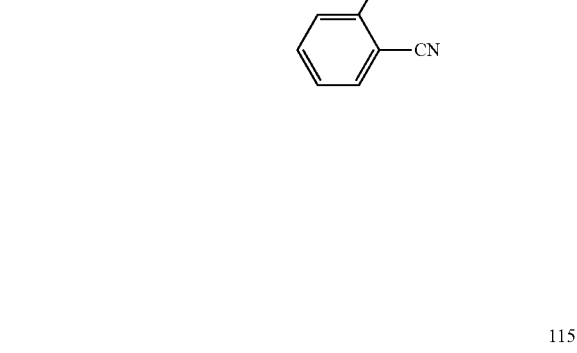

116
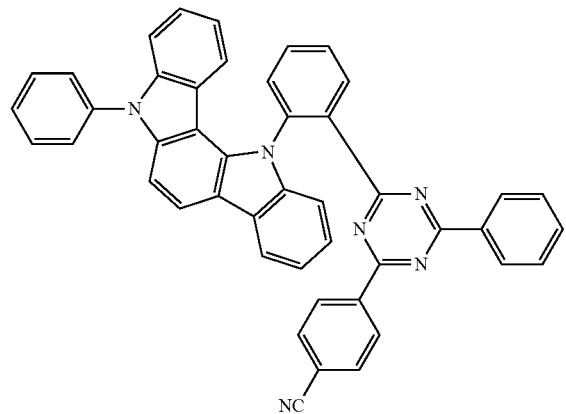
117
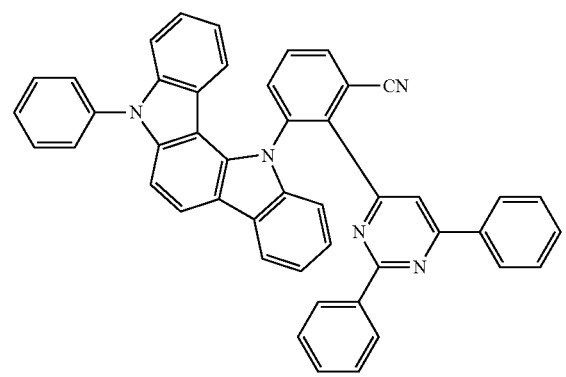
118
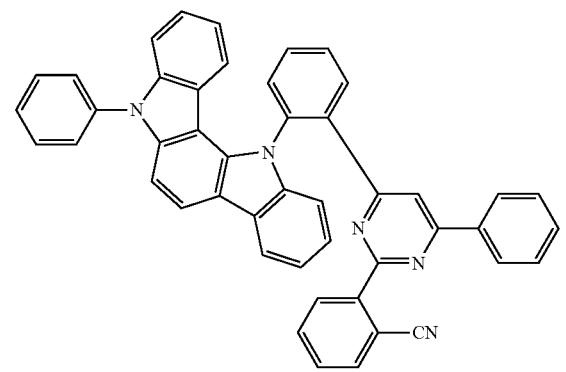
119
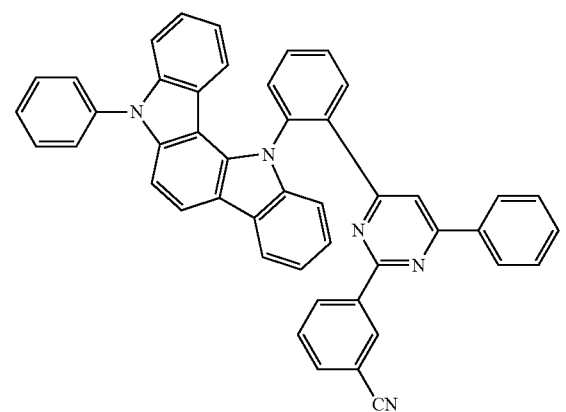
120
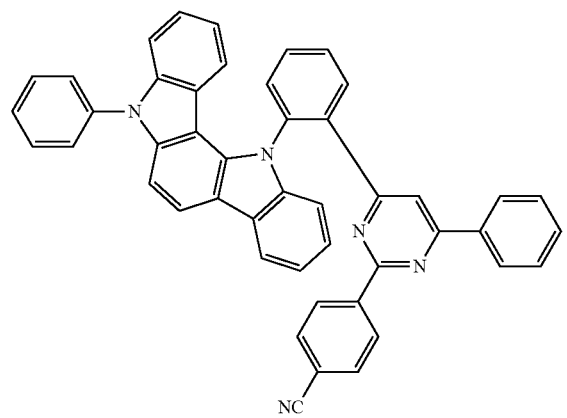
121
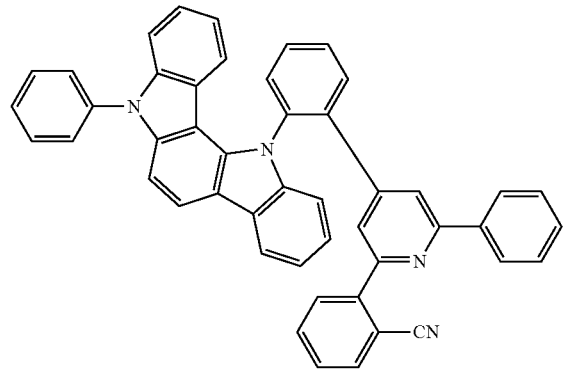
122

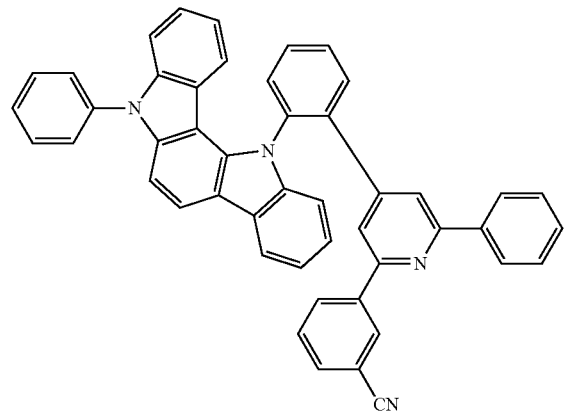
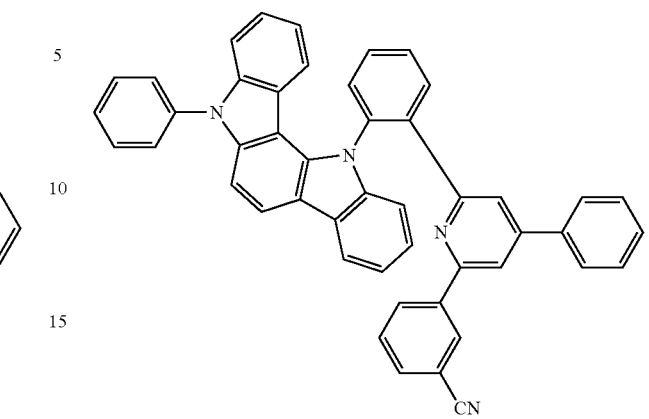

-continued
131
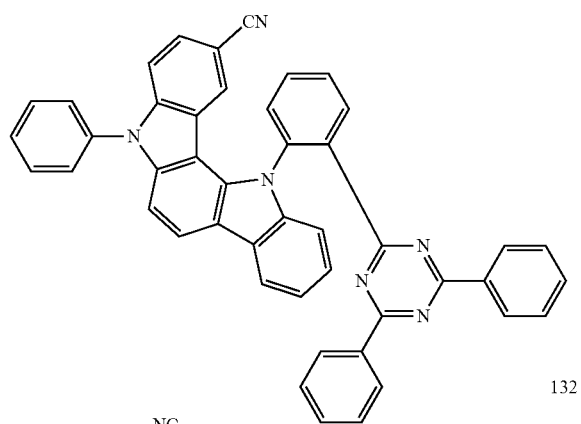
132
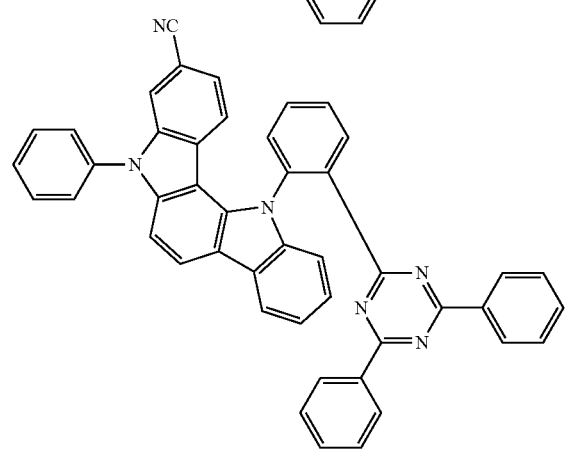
133
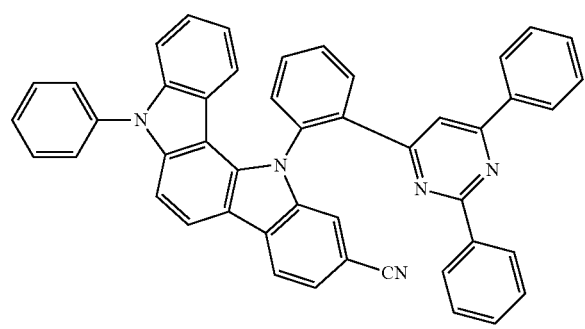
134
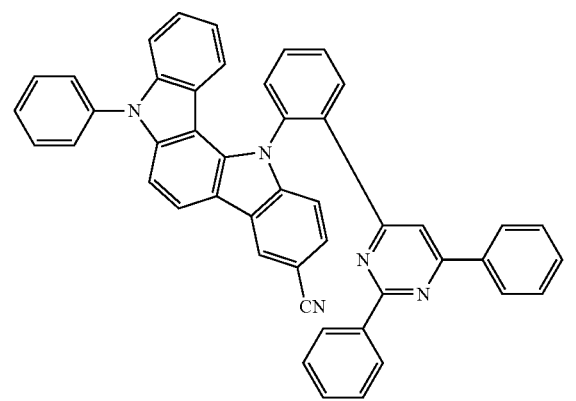
-continued
135
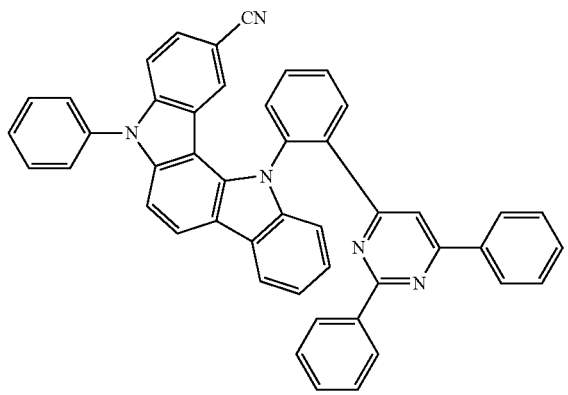
136
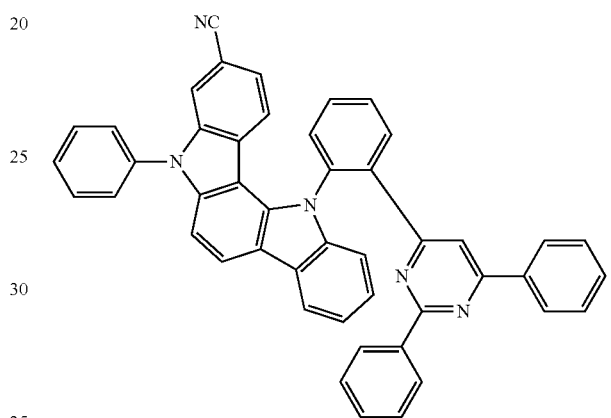
137
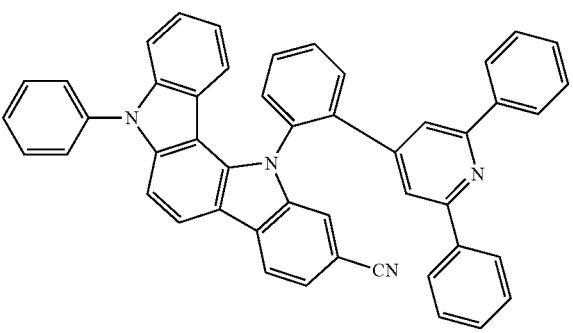
138
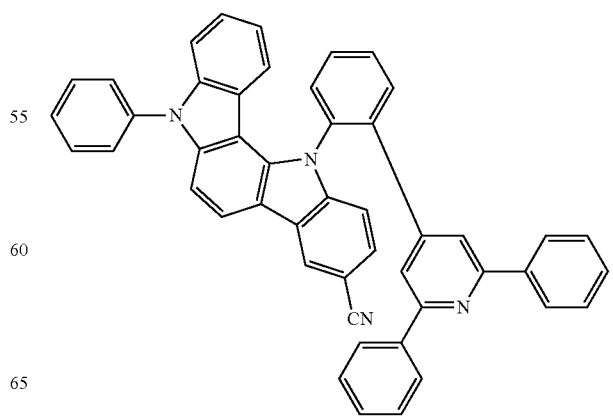

-continued
139
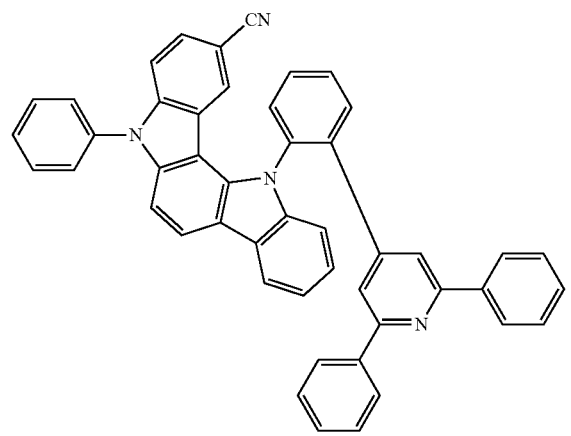
140
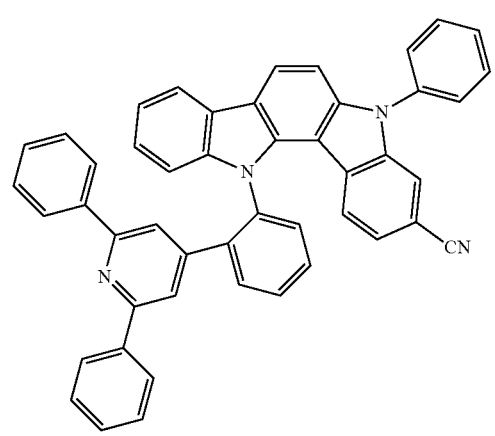
141
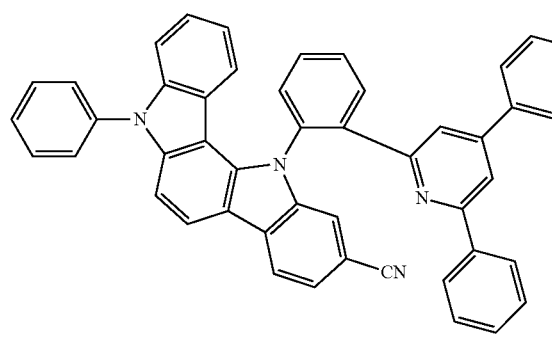
142
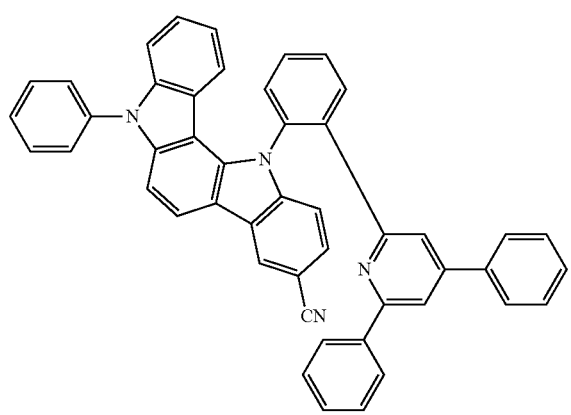
-continued
143
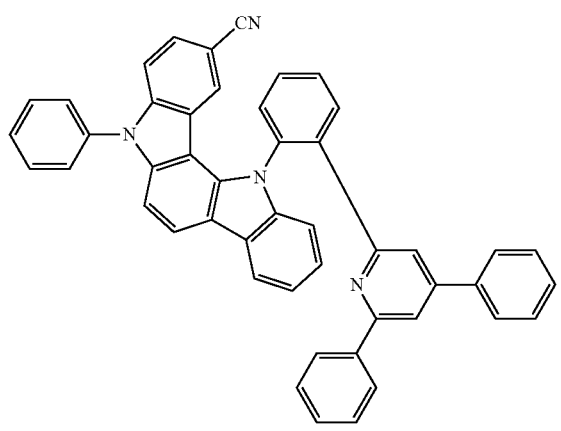
144
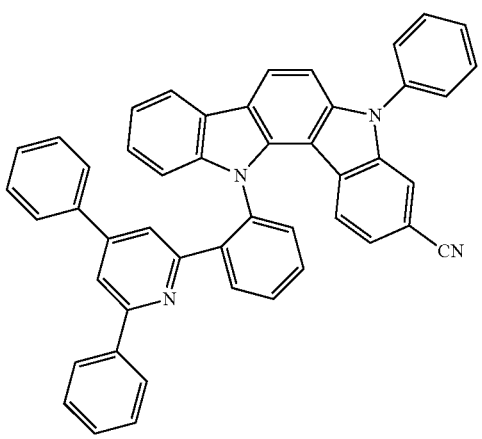
145
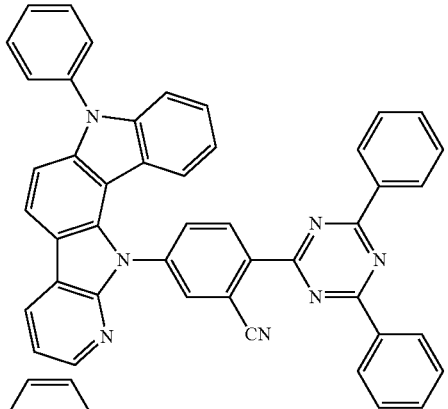
146
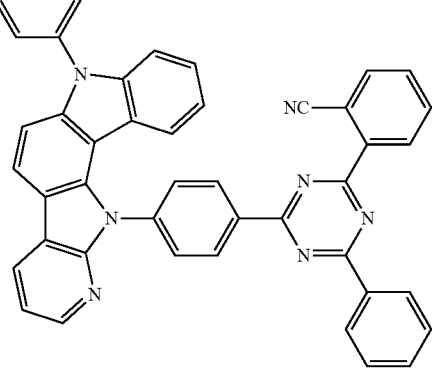

147
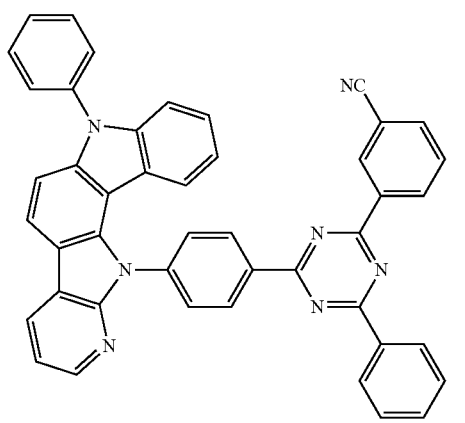
148
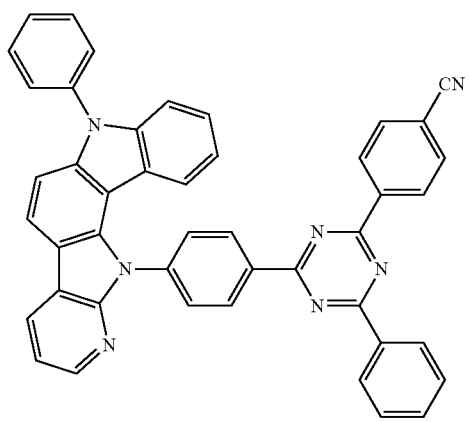
149
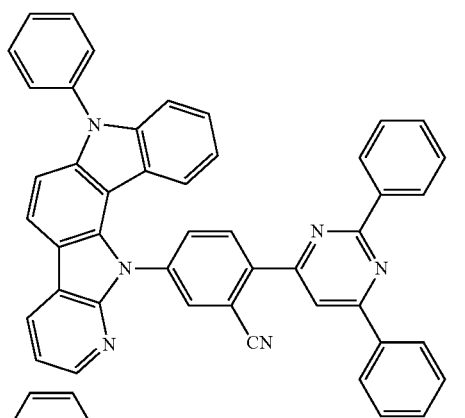
150
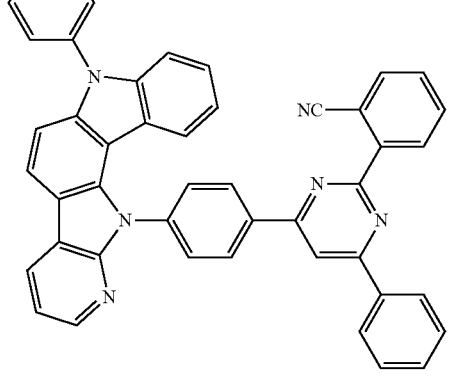
151
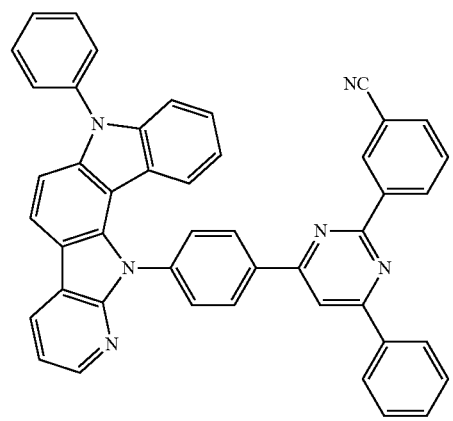
152
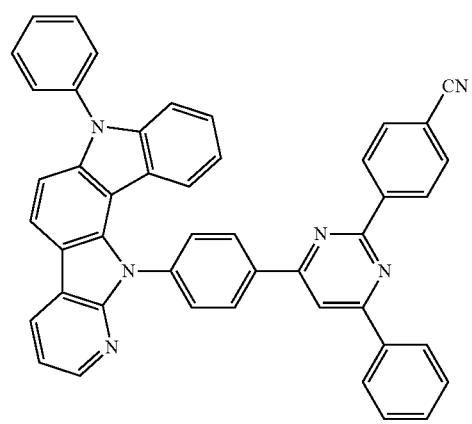
153
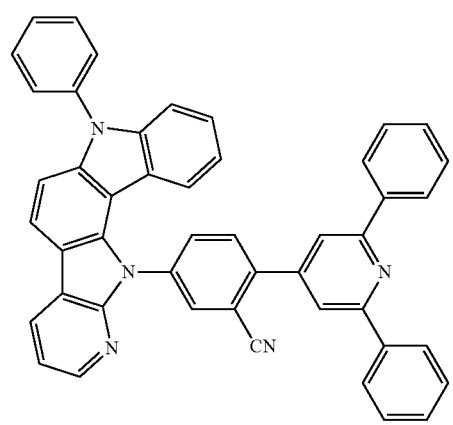
154
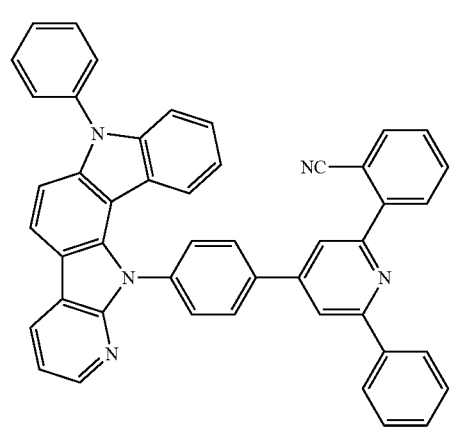

155
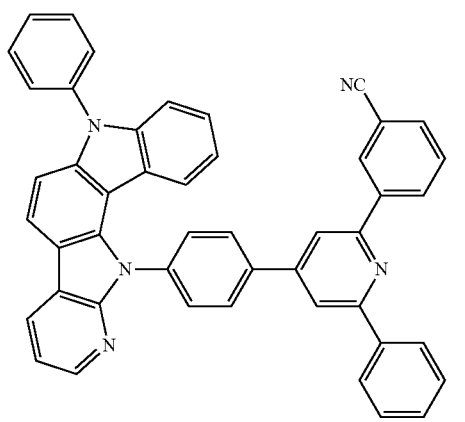
156
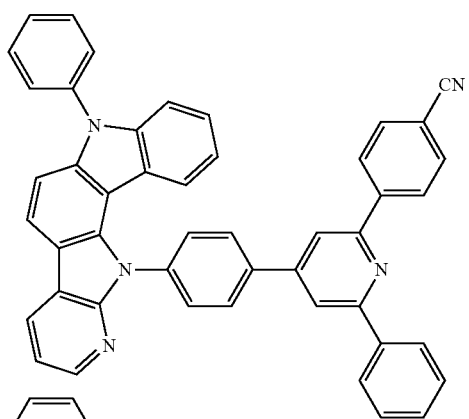
157
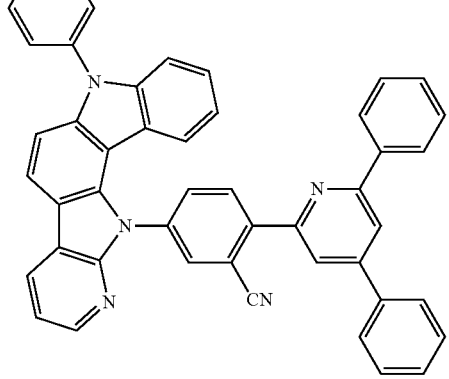
158
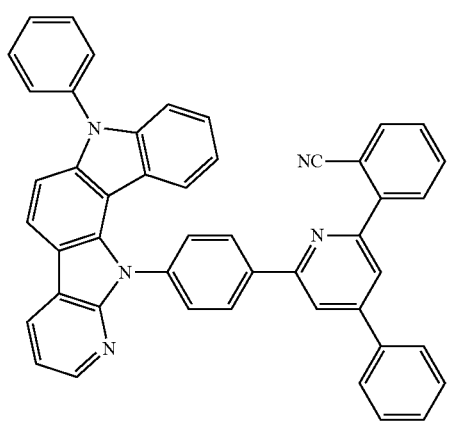
159
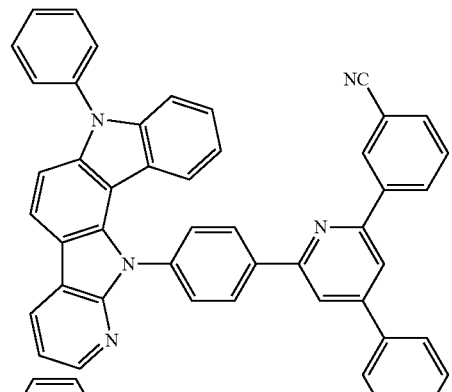
160
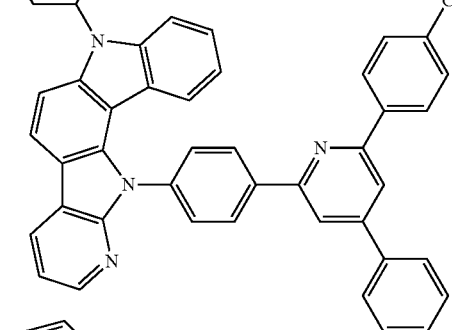
161
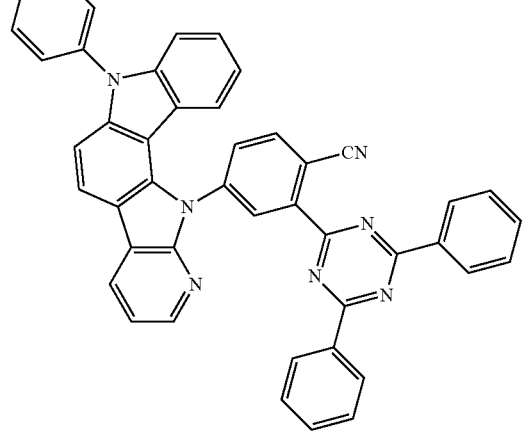
162
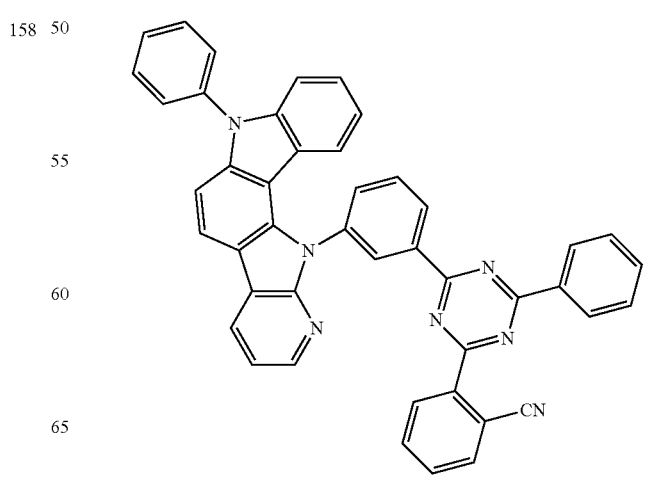

197
163
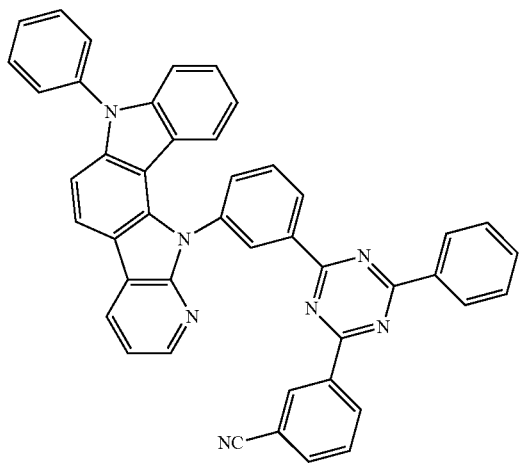
164
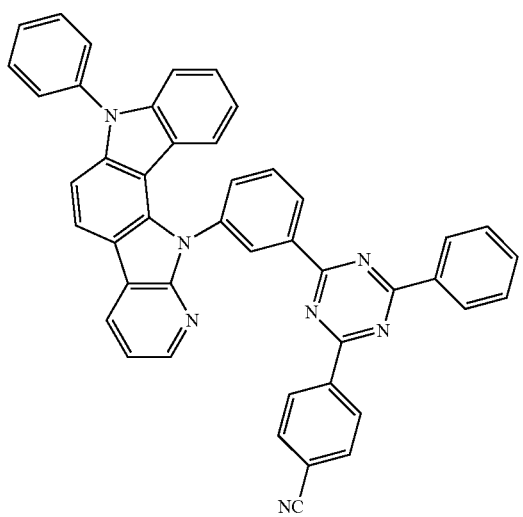
165
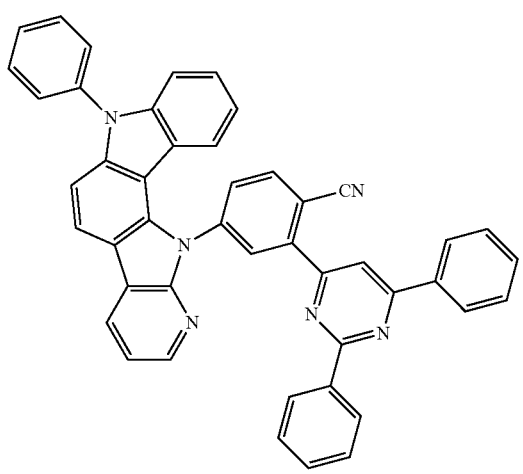
198
166
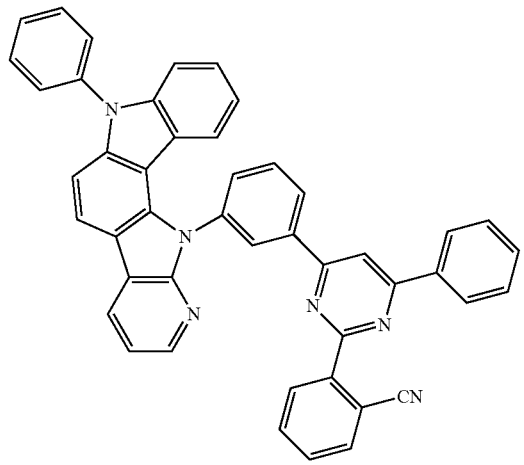
167
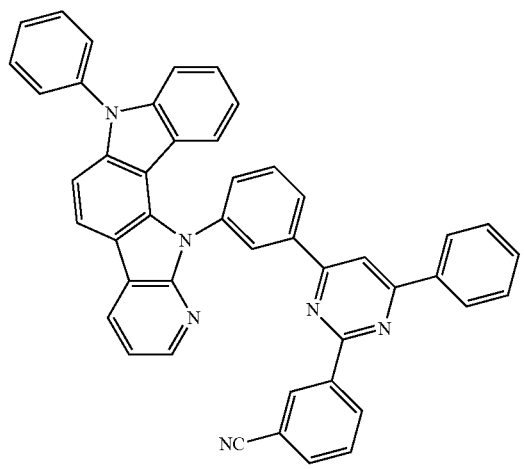
168
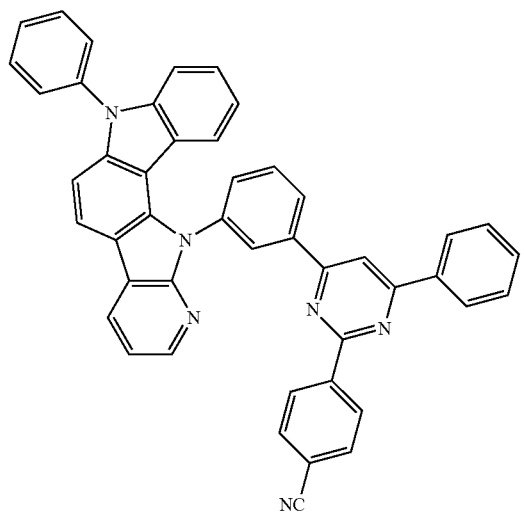

169
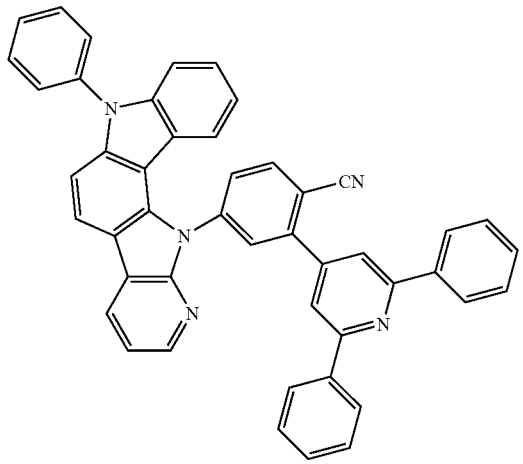
170
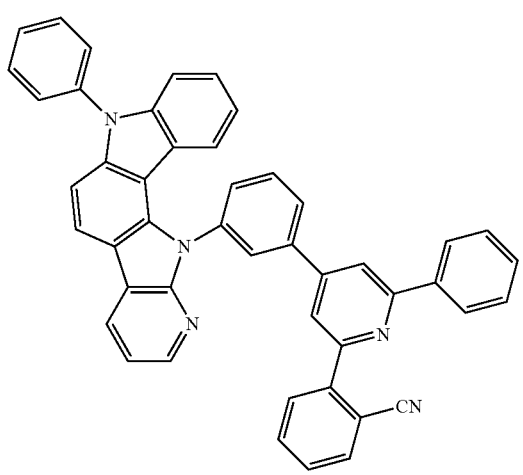
171
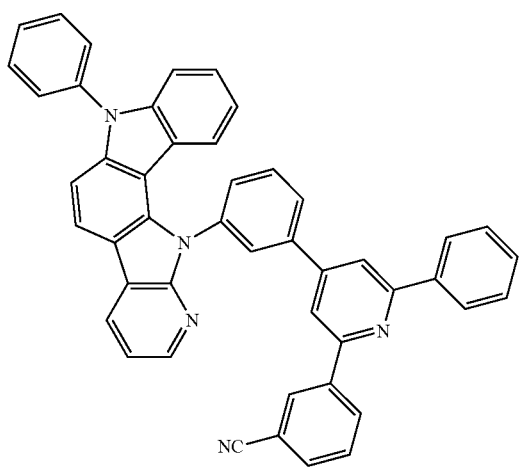
172
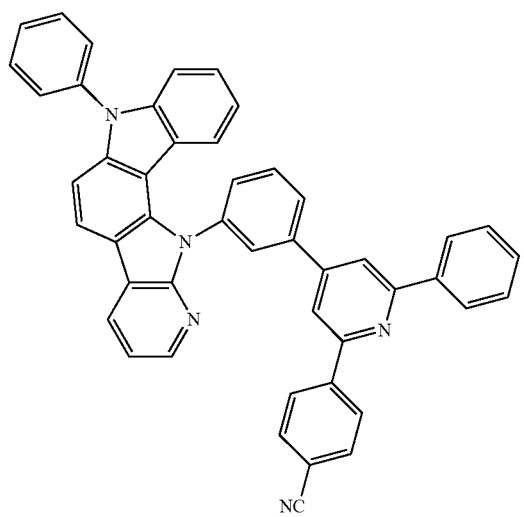
173
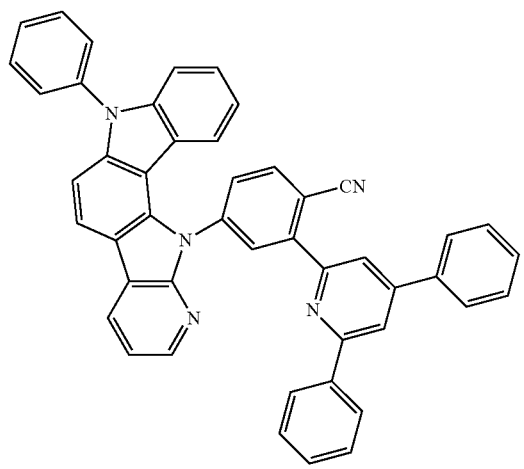
174
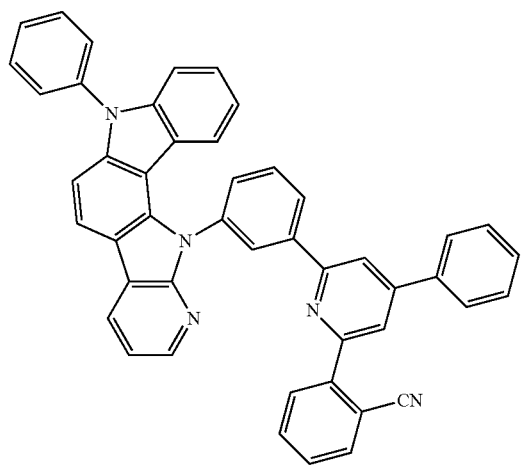

201
-continued
175
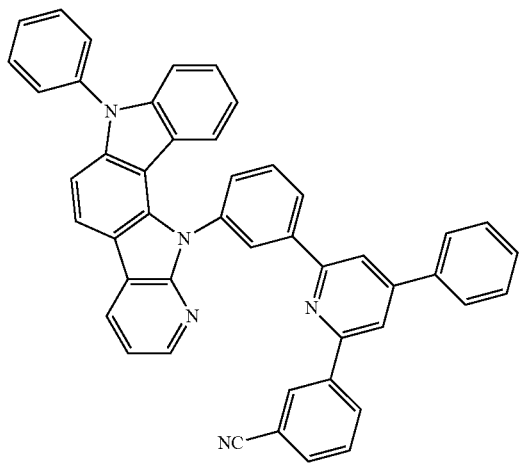
176
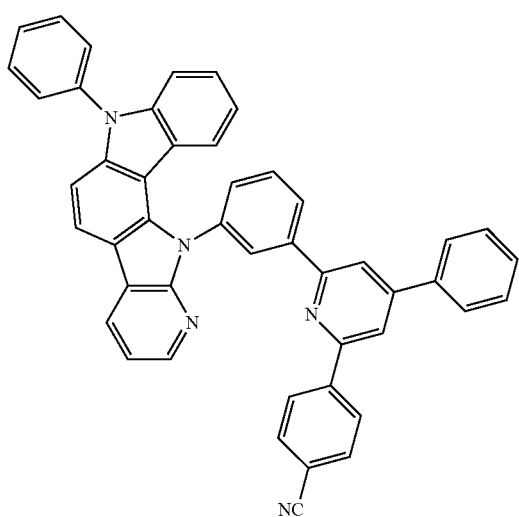
177
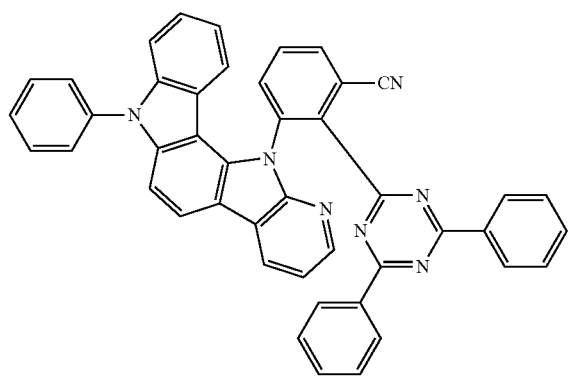
202
-continued
178
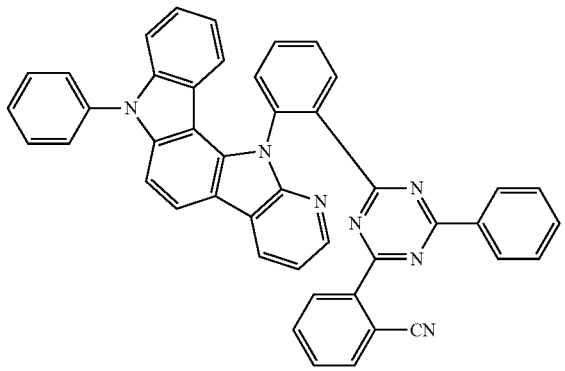
179
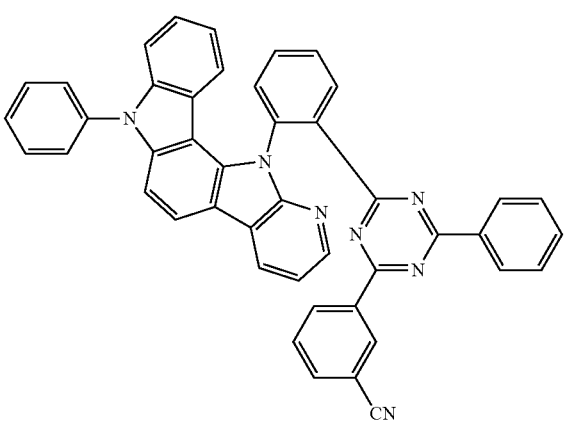
180
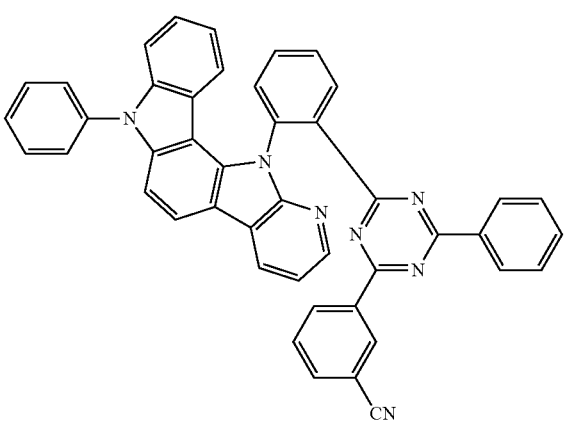
181
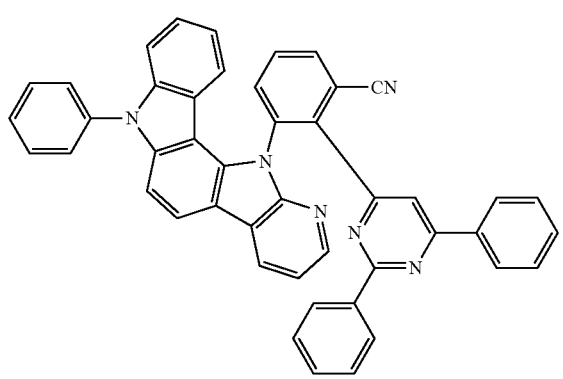

203
-continued
182
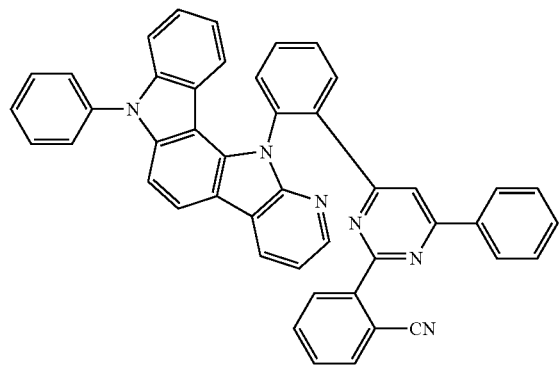
183
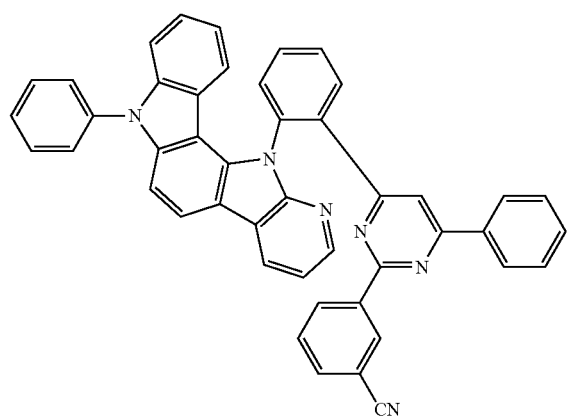
184
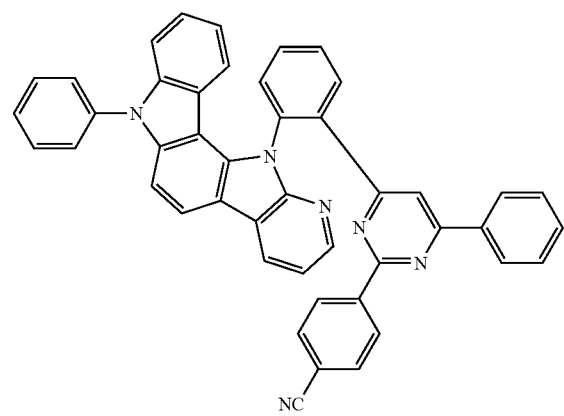
185
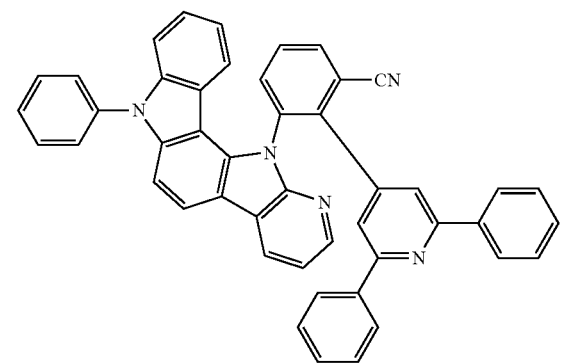
204
-continued
186
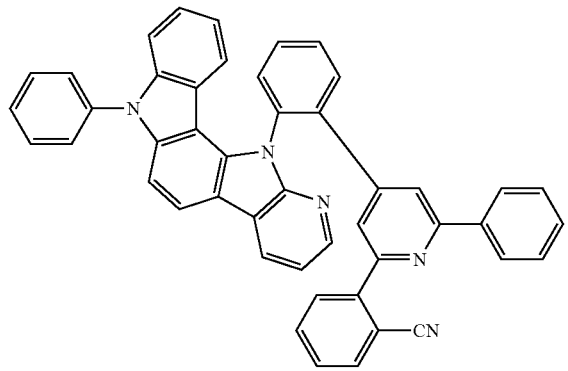
187
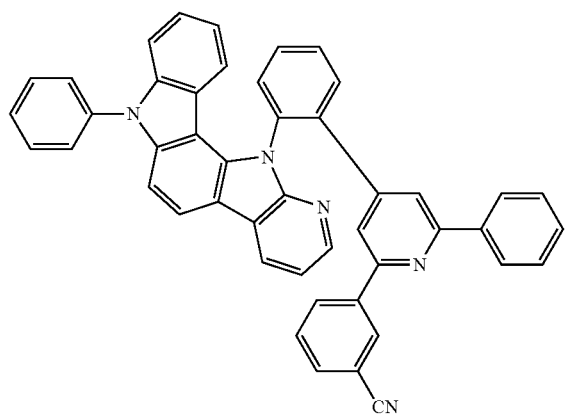
188
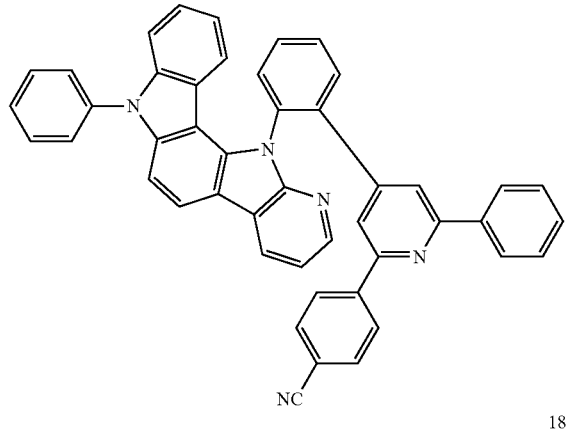
189
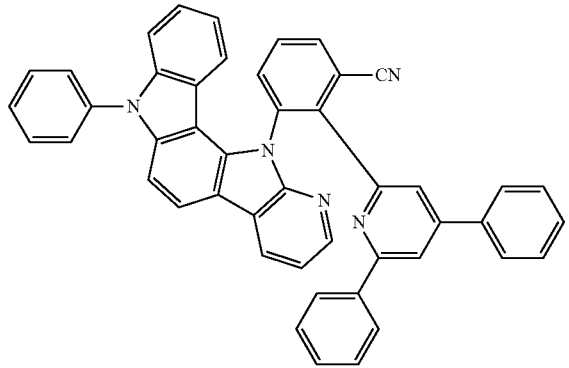

-continued

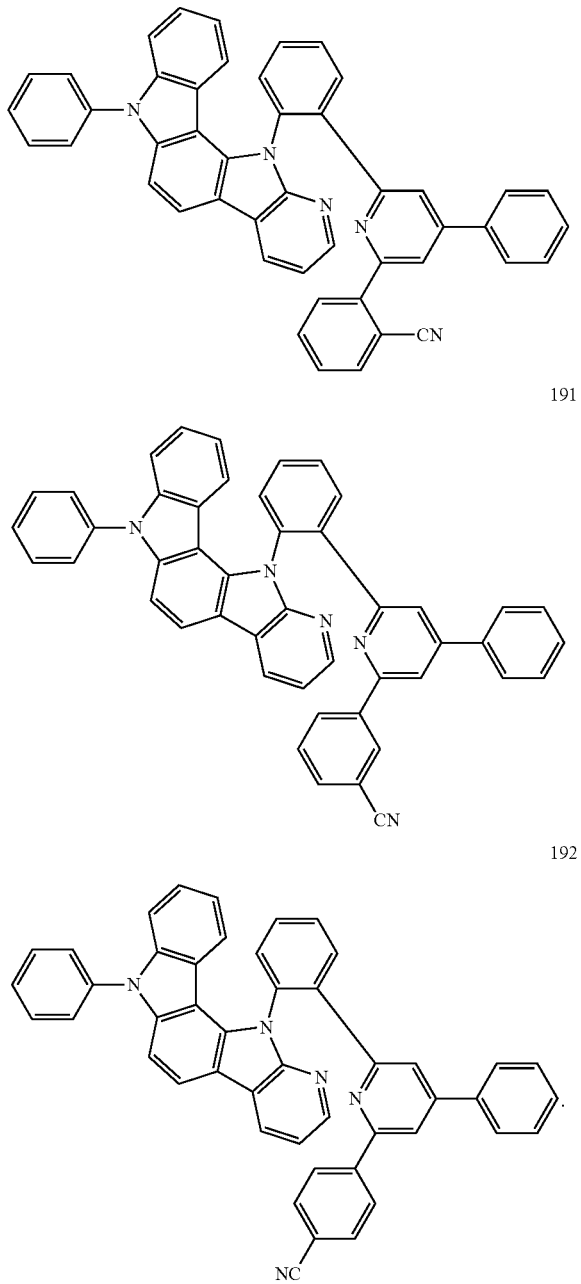

13. The organic light-emitting device of claim 1, wherein the host is selected from:
   a compound comprising at least one selected from a fluorene ring, a carbazole ring, a dibenzofuran ring, a dibenzothiophene ring, an indenocarbazole ring, an indolocarbazole ring, a benzofurocarbazole ring, a benzothienocarbazole ring, an acridine ring, a dihydroacridine ring, and a triindolobenzene ring; or
   a silicon compound and a phosphine oxide compound.

14. The organic light-emitting device of claim 1, wherein the host is selected from compounds represented by Formulae 11-1 to 11-3:

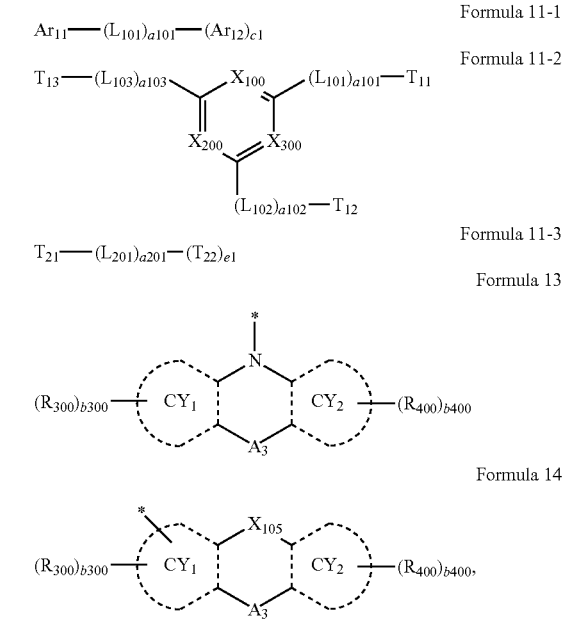

Formula 11-1

Formula 11-2

Formula 11-3

Formula 13

Formula 14 wherein, in Formulae 11-1 to 11-3, 13, and 14, $Ar_{11}$ and $Ar_{12}$ are each independently selected from groups represented by Formulae 13 and 14, $X_{105}$ is $N(R_{202})$, O, or S, $X_{100}$ is N or $C(T_{14})$, $X_{200}$ is N or $C(T_{15})$, and $X_{300}$ is N or $C(T_{16})$, wherein at least one selected from $X_{100}$ to $X_{300}$ is N, $T_{21}$ and $T_{22}$ are each independently selected from *-$(L_{201})_{a201}$-Si$(Q_{41})(Q_{42})(Q_{43})$ and *-$(L_{201})_{a201}$-P(=O)$(Q_{51})(Q_{52})$, $L_{101}$ to $L_{103}$ and $L_{201}$ are each independently selected from:

a single bond, O, S, Si$(Q_{61})(Q_{62})$, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —CF$_3$, —CF$_2$H, —CFH$_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si$(Q_{71})(Q_{72})(Q_{73})$;

a101 to a103 and a201 are each independently an integer selected from 0 to 5, wherein, when a101 is 2 or more, 2 or more groups $L_{101}$ are identical to or different from each other, when a102 is 2 or more, 2 or more groups $L_{102}$ are identical to or different from each other, when a103 is 2 or more, 2 or more groups $L_{103}$ are identical to or different from each other, and when a201 is 2 or more, 2 or more groups $L_{201}$ are identical to or different from each other, $CY_1$ and $CY_2$ are each independently selected from a benzene group, a naphthalene group, a fluorene group, a carbazole group, a benzocarbazole group, an indolocarbazole group, a dibenzofuran group, and a dibenzothiophene group, $A_3$ is selected from:

a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si($Q_{81}$)($Q_{82}$)($Q_{83}$), $T_{11}$ to $T_{16}$, $R_{202}$, $R_{300}$, and $R_{400}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, and —Si($Q_{91}$)($Q_{92}$)($Q_{93}$), b300 and b400 are each independently an integer selected from 0 to 10, c1 and e1 are each independently 0, 1, 2, or 3,

* indicates a binding site to a neighboring atom, at least one substituent selected from the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_7$-$C_{60}$ arylalkyl group, the substituted $C_1$-$C_{60}$ heteroaryl group, the substituted $C_1$-$C_{60}$ heteroaryloxy group, the substituted $C_1$-$C_{60}$ heteroarylthio group, the substituted $C_2$-$C_{60}$ heteroarylalkyl group, the substituted monovalent non-aromatic condensed polycyclic group, and the substituted monovalent non-aromatic condensed heteropolycyclic group is selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, and —Si($Q_{101}$)($Q_{102}$)($Q_{103}$), and $Q_{41}$ to $Q_{43}$, $Q_{51}$ to $Q_{52}$, $Q_{61}$ to $Q_{62}$, $Q_{71}$ to $Q_{73}$, $Q_{81}$ to $Q_{83}$, $Q_{91}$ to $Q_{93}$ and $Q_{101}$ to $Q_{103}$ are each independently selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

15. The organic light-emitting device of claim 14, wherein $Ar_{11}$ and $Ar_{12}$ are each independently selected from groups represented by Formulae 13-1 to 13-8 and 14-1 to 14-8:

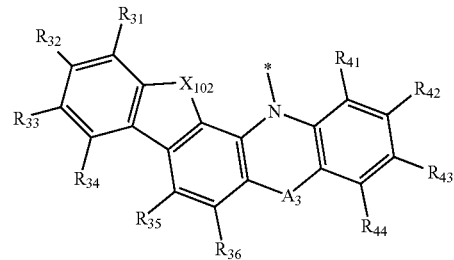

Formula 13-1

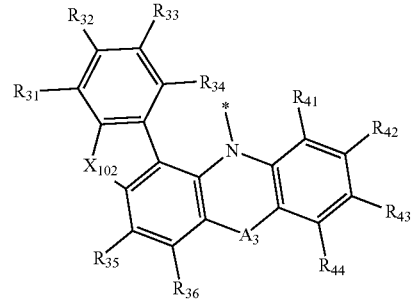

Formula 13-2

Formula 13-3
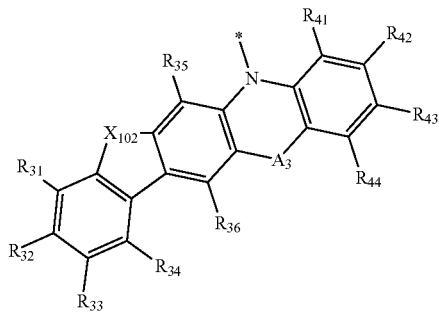
Formula 13-4
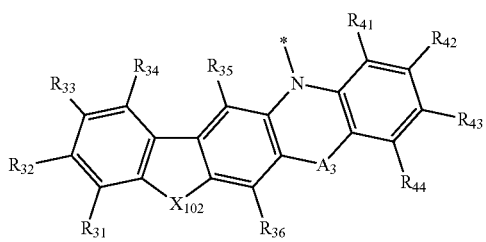
Formula 13-5
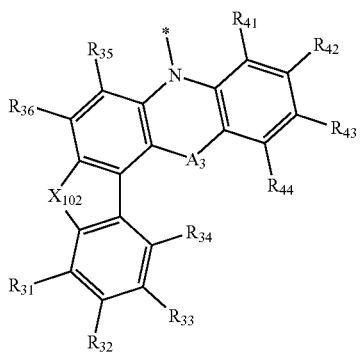
Formula 13-6
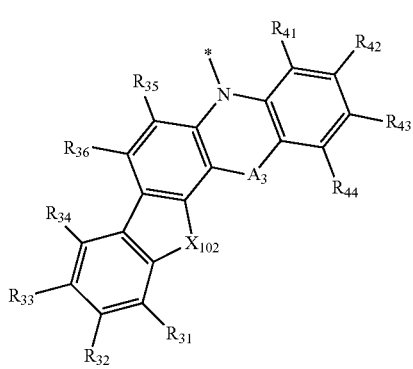
Formula 13-7
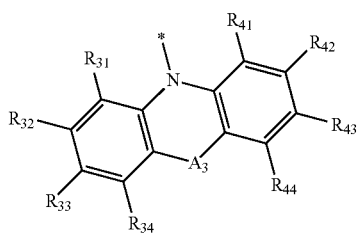
Formula 13-8
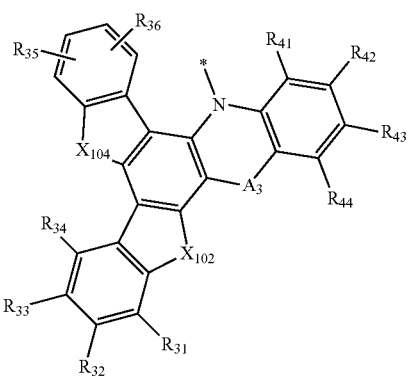
Formula 14-1
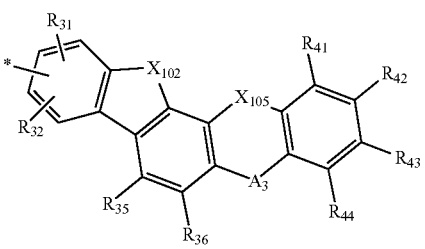
Formula 14-2
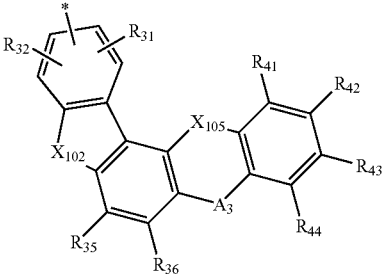
Formula 14-3
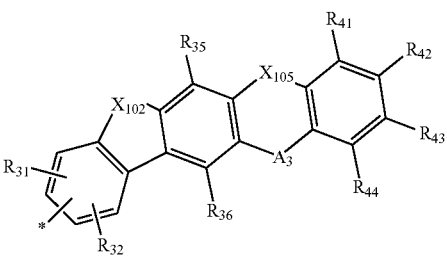
Formula 14-4
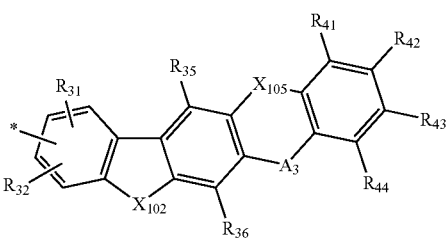

-continued

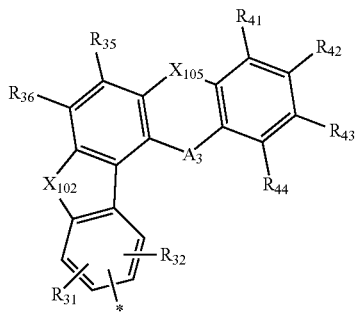
Formula 14-5

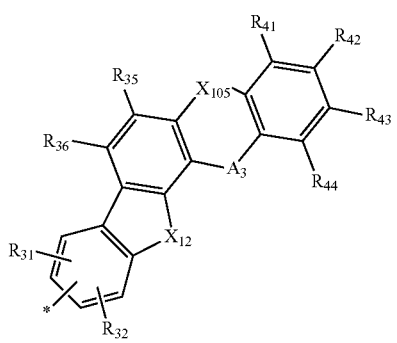
Formula 14-6

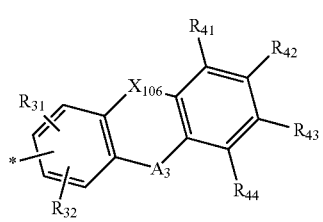
Formula 14-7

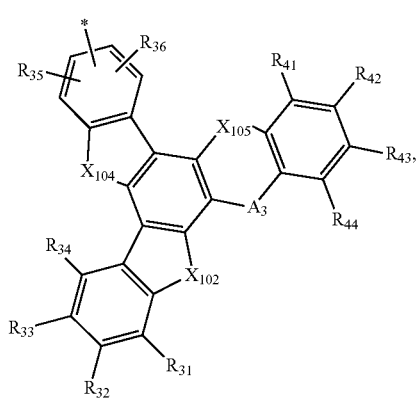
Formula 14-8 wherein, in Formulae 13-1 to 13-8 and 14-1 to 14-8,
$X_{102}$ and $X_{104}$ are each independently $C(R_{37})(R_{38})$, $N(R_{39})$, O, or S,
$X_{105}$ and $A_3$ are understood by referring to the descriptions thereof in claim 14,
$R_{31}$ to $R_{39}$ are each independently understood by referring to the description of $R_{300}$ in claim 14,
$R_{41}$ to $R_{44}$ are each independently understood by referring to the description of $R_{400}$ in claim 14, and
* indicates a binding site to a neighboring atom.

16. The organic light-emitting device of claim 14, wherein $Ar_{11}$ and $Ar_{12}$ are each independently selected from groups represented by Formulae 17-1 to 17-19 and 18-1 to 18-8:

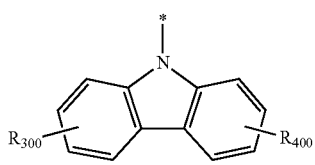
Formula 17-1

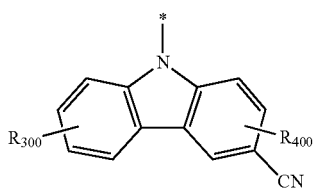
Formula 17-2

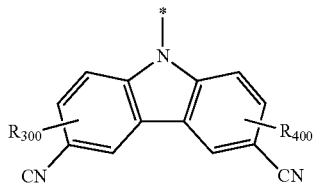
Formula 17-3

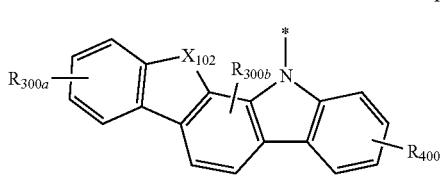
Formula 17-4

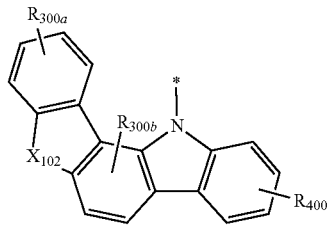
Formula 17-5

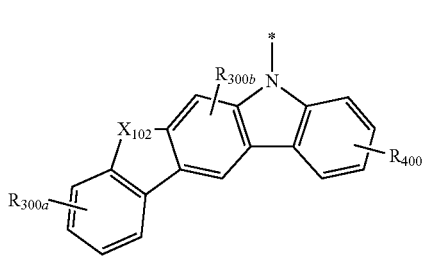
Formula 17-6

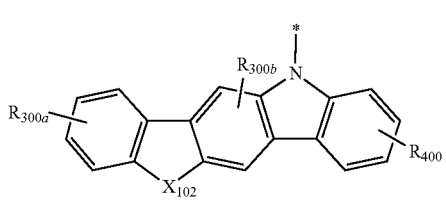
Formula 17-7

Formula 17-8
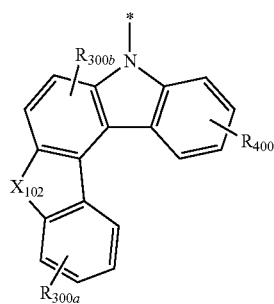
Formula 17-9
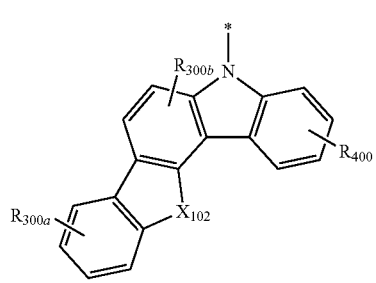
Formula 17-10
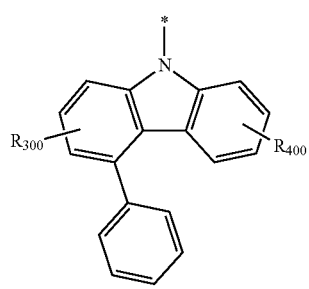
Formula 17-11
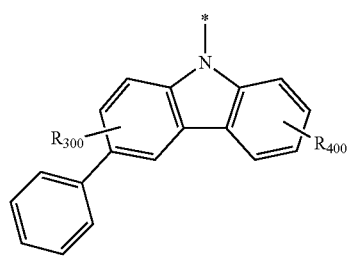
Formula 17-12
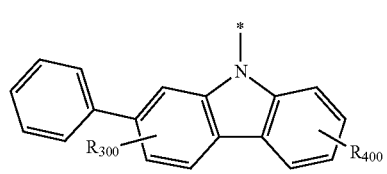
Formula 17-13
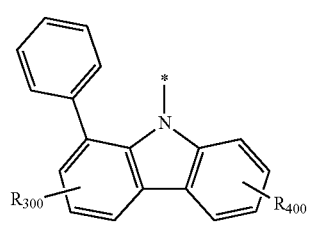
Formula 17-14
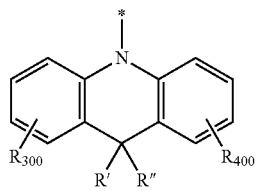
Formula 17-15
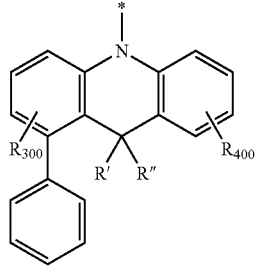
Formula 17-16
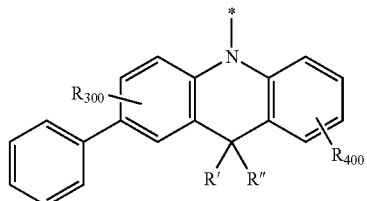
Formula 17-17
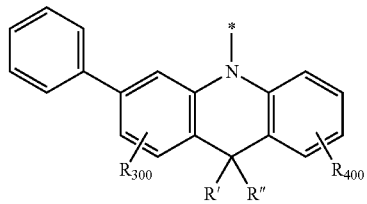
Formula 17-18
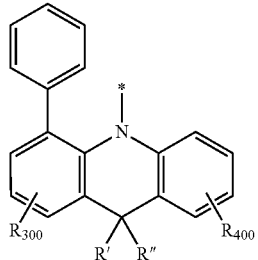
Formula 17-19
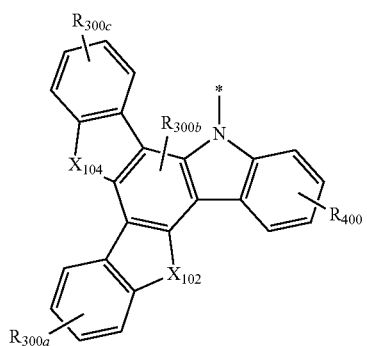

-continued

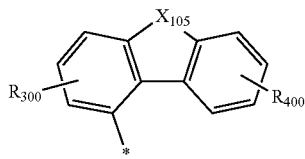
Formula 18-1

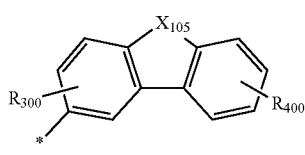
Formula 18-2

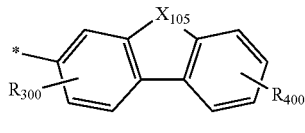
Formula 18-3

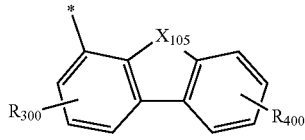
Formula 18-4

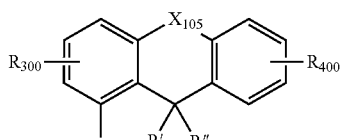
Formula 18-5

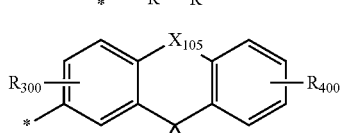
Formula 18-6

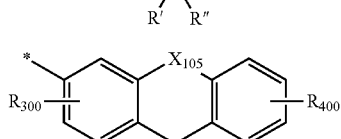
Formula 18-7

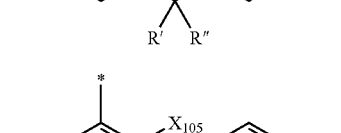
Formula 18-8

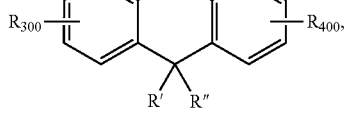

wherein, in Formulae 17-1 to 17-19 and 18-1 to 18-8,
$X_{102}$ and $X_{104}$ are each independently $C(R_{37})(R_{38})$, $N(R_{39})$, O, or S,
$X_{105}$ is $N(R_{202})$, O, or S,
R' and R'' are each independently selected from hydrogen, deuterium, a $C_1$-$C_{10}$ alkyl group, a $C_1$-$C_{10}$ alkoxy group, a phenyl group, a biphenyl group, a terphenyl group, a naphthyl group, a fluorenyl group, a carbazolyl group, a dibenzofuranyl group, and a dibenzothiophenyl group,
$R_{202}$, $R_{300}$, $R_{300a}$ to $R_{300c}$, and $R_{400}$ are each independently selected from
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$;
a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group;
a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, and —$CFH_2$, a phenyl group, a biphenyl group, a terphenyl group, a pyridinyl group, a pyrimidinyl group, a pyrazinyl group, a pyridazinyl group, a triazinyl group, a naphthyl group, a fluorenyl group, a carbazolyl group, a dibenzofuranyl group, and a dibenzothiophenyl group; and
—$Si(Q_{91})(Q_{92})(Q_{93})$,
$Q_{91}$ to $Q_{93}$ are each independently selected from hydrogen, a $C_1$-$C_{10}$ alkyl group, a $C_1$-$C_{10}$ alkoxy group, a phenyl group, a biphenyl group, a terphenyl group, and a naphthyl group, and
* indicates a binding site to a neighboring atom.

17. The organic light-emitting device of claim 14, wherein the groups represented by *-$(L_{101})_{a101}$-*', *-$(L_{102})_{a102}$-*', *-$(L_{103})_{a103}$-*' and *-$(L_{201})_{a201}$-*' are each independently selected from a single bond and groups represented by Formulae 4-1 to 4-42:

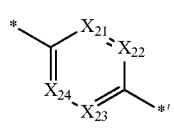
Formula 4-1

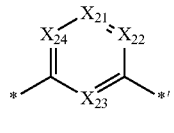
Formula 4-2

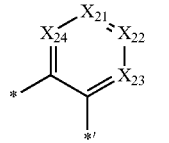
Formula 4-3

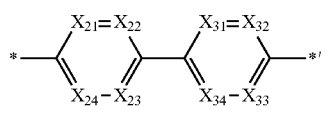
Formula 4-4

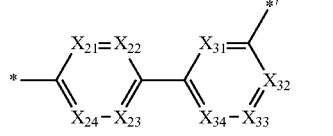
Formula 4-5

Formula 4-6

Formula 4-7

Formula 4-8

Formula 4-9

Formula 4-10

Formula 4-11

Formula 4-12

Formula 4-13

Formula 4-14

Formula 4-15

Formula 4-16

Formula 4-17

Formula 4-18

Formula 4-19

Formula 4-20

Formula 4-21

Formula 4-22

Formula 4-23
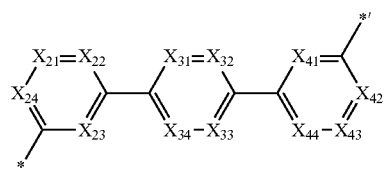
Formula 4-24
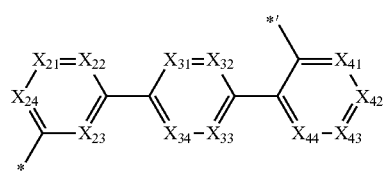
Formula 4-25
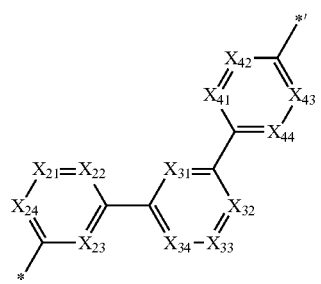
Formula 4-26
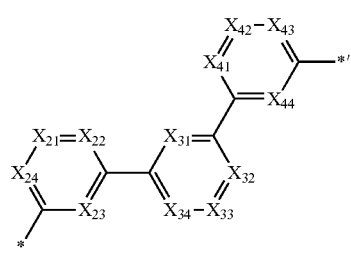
Formula 4-27
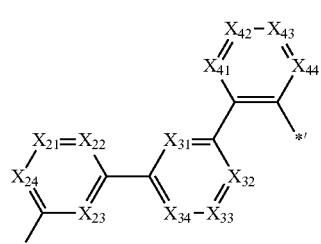
Formula 4-28
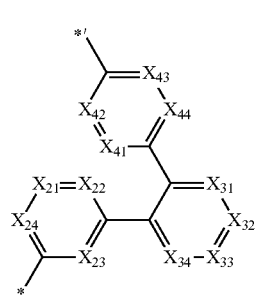
Formula 4-29
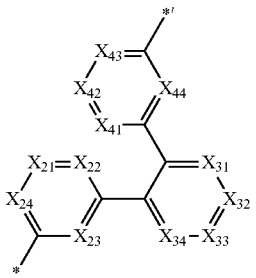
Formula 4-30
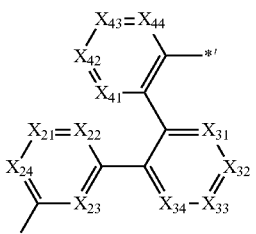
Formula 4-31
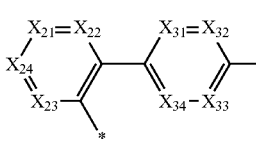
Formula 4-32
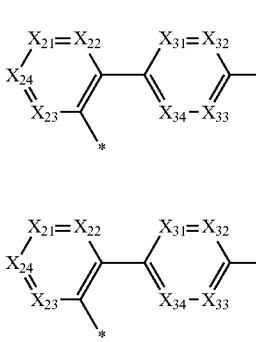
Formula 4-33
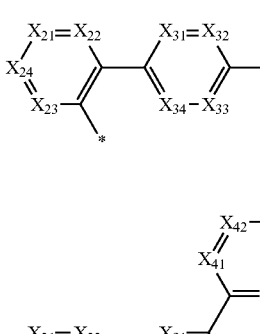
Formula 4-34
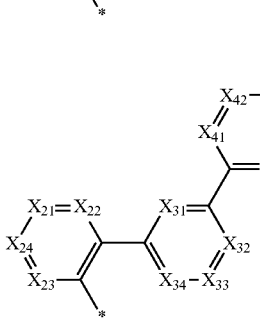
Formula 4-35
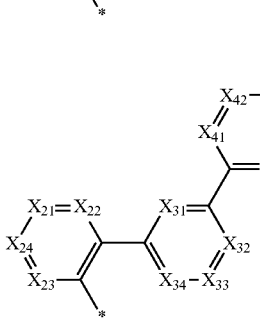

-continued

Formula 4-36

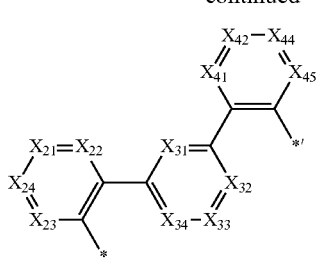

Formula 4-37

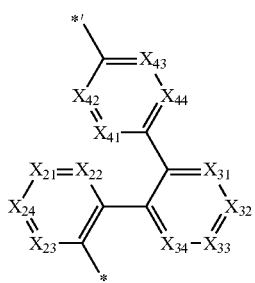

Formula 4-38

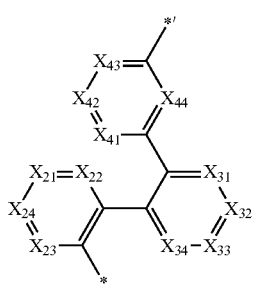

Formula 4-39

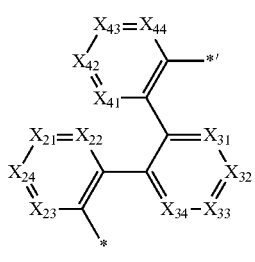

Formula 4-40

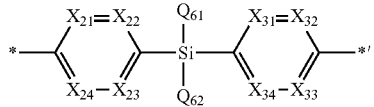

Formula 4-41

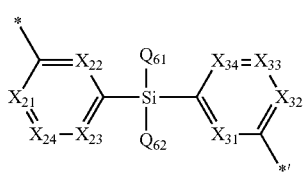

Formula 4-42

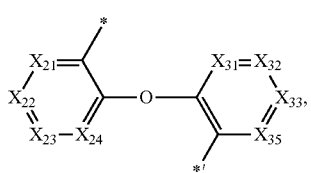

wherein, in Formulae 4-1 to 4-42,
$X_{41}$ is N or $C(Z_{41})$, $X_{42}$ is N or $C(Z_{42})$, $X_{43}$ is N or $C(Z_{43})$, $X_{44}$ is N or $C(Z_{44})$, $X_{51}$ is N or $C(Z_{51})$, $X_{52}$ is N or $C(Z_{52})$, $X_{53}$ is N or $C(Z_{53})$, $X_{54}$ is N or $C(Z_{54})$, $X_{61}$ is N or $C(Z_{61})$, $X_{62}$ is N or $C(Z_{62})$, $X_{63}$ is N or $C(Z_{63})$, and $X_{64}$ is N or $C(Z_{64})$, wherein a case where each of $X_{41}$ to $X_{44}$ is N, a case where each of $X_{51}$ to $X_{54}$ is N, and a case where each of $X_{61}$ to $X_{64}$ is N are excluded, $Z_{41}$ to $Z_{44}$, $Z_{51}$ to $Z_{54}$, and $Z_{61}$ to $Z_{64}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —$Si(Q_{71})(Q_{72})(Q_{73})$, $Q_{71}$ to $Q_{73}$ are each independently selected from hydrogen, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, and a dibenzothiophenyl group, and

* and *40 each indicate a binding site to a neighboring atom.

18. The organic light-emitting device of claim 14, wherein $T_{11}$ to $T_{16}$ are each independently selected from:
hydrogen, deuterium, —F, a cyano group, a $C_1$-$C_{10}$ alkyl group, a $C_1$-$C_{10}$ alkoxy group —$CF_3$, —$CF_2H$, and —$CFH_2$;
a $C_1$-$C_{10}$ alkyl group and a $C_1$-$C_{10}$ alkoxy group, each substituted with at least one selected from deuterium, —F, a cyano group —$CF_3$, —$CF_2H$, and —$CFH_2$;
a phenyl group, a biphenyl group, a terphenyl group, a pyridinyl group, a pyrimidinyl group, a triazinyl group, a carbazolyl group, a dibenzofuranyl group, and a dibenzothiophenyl group;
a phenyl group, a biphenyl group, a terphenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a $C_1$-$C_{10}$ alkyl group, a $C_1$-$C_{10}$ alkoxy group, —$CF_3$, —$CF_2H$, —$CFH_2$, a phenyl group, a biphenyl group, a terphenyl group, a pyridinyl group, a pyrimidinyl group, a triazinyl group, a carbazolyl group, a dibenzofuranyl group, and a dibenzothiophenyl group; and —$Si(Q_{91})(Q_{92})(Q_{93})$, $Q_{91}$ to $Q_{93}$ are each independently selected from hydrogen, a $C_1$-$C_{10}$ alkyl group, a $C_1$-$C_{10}$ alkoxy group, a phenyl group, a biphenyl group, a terphenyl group, a pyridinyl group, a pyrimidinyl group, a triazinyl group, a carbazolyl group, a dibenzofuranyl group, and a dibenzothiophenyl group, and $Q_{41}$ to $Q_{43}$ and $Q_{51}$ to $Q_{52}$ are each independently selected from:
a phenyl group, a biphenyl group, a terphenyl group, a pyridinyl group, a pyrimidinyl group, a triazinyl group, a carbazolyl group, a dibenzofuranyl group, and a dibenzothiophenyl group; and
a phenyl group, a biphenyl group, a terphenyl group, a pyridinyl group, a pyrimidinyl group, a triazinyl group, a carbazolyl group, a dibenzofuranyl group, and a dibenzothiophenyl group, each substituted with at least one selected from deuterium, —F, a cyano group, a C$_1$-C$_{10}$ alkyl group, a C$_1$-C$_{10}$ alkoxy group, —CF$_3$, —CF$_2$H, —CFH$_2$, a phenyl group, a biphenyl group, a terphenyl group, a pyridinyl group, a pyrimidinyl group, a triazinyl group, a carbazolyl group, a dibenzofuranyl group, and a dibenzothiophenyl group.

19. The organic light-emitting device of claim 1, wherein the host is selected from Compounds H1 to H24:

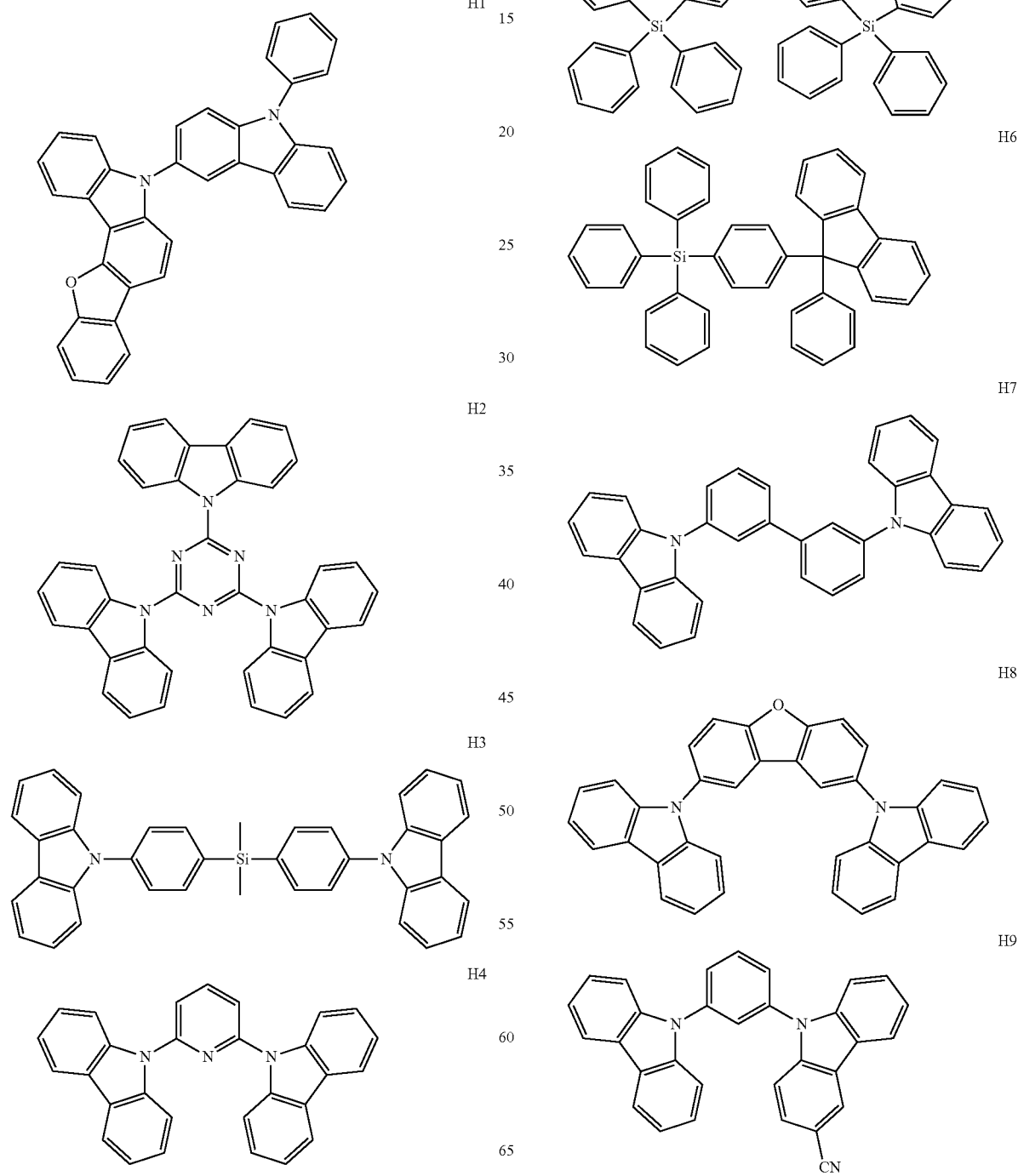

-continued
H10
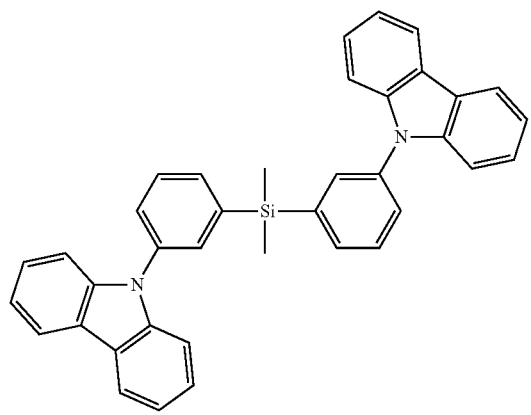
H11
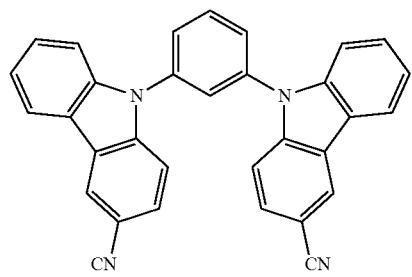
H12
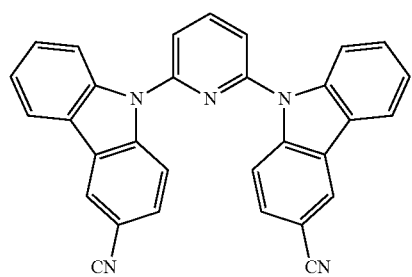
H13
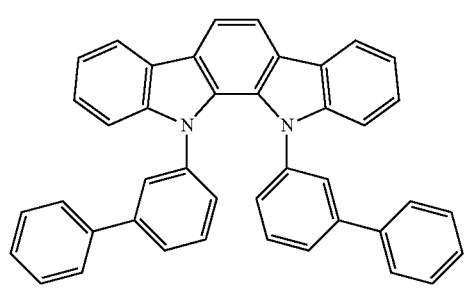
-continued
H15
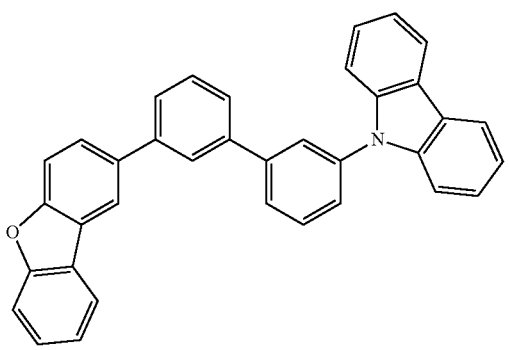
H16
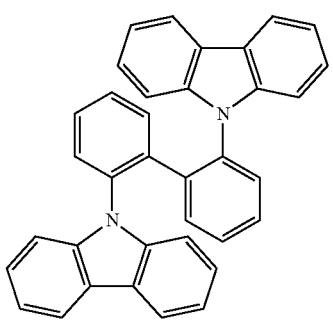
H17
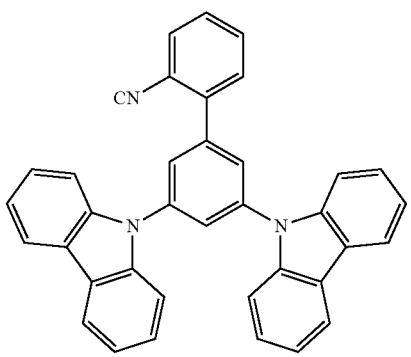
H18
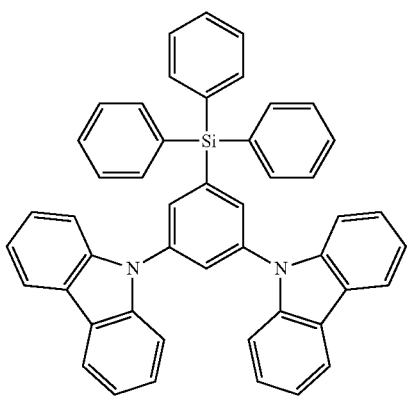

H19
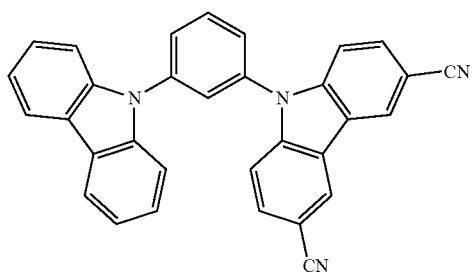

H20
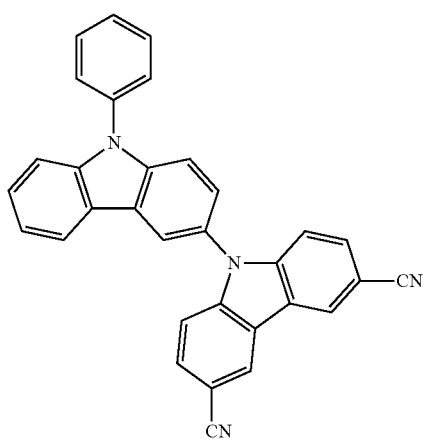

H21
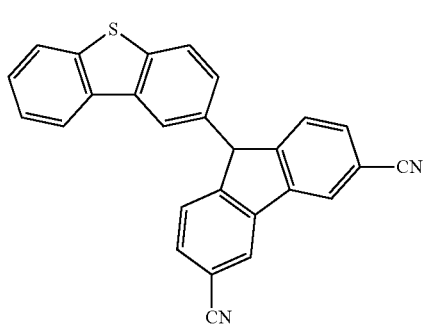

H22
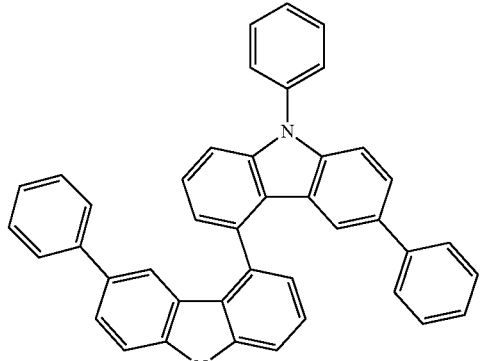

H23
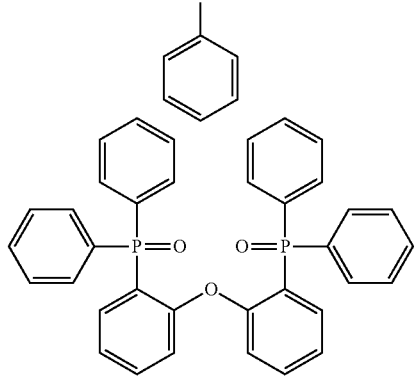

H24
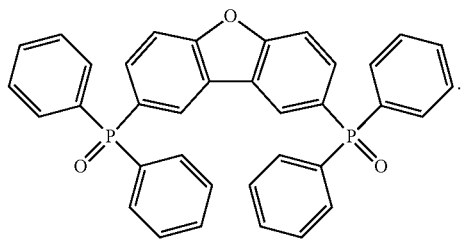

20. The organic light-emitting device of claim 1, wherein the dopant comprises a thermal activated delayed fluorescent dopant,
  wherein the thermal activated delayed fluorescent dopant is the condensed cyclic compound represented by Formula 1, which satisfies Equations 1 and 2:

$$E_{S1(TD)} - E_{T1(TD)} \leq 0.3 \text{ electron Volts} \qquad \text{Equation 1}$$

$$E_{S1(TD)} > 2.6 \text{ electron Volts}, \qquad \text{Equation 2}$$

wherein, in Equations 1 and 2,
  $E_{S1(TD)}$ denotes a singlet state ($S_1$) energy level (unit: eV) of the thermal activated delayed fluorescent dopant, and
  $E_{T1(TD)}$ denotes a triplet state ($T_1$) energy level (unit: eV) of the thermal activated delayed fluorescent dopant.

* * * * *